US006338852B1

(12) United States Patent
Reed et al.

(10) Patent No.: US 6,338,852 B1
(45) Date of Patent: *Jan. 15, 2002

(54) COMPOUNDS AND METHODS FOR DIAGNOSIS OF TUBERCULOSIS

(75) Inventors: Steven G. Reed, Bellevue; Yasir A. W. Skeiky, Seattle; Davin C. Dillon, Redmond; Antonio Campos-Neto, Bainbridge Island; Raymond Houghton, Bothell; Thomas S. Vedvick, Federal Way; Daniel R. Twardzik, Bainbridge Island, all of WA (US)

(73) Assignee: Corixa Corporation, Seattle, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/818,111

(22) Filed: Mar. 13, 1997

Related U.S. Application Data

(63) Continuation-in-part of application No. 08/729,622, filed as application No. PCT/US96/14675 on Aug. 30, 1996, and a continuation-in-part of application No. 08/680,574, filed on Jul. 12, 1996, which is a continuation-in-part of application No. 08/658,800, filed on Jun. 5, 1996, which is a continuation-in-part of application No. 08/620,280, filed on Mar. 22, 1996, now abandoned, which is a continuation-in-part of application No. 08/532,136, filed on Sep. 22, 1995, now abandoned, which is a continuation of application No. 08/523,435, filed on Sep. 1, 1995, now abandoned.

(51) Int. Cl.[7] .......................... A61K 39/04; A61K 49/00; C12N 15/00; C07K 1/00
(52) U.S. Cl. .......................... 424/248.1; 424/9.2; 435/7; 435/172.3; 435/320; 435/320.7; 530/350
(58) Field of Search .............................. 424/9.2, 248.1; 435/7, 172.3, 320, 320.7; 530/350

(56) References Cited

U.S. PATENT DOCUMENTS

| 3,943,119 A | 3/1976 | Tsumita et al. ....... 260/112.5 R |
| 4,689,397 A | 8/1987 | Shinnick et al. ............ 530/327 |
| 4,879,213 A | 11/1989 | Fox et al. ....................... 435/5 |
| 4,952,395 A | 8/1990 | Shinnick et al. .............. 424/92 |
| 5,108,745 A | 4/1992 | Horwitz ........................ 424/92 |
| 5,330,754 A | 7/1994 | Kapoor et al. ........... 424/190.1 |
| 5,478,726 A | 12/1995 | Shinnick et al. ............ 435/724 |

FOREIGN PATENT DOCUMENTS

| EP | 419 355 A1 | 3/1991 | |
| WO | WO 88/05823 | 8/1988 | |
| WO | WO 91/04272 | 4/1991 | |
| WO | WO 91/14448 | 10/1991 | |
| WO | WO 92/04049 | 3/1992 | |
| WO | WO 92/14823 | 9/1992 | |
| WO | WO 92/21758 | 12/1992 | |
| WO | WO 94/00493 | 1/1994 | |
| WO | WO 95/01440 | 1/1995 | |
| WO | WO 95/01441 | 1/1995 | |
| WO | WO 95/14713 | 6/1995 | |
| WO | WO 95/31216 | 11/1995 | .......... A61K/39/04 |
| WO | WO 96/15241 | 5/1996 | ........... C12N/15/11 |

OTHER PUBLICATIONS

Pal et al "Immunization with extracellular proteins of *Mycobacterium tuberculosis* induces cell–mediated immune responses substantial protective immunity in a guinea pig model of pulmonary tuberculosis", Infection and Immunity, vol. 60, No. 11, p. 4, Nov. 1, 1992.*

Lerner et al, "Cloning and structure of the *Bacillus subtilis* aspartate transcarbamylase gene (pyrB)", J. Biol. Chem., vol. 261, No. 24, pp. 11156–11165, Aug. 25, 1986.*

Andersen and Hansen, "Structure and Mapping of Antigenic Domains of Protein Antigen b, a 38,000–Molecular–Weight Protein of *Mycobacterium tuberculosis*," *Infection and Immunity* 37(8):2481–2488, 1989.

Andersen et al., "Identification of Immunodominant Antigens during Infection with *Mycobacterium tuberculosis*," *Scand. J. Immunol.* 36:823–831, 1992.

Andersen, P., "Effective Vaccination of Mice against *Mycobacterium tuberculosis* Infection with a Soluble Mixture of Secreted Mycobacterial Proteins," *Infection and Immunity* 62(6):2536–2544, 1994.

Ausebel et al., "Isolation of Proteins for Microsequence Analysis," in *Current Protocols in Molecular Biology*, Wiley & Sons, New York, 1993, pp. 10.19.1–10.19.12.

Barnes et al., "Immunoreactivity of a 10–kDa Antigen of *Mycobacterium tuberculosis*," *The Journal of Immunology* 148(6):1835–1840, 1992.

Boesen et al., "Human T–Cell Responses to Secreted Antigen Fractions of *Mycobacterium tuberculosis*," *Infection and Immunity* 63(4):1491–1497, 1995.

Borremans et al., "Cloning, Sequencing Determination, and Expression of a 32–Kilodalton–Protein Gene of *Mycobacterium tuberculosis*," *Infection and Immunity* 57(10):3123–3130, 1989.

(List continued on next page.)

*Primary Examiner*—Rodney P. Swartz
(74) *Attorney, Agent, or Firm*—Townsend and Townsend and Crew LLP

(57) ABSTRACT

Compounds and methods for diagnosing tuberculosis are disclosed. The compounds provided include polypeptides that contain at least one antigenic portion of one or more *M. tuberculosis* proteins, and DNA sequences encoding such polypeptides. Diagnostic kits containing such polypeptides or DNA sequences and a suitable detection reagent may be used for the detection of *M. tuberculosis* infection in patients and biological samples. Antibodies directed against such polypeptides are also provided.

93 Claims, 13 Drawing Sheets

OTHER PUBLICATIONS

Figures 1, 1A:
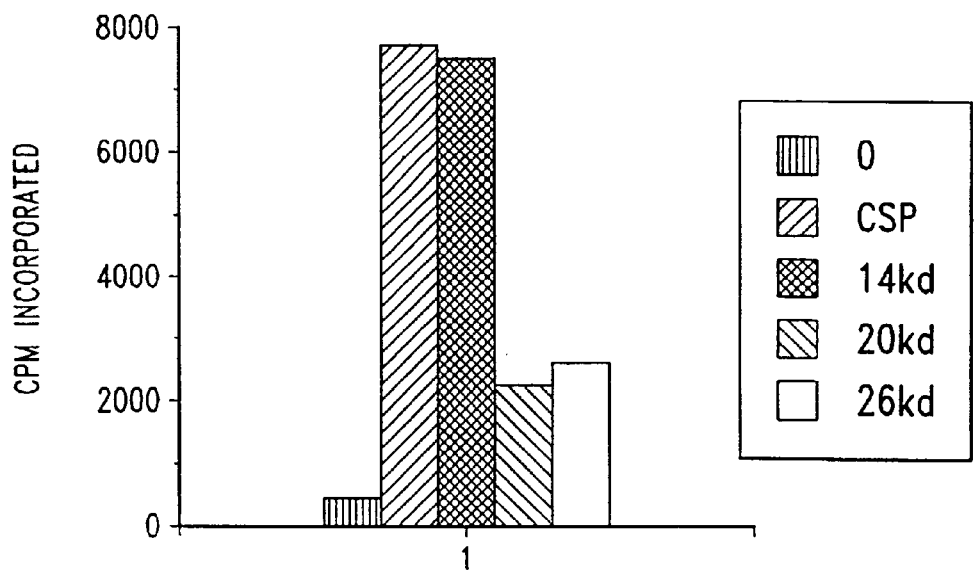
Figures 1, 1A, 2:
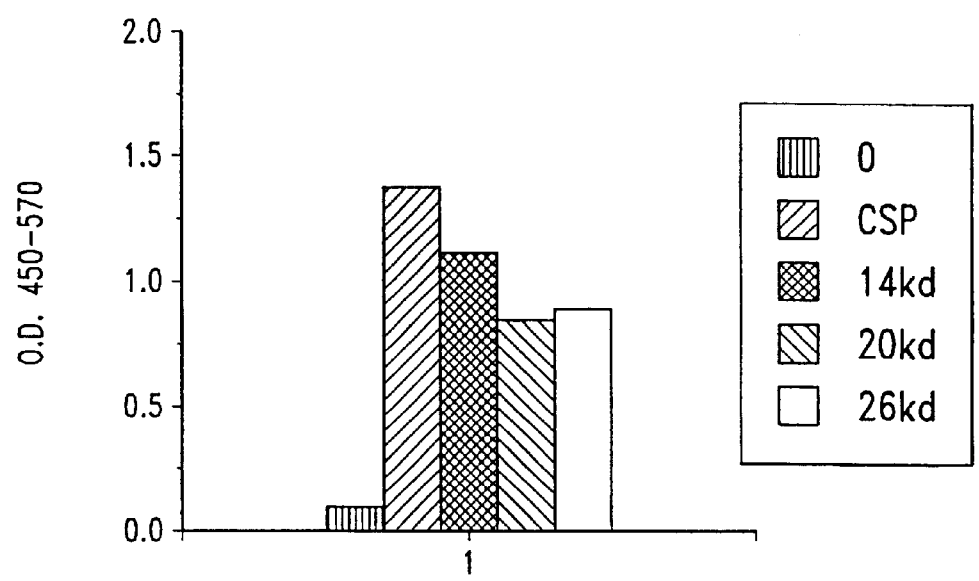
Figures 1, 1B:
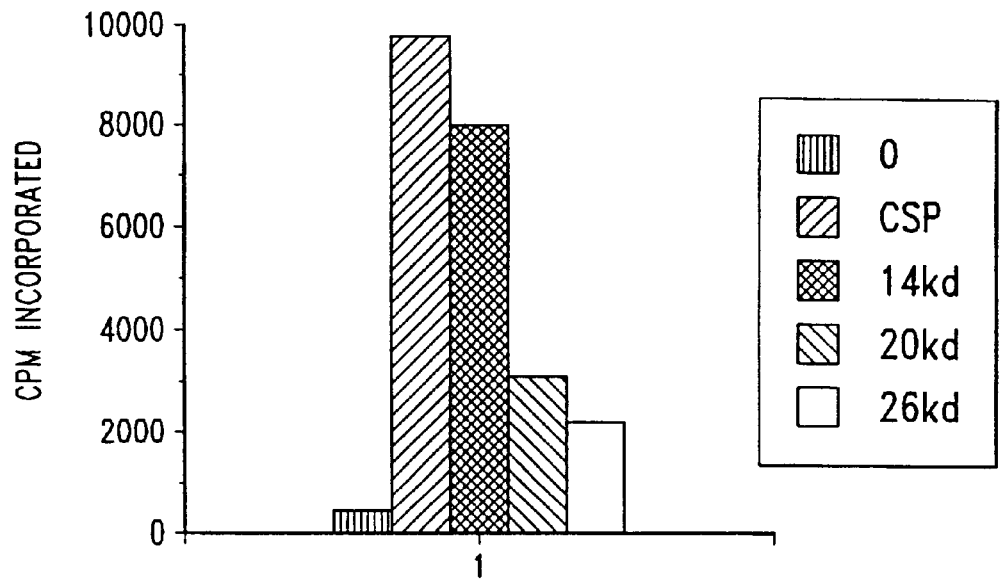
Figures 1, 1B, 2:
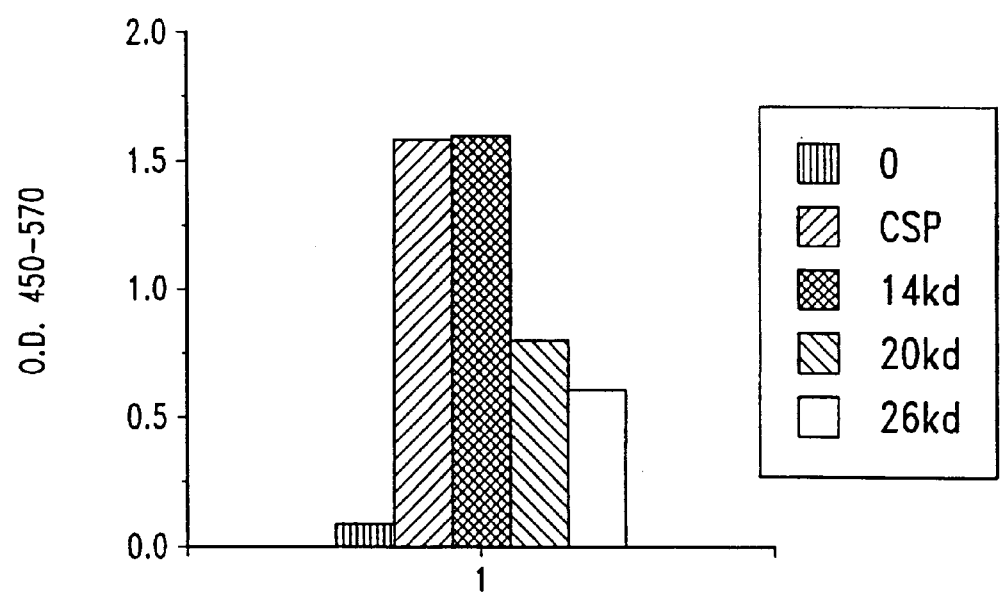

Content et al., "The Genes Coding for the Antigen 85 Complexes of *Mycobacterium tuberculosis* and *Mycobacterium bovis* BCG Are Members of a Gene Family: Cloning, Sequence Determination, and Genomic Orginization of the Gene Coding for Antigen 85–C of *M. tuberculosis,*" *Infection and Immunity* 59:3205–3212, 1991.

Horowitz et al., "Protective immunity against tuberculosis induced by vaccination with major extracellular proteins of *Mycobacterium tuberculosis,*" *Proc. Natl. Acad. Sci. USA* 92:1530–1534, 1995.

Lowrie et al., "Towards a DNA vaccine against tuberculosis," *Vaccine* 12(16):1537–1540, 1994.

Matsumoto et al., "Cloning and Sequencing of a Unique Antigen MPT70 from *Mycobacterium tuberculosis* H37Rv and Expression in BCG Using *E. coli*–Mycobacteria Shuttle Vector," *Scand. J. Immunol.* 41:281–287, 1995.

Nagai et al., "Isolation and Partial Characterization of Major Protein Antigens in the Culture Fluid of *Mycobacterium tuberculosis,*" *Infection and Immunity* 59(1):372–382, 1991.

Oettinger and Andersen, "Cloning and B–Cell–Epitope Mapping of MPT64 from *Mycobacterium tuberculosis* H37Rv," *Infection and Immunity* 62(5):2058–2064, 1994.

Pal and Horwitz, "Immunization with Extracellular Proteins of *Mycobacterium tuberculosis* Induces Cell–Mediated Immune Responses and Substantial Protective Immunity in a Guinea Pig Model of Pulmonary Tuberculosis," *Infection and Immunity* 60(11):4781–4792, 1992.

Romain et al., "Isolation of a proline–rich mycobacterial protein eliciting delayed–type hypersensitivity reactions only in guinea pigs immunized with living mycobacteria," *Proc. Natl. Acad. Sci. USA* 90:5322–5326, 1993.

Romain et al., "Preparation of Tuberculin Antigen L," *Ann. Inst. Pasteur/Microbiol.* 136B:235–248, 1985.

Wallis et al., "Identification of Antigens of *Mycobacterium tuberculosis* Using Human Monoclonal Antibodies," *J. Clin. Invest.* 84:214–219, 1989.

Wiker and Harboe, "The Antigen 85 Complex: a Major Secretion Product of *Mycobacterium tuberculosis,*" *Microbiological Reviews* 56(4):648–661, 1992.

Yamaguchi et al., "Cloning and Characterization of the Gene for Immunogenic Protein MPB64 of *Mycobacterium bovis* BCG," *Infection and Immunity* 57(1):283–288, 1989.

Young et al., "Screening of a Recombinant Mycobacterial DNA Library with Polyclonal Antiserum and Molecular Weight Analysis of Expressed Antigens," *Infection and Immunity* 55(6):1421–1425, 1987.

Sanderson et al. "Identification of a CD4+ TCell–stimulating Antigen of Pathogenic Bacteria by Expression Cloning" *J. Exp. Med.* 182(6):1751–1757 (1995).

Vega–Lopez et al. "Sequence and immunological characterization of a serine–rich antigen from *Mycobacterium leprae*" Infection and Immunity 61(5):2145–2153 (1993).

Wieles et al. "Characterization of a *Mycobacterium leprae* Antigen Related to the Secreted *Mycobacterium tuberculosis* Protein MPT32" *Infection and Immunity* 62(1):252–258 (1994).

Anderson and Heron "Specificity of a Protective Memory Immune Response against *Mycobacterium tuberculosis*" *Infection and Immunity* 61(3):844–851 (1993).

Burgess et al. "Possible Dissociation of the Heparin–binding and Mitogenic Activities of Heparin–Binding (Acidic Fibroblast) Growth Factor–1 from its Receptor–binding Activities by Site–Directed Mutagenesis of a Single Lysine Residue" *J. Cell. Biol.* 111:2129–2138 (1990).

Eiglmeier et al. "Use of an ordered cosmid library to deduce the genomic organization of *Mycobacterium leprae*" *Mol. Microbiol.* 7(2):197–206 (1993).

Fifis et al. "Purification and Characterization of Major Antigens from a *Mycobacterium bovis* Culture Filtrate" *Infection and Immunity* 59(3):800–807 (1991).

Geysen et al. "Cognitive features of continuous antigenic determinants" *J. Mol. Recognition* 1:32–41 (1988).

Greenway et al. "Enhancement of protective immune responses to Venezuelan equine encephalitis (VEE) virus with microencapsulated vaccine" *Vaccine* 13:1411–1420 (1995).

Kadival et al. "Radioimmunoassay of tuberculous antigen" *Indian J. Med. Res.* 75:765–770 (1982).

Lazar et al. "Transforming Growth Factor α: Mutation of Aspartic Acid 47 and Leucine 48 results in Different Biological Activities" *Mol. Cell. Biol.* 8(3):1247–1252 (1988).

Lee et al. "Characterization of the Major Membrane Protein of Virulent *Mycobacterium tuberculosis*" *Infection and Immunity* 60:2066–2074 (1992).

Mathur and Kolttukudy "Molecular cloning and sequencing of the gene for mycocerosic acid synthase, a novel fatty acid elongating multifunctional enzyme, from *Mycobacterium tuberculosis* var. *bovis* Bacillus Calmette–Guerin" *J. Biol. Chem.* 267:19388–19395 (1992).

Orme "Prospects for new vaccines against tuberculosis" *Trends in Microbiology* 3(10):401–404 (1995).

Pancholi et al. "Dendritic cells efficiently immunoselect mycobacterial–reactive T cells in human blood, including clonable antigen–reactive precursors" *Immunology* 76(2):217–224 (1992).

Philipp et al. "An integrated map of the genome of the tubercle bacillus, *Mycobacterium tuberculosis* H37Rv, and comparison with *Mycobacterium leprae*" *Proc. Natl. Acad. Sci. USA* 93(7):3132–3137 (1996).

Rinke de Wit et al. "A *Myconacterium leprae*–specific gene encoding an immunologically recognized 45 kDa protein" *Mol. Microbiol.* 10(4):829–838 (1993).

Rinke de Wit et al. "Mycobacteria contains two groEL genes: the second *Mycobacterium leprae* groEL gene is arranged in an operon with groES" *Mol. Microbiol.* 6(14):1995–2007 (1992).

Romain et al. "Identification of a *Mycobacterium bovis* BCG 45/47–Kilodalton Antigen Complex, an Immunodominant Target for Antibody Response after Immunization with Living Bacteria" *Infection and Immunity* 61(2):742–750 (1993).

* cited by examiner

SEQUENCE LISTING (1) GENERAL INFORMATION:

(iii) NUMBER OF SEQUENCES: 148

(2) INFORMATION FOR SEQ ID NO:1:

(i) SEQUENCE CHARACTERISTICS:
      (A) LENGTH: 766 base pairs
      (B) TYPE: nucleic acid
      (C) STRANDEDNESS: single
      (D) TOPOLOGY: linear (xi) SEQUENCE DESCRIPTION: SEQ ID NO:1:

```
CGAGGCACCG GTAGTTTGAA CCAAACGCAC AATCGACGGG CAAACGAACG GAAGAACACA      60

ACCATGAAGA TGGTGAAATC GATCGCCGCA GGTCTGACCG CCGCGGCTGC AATCGGCGCC     120

GCTGCGGCCG GTGTGACTTC GATCATGGCT GGCGGCCCGG TCGTATACCA GATGCAGCCG     180

GTCGTCTTCG GCGCGCCACT GCCGTTGGAC CCGGCATCCG CCCCTGACGT CCCGACCGCC     240

GCCCAGTTGA CCAGCCTGCT CAACAGCCTC GCCGATCCCA ACGTGTCGTT TGCGAACAAG     300

GGCAGTCTGG TCGAGGGCGG CATCGGGGGC ACCGAGGCGC GCATCGCCGA CCACAAGCTG     360

AAGAAGGCCG CCGAGCACGG GGATCTGCCG CTGTCGTTCA GCGTGACGAA CATCCAGCCG     420

GCGGCCGCCG GTTCGGCCAC CGCCGACGTT TCCGTCTCGG GTCCGAAGCT CTCGTCGCCG     480

GTCACGCAGA ACGTCACGTT CGTGAATCAA GGCGGCTGGA TGCTGTCACG CGCATCGGCG     540
```

```
ATGGAGTTGC TGCAGGCCGC AGGGNAACTG ATTGGCGGGC CGGNTTCAGC CCGCTGTTCA      600

GCTACGCCGC CCGCCTGGTG ACGCGTCCAT GTCGAACACT CGCGCGTGTA GCACGGTGCG      660

GTNTGCGCAG GGNCGCACGC ACCGCCCGGT GCAAGCCGTC CTCGAGATAG GTGGTGNCTC      720

GNCACCAGNG ANCACCCCCN NNTCGNCNNT TCTCGNTGNT GNATGA                      766
```

(2) INFORMATION FOR SEQ ID NO:2:

(i) SEQUENCE CHARACTERISTICS:
        (A) LENGTH: 752 base pairs
        (B) TYPE: nucleic acid
        (C) STRANDEDNESS: single
        (D) TOPOLOGY: linear (xi) SEQUENCE DESCRIPTION: SEQ ID NO:2:

```
ATGCATCACC ATCACCATCA CGATGAAGTC ACGGTAGAGA CGACCTCCGT CTTCCGCGCA       60

GACTTCCTCA GCGAGCTGGA CGCTCCTGCG CAAGCGGGTA CGGAGAGCGC GGTCTCCGGG      120

GTGGAAGGGC TCCCGCCGGG CTCGGCGTTG CTGGTAGTCA AACGAGGCCC CAACGCCGGG      180

TCCCGGTTCC TACTCGACCA AGCCATCACG TCGGCTGGTC GGCATCCCGA CAGCGACATA      240

TTTCTCGACG ACGTGACCGT GAGCCGTCGC CATGCTGAAT TCCGGTTGGA AAACAACGAA      300

TTCAATGTCG TCGATGTCGG GAGTCTCAAC GGCACCTACG TCAACCGCGA GCCCGTGGAT      360

TCGGCGGTGC TGGCGAACGG CGACGAGGTC CAGATCGGCA AGCTCCGGTT GGTGTTCTTG      420

ACCGGACCCA AGCAAGGCGA GGATGACGGG AGTACCGGGG GCCCGTGAGC GCACCCGATA      480

GCCCCGCGCT GGCCGGGATG TCGATCGGGG CGGTCCTCCG ACCTGCTACG ACCGGATTTT      540

CCCTGATGTC CACCATCTCC AAGATTCGAT TCTTGGGAGG CTTGAGGGTC NGGGTGACCC      600

CCCCGCGGGC CTCATTCNGG GGTNTCGGCN GGTTTCACCC CNTACCNACT GCCNCCCGGN      660

TTGCNAATTC NTTCTTCNCT GCCCNNAAAG GGACCNTTAN CTTGCCGCTN GAAANGGTNA      720

TCCNGGGCCC NTCCTNGAAN CCCCNTCCCC CT                                    752
```

(2) INFORMATION FOR SEQ ID NO:3:

(i) SEQUENCE CHARACTERISTICS:
        (A) LENGTH: 813 base pairs
        (B) TYPE: nucleic acid
        (C) STRANDEDNESS: single
        (D) TOPOLOGY: linear (xi) SEQUENCE DESCRIPTION: SEQ ID NO:3:

```
CATATGCATC ACCATCACCA TCACACTTCT AACCGCCCAG CGCGTCGGGG GCGTCGAGCA       60

CCACGCGACA CCGGGCCCGA TCGATCTGCT AGCTTGAGTC TGGTCAGGCA TCGTCGTCAG      120

CAGCGCGATG CCCTATGTTT GTCGTCGACT CAGATATCGC GGCAATCCAA TCTCCCGCCT      180

GCGGCCGGCG GTGCTGCAAA CTACTCCCGG AGGAATTTCG ACGTGCGCAT CAAGATCTTC      240

ATGCTGGTCA CGGCTGTCGT TTTGCTCTGT TGTTCGGGTG TGGCCACGGC CGCGCCCAAG      300

ACCTACTGCG AGGAGTTGAA AGGCACCGAT ACCGGCCAGG CGTGCCAGAT TCAAATGTCC      360

GACCCGGCCT ACAACATCAA CATCAGCCTG CCCAGTTACT ACCCCGACCA GAAGTCGCTG      420

GAAAATTACA TCGCCCAGAC GCGCGACAAG TTCCTCAGCG CGGCCACATC GTCCACTCCA      480

CGCGAAGCCC CCTACGAATT GAATATCACC TCGGCCACAT ACCAGTCCGC GATACCGCCG      540

CGTGGTACGC AGGCCGTGGT GCTCAMGGTC TACCACAACG CCGGCGGCAC GCACCCAACG      600

ACCACGTACA AGGCCTTCGA TTGGGACCAG GCCTATCGCA AGCCAATCAC CTATGACACG      660

CTGTGGCAGG CTGACACCGA TCCGCTGCCA GTCGTCTTCC CCATTGTTGC AAGGTGAACT      720
```

| | |
|---|---|
| GAGCAACGCA GACCGGGACA ACWGGTATCG ATAGCCGCCN AATGCCGGCT TGGAACCCNG | 780 |
| TGAAATTATC ACAACTTCGC AGTCACNAAA NAA | 813 |

(2) INFORMATION FOR SEQ ID NO:4:

(i) SEQUENCE CHARACTERISTICS:
        (A) LENGTH: 447 base pairs
        (B) TYPE: nucleic acid
        (C) STRANDEDNESS: single
        (D) TOPOLOGY: linear (xi) SEQUENCE DESCRIPTION: SEQ ID NO:4:

| | |
|---|---|
| CGGTATGAAC ACGGCCGCGT CCGATAACTT CCAGCTGTCC CAGGGTGGGC AGGGATTCGC | 60 |
| CATTCCGATC GGGCAGGCGA TGGCGATCGC GGGCCAGATC CGATCGGGTG GGGGGTCACC | 120 |
| CACCGTTCAT ATCGGGCCTA CCGCCTTCCT CGGCTTGGGT GTTGTCGACA ACAACGGCAA | 180 |
| CGGCGCACGA GTCCAACGCG TGGTCGGGAG CGCTCCGGCG GCAAGTCTCG GCATCTCCAC | 240 |
| CGGCGACGTG ATCACCGCGG TCGACGGCGC TCCGATCAAC TCGGCCACCG CGATGGCGGA | 300 |
| CGCGCTTAAC GGGCATCATC CCGGTGACGT CATCTCGGTG AACTGGCAAA CCAAGTCGGG | 360 |
| CGGCACGCGT ACAGGGAACG TGACATTGGC CGAGGGACCC CCGGCCTGAT TCGTCGYGG | 420 |
| ATACCACCCG CCGGCCGGCC AATTGGA | 447 |

(2) INFORMATION FOR SEQ ID NO:5:

(i) SEQUENCE CHARACTERISTICS:
        (A) LENGTH: 604 base pairs
        (B) TYPE: nucleic acid
        (C) STRANDEDNESS: single
        (D) TOPOLOGY: linear (xi) SEQUENCE DESCRIPTION: SEQ ID NO:5:

| | |
|---|---|
| GTCCCACTGC GGTCGCCGAG TATGTCGCCC AGCAAATGTC TGGCAGCCGC CCAACGGAAT | 60 |
| CCGGTGATCC GACGTCGCAG GTTGTCGAAC CCGCCGCCGC GGAAGTATCG GTCCATGCCT | 120 |
| AGCCCGGCGA CGGCGAGCGC CGGAATGGCG CGAGTGAGGA GGCGGGCAAT TTGGCGGGGC | 180 |
| CCGGCGACGG NGAGCGCCGG AATGGCGCGA GTGAGGAGGT GGNCAGTCAT GCCCAGNGTG | 240 |
| ATCCAATCAA CCTGNATTCG GNCTGNGGGN CCATTTGACA ATCGAGGTAG TGAGCGCAAA | 300 |
| TGAATGATGG AAAACGGGNG GNGACGTCCG NTGTTCTGGT GGTGNTAGGT GNCTGNCTGG | 360 |
| NGTNGNGGNT ATCAGGATGT TCTTCGNCGA AANCTGATGN CGAGGAACAG GGTGTNCCCG | 420 |
| NNANNCCNAN GGNGTCCNAN CCCNNNNTCC TCGNCGANAT CANANAGNCG NTTGATGNGA | 480 |
| NAAAAGGGTG GANCAGNNNN AANTNGNGGN CCNAANAANC NNNANNGNNG NNAGNTNGNT | 540 |
| NNNTNTTNNC ANNNNNNNTG NNGNNGNNCN NNNCAANCNN NTNNNNGNAA NNGGNTTNTT | 600 |
| NAAT | 604 |

(2) INFORMATION FOR SEQ ID NO:6:

(i) SEQUENCE CHARACTERISTICS:
        (A) LENGTH: 633 base pairs
        (B) TYPE: nucleic acid
        (C) STRANDEDNESS: single
        (D) TOPOLOGY: linear (xi) SEQUENCE DESCRIPTION: SEQ ID NO:6:

| | |
|---|---|
| TTGCANGTCG AACCACCTCA CTAAAGGGAA CAAAAGCTNG AGCTCCACCG CGGTGGCGGC | 60 |
| CGCTCTAGAA CTAGTGKATM YYYCKGGCTG CAGSAATYCG GYACGAGCAT TAGGACAGTC | 120 |

```
TAACGGTCCT GTTACGGTGA TCGAATGACC GACGACATCC TGCTGATCGA CACCGACGAA      180

CGGGTGCGAA CCCTCACCCT CAACCGGCCG CAGTCCCGYA ACGCGCTCTC GGCGGCGCTA      240

CGGGATCGGT TTTTCGCGGY GTTGGYCGAC GCCGAGGYCG ACGACGACAT CGACGTCGTC      300

ATCCTCACCG GYGCCGATCC GGTGTTCTGC GCCGGACTGG ACCTCAAGGT AGCTGGCCGG      360

GCAGACCGCG CTGCCGGACA TCTCACCGCG GTGGGCGGCC ATGACCAAGC CGGTGATCGG      420

CGCGATCAAC GGCGCCGCGG TCACCGGCGG GCTCGAACTG GCGCTGTACT GCGACATCCT      480

GATCGCCTCC GAGCACGCCC GCTTCGNCGA CACCCACGCC CGGGTGGGGC TGCTGCCCAC      540

CTGGGGACTC AGTGTGTGCT TGCCGCAAAA GGTCGGCATC GGNCTGGGCC GGTGGATGAG      600

CCTGACCGGC GACTACCTGT CCGTGACCGA CGC                                  633

(2) INFORMATION FOR SEQ ID NO:7:

(i) SEQUENCE CHARACTERISTICS:
        (A) LENGTH: 1362 base pairs
        (B) TYPE: nucleic acid
        (C) STRANDEDNESS: single
        (D) TOPOLOGY: linear (xi) SEQUENCE DESCRIPTION: SEQ ID NO:7:

CGACGACGAC GGCGCCGGAG AGCGGGCGCG AACGGCGATC GACGCGGCCC TGGCCAGAGT       60

CGGCACCACC CAGGAGGGAG TCGAATCATG AAATTTGTCA ACCATATTGA GCCCGTCGCG      120

CCCCGCCGAG CCGGCGGCGC GGTCGCCGAG GTCTATGCCG AGGCCCGCCG CGAGTTCGGC      180

CGGCTGCCCG AGCCGCTCGC CATGCTGTCC CCGGACGAGG GACTGCTCAC CGCCGGCTGG      240

GCGACGTTGC GCGAGACACT GCTGGTGGGC CAGGTGCCGG GTGGCCGCAA GGAAGCCGTC      300

GCCGCCGCCG TCGCGGCCAG CCTGCGCTGC CCCTGGTGCG TCGACGCACA CCACCACCATG     360

CTGTACGCGG CAGGCCAAAC CGACACCGCC GCGGCGATCT TGGCCGGCAC AGCACCTGCC      420

GCCGGTGACC CGAACGCGCC GTATGTGGCG TGGGCGGCAG GAACCGGGAC ACCGGCGGGA      480

CCGCCGGCAC CGTTCGGCCC GGATGTCGCC GCCGAATACC TGGGCACCGC GGTGCAATTC      540

CACTTCATCG CACGCCTGGT CCTGGTGCTG CTGGACGAAA CCTTCCTGCC GGGGGGCCCG      600

CGCGCCCAAC AGCTCATGCG CCGCGCCGGT GGACTGGTGT TCGCCCGCAA GGTGCGCGCG      660

GAGCATCGGC CGGGCCGCTC CACCCGCCGG CTCGAGCCGC GAACGCTGCC CGACGATCTG      720

GCATGGGCAA CACCGTCCGA GCCCATAGCA ACCGCGTTCG CCGCGCTCAG CCACCACCTG      780

GACACCGCGC CGCACCTGCC GCCACCGACT CGTCAGGTGG TCAGGCGGGT CGTGGGGTCG      840

TGGCACGGCG AGCCAATGCC GATGAGCAGT CGCTGGACGA ACGAGCACAC CGCCGAGCTG      900

CCCGCCGACC TGCACGCGCC CACCCGTCTT GCCCTGCTGA CCGGCCTGGC CCCGCATCAG      960

GTGACCGACG ACGACGTCGC CGCGGCCCGA TCCCTGCTCG ACACCGATGC GGCGCTGGTT     1020

GGCGCCCTGG CCTGGGCCGC CTTCACCGCC GCGCGGCGCA TCGGCACCTG GATCGGCGCC     1080

GCCGCCGAGG GCCAGGTGTC GCGGCAAAAC CCGACTGGGT GAGTGTGCGC GCCCTGTCGG     1140

TAGGGTGTCA TCGCTGGCCC GAGGGATCTC GCGGCGGCGA ACGGAGGTGG CGACACAGGT     1200

GGAAGCTGCG CCCACTGGCT TGCGCCCCAA CGCCGTCGTG GGCGTTCGGT TGGCCGCACT     1260

GGCCGATCAG GTCGGCGCCG GCCCTTGGCC GAAGGTCCAG CTCAACGTGC CGTCACCGAA     1320

GGACCGGACG TCACCGGGG GTCACCCTGC GCGCCCAAGG AA                        1362

(2) INFORMATION FOR SEQ ID NO:8:
```

(i) SEQUENCE CHARACTERISTICS:
    (A) LENGTH: 1458 base pairs
    (B) TYPE: nucleic acid
    (C) STRANDEDNESS: single
    (D) TOPOLOGY: linear (xi) SEQUENCE DESCRIPTION: SEQ ID NO:8:

| | | | | | |
|---|---|---|---|---|---|
| GCGACGACCC | CGATATGCCG | GGCACCGTAG | CGAAAGCCGT | CGCCGACGCA | CTCGGGCGCG | 60 |
| GTATCGCTCC | CGTTGAGGAC | ATTCAGGACT | GCGTGGAGGC | CCGGCTGGGG | GAAGCCGGTC | 120 |
| TGGATGACGT | GGCCCGTGTT | TACATCATCT | ACCGGCAGCG | GCGCGCCGAG | CTGCGGACGG | 180 |
| CTAAGGCCTT | GCTCGGCGTG | CGGGACGAGT | TAAAGCTGAG | CTTGGCGGCC | GTGACGGTAC | 240 |
| TGCGCGAGCG | CTATCTGCTG | CACGACGAGC | AGGGCCGGCC | GGCCGAGTCG | ACCGGCGAGC | 300 |
| TGATGGACCG | ATCGGCGCGC | TGTGTCGCGG | CGGCCGAGGA | CCAGTATGAG | CCGGGCTCGT | 360 |
| CGAGGCGGTG | GGCCGAGCGG | TTCGCCACGC | TATTACGCAA | CCTGGAATTC | CTGCCGAATT | 420 |
| CGCCCACGTT | GATGAACTCT | GGCACCGACC | TGGGACTGCT | CGCCGGCTGT | TTTGTTCTGC | 480 |
| CGATTGAGGA | TTCGCTGCAA | TCGATCTTTG | CGACGCTGGG | ACAGGCCGCC | GAGCTGCAGC | 540 |
| GGGCTGGAGG | CGGCACCGGA | TATGCGTTCA | GCCACCTGCG | ACCCGCCGGG | GATCGGGTGG | 600 |
| CCTCCACGGG | CGGCACGGCC | AGCGGACCGG | TGTCGTTTCT | ACGGCTGTAT | GACAGTGCCG | 660 |
| CGGGTGTGGT | CTCCATGGGC | GGTCGCCGGC | GTGGCGCCTG | TATGGCTGTG | CTTGATGTGT | 720 |
| CGCACCCGGA | TATCTGTGAT | TTCGTCACCG | CCAAGGCCGA | ATCCCCAGC | GAGCTCCCGC | 780 |
| ATTTCAACCT | ATCGGTTGGT | GTGACCGACG | CGTTCCTGCG | GGCCGTCGAA | CGCAACGGCC | 840 |
| TACACCGGCT | GGTCAATCCG | CGAACCGGCA | AGATCGTCGC | GCGGATGCCC | GCCGCCGAGC | 900 |
| TGTTCGACGC | CATCTGCAAA | GCCGCGCACG | CCGGTGGCGA | TCCCGGGCTG | GTGTTTCTCG | 960 |
| ACACGATCAA | TAGGGCAAAC | CCGGTGCCGG | GGAGAGGCCG | CATCGAGGCG | ACCAACCCGT | 1020 |
| GCGGGGAGGT | CCCACTGCTG | CCTTACGAGT | CATGTAATCT | CGGCTCGATC | AACCTCGCCC | 1080 |
| GGATGCTCGC | CGACGGTCGC | GTCGACTGGG | ACCGGCTCGA | GGAGGTCGCC | GGTGTGGCGG | 1140 |
| TGCGGTTCCT | TGATGACGTC | ATCGATGTCA | GCCGCTACCC | CTTCCCCGAA | CTGGGTGAGG | 1200 |
| CGGCCCGCGC | CACCCGCAAG | ATCGGGCTGG | GAGTCATGGG | TTTGGCGGAA | CTGCTTGCCG | 1260 |
| CACTGGGTAT | TCCGTACGAC | AGTGAAGAAG | CCGTGCGGTT | AGCCACCCGG | CTCATGCGTC | 1320 |
| GCATACAGCA | GGCGGCGCAC | ACGGCATCGC | GGAGGCTGGC | CGAAGAGCGG | GGCGCATTCC | 1380 |
| CGGCGTTCAC | CGATAGCCGG | TTCGCGCGGT | CGGGCCCGAG | GCGCAACGCA | CAGGTCACCT | 1440 |
| CCGTCGCTCC | GACGGGCA | | | | | 1458 |

(2) INFORMATION FOR SEQ ID NO:9:

(i) SEQUENCE CHARACTERISTICS:
        (A) LENGTH: 862 base pairs
        (B) TYPE: nucleic acid
        (C) STRANDEDNESS: single
        (D) TOPOLOGY: linear (xi) SEQUENCE DESCRIPTION: SEQ ID NO:9:

| | | | | | |
|---|---|---|---|---|---|
| ACGGTGTAAT | CGTGCTGGAT | CTGGAACCGC | GTGGCCCGCT | ACCTACCGAG | ATCTACTGGC | 60 |
| GGCGCAGGGG | GCTGGCCCTG | GGCATCGCGG | TCGTCGTAGT | CGGGATCGCG | GTGGCCATCG | 120 |
| TCATCGCCTT | CGTCGACAGC | AGCGCCGGTG | CCAAACCGGT | CAGCGCCGAC | AAGCCGGCCT | 180 |
| CCGCCCAGAG | CCATCCGGGC | TCGCCGGCAC | CCCAAGCACC | CCAGCCGGCC | GGGCAAACCG | 240 |
| AAGGTAACGC | CGCCGCGGCC | CCGCCGCAGG | GCCAAAACCC | CGAGACACCC | ACGCCCACCG | 300 |

-continued

```
CCGCGGTGCA GCCGCCGCCG GTGCTCAAGG AAGGGGACGA TTGCCCCGAT TCGACGCTGG    360

CCGTCAAAGG TTTGACCAAC GCGCCGCAGT ACTACGTCGG CGACCAGCCG AAGTTCACCA    420

TGGTGGTCAC CAACATCGGC CTGGTGTCCT GTAAACGCGA CGTTGGGGCC GCGGTGTTGG    480

CCGCCTACGT TTACTCGCTG ACAACAAGC GGTTGTGGTC CAACCTGGAC TGCGCGCCCT     540

CGAATGAGAC GCTGGTCAAG ACGTTTTCCC CCGGTGAGCA GGTAACGACC GCGGTGACCT    600

GGACCGGGAT GGGATCGGCG CCGCGCTGCC CATTGCCGCG GCCGGCGATC GGGCCGGGCA    660

CCTACAATCT CGTGGTACAA CTGGGCAATC TGCGCTCGCT GCCGGTTCCG TTCATCCTGA    720

ATCAGCCGCC GCCGCCGCCC GGGCCGGTAC CCGCTCCGGG TCCAGCGCAG GCGCCTCCGC    780

CGGAGTCTCC CGCGCAAGGC GGATAATTAT TGATCGCTGA TGGTCGATTC CGCCAGCTGT    840

GACAACCCCT CGCCTCGTGC CG                                             862
```

(2) INFORMATION FOR SEQ ID NO:10:

(i) SEQUENCE CHARACTERISTICS:
        (A) LENGTH: 622 base pairs
        (B) TYPE: nucleic acid
        (C) STRANDEDNESS: single
        (D) TOPOLOGY: linear (xi) SEQUENCE DESCRIPTION: SEQ ID NO:10:

```
TTGATCAGCA CCGGCAAGGC GTCACATGCC TCCCTGGGTG TGCAGGTGAC CAATGACAAA     60

GACACCCCGG GCGCCAAGAT CGTCGAAGTA GTGGCCGGTG GTGCTGCCGC GAACGCTGGA    120

GTGCCGAAGG GCGTCGTTGT CACCAAGGTC GACGACCGCC CGATCAACAG CGCGGACGCG    180

TTGGTTGCCG CCGTGCGGTC CAAAGCGCCG GGCGCCACGG TGGCGCTAAC CTTTCAGGAT    240

CCCTCGGGCG GTAGCCGCAC AGTGCAAGTC ACCCTCGGCA AGGCGGAGCA GTGATGAAGG    300

TCGCCGCGCA GTGTTCAAAG CTCGGATATA CGGTGGCACC CATGGAACAG CGTGCGGAGT    360

TGGTGGTTGG CCGGGCACTT GTCGTCGTCG TTGACGATCG CACGGCGCAC GGCGATGAAG    420

ACCACAGCGG GCCGCTTGTC ACCGAGCTGC TCACCGAGGC CGGGTTTGTT GTCGACGGCG    480

TGGTGGCGGT GTCGGCCGAC GAGGTCGAGA TCCGAAATGC GCTGAACACA GCGGTGATCG    540

GCGGGGTGGA CCTGGTGGTG TCGGTCGGCG GGACCGGNGT GACGNCTCGC GATGTCACCC    600

CGGAAGCCAC CCGNGACATT CT                                             622
```

(2) INFORMATION FOR SEQ ID NO:11:

(i) SEQUENCE CHARACTERISTICS:
        (A) LENGTH: 1200 base pairs
        (B) TYPE: nucleic acid
        (C) STRANDEDNESS: single
        (D) TOPOLOGY: linear (xi) SEQUENCE DESCRIPTION: SEQ ID NO:11:

```
GGCGCAGCGG TAAGCCTGTT GGCCGCCGGC ACACTGGTGT TGACAGCATG CGGCGGTGGC     60

ACCAACAGCT CGTCGTCAGG CGCAGGCGGA ACGTCTGGGT CGGTGCACTG CGGCGGCAAG    120

AAGGAGCTCC ACTCCAGCGG CTCGACCGCA CAAGAAAATG CCATGGAGCA GTTCGTCTAT    180

GCCTACGTGC GATCGTGCCC GGGCTACACG TTGGACTACA CGCCAACGG GTCCGGTGCC     240

GGGGTGACCC AGTTTCTCAA CAACGAAACC GATTTCGCCG GCTCGGATGT CCCGTTGAAT    300

CCGTCGACCG GTCAACCTGA CCGGTCGGCG GAGCGGTGCG GTTCCCCGGC ATGGGACCTG    360

CCGACGGTGT TCGGCCCGAT CGCGATCACC TACAATATCA AGGGCGTGAG CACGCTGAAT    420

CTTGACGGAC CCACTACCGC CAAGATTTTC AACGGCACCA TCACCGTGTG GAATGATCCA    480
```

```
CAGATCCAAG CCCTCAACTC CGGCACCGAC CTGCCGCCAA CACCGATTAG CGTTATCTTC      540

CGCAGCGACA AGTCCGGTAC GTCGGACAAC TTCCAGAAAT ACCTCGACGG TGTATCCAAC      600

GGGGCGTGGG GCAAAGGCGC CAGCGAAACG TTCAGCGGGG GCGTCGGCGT CGGCGCCAGC      660

GGGAACAACG GAACGTCGGC CCTACTGCAG ACGACCGACG GGTCGATCAC CTACAACGAG      720

TGGTCGTTTG CGGTGGGTAA GCAGTTGAAC ATGGCCCAGA TCATCACGTC GGCGGGTCCG      780

GATCCAGTGG CGATCACCAC CGAGTCGGTC GGTAAGACAA TCGCCGGGGC CAAGATCATG      840

GGACAAGGCA ACGACCTGGT ATTGGACACG TCGTCGTTCT ACAGACCCAC CCAGCCTGGC      900

TCTTACCCGA TCGTGCTGGC GACCTATGAG ATCGTCTGCT CGAAATACCC GGATGCGACG      960

ACCGGTACTG CGGTAAGGGC GTTTATGCAA GCCGCGATTG GTCCAGGCCA AGAAGGCCTG     1020

GACCAATACG GCTCCATTCC GTTGCCCAAA TCGTTCCAAG CAAAATTGGC GGCCGCGGTG     1080

AATGCTATTT CTTGACCTAG TGAAGGGAAT TCGACGGTGA GCGATGCCGT TCCGCAGGTA     1140

GGGTCGCAAT TTGGGCCGTA TCAGCTATTG CGGCTGCTGG GCCGAGGCGG GATGGGCGAG     1200
```

(2) INFORMATION FOR SEQ ID NO:12:

(i) SEQUENCE CHARACTERISTICS:
        (A) LENGTH: 1155 base pairs
        (B) TYPE: nucleic acid
        (C) STRANDEDNESS: single
        (D) TOPOLOGY: linear (xi) SEQUENCE DESCRIPTION: SEQ ID NO:12:

```
GCAAGCAGCT GCAGGTCGTG CTGTTCGACG AACTGGGCAT GCCGAAGACC AAACGCACCA       60

AGACCGGCTA CACCACGGAT GCCGACGCGC TGCAGTCGTT GTTCGACAAG ACCGGGCATC      120

CGTTTCTGCA ACATCTGCTC GCCCACCGCG ACGTCACCCG GCTCAAGGTC ACCGTCGACG      180

GGTTGCTCCA AGCGGTGGCC GCCGACGGCC GCATCCACAC CACGTTCAAC CAGACGATCG      240

CCGCGACCGG CCGGCTCTCC TCGACCGAAC CCAACCTGCA GAACATCCCG ATCCGCACCG      300

ACGCGGGCCG GCGGATCCGG GACGCGTTCG TGGTCGGGGA CGGTTACGCC GAGTTGATGA      360

CGGCCGACTA CAGCCAGATC GAGATGCGGA TCATGGGCA CCTGTCCGGG GACGAGGGCC       420

TCATCGAGGC GTTCAACACC GGGGAGGACC TGTATTCGTT CGTCGCGTCC CGGGTGTTCG      480

GTGTGCCCAT CGACGAGGTC ACCGGCGAGT TGCGGCGCCG GGTCAAGGCG ATGTCCTACG      540

GGCTGGTTTA CGGGTTGAGC GCCTACGCCC TGTCGCAGCA GTTGAAAATC TCCACCGAGG      600

AAGCCAACGA GCAGATGGAC GCGTATTTCG CCCGATTCGG CGGGGTGCGC GACTACCTGC      660

GCGCCGTAGT CGAGCGGGCC CGCAAGGACG GCTACACCTC GACGGTGCTG GGCCGTCGCC      720

GCTACCTGCC CGAGCTGGAC AGCAGCAACC GTCAAGTGCG GGAGGCCGCC GAGCGGGCGG      780

CGCTGAACGC GCCGATCCAG GGCAGCGCGG CCGACATCAT CAAGGTGGCC ATGATCCAGG      840

TCGACAAGGC GCTCAACGAG GCACAGCTGG CGTCGCGCAT GCTGCTGCAG GTCCACGACG      900

AGCTGCTGTT CGAAATCGCC CCCGGTGAAC GCGAGCGGGT CGAGGCCCTG GTGCGCGACA      960

AGATGGGCGG CGCTTACCCG CTCGACGTCC CGCTGGAGGT GTCGGTGGGC TACGGCCGCA     1020

GCTGGGACGC GGCGGCGCAC TGAGTGCCGA GCGTGCATCT GGGGCGGGAA TTCGGCGATT     1080

TTTCCGCCCT GAGTTCACGC TCGGCGCAAT CGGGACCGAG TTTGTCCAGC GTGTACCCGT     1140

CGAGTAGCCT CGTCA                                                     1155
```

(2) INFORMATION FOR SEQ ID NO:13:

(i) SEQUENCE CHARACTERISTICS:
(A) LENGTH: 1771 base pairs
(B) TYPE: nucleic acid
(C) STRANDEDNESS: single
(D) TOPOLOGY: linear (xi) SEQUENCE DESCRIPTION: SEQ ID NO:13:

```
GAGCGCCGTC TGGTGTTTGA ACGGTTTTAC CGGTCGGCAT CGGCACGGGC GTTGCCGGGT      60
TCGGGCCTCG GGTTGGCGAT CGTCAAACAG GTGGTGCTCA ACCACGGCGG ATTGCTGCGC     120
ATCGAAGACA CCGACCCAGG CGGCCAGCCC CCTGGAACGT CGATTTACGT GCTGCTCCCC     180
GGCCGTCGGA TGCCGATTCC GCAGCTTCCC GGTGCGACGG CTGGCGCTCG GAGCACGGAC     240
ATCGAGAACT CTCGGGGTTC GGCGAACGTT ATCTCAGTGG AATCTCAGTC CACGCGCGCA     300
ACCTAGTTGT GCAGTTACTG TTGAAAGCCA CACCCATGCC AGTCCACGCA TGGCCAAGTT     360
GGCCCGAGTA GTGGGCCTAG TACAGGAAGA GCAACCTAGC GACATGACGA ATCACCCACG     420
GTATTCGCCA CCGCCGCAGC AGCCGGGAAC CCCAGGTTAT GCTCAGGGGC AGCAGCAAAC     480
GTACAGCCAG CAGTTCGACT GGCGTTACCC ACCGTCCCCG CCCCCGCAGC CAACCCAGTA     540
CCGTCAACCC TACGAGGCGT TGGGTGGTAC CCGGCCGGGT CTGATACCTG GCGTGATTCC     600
GACCATGACG CCCCCTCCTG GGATGGTTCG CCAACGCCCT CGTGCAGGCA TGTTGGCCAT     660
CGGCGCGGTG ACGATAGCGG TGGTGTCCGC CGGCATCGGC GGCGCGGCCG CATCCCTGGT     720
CGGGTTCAAC CGGGCACCCG CCGGCCCCAG CGGCGGCCCA GTGGCTGCCA GCGCGGCGCC     780
AAGCATCCCC GCAGCAAACA TGCCGCCGGG GTCGGTCGAA CAGGTGGCGG CCAAGGTGGT     840
GCCCAGTGTC GTCATGTTGG AAACCGATCT GGGCCGCCAG TCGGAGGAGG GCTCCGGCAT     900
CATTCTGTCT GCCGAGGGGC TGATCTTGAC CAACAACCAC GTGATCGCGG CGGCCGCCAA     960
GCCTCCCCTG GGCAGTCCGC CGCCGAAAAC GACGGTAACC TTCTCTGACG GCGGACCGC    1020
ACCCTTCACG GTGGTGGGGG CTGACCCCAC CAGTGATATC GCCGTCGTCC GTGTTCAGGG    1080
CGTCTCCGGG CTCACCCCGA TCTCCCTGGG TTCCTCCTCG GACCTGAGGG TCGGTCAGCC    1140
GGTGCTGGCG ATCGGGTCGC CGCTCGGTTT GGAGGGCACC GTGACCACGG GATCGTCAG    1200
CGCTCTCAAC CGTCCAGTGT CGACGACCGG CGAGGCCGGC AACCAGAACA CCGTGCTGGA    1260
CGCCATTCAG ACCGACGCCG CGATCAACCC CGGTAACTCC GGGGGCGCGC TGGTGAACAT    1320
GAACGCTCAA CTCGTCGGAG TCAACTCGGC CATTGCCACG CTGGGCGCGG ACTCAGCCGA    1380
TGCGCAGAGC GGCTCGATCG GTCTCGGTTT TGCGATTCCA GTCGACCAGG CCAAGCGCAT    1440
CGCCGACGAG TTGATCAGCA CCGGCAAGGC GTCACATGCC TCCCTGGGTG TGCAGGTGAC    1500
CAATGACAAA GACACCCCGG CGCCAAGAT CGTCGAAGTA GTGGCCGGTG GTGCTGCCGC     1560
GAACGCTGGA GTGCCGAAGG GCGTCGTTGT CACCAAGGTC GACGACCGCC CGATCAACAG    1620
CGCGGACGCG TTGGTTGCCG CCGTGCGGTC CAAAGCGCCG GGCGCCACGG TGGCGCTAAC    1680
CTTTCAGGAT CCCTCGGGCG GTAGCCGCAC AGTGCAAGTC ACCCTCGGCA AGGCGGAGCA    1740
GTGATGAAGG TCGCCGCGCA GTGTTCAAAG C                                   1771
```

(2) INFORMATION FOR SEQ ID NO:14:

(i) SEQUENCE CHARACTERISTICS:
(A) LENGTH: 1058 base pairs
(B) TYPE: nucleic acid
(C) STRANDEDNESS: single
(D) TOPOLOGY: linear (xi) SEQUENCE DESCRIPTION: SEQ ID NO:14:

-continued

```
CTCCACCGCG GTGGCGGCCG CTCTAGAACT AGTGGATCCC CCGGGCTGCA GGAATTCGGC      60

ACGAGGATCC GACGTCGCAG GTTGTCGAAC CCGCCGCCGC GGAAGTATCG GTCCATGCCT     120

AGCCCGGCGA CGGCGAGCGC CGGAATGGCG CGAGTGAGGA GGCGGGCAAT TTGGCGGGGC     180

CCGGCGACGG CGAGCGCCGG AATGGCGCGA GTGAGGAGGC GGGCAGTCAT GCCCAGCGTG     240

ATCCAATCAA CCTGCATTCG GCCTGCGGGC CCATTTGACA ATCGAGGTAG TGAGCGCAAA     300

TGAATGATGG AAAACGGGCG GTGACGTCCG CTGTTCTGGT GGTGCTAGGT GCCTGCCTGG     360

CGTTGTGGCT ATCAGGATGT TCTTCGCCGA AACCTGATGC CGAGGAACAG GGTGTTCCCG     420

TGAGCCCGAC GGCGTCCGAC CCCGCGCTCC TCGCCGAGAT CAGGCAGTCG CTTGATGCGA     480

CAAAAGGGTT GACCAGCGTG CACGTAGCGG TCCAACAAC CGGGAAAGTC GACAGCTTGC      540

TGGGTATTAC CAGTGCCGAT GTCGACGTCC GGGCCAATCC GCTCGCGGCA AAGGGCGTAT     600

GCACCTACAA CGACGAGCAG GGTGTCCCGT TTCGGGTACA AGGCGACAAC ATCTCGGTGA     660

AACTGTTCGA CGACTGGAGC AATCTCGGCT CGATTTCTGA ACTGTCAACT TCACGCGTGC     720

TCGATCCTGC CGCTGGGGTG ACGCAGCTGC TGTCCGGTGT CACGAACCTC CAAGCGCAAG     780

GTACCGAAGT GATAGACGGA ATTTCGACCA CCAAAATCAC CGGGACCATC CCCGCGAGCT     840

CTGTCAAGAT GCTTGATCCT GGCGCCAAGA GTGCAAGGCC GGCGACCGTG TGGATTGCCC     900

AGGACGGCTC GCACCACCTC GTCCGAGCGA GCATCGACCT CGGATCCGGG TCGATTCAGC     960

TCACGCAGTC GAAATGGAAC GAACCCGTCA ACGTCGACTA GGCCGAAGTT GCGTCGACGC    1020

GTTGNTCGAA ACGCCCTTGT GAACGGTGTC AACGGNAC                            1058
```

(2) INFORMATION FOR SEQ ID NO:15:

(i) SEQUENCE CHARACTERISTICS:
        (A) LENGTH: 542 base pairs
        (B) TYPE: nucleic acid
        (C) STRANDEDNESS: single
        (D) TOPOLOGY: linear (xi) SEQUENCE DESCRIPTION: SEQ ID NO:15:

```
GAATTCGGCA CGAGAGGTGA TCGACATCAT CGGGACCAGC CCCACATCCT GGGAACAGGC      60

GGCGGCGGAG GCGGTCCAGC GGGCGCGGGA TAGCGTCGAT GACATCCGCG TCGCTCGGGT     120

CATTGAGCAG GACATGGCCG TGGACAGCGC CGGCAAGATC ACCTACCGCA TCAAGCTCGA     180

AGTGTCGTTC AAGATGAGGC CGGCGCAACC GCGCTAGCAC GGGCCGGCGA GCAAGACGCA     240

AAATCGCACG GTTTGCGGTT GATTCGTGCG ATTTTGTGTC TGCTCGCCGA GGCCTACCAG     300

GCGCGGCCCA GGTCCGCGTG CTGCCGTATC CAGGCGTGCA TCGCGATTCC GGCGGCCACG     360

CCGGAGTTAA TGCTTCGCGT CGACCCGAAC TGGGCGATCC GCCGGNGAGC TGATCGATGA     420

CCGTGGCCAG CCCGTCGATG CCCGAGTTGC CCGAGGAAAC GTGCTGCCAG GCCGGTAGGA     480

AGCGTCCGTA GGCGGCGGTG CTGACCGGCT CTGCCTGCGC CCTCAGTGCG GCCAGCGAGC     540

GG                                                                    542
```

(2) INFORMATION FOR SEQ ID NO:16:

(i) SEQUENCE CHARACTERISTICS:
        (A) LENGTH: 913 base pairs
        (B) TYPE: nucleic acid
        (C) STRANDEDNESS: single
        (D) TOPOLOGY: linear (xi) SEQUENCE DESCRIPTION: SEQ ID NO:16:

```
CGGTGCCGCC CGCGCCTCCG TTGCCCCCAT TGCCGCCGTC GCCGATCAGC TGCGCATCGC       60
```

```
CACCATCACC GCCTTTGCCG CCGGCACCGC CGGTGGCGCC GGGGCCGCCG ATGCCACCGC      120

TTGACCCTGG CCGCCGGCGC CGCCATTGCC ATACAGCACC CCGCCGGGGG CACCGTTACC      180

GCCGTCGCCA CCGTCGCCGC CGCTGCCGTT TCAGGCCGGG GAGGCCGAAT GAACCGCCGC      240

CAAGCCCGCC GCCGGCACCG TTGCCGCCTT TTCCGCCCGC CCCGCCGGCG CCGCCAATTG      300

CCGAACAGCC AMGCACCGTT GCCGCCAGCC CCGCCGCCGT TAACGGCGCT GCCGGGCGCC      360

GCCGCCGGAC CCGCCATTAC CGCCGTTCCC GTTCGGTGCC CCGCCGTTAC CGGCGCCGCC      420

GTTTGCCGCC AATATTCGGC GGGCACCGCC AGACCCGCCG GGGCCACCAT TGCCGCCGGG      480

CACCGAAACA ACAGCCCAAC GGTGCCGCCG GCCCCGCCGT TTGCCGCCAT CACCGGCCAT      540

TCACCGCCAG CACCGCCGTT AATGTTTATG AACCCGGTAC CGCCAGCGCG GCCCCTATTG      600

CCGGGCGCCG GAGNGCGTGC CCGCCGGCGC CGCCAACGCC CAAAAGCCCG GGGTTGCCAC      660

CGGCCCCGCC GGACCCACCG GTCCCGCCGA TCCCCCCGTT GCCGCCGGTG CCGCCGCCAT      720

TGGTGCTGCT GAAGCCGTTA GCGCCGGTTC CGCSGGTTCC GGCGGTGGCG CCNTGGCCGC      780

CGGCCCCGCC GTTGCCGTAC AGCCACCCCC CGGTGGCGCC GTTGCCGCCA TTGCCGCCAT      840

TGCCGCCGTT GCCGCCATTG CCGCCGTTCC CGCCGCCACC GCCGGNTTGG CCGCCGGCGC      900

CGCCGGCGGC CGC                                                        913

(2) INFORMATION FOR SEQ ID NO:17:

(i) SEQUENCE CHARACTERISTICS:
        (A) LENGTH: 1872 base pairs
        (B) TYPE: nucleic acid
        (C) STRANDEDNESS: single
        (D) TOPOLOGY: linear (xi) SEQUENCE DESCRIPTION: SEQ ID NO:17:

GACTACGTTG GTGTAGAAAA ATCCTGCCGC CCGGACCCTT AAGGCTGGGA CAATTTCTGA       60

TAGCTACCCC GACACAGGAG GTTACGGGAT GAGCAATTCG CGCCGCCGCT CACTCAGGTG      120

GTCATGGTTG CTGAGCGTGC TGGCTGCCGT CGGGCTGGGC CTGGCCACGG CGCCGGCCCA      180

GGCGGCCCCG CCGGCCTTGT CGCAGGACCG GTTCGCCGAC TTCCCCGCGC TGCCCCTCGA      240

CCCGTCCGCG ATGGTCGCCC AAGTGGCGCC ACAGGTGGTC AACATCAACA CCAAACTGGG      300

CTACAACAAC GCCGTGGGCG CCGGGACCGG CATCGTCATC GATCCCAACG GTGTCGTGCT      360

GACCAACAAC CACGTGATCG CGGGCGCCAC CGACATCAAT GCGTTCAGCG TCGGCTCCGG      420

CCAAACCTAC GGCGTCGATG TGGTCGGGTA TGACCGCACC CAGGATGTCG CGGTGCTGCA      480

GCTGCGCGGT GCCGGTGGCC TGCCGTCGGC GGCGATCGGT GGCGGCGTCG CGGTTGGTGA      540

GCCCGTCGTC GCGATGGGCA ACAGCGGTGG GCAGGGCGGA ACGCCCCGTG CGGTGCCTGG      600

CAGGGTGGTC GCGCTCGGCC AAACCGTGCA GGCGTCGGAT TCGCTGACCG GTGCCGAAGA      660

GACATTGAAC GGGTTGATCC AGTTCGATGC CGCAATCCAG CCCGGTGATT CGGGCGGGCC      720

CGTCGTCAAC GGCCTAGGAC AGGTGGTCGG TATGAACACG GCCGCGTCCG ATAACTTCCA      780

GCTGTCCCAG GGTGGGCAGG GATTCGCCAT TCCGATCGGG CAGGCGATGG CGATCGCGGG      840

CCAAATCCGA TCGGGTGGGG GGTCACCCAC CGTTCATATC GGGCCTACCG CCTTCCTCGG      900

CTTGGGTGTT GTCGACAACA ACGGCAACGG CGCACGAGTC CAACGCGTGG TCGGAAGCGC      960

TCCGGCGGCA AGTCTCGGCA TCTCCACCGG CGACGTGATC ACCGCGGTCG ACGGCGCTCC     1020

GATCAACTCG GCCACCGCGA TGGCGGACGC GCTTAACGGG CATCATCCCG GTGACGTCAT     1080

CTCGGTGAAC TGGCAAACCA AGTCGGGCGG CACGCGTACA GGGAACGTGA CATTGGCCGA     1140
```

-continued

```
GGGACCCCCG GCCTGATTTG TCGCGGATAC CACCCGCCGG CCGGCCAATT GGATTGGCGC   1200

CAGCCGTGAT TGCCGCGTGA GCCCCCGAGT TCCGTCTCCC GTGCGCGTGG CATTGTGGAA   1260

GCAATGAACG AGGCAGAACA CAGCGTTGAG CACCCTCCCG TGCAGGGCAG TTACGTCGAA   1320

GGCGGTGTGG TCGAGCATCC GGATGCCAAG GACTTCGGCA GCGCCGCCGC CCTGCCCGCC   1380

GATCCGACCT GGTTTAAGCA CGCCGTCTTC TACGAGGTGC TGGTCCGGGC GTTCTTCGAC   1440

GCCAGCGCGG ACGGTTCCGN CGATCTGCGT GGACTCATCG ATCGCCTCGA CTACCTGCAG   1500

TGGCTTGGCA TCGACTGCAT CTGTTGCCGC CGTTCCTACG ACTCACCGCT GCGCGACGGC   1560

GGTTACGACA TTCGCGACTT CTACAAGGTG CTGCCCGAAT TCGGCACCGT CGACGATTTC   1620

GTCGCCCTGG TCGACACCGC TCACCGGCGA GGTATCCGCA TCATCACCGA CCTGGTGATG   1680

AATCACACCT CGGAGTCGCA CCCCTGGTTT CAGGAGTCCC GCCGCGACCC AGACGGACCG   1740

TACGGTGACT ATTACGTGTG GAGCGACACC AGCGAGCGCT ACACCGACGC CCGGATCATC   1800

TTCGTCGACA CCGAAGAGTC GAACTGGTCA TTCGATCCTG TCCGCCGACA GTTNCTACTG   1860

GCACCGATTC TT                                                      1872
```

(2) INFORMATION FOR SEQ ID NO:18:

(i) SEQUENCE CHARACTERISTICS:
        (A) LENGTH: 1482 base pairs
        (B) TYPE: nucleic acid
        (C) STRANDEDNESS: single
        (D) TOPOLOGY: linear (xi) SEQUENCE DESCRIPTION: SEQ ID NO:18:

```
CTTCGCCGAA ACCTGATGCC GAGGAACAGG GTGTTCCCGT GAGCCCGACG GCGTCCGACC     60

CCGCGCTCCT CGCCGAGATC AGGCAGTCGC TTGATGCGAC AAAAGGGTTG ACCAGCGTGC    120

ACGTAGCGGT CCGAACAACC GGGAAAGTCG ACAGCTTGCT GGGTATTACC AGTGCCGATG    180

TCGACGTCCG GGCCAATCCG CTCGCGGCAA AGGGCGTATG CACCTACAAC GACGAGCAGG    240

GTGTCCCGTT TCGGGTACAA GGCGACAACA TCTCGGTGAA ACTGTTCGAC GACTGGAGCA    300

ATCTCGGCTC GATTTCTGAA CTGTCAACTT CACGCGTGCT CGATCCTGCC GCTGGGGTGA    360

CGCAGCTGCT GTCCGGTGTC ACGAACCTCC AAGCGCAAGG TACCGAAGTG ATAGACGGAA    420

TTTCGACCAC CAAAATCACC GGGACCATCC CCGCGAGCTC TGTCAAGATG CTTGATCCTG    480

GCGCCAAGAG TGCAAGGCCG GCGACCGTGT GGATTGCCCA GGACGGCTCG CACCACCTCG    540

TCCGAGCGAG CATCGACCTC GGATCCGGGT CGATTCAGCT CACGCAGTCG AAATGGAACG    600

AACCCGTCAA CGTCGACTAG GCCGAAGTTG CGTCGACGCG TTGCTCGAAA CGCCCTTGTG    660

AACGGTGTCA ACGGCACCCG AAAACTGACC CCCTGACGGC ATCTGAAAAT TGACCCCCTA    720

GACCGGGCGG TTGGTGGTTA TTCTTCGGTG GTTCCGGCTG GTGGGACGCG GCCGAGGTCG    780

CGGTCTTTGA GCCGGTAGCT GTCGCCTTTG AGGGCGACGA CTTCAGCATG GTGGACGAGG    840

CGGTCGATCA TGGCGGCAGC AACGACGTCG TCGCCGCCGA AAACCTCGCC CCACCGGCCG    900

AAGGCCTTAT TGGACGTGAC GATCAAGCTG GCCCGCTCAT ACCGGGAGGA CACCAGCTGG    960

AAGAAGAGGT TGGCGGCCTC GGGCTCAAAC GGAATGTAAC CGACTTCGTC AACCACCAGG   1020

AGCGGATAGC GGCCAAACCG GGTGAGTTCG GCGTAGATGC GCCCGGCGTG GTGAGCCTCG   1080

GCGAACCGTG CTACCCATTC GGCGGCGGTG GCGAACAGCA CCCGATGACC GGCCTGACAC   1140

GCGCGTATCG CCAGGCCGAC CGCAAGATGA GTCTTCCCGG TGCCAGGCGG GGCCCAAAAA   1200

CACGACGTTA TCGCGGGCGG TGATGAAATC CAGGGTGCCC AGATGTGCGA TGGTGTCGCG   1260
```

| | |
|---|---|
| TTTGAGGCCA CGAGCATGCT CAAAGTCGAA CTCTTCCAAC GACTTCCGAA CCGGGAAGCG | 1320 |
| GGCGGCGCGG ATGCGGCCCT CACCACCATG GGACTCCCGG GCTGACACTT CCCGCTGCAG | 1380 |
| GCAGGCGGCC AGGTATTCTT CGTGGCTCCA GTTCTCGGCG CGGGCGCGAT CGGCCAGCCG | 1440 |
| GGACACTGAC TCACGCAGGG TGGGAGCTTT CAATGCTCTT GT | 1482 |

(2) INFORMATION FOR SEQ ID NO:19:

(i) SEQUENCE CHARACTERISTICS:
        (A) LENGTH: 876 base pairs
        (B) TYPE: nucleic acid
        (C) STRANDEDNESS: single
        (D) TOPOLOGY: linear (xi) SEQUENCE DESCRIPTION: SEQ ID NO:19:

| | |
|---|---|
| GAATTCGGCA CGAGCCGGCG ATAGCTTCTG GGCCGCGGCC GACCAGATGG CTCGAGGGTT | 60 |
| CGTGCTCGGG GCCACCGCCG GGCGCACCAC CCTGACCGGT GAGGGCCTGC AACACGCCGA | 120 |
| CGGTCACTCG TTGCTGCTGG ACGCCACCAA CCCGGCGGTG GTTGCCTACG ACCCGGCCTT | 180 |
| CGCCTACGAA ATCGGCTACA TCGNGGAAAG CGGACTGGCC AGGATGTGCG GGGAGAACCC | 240 |
| GGAGAACATC TTCTTCTACA TCACCGTCTA CAACGAGCCG TACGTGCAGC CGCCGGAGCC | 300 |
| GGAGAACTTC GATCCCGAGG GCGTGCTGGG GGGTATCTAC CGNTATCACG CGGCCACCGA | 360 |
| GCAACGCACC AACAAGGNGC AGATCCTGGC CTCCGGGGTA GCGATGCCCG CGGCGCTGCG | 420 |
| GGCAGCACAG ATGCTGGCCG CCGAGTGGGA TGTCGCCGCC GACGTGTGGT CGGTGACCAG | 480 |
| TTGGGGCGAG CTAAACCGCG ACGGGGTGGT CATCGAGACC GAGAAGCTCC GCCACCCCGA | 540 |
| TCGGCCGGCG GGCGTGCCCT ACGTGACGAG AGCGCTGGAG AATGCTCGGG GCCCGGTGAT | 600 |
| CGCGGTGTCG GACTGGATGC GCGCGGTCCC CGAGCAGATC CGACCGTGGG TGCCGGGCAC | 660 |
| ATACCTCACG TTGGGCACCG ACGGGTTCGG TTTTTCCGAC ACTCGGCCCG CCGGTCGTCG | 720 |
| TTACTTCAAC ACCGACGCCG AATCCCAGGT TGGTCGCGGT TTTGGGAGGG GTTGGCCGGG | 780 |
| TCGACGGGTG AATATCGACC CATTCGGTGC CGGTCGTGGG CCGCCCGCCC AGTTACCCGG | 840 |
| ATTCGACGAA GGTGGGGGGT TGCGCCCGAN TAAGTT | 876 |

(2) INFORMATION FOR SEQ ID NO:20:

(i) SEQUENCE CHARACTERISTICS:
        (A) LENGTH: 1021 base pairs
        (B) TYPE: nucleic acid
        (C) STRANDEDNESS: single
        (D) TOPOLOGY: linear (xi) SEQUENCE DESCRIPTION: SEQ ID NO:20:

| | |
|---|---|
| ATCCCCCCGG GCTGCAGGAA TTCGGCACGA GAGACAAAAT TCCACGCGTT AATGCAGGAA | 60 |
| CAGATTCATA ACGAATTCAC AGCGGCACAA CAATATGTCG CGATCGCGGT TTATTTCGAC | 120 |
| AGCGAAGACC TGCCGCAGTT GGCGAAGCAT TTTTACAGCC AAGCGGTCGA GGAACGAAAC | 180 |
| CATGCAATGA TGCTCGTGCA ACACCTGCTC GACCGCGACC TTCGTGTCGA AATTCCCGGC | 240 |
| GTAGACACGG TGCGAAACCA GTTCGACAGA CCCCGCGAGG CACTGGCGCT GGCGCTCGAT | 300 |
| CAGGAACGCA CAGTCACCGA CCAGGTCGGT CGGCTGACAG CGGTGGCCCG CGACGAGGGC | 360 |
| GATTTCCTCG GCGAGCAGTT CATGCAGTGG TTCTTGCAGG AACAGATCGA AGAGGTGGCC | 420 |
| TTGATGGCAA CCCTGGTGCG GGTTGCCGAT CGGGCCGGGG CCAACCTGTT CGAGCTAGAG | 480 |
| AACTTCGTCG CACGTGAAGT GGATGTGGCG CCGGCCGCAT CAGGCGCCCC GCACGCTGCC | 540 |

-continued

```
GGGGGCCGCC TCTAGATCCC TGGGGGGGAT CAGCGAGTGG TCCCGTTCGC CCGCCCGTCT    600

TCCAGCCAGG CCTTGGTGCG GCCGGGGTGG TGAGTACCAA TCCAGGCCAC CCCGACCTCC    660

CGGNAAAAGT CGATGTCCTC GTACTCATCG ACGTTCCAGG AGTACACCGC CCGGCCCTGA    720

GCTGCCGAGC GGTCAACGAG TTGCGGATAT TCCTTTAACG CAGGCAGTGA GGGTCCCACG    780

GCGGTTGGCC CGACCGCCGT GGCCGCACTG CTGGTCAGGT ATCGGGGGGT CTTGGCGAGC    840

AACAACGTCG GCAGGAGGGG TGGAGCCCGC CGGATCCGCA GACCGGGGGG GCGAAAACGA    900

CATCAACACC GCACGGGATC GATCTGCGGA GGGGGGTGCG GGAATACCGA ACCGGTGTAG    960

GAGCGCCAGC AGTTGTTTTT CCACCAGCGA AGCGTTTTCG GGTCATCGGN GGCNNTTAAG   1020

T                                                                   1021
```

(2) INFORMATION FOR SEQ ID NO:21:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO:21:

```
CGTGCCGACG AACGGAAGAA CACAACCATG AAGATGGTGA AATCGATCGC CGCAGGTCTG     60

ACCGCCGCGG CTGCAATCGG CGCCGCTGCG GCCGGTGTGA CTTCGATCAT GGCTGGCGGN    120

CCGGTCGTAT ACCAGATGCA GCCGGTCGTC TTCGGCGCGC CACTGCCGTT GGACCCGGNA    180

TCCGCCCCTG ANGTCCCGAC CGCCGCCCAG TGGACCAGNC TGCTCAACAG NCTCGNCGAT    240

CCCAACGTGT CGTTTGNGAA CAAGGGNAGT CTGGTCGAGG GNGGNATCGG NGGNANCGAG    300

GGNGNGNATC GNCGANCACA A                                              321
```

(2) INFORMATION FOR SEQ ID NO:22:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (xi) SEQUENCE DESCRIPTION: SEQ ID NO:22:

```
TCTTATCGGT TCCGGTTGGC GACGGGTTTT GGGNGCGGGT GGTTAACCCG CTCGGCCAGC     60

CGATCGACGG GCGCGGAGAC GTCGACTCCG ATACTCGGCG CGCGCTGGAG CTCCAGGCGC    120

CCTCGGTGGT GNACCGGCAA GGCGTGAAGG AGCCGTTGNA GACCGGGATC AAGGCGATTG    180

ACGCGATGAC CCCGATCGGC CGCGGGCAGC GCCAGCTGAT CATCGGGGAC CGCAAGACCG    240

GCAAAAACCG CCGTCTGTGT CGGACACCAT CCTCAAACCA GCGGGAAGAA CTGGGAGTCC    300

GGTGGATCCC AAGAAGCAGG TGCGCTTGTG TATACGTTGG CCATCGGGCA AGAAGGGGAA    360

CTTACCATCG CCG                                                       373
```

(2) INFORMATION FOR SEQ ID NO:23:

(i) SEQUENCE CHARACTERISTICS:
        (A) LENGTH: 352 base pairs
        (B) TYPE: nucleic acid
        (C) STRANDEDNESS: single
        (D) TOPOLOGY: linear (xi) SEQUENCE DESCRIPTION: SEQ ID NO:23:

```
GTGACGCCGT GATGGGATTC CTGGGCGGGG CCGGTCCGCT GGCGGTGGTG GATCAGCAAC     60
```

```
TGGTTACCCG GGTGCCGCAA GGCTGGTCGT TTGCTCAGGC AGCCGCTGTG CCGGTGGTGT      120

TCTTGACGGC CTGGTACGGG TTGGCCGATT TAGCCGAGAT CAAGGCGGGC GAATCGGTGC      180

TGATCCATGC CGGTACCGGC GGTGTGGGCA TGGCGGCTGT GCAGCTGGCT CGCCAGTGGG      240

GCGTGGAGGT TTTCGTCACC GCCAGCCGTG GNAAGTGGGA CACGCTGCGC GCCATNGNGT      300

TTGACGACGA NCCATATCGG NGATTCCCNC ACATNCGAAG TTCCGANGGA GA              352
```

(2) INFORMATION FOR SEQ ID NO:24:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (xi) SEQUENCE DESCRIPTION: SEQ ID NO:24:

```
GAAATCCGCG TTCATTCCGT TCGACCAGCG GCTGGCGATA ATCGACGAAG TGATCAAGCC       60

GCGGTTCGCG GCGCTCATGG GTCACAGCGA GTAATCAGCA AGTTCTCTGG TATATCGCAC      120

CTAGCGTCCA GTTGCTTGCC AGATCGCTTT CGTACCGTCA TCGCATGTAC CGGTTCGCGT      180

GCCGCACGCT CATGCTGGCG GCGTGCATCC TGGCCACGGG TGTGGCGGGT CTCGGGGTCG      240

GCGCGCAGTC CGCAGCCCAA ACCGCGCCGG TGCCCGACTA CTACTGGTGC CCGGGGCAGC      300

CTTTCGACCC CGCATGGGGG CCCAACTGGG ATCCCTACAC CTGCCATGAC GACTTCCACC      360

GCGACAGCGA CGGCCCCGAC CACAGCCGCG ACTACCCCGG ACCCATCCTC GAAGGTCCCG      420

TGCTTGACGA TCCCGGTGCT GCGCCGCCGC CCCCGGCTGC CGGTGGCGGC GCATAGCGCT      480

CGTTGACCGG GCCGCATCAG CGAATACGCG TATAAACCCG GGCGTGCCCC CGGCAAGCTA      540

CGACCCCCGG CGGGGCAGAT TTACGCTCCC GTGCCGATGG ATCGCGCCGT CCGATGACAG      600

AAAATAGGCG ACGGTTTTGG CAACCGCTTG GAGGACGCTT GAAGGGAACC TGTCATGAAC      660

GGCGACAGCG CCTCCACCAT CGACATCGAC AAGGTTGTTA CCCGCACACC CGTTCGCCGG      720

ATCGTG                                                                 726
```

(2) INFORMATION FOR SEQ ID NO:25:

(i) SEQUENCE CHARACTERISTICS:
        (A) LENGTH: 580 base pairs
        (B) TYPE: nucleic acid
        (C) STRANDEDNESS: single
        (D) TOPOLOGY: linear (xi) SEQUENCE DESCRIPTION: SEQ ID NO:25:

```
CGCGACGACG ACGAACGTCG GGCCCACCAC CGCCTATGCG TTGATGCAGG CGACCGGGAT       60

GGTCGCCGAC CATATCCAAG CATGCTGGGT GCCCACTGAG CGACCTTTTG ACCAGCCGGG      120

CTGCCCGATG GCGGCCCGGT GAAGTCATTG CGCCGGGGCT TGTGCACCTG ATGAACCCGA      180

ATAGGGAACA ATAGGGGGGT GATTTGGCAG TTCAATGTCG GGTATGGCTG GAAATCCAAT      240

GGCGGGGCAT GCTCGGCGCC GACCAGGCTC GCGCAGGCGG GCCAGCCCGA ATCTGGAGGG      300

AGCACTCAAT GGCGGCGATG AAGCCCCGGA CCGGCGACGG TCCTTTGGAA GCAACTAAGG      360

AGGGGCGCGG CATTGTGATG CGAGTACCAC TTGAGGGTGG CGGTCGCCTG GTCGTCGAGC      420

TGACACCCGA CGAAGCCGCC GCACTGGGTG ACGAACTCAA AGGCGTTACT AGCTAAGACC      480

AGCCCAACGG CGAATGGTCG GCGTTACGCG CACACCTTCC GGTAGATGTC CAGTGTCTGC      540

TCGGCGATGT ATGCCCAGGA GAACTCTTGG ATACAGCGCT                            580
```

(2) INFORMATION FOR SEQ ID NO:26:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (xi) SEQUENCE DESCRIPTION: SEQ ID NO:26:

```
AACGGAGGCG CCGGGGGTTT TGGCGGGGCC GGGGCGGTCG GCGGCAACGG CGGGGCCGGC      60

GGTACCGCCG GGTTGTTCGG TGTCGGCGGG GCCGGTGGGG CCGGAGGCAA CGGCATCGCC     120

GGTGTCACGG GTACGTCGGC CAGCACACCG GGTGGATCCG                          160
```

(2) INFORMATION FOR SEQ ID NO:27:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (xi) SEQUENCE DESCRIPTION: SEQ ID NO:27:

```
GACACCGATA CGATGGTGAT GTACGCCAAC GTTGTCGACA CGCTCGAGGC GTTCACGATC      60

CAGCGCACAC CCGACGGCGT GACCATCGGC GATGCGGCCC CGTTCGCGGA GGCGGCTGCC     120

AAGGCGATGG GAATCGACAA GCTGCGGGTA ATTCATACCG GAATGGACCC CGTCGTCGCT     180

GAACGCGAAC AGTGGGACGA CGGCAACAAC ACGTTGGCGT TGGCGCCCGG TGTCGTTGTC     240

GCCTACGAGC GCAACGTACA GACCAACGCC CG                                  272
```

(2) INFORMATION FOR SEQ ID NO:28:

(i) SEQUENCE CHARACTERISTICS:
        (A) LENGTH: 317 base pairs
        (B) TYPE: nucleic acid
        (C) STRANDEDNESS: single
        (D) TOPOLOGY: linear (xi) SEQUENCE DESCRIPTION: SEQ ID NO:28:

```
GCAGCCGGTG GTTCTCGGAC TATCTGCGCA CGGTGACGCA GCGCGACGTG CGCGAGCTGA      60

AGCGGATCGA GCAGACGGAT CGCCTGCCGC GGTTCATGCG CTACCTGGCC GCTATCACCG     120

CGCAGGAGCT GAACGTGGCC GAAGCGGCGC GGGTCATCGG GGTCGACGCG GGACGATCC     180

GTTCGGATCT GGCGTGGTTC GAGACGGTCT ATCTGGTACA TCGCCTGCCC GCCTGGTCGC     240

GGAATCTGAC CGCGAAGATC AAGAAGCGGT CAAAGATCCA CGTCGTCGAC AGTGGCTTCG     300

CGGCCTGGTT GCGCGGG                                                   317
```

(2) INFORMATION FOR SEQ ID NO:29:

(i) SEQUENCE CHARACTERISTICS:
        (A) LENGTH: 182 base pairs
        (B) TYPE: nucleic acid
        (C) STRANDEDNESS: single
        (D) TOPOLOGY: linear (xi) SEQUENCE DESCRIPTION: SEQ ID NO:29:

```
GATCGTGGAG CTGTCGATGA ACAGCGTTGC CGGACGCGCG GCGGCCAGCA CGTCGGTGTA      60

GCAGCGCCGG ACCACCTCGC CGGTGGGCAG CATGGTGATG ACCACGTCGG CCTCGGCCAC     120

CGCTTCGGGC GCGCTACGAA ACACCGCGAC ACCGTGCGCG GCGGCGCCGG ACGCCGCCGT     180

GG                                                                   182
```

(2) INFORMATION FOR SEQ ID NO:30:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (xi) SEQUENCE DESCRIPTION: SEQ ID NO:30:

```
GATCGCGAAG TTTGGTGAGC AGGTGGTCGA CGCGAAAGTC TGGGCGCCTG CGAAGCGGGT      60

CGGCGTTCAC GAGGCGAAGA CACGCCTGTC CGAGCTGCTG CGGCTCGTCT ACGGCGGGCA     120

GAGGTTGAGA TTGCCCGCCG CGGCGAGCCG GTAGCAAAGC TTGTGCCGCT GCATCCTCAT     180

GAGACTCGGC GGTTAGGCAT TGACCATGGC GTGTACCGCG TGCCCGACGA TTTGGACGCT     240

CCGTTGTCAG ACGACGTGCT CGAACGCTTT CACCGGTGAA GCGCTACCTC ATCGACACCC     300

ACGTTTGG                                                              308
```

(2) INFORMATION FOR SEQ ID NO:31:

(i) SEQUENCE CHARACTERISTICS:
        (A) LENGTH: 267 base pairs
        (B) TYPE: nucleic acid
        (C) STRANDEDNESS: single
        (D) TOPOLOGY: linear (xi) SEQUENCE DESCRIPTION: SEQ ID NO:31:

```
CCGACGACGA GCAACTCACG TGGATGATGG TCGGCAGCGG CATTGAGGAC GGAGAGAATC      60

CGGCCGAAGC TGCCGCGCGG CAAGTGCTCA TAGTGACCGG CCGTAGAGGG CTCCCCCGAT     120

GGCACCGGAC TATTCTGGTG TGCCGCTGGC CGGTAAGAGC GGGTAAAAGA ATGTGAGGGG     180

ACACGATGAG CAATCACACC TACCGAGTGA TCGAGATCGT CGGGACCTCG CCCGACGGCG     240

TCGACGCGGC AATCCAGGGC GGTCTGG                                         267
```

(2) INFORMATION FOR SEQ ID NO:32:

(i) SEQUENCE CHARACTERISTICS:
        (A) LENGTH: 1539 base pairs
        (B) TYPE: nucleic acid
        (C) STRANDEDNESS: single
        (D) TOPOLOGY: linear (xi) SEQUENCE DESCRIPTION: SEQ ID NO:32:

```
CTCGTGCCGA AAGAATGTGA GGGGACACGA TGAGCAATCA CACCTACCGA GTGATCGAGA      60

TCGTCGGGAC CTCGCCCGAC GGCGTCGACG CGGCAATCCA GGGCGGTCTG GCCCGAGCTG     120

CGCAGACCAT GCGCGCGCTG GACTGGTTCG AAGTACAGTC AATTCGAGGC CACCTGGTCG     180

ACGGAGCGGT CGCGCACTTC CAGGTGACTA TGAAAGTCGG CTTCCGCTGG AGGATTCCTG     240

AACCTTCAAG CGCGGCCGAT AACTGAGGTG CATCATTAAG CGACTTTTCC AGAACATCCT     300

GACGCGCTCG AAACGCGGTT CAGCCGACGG TGGCTCCGCC GAGGCGCTGC CTCCAAAATC     360

CCTGCGACAA TTCGTCGGCG GCGCCTACAA GGAAGTCGGT GCTGAATTCG TCGGGTATCT     420

GGTCGACCTG TGTGGGCTGC AGCCGGACGA AGCGGTGCTC GACGTCGGCT GCGGCTCGGG     480

GCGGATGGCG TTGCCGCTCA CCGGCTATCT GAACAGCGAG GGACGCTACG CCGGCTTCGA     540

TATCTCGCAG AAAGCCATCG CGTGGTGCCA GGAGCACATC ACCTCGGCGC ACCCCAACTT     600

CCAGTTCGAG GTCTCCGACA TCTACAACTC GCTGTACAAC CCGAAAGGGA ATACCAGTC      660

ACTAGACTTT CGCTTTCCAT ATCCGGATGC GTCGTTCGAT GTGGTGTTTC TTACCTCGGT     720
```

```
GTTCACCCAC ATGTTTCCGC CGGACGTGGA GCACTATCTG ACGAGATCT  CCCGCGTGCT    780

GAAGCCCGGC GGACGATGCC TGTGCACGTA CTTCTTGCTC AATGACGAGT CGTTAGCCCA    840

CATCGCGGAA GGAAAGAGTG CGCACAACTT CCAGCATGAG GGACCGGGTT ATCGGACAAT    900

CCACAAGAAG CGGCCCGAAG AAGCAATCGG CTTGCCGGAG ACCTTCGTCA GGGATGTCTA    960

TGGCAAGTTC GGCCTCGCCG TGCACGAACC ATTGCACTAC GGCTCATGGA GTGGCCGGGA   1020

ACCACGCCTA AGCTTCCAGG ACATCGTCAT CGCGACCAAA ACCGCGAGCT AGGTCGGCAT   1080

CCGGGAAGCA TCGCGACACC GTGGCGCCGA GCGCCGCTGC CGGCAGGCCG ATTAGGCGGG   1140

CAGATTAGCC CGCCGCGGCT CCCGGCTCCG AGTACGGCGC CCCGAATGGC GTCACCGGCT   1200

GGTAACCACG CTTGCGCGCC TGGGCGGCGG CCTGCCGGAT CAGGTGGTAG ATGCCGACAA   1260

AGCCTGCGTG ATCGGTCATC ACCAACGGTG ACAGCAGCCG GTTGTGCACC AGCGCGAACG   1320

CCACCCCGGT CTCCGGGTCT GTCCAGCCGA TCGAGCCGCC CAAGCCCACA TGACCAAACC   1380

CCGGCATCAC GTTGCCGATC GGCATACCGT GATAGCCAAG ATGAAAATTT AAGGGCACCA   1440

ATAGATTTCG ATCCGGCAGA ACTTGCCGTC GGTTGCGGGT CAGGCCCGTG ACCAGCTCCC   1500

GCGACAAGAA CCGTATGCCG TCGATCTCGC CTCGTGCCG                          1539

(2) INFORMATION FOR SEQ ID NO:33:

(i) SEQUENCE CHARACTERISTICS:
        (A) LENGTH: 851 base pairs
        (B) TYPE: nucleic acid
        (C) STRANDEDNESS: single
        (D) TOPOLOGY: linear (xi) SEQUENCE DESCRIPTION: SEQ ID NO:33:

CTGCAGGGTG GCGTGGATGA GCGTCACCGC GGGGCAGGCC GAGCTGACCG CCGCCCAGGT     60

CCGGGTTGCT GCGGCGGCCT ACGAGACGGC GTATGGGCTG ACGGTGCCCC CGCCGGTGAT    120

CGCCGAGAAC CGTGCTGAAC TGATGATTCT GATAGCGACC AACCTCTTGG GGCAAAACAC    180

CCCGGCGATC GCGGTCAACG AGGCCGAATA CGGCGAGATG TGGGCCCAAG ACGCCGCCGC    240

GATGTTTGGC TACGCCGCGG CGACGGCGAC GGCGACGGCG ACGTTGCTGC CGTTCGAGGA    300

GGCGCCGGAG ATGACCAGCG CGGGTGGGCT CCTCGAGCAG GCCGCCGCGG TCGAGGAGGC    360

CTCCGACACC GCCGCGGCGA ACCAGTTGAT GAACAATGTG CCCCAGGCGC TGAAACAGTT    420

GGCCCAGCCC ACGCAGGGCA CCACGCCTTC TTCCAAGCTG GGTGGCCTGT GGAAGACGGT    480

CTCGCCGCAT CGGTCGCCGA TCAGCAACAT GGTGTCGATG GCCAACAACC ACATGTCGAT    540

GACCAACTCG GGTGTGTCGA TGACCAACAC CTTGAGCTCG ATGTTGAAGG GCTTTGCTCC    600

GGCGGCGGCC GCCCAGGCCG TGCAAACCGC GGCGCAAAAC GGGGTCCGGG CGATGAGCTC    660

GCTGGGCAGC TCGCTGGGTT CTTCGGGTCT GGGCGGTGGG GTGGCCGCCA ACTTGGGTCG    720

GGCGGCCTCG GTACGGTATG GTCACCGGGA TGGCGGAAAA TATGCANAGT CTGGTCGGCG    780

GAACGGTGGT CCGGCGTAAG GTTTACCCCC GTTTTCTGGA TGCGGTGAAC TTCGTCAACG    840

GAAACAGTTA C                                                        851

(2) INFORMATION FOR SEQ ID NO:34:

(i) SEQUENCE CHARACTERISTICS:
        (A) LENGTH: 254 base pairs
        (B) TYPE: nucleic acid
        (C) STRANDEDNESS: single
        (D) TOPOLOGY: linear (xi) SEQUENCE DESCRIPTION: SEQ ID NO:34:
```

```
GATCGATCGG GCGGAAATTT GGACCAGATT CGCCTCCGGC GATAACCCAA TCAATCGAAC        60

CTAGATTTAT TCCGTCCAGG GGCCCGAGTA ATGGCTCGCA GGAGAGGAAC CTTACTGCTG       120

CGGGCACCTG TCGTAGGTCC TCGATACGGC GGAAGGCGTC GACATTTTCC ACCGACACCC       180

CCATCCAAAC GTTCGAGGGC CACTCCAGCT TGTGAGCGAG GCGACGCAGT CGCAGGCTGC       240

GCTTGGTCAA GATC                                                        254
```

(2) INFORMATION FOR SEQ ID NO:35:

(i) SEQUENCE CHARACTERISTICS:
        (A) LENGTH: 1227 base pairs
        (B) TYPE: nucleic acid
        (C) STRANDEDNESS: single
        (D) TOPOLOGY: linear (xi) SEQUENCE DESCRIPTION: SEQ ID NO:35:

```
GATCCTGACC GAAGCGGCCG CCGCCAAGGC GAAGTCGCTG TTGGACCAGG AGGGACGGGA        60

CGATCTGGCG CTGCGGATCG CGGTTCAGCC GGGGGGGTGC GCTGGATTGC GCTATAACCT       120

TTTCTTCGAC GACCGGACGC TGGATGGTGA CCAAACCGCG GAGTTCGGTG GTGTCAGGTT       180

GATCGTGGAC CGGATGAGCG CGCCGTATGT GGAAGGCGCG TCGATCGATT TCGTCGACAC       240

TATTGAGAAG CAAGGTTCAC CATCGACAAT CCCAACGCCA CCGGCTCCTG CGCGTGCGGG       300

GATTCGTTCA ACTGATAAAA CGCTAGTACG ACCCCGCGGT GCGCAACACG TACGAGCACA       360

CCAAGACCTG ACCGCGCTGG AAAAGCAACT GAGCGATGCC TTGCACCTGA CCGCGTGGCG       420

GGCCGCCGGC GGCAGGTGTC ACCTGCATGG TGAACAGCAC CTGGGCCTGA TATTGCGACC       480

AGTACACGAT TTTGTCGATC GAGGTCACTT CGACCTGGGA GAACTGCTTG CGGAACGCGT       540

CGCTGCTCAG CTTGGCCAAG GCCTGATCGG AGCGCTTGTC GCGCACGCCG TCGTGGATAC       600

CGCACAGCGC ATTGCGAACG ATGGTGTCCA CATCGCGGTT CTCCAGCGCG TTGAGGTATC       660

CCTGAATCGC GGTTTTGGCC GGTCCCTCCG AGAATGTGCC TGCCGTGTTG GCTCCGTTGG       720

TGCGGACCCC GTATATGATC GCCGCCGTCA TAGCCGACAC CAGCGCGAGG GCTACCACAA       780

TGCCGATCAG CAGCCGCTTG TGCCGTCGCT TCGGGTAGGA CACCTGCGGC GGCACGCCGG       840

GATATGCGGC GGGCGGCAGC GCCGCGTCGT CTGCCGGTCC CGGGGCGAAG GCCGGTTCGG       900

CGGCGCCGAG GTCGTGGGGG TAGTCCAGGG CTTGGGGTTC GTGGGATGAG GGCTCGGGGT       960

ACGGCGCCGG TCCGTTGGTG CCGACACCGG GGTTCGGCGA GTGGGACCGG GGCATTGTGG      1020

TTCTCCTAGG GTGGTGGACG GGACCAGCTG CTAGGGCGAC AACCGCCCGT CGCGTCAGCC      1080

GGCAGCATCG GCAATCAGGT GAGCTCCCTA GGCAGGCTAG CGCAACAGCT GCCGTCAGCT      1140

CTCAACGCGA CGGGGCGGGC CGCGGCGCCG ATAATGTTGA AGACTAGGC AACCTTAGGA      1200

ACGAAGGACG GAGATTTTGT GACGATC                                         1227
```

(2) INFORMATION FOR SEQ ID NO:36:

(i) SEQUENCE CHARACTERISTICS:
        (A) LENGTH: 181 base pairs
        (B) TYPE: nucleic acid
        (C) STRANDEDNESS: single
        (D) TOPOLOGY: linear (xi) SEQUENCE DESCRIPTION: SEQ ID NO:36:

```
GCGGTGTCGG CGGATCCGGC GGGTGGTTGA ACGGCAACGG CGGGGCCGGC GGGGCCGGCG        60

GGACCGGCGC TAACGGTGGT GCCGGCGGCA ACGCCTGGTT GTTCGGGGCC GGCGGGTCCG       120
```

GCGGNGCCGG CACCAATGGT GGNGTCGGCG GGTCCGGCGG ATTTGTCTAC GGCAACGGCG    180

G    181

(2) INFORMATION FOR SEQ ID NO:37:

(i) SEQUENCE CHARACTERISTICS:
        (A) LENGTH: 290 base pairs
        (B) TYPE: nucleic acid
        (C) STRANDEDNESS: single
        (D) TOPOLOGY: linear (xi) SEQUENCE DESCRIPTION: SEQ ID NO:37:

GCGGTGTCGG CGGATCCGGC GGGTGGTTGA ACGGCAACGG CGGTGTCGGC GGCCGGGGCG    60

GCGACGGCGT CTTTGCCGGT GCCGGCGGCC AGGGCGGCCT CGGTGGGCAG GCGGCAATG    120

GCGGCGGCTC CACCGGCGGC AACGGCGGTC TTGGCGGCGC GGGCGGTGGC GGAGGCAACG    180

CCCCGGACGG CGGCTTCGGT GGCAACGGCG GTAAGGGTGG CCAGGGCGGN ATTGGCGGCG    240

GCACTCAGAG CGCGACCGGC CTCGGNGGTG ACGGCGGTGA CGGCGGTGAC    290

(2) INFORMATION FOR SEQ ID NO:38:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:38:

GATCCAGTGG CATGGNGGGT GTCAGTGGAA GCAT    34

(2) INFORMATION FOR SEQ ID NO:39:

(i) SEQUENCE CHARACTERISTICS:
        (A) LENGTH: 155 base pairs
        (B) TYPE: nucleic acid
        (C) STRANDEDNESS: single
        (D) TOPOLOGY: linear (xi) SEQUENCE DESCRIPTION: SEQ ID NO:39:

GATCGCTGCT CGTCCCCCCC TTGCCGCCGA CGCCACCGGT CCCACCGTTA CCGAACAAGC    60

TGGCGTGGTC GCCAGCACCC CCGGCACCGC CGACGCCGGA GTCGAACAAT GGCACCGTCG    120

TATCCCCACC ATTGCCGCCG GNCCCACCGG CACCG    155

(2) INFORMATION FOR SEQ ID NO:40:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (xi) SEQUENCE DESCRIPTION: SEQ ID NO:40:

ATGGCGTTCA CGGGGCGCCG GGGACCGGGC AGCCCGGNGG GGCCGGGGGG TGG    53

(2) INFORMATION FOR SEQ ID NO:41:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (xi) SEQUENCE DESCRIPTION: SEQ ID NO:41:

-continued

```
GATCCACCGC GGGTGCAGAC GGTGCCCGCG GCGCCACCCC GACCAGCGGC GGCAACGGCG      60

GCACCGGCGG CAACGGCGCG AACGCCACCG TCGTCGGNGG GGCCGGCGGG GCCGGCGGCA     120

AGGGCGGCAA CG                                                        132
```

(2) INFORMATION FOR SEQ ID NO:42:

(i) SEQUENCE CHARACTERISTICS:
  (A) LENGTH: 132 base pairs
  (B) TYPE: nucleic acid
  (C) STRANDEDNESS: single
  (D) TOPOLOGY: linear (xi) SEQUENCE DESCRIPTION: SEQ ID NO:42:

```
GATCGGCGGC CGGNACGGNC GGGGACGGCG GCAAGGGCGG NAACGGGGGC GCCGNAGCCA      60

CCNGCCAAGA ATCCTCCGNG TCCNCCAATG GCGCGAATGG CGGACAGGGC GGCAACGGCG     120

GCANCGGCGG CA                                                        132
```

(2) INFORMATION FOR SEQ ID NO:43:

(i) SEQUENCE CHARACTERISTICS:
  (A) LENGTH: 702 base pairs
  (B) TYPE: nucleic acid
  (C) STRANDEDNESS: single
  (D) TOPOLOGY: linear (xi) SEQUENCE DESCRIPTION: SEQ ID NO:43:

```
CGGCACGAGG ATCGGTACCC CGCGGCATCG GCAGCTGCCG ATTCGCCGGG TTTCCCCACC      60

CGAGGAAAGC CGCTACCAGA TGGCGCTGCC GAAGTAGGGC GATCCGTTCG CGATGCCGGC     120

ATGAACGGGC GGCATCAAAT TAGTGCAGGA ACCTTTCAGT TTAGCGACGA TAATGGCTAT     180

AGCACTAAGG AGGATGATCC GATATGACGC AGTCGCAGAC CGTGACGGTG GATCAGCAAG     240

AGATTTTGAA CAGGGCCAAC GAGGTGGAGG CCCCGATGGC GGACCCACCG ACTGATGTCC     300

CCATCACACC GTGCGAACTC ACGGNGGNTA AAAACGCCGC CAACAGNTG GTNTTGTCCG      360

CCGACAACAT GCGGGAATAC CTGGCGGCCG GTGCCAAAGA GCGGCAGCGT CTGGCGACCT     420

CGCTGCGCAA CGCGGCCAAG GNGTATGGCG AGGTTGATGA GGAGGCTGCG ACCGCGCTGG     480

ACAACGACGG CGAAGGAACT GTGCAGGCAG AATCGGCCGG GGCCGTCGGA GGGGACAGTT     540

CGGCCGAACT AACCGATACG CCGAGGGTGG CCACGGCCGG TGAACCCAAC TTCATGGATC     600

TCAAAGAAGC GGCAAGGAAG CTCGAAACGG GCGACCAAGG CGCATCGCTC GCGCACTGNG     660

GGGATGGGTG GAACACTTNC ACCCTGACGC TGCAAGGCGA CG                       702
```

(2) INFORMATION FOR SEQ ID NO:44:

(i) SEQUENCE CHARACTERISTICS:
  (A) LENGTH: 298 base pairs
  (B) TYPE: nucleic acid
  (C) STRANDEDNESS: single
  (D) TOPOLOGY: linear (xi) SEQUENCE DESCRIPTION: SEQ ID NO:44:

```
GAAGCCGCAG CGCTGTCGGG CGACGTGGCG GTCAAAGCGG CATCGCTCGG TGGCGGTGGA      60

GCGGCGGGG TGCCGTCGGC GCCGTTGGGA TCCGCGATCG GGGCGCCGA ATCGGTGCGG      120

CCCGCTGGCG CTGGTGACAT TGCCGGCTTA GGCCAGGGAA GGGCCGGCGG CGGCGCCGCG     180

CTGGGCGGCG GTGGCATGGG AATGCCGATG GGTGCCGCGC ATCAGGGACA AGGGGGCGCC     240

AAGTCCAAGG GTTCTCAGCA GGAAGACGAG GCGCTCTACA CCGAGGATCC TCGTGCCG       298
```

(2) INFORMATION FOR SEQ ID NO:45:

(i) SEQUENCE CHARACTERISTICS:
        (A) LENGTH: 1058 base pairs
        (B) TYPE: nucleic acid
        (C) STRANDEDNESS: single
        (D) TOPOLOGY: linear (xi) SEQUENCE DESCRIPTION: SEQ ID NO:45:

```
CGGCACGAGG ATCGAATCGC GTCGCCGGGA GCACAGCGTC GCACTGCACC AGTGGAGGAG      60
CCATGACCTA CTCGCCGGGT AACCCCGGAT ACCCGCAAGC GCAGCCCGCA GGCTCCTACG     120
GAGGCGTCAC ACCCTCGTTC GCCCACGCCG ATGAGGGTGC GAGCAAGCTA CCGATGTACC     180
TGAACATCGC GGTGGCAGTG CTCGGTCTGG CTGCGTACTT CGCCAGCTTC GGCCCAATGT     240
TCACCCTCAG TACCGAACTC GGGGGGGGTG ATGGCGCAGT GTCCGGTGAC ACTGGGCTGC     300
CGGTCGGGGT GGCTCTGCTG GCTGCGCTGC TTGCCGGGGT GGTTCTGGTG CCTAAGGCCA     360
AGAGCCATGT GACGGTAGTT GCGGTGCTCG GGGTACTCGG CGTATTTCTG ATGGTCTCGG     420
CGACGTTTAA CAAGCCCAGC GCCTATTCGA CCGGTTGGGC ATTGTGGGTT GTGTTGGCTT     480
TCATCGTGTT CCAGGCGGTT GCGGCAGTCC TGGCGCTCTT GGTGGAGACC GGCGCTATCA     540
CCGCGCCGGC GCCGCGGCCC AAGTTCGACC CGTATGGACA GTACGGGCGG TACGGGCAGT     600
ACGGGCAGTA CGGGGTGCAG CCGGGTGGGT ACTACGGTCA GCAGGGTGCT CAGCAGGCCG     660
CGGGACTGCA GTCGCCCGGC CCGCAGCAGT CTCCGCAGCC TCCCGGATAT GGGTCGCAGT     720
ACGGCGGCTA TTCGTCCAGT CCGAGCCAAT CGGGCAGTGG ATACACTGCT CAGCCCCCGG     780
CCCAGCCGCC GGCGCAGTCC GGGTCGCAAC AATCGCACCA GGGCCCATCC ACGCCACCTA     840
CCGGCTTTCC GAGCTTCAGC CCACCACCAC CGGTCAGTGC CGGGACGGGG TCGCAGGCTG     900
GTTCGGCTCC AGTCAACTAT TCAAACCCCA GCGGGGGCGA GCAGTCGTCG TCCCCCGGGG     960
GGGCGCCGGT CTAACCGGGC GTTCCCGCGT CCGGTCGCGC GTGTGCGCGA AGAGTGAACA    1020
GGGTGTCAGC AAGCGCGGAC GATCCTCGTG CCGAATTC                           1058
```

(2) INFORMATION FOR SEQ ID NO:46:

(i) SEQUENCE CHARACTERISTICS:
        (A) LENGTH: 327 base pairs
        (B) TYPE: nucleic acid
        (C) STRANDEDNESS: single
        (D) TOPOLOGY: linear (xi) SEQUENCE DESCRIPTION: SEQ ID NO:46:

```
CGGCACGAGA GACCGATGCC GCTACCCTCG CGCAGGAGGC AGGTAATTTC GAGCGGATCT      60
CCGGCGACCT GAAAACCCAG ATCGACCAGG TGGAGTCGAC GGCAGGTTCG TTGCAGGGCC     120
AGTGGCGCGG CGCGGCGGGG ACGGCCGCCC AGGCCGCGGT GGTGCGCTTC CAAGAAGCAG     180
CCAATAAGCA GAAGCAGGAA CTCGACGAGA TCTCGACGAA TATTCGTCAG GCCGGCGTCC     240
AATACTCGAG GGCCGACGAG GAGCAGCAGC AGGCGCTGTC CTCGCAAATG GGCTTCTGAC     300
CCGCTAATAC GAAAAGAAAC GGAGCAA                                         327
```

(2) INFORMATION FOR SEQ ID NO:47:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (xi) SEQUENCE DESCRIPTION: SEQ ID NO:47:

CGGTCGCGAT GATGGCGTTG TCGAACGTGA CCGATTCTGT ACCGCCGTCG TTGAGATCAA      60

CCAACAACGT GTTGGCGTCG GCAAATGTGC CGNACCCGTG GATCTCGGTG ATCTTGTTCT     120

TCTTCATCAG GAAGTGCACA CCGGCCACCC TGCCCTCGGN TACCTTTCGG                170

(2) INFORMATION FOR SEQ ID NO:48:

(i) SEQUENCE CHARACTERISTICS:
        (A) LENGTH: 127 base pairs
        (B) TYPE: nucleic acid
        (C) STRANDEDNESS: single
        (D) TOPOLOGY: linear (xi) SEQUENCE DESCRIPTION: SEQ ID NO:48:

GATCCGGCGG CACGGGGGGT GCCGGCGGCA GCACCGCTGG CGCTGGCGGC AACGGCGGGG      60

CCGGGGGTGG CGGCGGAACC GGTGGGTTGC TCTTCGGCAA CGGCGGTGCC GGCGGGCACG     120

GGGCCGT                                                              127

(2) INFORMATION FOR SEQ ID NO:49:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:49:

CGGCGGCAAG GCGGCACCG CCGGCAACGG GAGCGGCGCG GCCGGCGGCA ACGGCGGCAA       60

CGGCGGCTCC GGCCTCAACG G                                               81

(2) INFORMATION FOR SEQ ID NO:50:

(i) SEQUENCE CHARACTERISTICS:
        (A) LENGTH: 149 base pairs
        (B) TYPE: nucleic acid
        (C) STRANDEDNESS: single
        (D) TOPOLOGY: linear (xi) SEQUENCE DESCRIPTION: SEQ ID NO:50:

GATCAGGGCT GGCCGGCTCC GGCCAGAAGG GCGGTAACGG AGGAGCTGCC GGATTGTTTG      60

GCAACGGCGG GGCCGGNGGT GCCGGCGCGT CCAACCAAGC CGGTAACGGC GGNGCCGGCG     120

GAAACGGTGG TGCCGGTGGG CTGATCTGG                                      149

(2) INFORMATION FOR SEQ ID NO:51:

(i) SEQUENCE CHARACTERISTICS:
        (A) LENGTH: 355 base pairs
        (B) TYPE: nucleic acid
        (C) STRANDEDNESS: single
        (D) TOPOLOGY: linear (xi) SEQUENCE DESCRIPTION: SEQ ID NO:51:

CGGCACGAGA TCACACCTAC CGAGTGATCG AGATCGTCGG GACCTCGCCC GACGGTGTCG      60

ACGCGGNAAT CCAGGGCGGT CTGGCCCGAG CTGCGCAGAC CATGCGCGCG CTGGACTGGT     120

TCGAAGTACA GTCAATTCGA GGCCACCTGG TCGACGGAGC GGTCGCGCAC TTCCAGGTGA     180

CTATGAAAGT CGGCTTCCGC CTGGAGGATT CCTGAACCTT CAAGCGCGGC CGATAACTGA     240

GGTGCATCAT TAAGCGACTT TTCCAGAACA TCCTGACGCG CTCGAAACGC GGTTCAGCCG     300

ACGGTGGCTC CGCCGAGGCG CTGCCTCCAA AATCCCTGCG ACAATTCGTC GGCGG          355

(2) INFORMATION FOR SEQ ID NO:52:

(i) SEQUENCE CHARACTERISTICS:
        (A) LENGTH: 999 base pairs
        (B) TYPE: nucleic acid
        (C) STRANDEDNESS: single
        (D) TOPOLOGY: linear (xi) SEQUENCE DESCRIPTION: SEQ ID NO:52:

```
ATGCATCACC ATCACCATCA CATGCATCAG GTGGACCCCA ACTTGACACG TCGCAAGGGA      60
CGATTGGCGG CACTGGCTAT CGCGGCGATG GCCAGCGCCA GCCTGGTGAC CGTTGCGGTG     120
CCCGCGACCG CCAACGCCGA TCCGGAGCCA GCGCCCCCGG TACCCACAAC GGCCGCCTCG     180
CCGCCGTCGA CCGCTGCAGC GCCACCCGCA CCGGCGACAC CTGTTGCCCC CCCACCACCG     240
GCCGCCGCCA ACACGCCGAA TGCCCAGCCG GGCGATCCCA ACGCAGCACC TCCGCCGGCC     300
GACCCGAACG CACCGCCGCC ACCTGTCATT GCCCCAAACG CACCCCAACC TGTCCGGATC     360
GACAACCCGG TTGGAGGATT CAGCTTCGCG CTGCCTGCTG GCTGGGTGGA GTCTGACGCC     420
GCCCACTTCG ACTACGGTTC AGCACTCCTC AGCAAAACCA CCGGGGACCC GCCATTTCCC     480
GGACAGCCGC CGCCGGTGGC CAATGACACC CGTATCGTGC TCGGCCGGCT AGACCAAAAG     540
CTTTACGCCA GCGCCGAAGC CACCGACTCC AAGGCCGCGG CCCGGTTGGG CTCGGACATG     600
GGTGAGTTCT ATATGCCCTA CCCGGGCACC CGGATCAACC AGGAAACCGT CTCGCTCGAC     660
GCCAACGGGG TGTCTGGAAG CGCGTCGTAT TACGAAGTCA AGTTCAGCGA TCCGAGTAAG     720
CCGAACGGCC AGATCTGGAC GGGCGTAATC GGCTCGCCCG CGGCGAACGC ACCGGACGCC     780
GGGCCCCCTC AGCGCTGGTT TGTGGTATGG CTCGGGACCC CAACAACCC GGTGGACAAG     840
GGCGCGGCCA AGGCGCTGGC CGAATCGATC CGGCCTTTGG TCGCCCCGCC GCCGGCGCCG     900
GCACCGGCTC CTGCAGAGCC CGCTCCGGCG CCGGCGCCGG CCGGGGAAGT CGCTCCTACC     960
CCGACGACAC CGACACCGCA GCGGACCTTA CCGGCCTGA                            999
```

(2) INFORMATION FOR SEQ ID NO:53:

(i) SEQUENCE CHARACTERISTICS:
        (A) LENGTH: 332 amino acids
        (B) TYPE: amino acid
        (C) STRANDEDNESS: single
        (D) TOPOLOGY: linear (xi) SEQUENCE DESCRIPTION: SEQ ID NO:53:

```
Met His His His His His His Met His Gln Val Asp Pro Asn Leu Thr
1               5                   10                  15

Arg Arg Lys Gly Arg Leu Ala Ala Leu Ala Ile Ala Ala Met Ala Ser
            20                  25                  30

Ala Ser Leu Val Thr Val Ala Val Pro Ala Thr Ala Asn Ala Asp Pro
        35                  40                  45

Glu Pro Ala Pro Pro Val Pro Thr Thr Ala Ala Ser Pro Pro Ser Thr
    50                  55                  60

Ala Ala Ala Pro Pro Ala Pro Ala Thr Pro Val Ala Pro Pro Pro
65                  70                  75                  80

Ala Ala Ala Asn Thr Pro Asn Ala Gln Pro Gly Asp Pro Asn Ala Ala
                85                  90                  95

Pro Pro Pro Ala Asp Pro Asn Ala Pro Pro Pro Val Ile Ala Pro
            100                 105                 110

Asn Ala Pro Gln Pro Val Arg Ile Asp Asn Pro Val Gly Gly Phe Ser
```

```
                115                 120                 125
Phe Ala Leu Pro Ala Gly Trp Val Glu Ser Asp Ala His Phe Asp
        130                 135                 140

Tyr Gly Ser Ala Leu Leu Ser Lys Thr Thr Gly Asp Pro Pro Phe Pro
145                 150                 155                 160

Gly Gln Pro Pro Val Ala Asn Asp Thr Arg Ile Val Leu Gly Arg
                165                 170                 175

Leu Asp Gln Lys Leu Tyr Ala Ser Ala Glu Ala Thr Asp Ser Lys Ala
                180                 185                 190

Ala Ala Arg Leu Gly Ser Asp Met Gly Glu Phe Tyr Met Pro Tyr Pro
            195                 200                 205

Gly Thr Arg Ile Asn Gln Glu Thr Val Ser Leu Asp Ala Asn Gly Val
            210                 215                 220

Ser Gly Ser Ala Ser Tyr Tyr Glu Val Lys Phe Ser Asp Pro Ser Lys
225                 230                 235                 240

Pro Asn Gly Gln Ile Trp Thr Gly Val Ile Gly Ser Pro Ala Ala Asn
                245                 250                 255

Ala Pro Asp Ala Gly Pro Pro Gln Arg Trp Phe Val Val Trp Leu Gly
            260                 265                 270

Thr Ala Asn Asn Pro Val Asp Lys Gly Ala Ala Lys Ala Leu Ala Glu
            275                 280                 285

Ser Ile Arg Pro Leu Val Ala Pro Pro Ala Pro Ala Pro Ala Pro
290                 295                 300

Ala Glu Pro Ala Pro Ala Pro Ala Gly Glu Val Ala Pro Thr
305                 310                 315                 320

Pro Thr Thr Pro Thr Pro Gln Arg Thr Leu Pro Ala
                325                 330
```

(2) INFORMATION FOR SEQ ID NO:54:

(i) SEQUENCE CHARACTERISTICS:
        (A) LENGTH: 20 amino acids
        (B) TYPE: amino acid
        (C) STRANDEDNESS:
        (D) TOPOLOGY: linear (xi) SEQUENCE DESCRIPTION: SEQ ID NO:54:

```
Asp Pro Val Asp Ala Val Ile Asn Thr Thr Xaa Asn Tyr Gly Gln Val
1               5                   10                  15

Val Ala Ala Leu
            20
```

(2) INFORMATION FOR SEQ ID NO:55:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:55:

```
Ala Val Glu Ser Gly Met Leu Ala Leu Gly Thr Pro Ala Pro Ser
1               5                   10                  15
```

(2) INFORMATION FOR SEQ ID NO:56:

(i) SEQUENCE CHARACTERISTICS:
        (A) LENGTH: 19 amino acids
        (B) TYPE: amino acid
        (C) STRANDEDNESS:

(D) TOPOLOGY: linear (xi) SEQUENCE DESCRIPTION: SEQ ID NO:56:

Ala Ala Met Lys Pro Arg Thr Gly Asp Gly Pro Leu Glu Ala Ala Lys
1               5                  10                  15

Glu Gly Arg (2) INFORMATION FOR SEQ ID NO:57:

(i) SEQUENCE CHARACTERISTICS:
          (A) LENGTH: 15 amino acids
          (B) TYPE: amino acid
          (C) STRANDEDNESS:
          (D) TOPOLOGY: linear (xi) SEQUENCE DESCRIPTION: SEQ ID NO:57:

Tyr Tyr Trp Cys Pro Gly Gln Pro Phe Asp Pro Ala Trp Gly Pro
1               5                  10                  15

(2) INFORMATION FOR SEQ ID NO:58:

(i) SEQUENCE CHARACTERISTICS:
          (A) LENGTH: 14 amino acids
          (B) TYPE: amino acid
          (C) STRANDEDNESS:
          (D) TOPOLOGY: linear (xi) SEQUENCE DESCRIPTION: SEQ ID NO:58:

Asp Ile Gly Ser Glu Ser Thr Glu Asp Gln Gln Xaa Ala Val
1               5                  10

(2) INFORMATION FOR SEQ ID NO:59:

(i) SEQUENCE CHARACTERISTICS:
          (A) LENGTH: 13 amino acids
          (B) TYPE: amino acid
          (C) STRANDEDNESS:
          (D) TOPOLOGY: linear (xi) SEQUENCE DESCRIPTION: SEQ ID NO:59:

Ala Glu Glu Ser Ile Ser Thr Xaa Glu Xaa Ile Val Pro
1               5                  10

(2) INFORMATION FOR SEQ ID NO:60:

(i) SEQUENCE CHARACTERISTICS:
          (A) LENGTH: 17 amino acids
          (B) TYPE: amino acid
          (C) STRANDEDNESS:
          (D) TOPOLOGY: linear (xi) SEQUENCE DESCRIPTION: SEQ ID NO:60:

Asp Pro Glu Pro Ala Pro Pro Val Pro Thr Ala Ala Ala Ala Pro Pro
1               5                  10                  15

Ala (2) INFORMATION FOR SEQ ID NO:61:

(i) SEQUENCE CHARACTERISTICS:
          (A) LENGTH: 15 amino acids
          (B) TYPE: amino acid
          (C) STRANDEDNESS:
          (D) TOPOLOGY: linear (xi) SEQUENCE DESCRIPTION: SEQ ID NO:61:

Ala Pro Lys Thr Tyr Xaa Glu Glu Leu Lys Gly Thr Asp Thr Gly (2) INFORMATION FOR SEQ ID NO:62:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:62:

```
Asp Pro Ala Ser Ala Pro Asp Val Pro Thr Ala Ala Gln Gln Thr Ser
 1               5                  10                  15
Leu Leu Asn Asn Leu Ala Asp Pro Asp Val Ser Phe Ala Asp
            20                  25                  30
```

(2) INFORMATION FOR SEQ ID NO:63:

(i) SEQUENCE CHARACTERISTICS:
        (A) LENGTH: 24 amino acids
        (B) TYPE: amino acid
        (C) STRANDEDNESS:
        (D) TOPOLOGY: linear (xi) SEQUENCE DESCRIPTION: SEQ ID NO:63:

```
Gly Cys Gly Asp Arg Ser Gly Gly Asn Leu Asp Gln Ile Arg Leu Arg
 1               5                  10                  15
Arg Asp Arg Ser Gly Gly Asn Leu
            20
```

(2) INFORMATION FOR SEQ ID NO:64:

(i) SEQUENCE CHARACTERISTICS:
        (A) LENGTH: 187 amino acids
        (B) TYPE: amino acid
        (C) STRANDEDNESS: single
        (D) TOPOLOGY: linear (xi) SEQUENCE DESCRIPTION: SEQ ID NO:64:

```
Thr Gly Ser Leu Asn Gln Thr His Asn Arg Arg Ala Asn Glu Arg Lys
 1               5                  10                  15
Asn Thr Thr Met Lys Met Val Lys Ser Ile Ala Ala Gly Leu Thr Ala
            20                  25                  30
Ala Ala Ala Ile Gly Ala Ala Ala Gly Val Thr Ser Ile Met Ala
            35                  40                  45
Gly Gly Pro Val Val Tyr Gln Met Gln Pro Val Val Phe Gly Ala Pro
    50                  55                  60
Leu Pro Leu Asp Pro Ala Ser Ala Pro Asp Val Pro Thr Ala Ala Gln
65                  70                  75                  80
Leu Thr Ser Leu Leu Asn Ser Leu Ala Asp Pro Asn Val Ser Phe Ala
            85                  90                  95
Asn Lys Gly Ser Leu Val Glu Gly Ile Gly Gly Thr Glu Ala Arg
            100                 105                 110
Ile Ala Asp His Lys Leu Lys Ala Ala Glu His Gly Asp Leu Pro
            115                 120                 125
Leu Ser Phe Ser Val Thr Asn Ile Gln Pro Ala Ala Gly Ser Ala
            130                 135                 140
Thr Ala Asp Val Ser Val Ser Gly Pro Lys Leu Ser Ser Pro Val Thr
145                 150                 155                 160
Gln Asn Val Thr Phe Val Asn Gln Gly Gly Trp Met Leu Ser Arg Ala
            165                 170                 175
```

Ser Ala Met Glu Leu Leu Gln Ala Ala Gly Xaa
        180                 185

(2) INFORMATION FOR SEQ ID NO:65:

(i) SEQUENCE CHARACTERISTICS:
        (A) LENGTH: 148 amino acids
        (B) TYPE: amino acid
        (C) STRANDEDNESS: single
        (D) TOPOLOGY: linear (xi) SEQUENCE DESCRIPTION: SEQ ID NO:65:

Asp Glu Val Thr Val Glu Thr Thr Ser Val Phe Arg Ala Asp Phe Leu
1               5                   10                  15

Ser Glu Leu Asp Ala Pro Ala Gln Ala Gly Thr Glu Ser Ala Val Ser
            20                  25                  30

Gly Val Glu Gly Leu Pro Pro Gly Ser Ala Leu Leu Val Val Lys Arg
        35                  40                  45

Gly Pro Asn Ala Gly Ser Arg Phe Leu Leu Asp Gln Ala Ile Thr Ser
    50                  55                  60

Ala Gly Arg His Pro Asp Ser Asp Ile Phe Leu Asp Asp Val Thr Val
65                  70                  75                  80

Ser Arg Arg His Ala Glu Phe Arg Leu Glu Asn Asn Glu Phe Asn Val
                85                  90                  95

Val Asp Val Gly Ser Leu Asn Gly Thr Tyr Val Asn Arg Glu Pro Val
            100                 105                 110

Asp Ser Ala Val Leu Ala Asn Gly Asp Glu Val Gln Ile Gly Lys Leu
        115                 120                 125

Arg Leu Val Phe Leu Thr Gly Pro Lys Gln Gly Glu Asp Asp Gly Ser
    130                 135                 140

Thr Gly Gly Pro
145

(2) INFORMATION FOR SEQ ID NO:66:

(i) SEQUENCE CHARACTERISTICS:
        (A) LENGTH: 230 amino acids
        (B) TYPE: amino acid
        (C) STRANDEDNESS: single
        (D) TOPOLOGY: linear (xi) SEQUENCE DESCRIPTION: SEQ ID NO:66:

Thr Ser Asn Arg Pro Ala Arg Arg Gly Arg Arg Ala Pro Arg Asp Thr
1               5                   10                  15

Gly Pro Asp Arg Ser Ala Ser Leu Ser Leu Val Arg His Arg Arg Gln
            20                  25                  30

Gln Arg Asp Ala Leu Cys Leu Ser Ser Thr Gln Ile Ser Arg Gln Ser
        35                  40                  45

Asn Leu Pro Pro Ala Ala Gly Gly Ala Ala Asn Tyr Ser Arg Arg Asn
    50                  55                  60

Phe Asp Val Arg Ile Lys Ile Phe Met Leu Val Thr Ala Val Val Leu
65                  70                  75                  80

Leu Cys Cys Ser Gly Val Ala Thr Ala Ala Pro Lys Thr Tyr Cys Glu
                85                  90                  95

Glu Leu Lys Gly Thr Asp Thr Gly Gln Ala Cys Gln Ile Gln Met Ser
            100                 105                 110

Asp Pro Ala Tyr Asn Ile Asn Ile Ser Leu Pro Ser Tyr Tyr Pro Asp
        115                 120                 125

```
Gln Lys Ser Leu Glu Asn Tyr Ile Ala Gln Thr Arg Asp Lys Phe Leu
    130                 135                 140

Ser Ala Ala Thr Ser Ser Thr Pro Arg Glu Ala Pro Tyr Glu Leu Asn
145                 150                 155                 160

Ile Thr Ser Ala Thr Tyr Gln Ser Ala Ile Pro Pro Arg Gly Thr Gln
                165                 170                 175

Ala Val Val Leu Xaa Val Tyr His Asn Ala Gly Thr His Pro Thr
                180                 185                 190

Thr Thr Tyr Lys Ala Phe Asp Trp Asp Gln Ala Tyr Arg Lys Pro Ile
        195                 200                 205

Thr Tyr Asp Thr Leu Trp Gln Ala Asp Thr Asp Pro Leu Pro Val Val
    210                 215                 220

Phe Pro Ile Val Ala Arg
225             230

(2) INFORMATION FOR SEQ ID NO:67:

(i) SEQUENCE CHARACTERISTICS:
        (A) LENGTH: 132 amino acids
        (B) TYPE: amino acid
        (C) STRANDEDNESS: single
        (D) TOPOLOGY: linear (xi) SEQUENCE DESCRIPTION: SEQ ID NO:67:

Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile Arg Ser
                20                  25                  30

Gly Gly Gly Ser Pro Thr Val His Ile Gly Pro Thr Ala Phe Leu Gly
            35                  40                  45

Leu Gly Val Val Asp Asn Asn Gly Asn Gly Ala Arg Val Gln Arg Val
        50                  55                  60

Val Gly Ser Ala Pro Ala Ala Ser Leu Gly Ile Ser Thr Gly Asp Val
65                  70                  75                  80

Ile Thr Ala Val Asp Gly Ala Pro Ile Asn Ser Ala Thr Ala Met Ala
                85                  90                  95

Asp Ala Leu Asn Gly His His Pro Gly Asp Val Ile Ser Val Asn Trp
                100                 105                 110

Gln Thr Lys Ser Gly Gly Thr Arg Thr Gly Asn Val Thr Leu Ala Glu
            115                 120                 125

Gly Pro Pro Ala
        130

(2) INFORMATION FOR SEQ ID NO:68:

(i) SEQUENCE CHARACTERISTICS:
        (A) LENGTH: 100 amino acids
        (B) TYPE: amino acid
        (C) STRANDEDNESS: single
        (D) TOPOLOGY: linear (xi) SEQUENCE DESCRIPTION: SEQ ID NO:68:

Val Pro Leu Arg Ser Pro Ser Met Ser Pro Ser Lys Cys Leu Ala Ala
1               5                   10                  15

Ala Gln Arg Asn Pro Val Ile Arg Arg Arg Arg Leu Ser Asn Pro Pro
                20                  25                  30

Pro Arg Lys Tyr Arg Ser Met Pro Ser Pro Ala Thr Ala Ser Ala Gly
            35                  40                  45
```

```
Met Ala Arg Val Arg Arg Ala Ile Trp Arg Gly Pro Ala Thr Xaa
    50                  55                  60

Ser Ala Gly Met Ala Arg Val Arg Arg Trp Xaa Val Met Pro Xaa Val
65                  70                  75                  80

Ile Gln Ser Thr Xaa Ile Arg Xaa Xaa Gly Pro Phe Asp Asn Arg Gly
                85                  90                  95

Ser Glu Arg Lys
            100
```

(2) INFORMATION FOR SEQ ID NO:69:

(i) SEQUENCE CHARACTERISTICS:
        (A) LENGTH: 163 amino acids
        (B) TYPE: amino acid
        (C) STRANDEDNESS: single
        (D) TOPOLOGY: linear (xi) SEQUENCE DESCRIPTION: SEQ ID NO:69:

```
Met Thr Asp Asp Ile Leu Leu Ile Asp Thr Asp Glu Arg Val Arg Thr
1               5                   10                  15

Leu Thr Leu Asn Arg Pro Gln Ser Arg Asn Ala Leu Ser Ala Ala Leu
                20                  25                  30

Arg Asp Arg Phe Phe Ala Xaa Leu Xaa Asp Ala Glu Xaa Asp Asp
                35                  40                  45

Ile Asp Val Val Ile Leu Thr Gly Ala Asp Pro Val Phe Cys Ala Gly
    50                  55                  60

Leu Asp Leu Lys Val Ala Gly Arg Ala Asp Arg Ala Ala Gly His Leu
65                  70                  75                  80

Thr Ala Val Gly Gly His Asp Gln Ala Gly Asp Arg Arg Asp Gln Arg
                85                  90                  95

Arg Arg Gly His Arg Arg Ala Arg Thr Gly Ala Val Leu Arg His Pro
                100                 105                 110

Asp Arg Leu Arg Ala Arg Pro Leu Arg Arg His Pro Arg Pro Gly Gly
                115                 120                 125

Ala Ala Ala His Leu Gly Thr Gln Cys Val Leu Ala Ala Lys Gly Arg
                130                 135                 140

His Arg Xaa Gly Pro Val Asp Glu Pro Asp Arg Arg Leu Pro Val Arg
145                 150                 155                 160

Asp Arg Arg
```

(2) INFORMATION FOR SEQ ID NO:70:

(i) SEQUENCE CHARACTERISTICS:
        (A) LENGTH: 344 amino acids
        (B) TYPE: amino acid
        (C) STRANDEDNESS: single
        (D) TOPOLOGY: linear (xi) SEQUENCE DESCRIPTION: SEQ ID NO:70:

```
Met Lys Phe Val Asn His Ile Glu Pro Val Ala Pro Arg Arg Ala Gly
1               5                   10                  15

Gly Ala Val Ala Glu Val Tyr Ala Glu Ala Arg Arg Glu Phe Gly Arg
                20                  25                  30

Leu Pro Glu Pro Leu Ala Met Leu Ser Pro Asp Glu Gly Leu Leu Thr
                35                  40                  45

Ala Gly Trp Ala Thr Leu Arg Glu Thr Leu Leu Val Gly Gln Val Pro
    50                  55                  60
```

-continued

```
Arg Gly Arg Lys Glu Ala Val Ala Ala Val Ala Ala Ser Leu Arg
65              70                  75                  80

Cys Pro Trp Cys Val Asp Ala His Thr Thr Met Leu Tyr Ala Ala Gly
                85                  90                  95

Gln Thr Asp Thr Ala Ala Ala Ile Leu Ala Gly Thr Ala Pro Ala Ala
                100                 105                 110

Gly Asp Pro Asn Ala Pro Tyr Val Ala Trp Ala Ala Gly Thr Gly Thr
                115                 120                 125

Pro Ala Gly Pro Pro Ala Pro Phe Gly Pro Asp Val Ala Ala Glu Tyr
            130                 135                 140

Leu Gly Thr Ala Val Gln Phe His Phe Ile Ala Arg Leu Val Leu Val
145                 150                 155                 160

Leu Leu Asp Glu Thr Phe Leu Pro Gly Gly Pro Arg Ala Gln Gln Leu
                165                 170                 175

Met Arg Arg Ala Gly Gly Leu Val Phe Ala Arg Lys Val Arg Ala Glu
                180                 185                 190

His Arg Pro Gly Arg Ser Thr Arg Arg Leu Glu Pro Arg Thr Leu Pro
            195                 200                 205

Asp Asp Leu Ala Trp Ala Thr Pro Ser Glu Pro Ile Ala Thr Ala Phe
210                 215                 220

Ala Ala Leu Ser His His Leu Asp Thr Ala Pro His Leu Pro Pro Pro
225                 230                 235                 240

Thr Arg Gln Val Val Arg Arg Val Val Gly Ser Trp His Gly Glu Pro
                245                 250                 255

Met Pro Met Ser Ser Arg Trp Thr Asn Glu His Thr Ala Glu Leu Pro
                260                 265                 270

Ala Asp Leu His Ala Pro Thr Arg Leu Ala Leu Leu Thr Gly Leu Ala
            275                 280                 285

Pro His Gln Val Thr Asp Asp Val Ala Ala Ala Arg Ser Leu Leu
            290                 295                 300

Asp Thr Asp Ala Ala Leu Val Gly Ala Leu Ala Trp Ala Ala Phe Thr
305                 310                 315                 320

Ala Ala Arg Arg Ile Gly Thr Trp Ile Gly Ala Ala Ala Glu Gly Gln
                325                 330                 335

Val Ser Arg Gln Asn Pro Thr Gly
            340
```

(2) INFORMATION FOR SEQ ID NO:71:

(i) SEQUENCE CHARACTERISTICS:
        (A) LENGTH: 485 amino acids
        (B) TYPE: amino acid
        (C) STRANDEDNESS: single
        (D) TOPOLOGY: linear (xi) SEQUENCE DESCRIPTION: SEQ ID NO:71:

```
Asp Asp Pro Asp Met Pro Gly Thr Val Ala Lys Ala Val Ala Asp Ala
1               5                   10                  15

Leu Gly Arg Gly Ile Ala Pro Val Glu Asp Ile Gln Asp Cys Val Glu
            20                  25                  30

Ala Arg Leu Gly Glu Ala Gly Leu Asp Asp Val Ala Arg Val Tyr Ile
            35                  40                  45

Ile Tyr Arg Gln Arg Arg Ala Glu Leu Arg Thr Ala Lys Ala Leu Leu
            50                  55                  60

Gly Val Arg Asp Glu Leu Lys Leu Ser Leu Ala Ala Val Thr Val Leu
65                  70                  75                  80
```

-continued

```
Arg Glu Arg Tyr Leu Leu His Asp Glu Gln Gly Arg Pro Ala Glu Ser
                 85                  90                  95
Thr Gly Glu Leu Met Asp Arg Ser Ala Arg Cys Val Ala Ala Ala Glu
            100                 105                 110
Asp Gln Tyr Glu Pro Gly Ser Ser Arg Arg Trp Ala Glu Arg Phe Ala
        115                 120                 125
Thr Leu Leu Arg Asn Leu Glu Phe Leu Pro Asn Ser Pro Thr Leu Met
    130                 135                 140
Asn Ser Gly Thr Asp Leu Gly Leu Leu Ala Gly Cys Phe Val Leu Pro
145                 150                 155                 160
Ile Glu Asp Ser Leu Gln Ser Ile Phe Ala Thr Leu Gly Gln Ala Ala
                165                 170                 175
Glu Leu Gln Arg Ala Gly Gly Thr Gly Tyr Ala Phe Ser His Leu
            180                 185                 190
Arg Pro Ala Gly Asp Arg Val Ala Ser Thr Gly Gly Thr Ala Ser Gly
        195                 200                 205
Pro Val Ser Phe Leu Arg Leu Tyr Asp Ser Ala Ala Gly Val Val Ser
    210                 215                 220
Met Gly Gly Arg Arg Arg Gly Ala Cys Met Ala Val Leu Asp Val Ser
225                 230                 235                 240
His Pro Asp Ile Cys Asp Phe Val Thr Ala Lys Ala Glu Ser Pro Ser
                245                 250                 255
Glu Leu Pro His Phe Asn Leu Ser Val Gly Val Thr Asp Ala Phe Leu
            260                 265                 270
Arg Ala Val Glu Arg Asn Gly Leu His Arg Leu Val Asn Pro Arg Thr
        275                 280                 285
Gly Lys Ile Val Ala Arg Met Pro Ala Ala Glu Leu Phe Asp Ala Ile
    290                 295                 300
Cys Lys Ala Ala His Ala Gly Gly Asp Pro Gly Leu Val Phe Leu Asp
305                 310                 315                 320
Thr Ile Asn Arg Ala Asn Pro Val Pro Gly Arg Gly Arg Ile Glu Ala
                325                 330                 335
Thr Asn Pro Cys Gly Glu Val Pro Leu Leu Pro Tyr Glu Ser Cys Asn
            340                 345                 350
Leu Gly Ser Ile Asn Leu Ala Arg Met Leu Ala Asp Gly Arg Val Asp
        355                 360                 365
Trp Asp Arg Leu Glu Glu Val Ala Gly Val Ala Val Arg Phe Leu Asp
    370                 375                 380
Asp Val Ile Asp Val Ser Arg Tyr Pro Phe Pro Glu Leu Gly Glu Ala
385                 390                 395                 400
Ala Arg Ala Thr Arg Lys Ile Gly Leu Gly Val Met Gly Leu Ala Glu
                405                 410                 415
Leu Leu Ala Ala Leu Gly Ile Pro Tyr Asp Ser Glu Glu Ala Val Arg
            420                 425                 430
Leu Ala Thr Arg Leu Met Arg Arg Ile Gln Gln Ala Ala His Thr Ala
        435                 440                 445
Ser Arg Arg Leu Ala Glu Glu Arg Gly Ala Phe Pro Ala Phe Thr Asp
    450                 455                 460
Ser Arg Phe Ala Arg Ser Gly Pro Arg Arg Asn Ala Gln Val Thr Ser
465                 470                 475                 480
Val Ala Pro Thr Gly
                485
```

(2) INFORMATION FOR SEQ ID NO:72:

(i) SEQUENCE CHARACTERISTICS:
        (A) LENGTH: 267 amino acids
        (B) TYPE: amino acid
        (C) STRANDEDNESS: single
        (D) TOPOLOGY: linear (xi) SEQUENCE DESCRIPTION: SEQ ID NO:72:

```
Gly Val Ile Val Leu Asp Leu Glu Pro Arg Gly Pro Leu Pro Thr Glu
1               5                   10                  15

Ile Tyr Trp Arg Arg Gly Leu Ala Leu Gly Ile Ala Val Val Val
                20                  25                  30

Val Gly Ile Ala Val Ala Ile Val Ile Ala Phe Val Asp Ser Ser Ala
            35                  40                  45

Gly Ala Lys Pro Val Ser Ala Asp Lys Pro Ala Ser Ala Gln Ser His
    50                  55                  60

Pro Gly Ser Pro Ala Pro Gln Ala Pro Gln Pro Ala Gly Gln Thr Glu
65                  70                  75                  80

Gly Asn Ala Ala Ala Pro Pro Gln Gly Gln Asn Pro Glu Thr Pro
                85                  90                  95

Thr Pro Thr Ala Ala Val Gln Pro Pro Val Leu Lys Glu Gly Asp
                100                 105                 110

Asp Cys Pro Asp Ser Thr Leu Ala Val Lys Gly Leu Thr Asn Ala Pro
        115                 120                 125

Gln Tyr Tyr Val Gly Asp Gln Pro Lys Phe Thr Met Val Val Thr Asn
    130                 135                 140

Ile Gly Leu Val Ser Cys Lys Arg Asp Val Gly Ala Ala Val Leu Ala
145                 150                 155                 160

Ala Tyr Val Tyr Ser Leu Asp Asn Lys Arg Leu Trp Ser Asn Leu Asp
                165                 170                 175

Cys Ala Pro Ser Asn Glu Thr Leu Val Lys Thr Phe Ser Pro Gly Glu
                180                 185                 190

Gln Val Thr Thr Ala Val Thr Trp Thr Gly Met Gly Ser Ala Pro Arg
            195                 200                 205

Cys Pro Leu Pro Arg Pro Ala Ile Gly Pro Gly Thr Tyr Asn Leu Val
            210                 215                 220

Val Gln Leu Gly Asn Leu Arg Ser Leu Pro Val Pro Phe Ile Leu Asn
225                 230                 235                 240

Gln Pro Pro Pro Pro Gly Pro Val Pro Ala Pro Gly Pro Ala Gln
                245                 250                 255

Ala Pro Pro Pro Glu Ser Pro Ala Gln Gly Gly
                260                 265
```

(2) INFORMATION FOR SEQ ID NO:73:

(i) SEQUENCE CHARACTERISTICS:
        (A) LENGTH: 97 amino acids
        (B) TYPE: amino acid
        (C) STRANDEDNESS: single
        (D) TOPOLOGY: linear (xi) SEQUENCE DESCRIPTION: SEQ ID NO:73:

```
Leu Ile Ser Thr Gly Lys Ala Ser His Ala Ser Leu Gly Val Gln Val
1               5                   10                  15

Thr Asn Asp Lys Asp Thr Pro Gly Ala Lys Ile Val Glu Val Val Ala
                20                  25                  30
```

```
Gly Gly Ala Ala Ala Asn Ala Gly Val Pro Lys Gly Val Val Thr
        35                  40                  45

Lys Val Asp Asp Arg Pro Ile Asn Ser Ala Asp Ala Leu Val Ala Ala
    50                  55                  60

Val Arg Ser Lys Ala Pro Gly Ala Thr Val Ala Leu Thr Phe Gln Asp
65                  70                  75                  80

Pro Ser Gly Gly Ser Arg Thr Val Gln Val Thr Leu Gly Lys Ala Glu
                85                  90                  95

Gln
```

(2) INFORMATION FOR SEQ ID NO:74:

(i) SEQUENCE CHARACTERISTICS:
        (A) LENGTH: 364 amino acids
        (B) TYPE: amino acid
        (C) STRANDEDNESS: single
        (D) TOPOLOGY: linear (xi) SEQUENCE DESCRIPTION: SEQ ID NO:74:

```
Gly Ala Ala Val Ser Leu Leu Ala Ala Gly Thr Leu Val Leu Thr Ala
1               5                   10                  15

Cys Gly Gly Gly Thr Asn Ser Ser Ser Gly Ala Gly Gly Thr Ser
                20                  25                  30

Gly Ser Val His Cys Gly Gly Lys Lys Glu Leu His Ser Ser Gly Ser
            35                  40                  45

Thr Ala Gln Glu Asn Ala Met Glu Gln Phe Val Tyr Ala Tyr Val Arg
    50                  55                  60

Ser Cys Pro Gly Tyr Thr Leu Asp Tyr Asn Ala Asn Gly Ser Gly Ala
65                  70                  75                  80

Gly Val Thr Gln Phe Leu Asn Asn Glu Thr Asp Phe Ala Gly Ser Asp
                85                  90                  95

Val Pro Leu Asn Pro Ser Thr Gly Gln Pro Asp Arg Ser Ala Glu Arg
            100                 105                 110

Cys Gly Ser Pro Ala Trp Asp Leu Pro Thr Val Phe Gly Pro Ile Ala
            115                 120                 125

Ile Thr Tyr Asn Ile Lys Gly Val Ser Thr Leu Asn Leu Asp Gly Pro
    130                 135                 140

Thr Thr Ala Lys Ile Phe Asn Gly Thr Ile Thr Val Trp Asn Asp Pro
145                 150                 155                 160

Gln Ile Gln Ala Leu Asn Ser Gly Thr Asp Leu Pro Pro Thr Pro Ile
                165                 170                 175

Ser Val Ile Phe Arg Ser Asp Lys Ser Gly Thr Ser Asp Asn Phe Gln
            180                 185                 190

Lys Tyr Leu Asp Gly Val Ser Asn Gly Ala Trp Gly Lys Gly Ala Ser
        195                 200                 205

Glu Thr Phe Ser Gly Gly Val Gly Val Gly Ala Ser Gly Asn Asn Gly
    210                 215                 220

Thr Ser Ala Leu Leu Gln Thr Thr Asp Gly Ser Ile Thr Tyr Asn Glu
225                 230                 235                 240

Trp Ser Phe Ala Val Gly Lys Gln Leu Asn Met Ala Gln Ile Ile Thr
                245                 250                 255

Ser Ala Gly Pro Asp Pro Val Ala Ile Thr Thr Glu Ser Val Gly Lys
            260                 265                 270

Thr Ile Ala Gly Ala Lys Ile Met Gly Gln Gly Asn Asp Leu Val Leu
        275                 280                 285
```

```
Asp Thr Ser Ser Phe Tyr Arg Pro Thr Gln Pro Gly Ser Tyr Pro Ile
        290                 295                 300

Val Leu Ala Thr Tyr Glu Ile Val Cys Ser Lys Tyr Pro Asp Ala Thr
305                 310                 315                 320

Thr Gly Thr Ala Val Arg Ala Phe Met Gln Ala Ala Ile Gly Pro Gly
                    325                 330                 335

Gln Glu Gly Leu Asp Gln Tyr Gly Ser Ile Pro Leu Pro Lys Ser Phe
                340                 345                 350

Gln Ala Lys Leu Ala Ala Ala Val Asn Ala Ile Ser
            355                 360
```

(2) INFORMATION FOR SEQ ID NO:75:

(i) SEQUENCE CHARACTERISTICS:
        (A) LENGTH: 309 amino acids
        (B) TYPE: amino acid
        (C) STRANDEDNESS: single
        (D) TOPOLOGY: linear (xi) SEQUENCE DESCRIPTION: SEQ ID NO:75:

```
Gln Ala Ala Ala Gly Arg Ala Val Arg Arg Thr Gly His Ala Glu Asp
1               5                   10                  15

Gln Thr His Gln Asp Arg Leu His His Gly Cys Arg Arg Ala Ala Val
            20                  25                  30

Val Val Arg Gln Asp Arg Ala Ser Val Ser Ala Thr Ser Ala Arg Pro
        35                  40                  45

Pro Arg Arg His Pro Ala Gln Gly His Arg Arg Val Ala Pro Ser
    50                  55                  60

Gly Gly Arg Arg Arg Pro His Pro His His Val Gln Pro Asp Asp Arg
65                  70                  75                  80

Arg Asp Arg Pro Ala Leu Leu Asp Arg Thr Gln Pro Ala Glu His Pro
                85                  90                  95

Asp Pro His Arg Arg Gly Pro Ala Asp Pro Gly Arg Val Arg Gly Arg
                100                 105                 110

Gly Arg Leu Arg Arg Val Asp Asp Gly Arg Leu Gln Pro Asp Arg Asp
            115                 120                 125

Ala Asp His Gly Ala Pro Val Arg Gly Arg Gly Pro His Arg Gly Val
        130                 135                 140

Gln His Arg Gly Gly Pro Val Phe Val Arg Arg Val Pro Gly Val Arg
145                 150                 155                 160

Cys Ala His Arg Arg Gly His Arg Arg Val Ala Pro Gly Gln Gly
                165                 170                 175

Asp Val Leu Arg Ala Gly Leu Arg Val Glu Arg Leu Pro Val Ala
            180                 185                 190

Ala Val Glu Asn Leu His Arg Gly Ser Gln Arg Ala Asp Gly Arg Val
        195                 200                 205

Phe Arg Pro Ile Arg Arg Gly Ala Arg Leu Pro Ala Arg Ser Arg
210                 215                 220

Ala Gly Pro Gln Gly Arg Leu His Leu Asp Gly Ala Gly Pro Ser Pro
225                 230                 235                 240

Leu Pro Ala Arg Ala Gly Gln Gln Gln Pro Ser Ser Ala Gly Gly Arg
                245                 250                 255

Arg Ala Gly Gly Ala Glu Arg Ala Asp Pro Gly Gln Arg Gly Arg His
            260                 265                 270

His Gln Gly Gly His Asp Pro Gly Arg Gln Gly Ala Gln Arg Gly Thr
        275                 280                 285
```

```
Ala Gly Val Ala His Ala Ala Gly Pro Arg Ala Ala Val Arg
    290             295             300

Asn Arg Pro Arg Arg
305

(2) INFORMATION FOR SEQ ID NO:76:

(i) SEQUENCE CHARACTERISTICS:
        (A) LENGTH: 580 amino acids
        (B) TYPE: amino acid
        (C) STRANDEDNESS: single
        (D) TOPOLOGY: linear (xi) SEQUENCE DESCRIPTION: SEQ ID NO:76:

Ser Ala Val Trp Cys Leu Asn Gly Phe Thr Gly Arg His Arg His Gly
1               5                   10                  15

Arg Cys Arg Val Arg Ala Ser Gly Trp Arg Ser Ser Asn Arg Trp Cys
            20                  25                  30

Ser Thr Thr Ala Asp Cys Cys Ala Ser Lys Thr Pro Thr Gln Ala Ala
            35                  40                  45

Ser Pro Leu Glu Arg Arg Phe Thr Cys Cys Ser Pro Ala Val Gly Cys
    50                  55                  60

Arg Phe Arg Ser Phe Pro Val Arg Leu Ala Leu Gly Ala Arg Thr
65                  70                  75                  80

Ser Arg Thr Leu Gly Val Arg Arg Thr Leu Ser Gln Trp Asn Leu Ser
                85                  90                  95

Pro Arg Ala Gln Pro Ser Cys Ala Val Thr Val Glu Ser His Thr His
            100                 105                 110

Ala Ser Pro Arg Met Ala Lys Leu Ala Arg Val Val Gly Leu Val Gln
            115                 120                 125

Glu Glu Gln Pro Ser Asp Met Thr Asn His Pro Arg Tyr Ser Pro Pro
    130                 135                 140

Pro Gln Gln Pro Gly Thr Pro Gly Tyr Ala Gln Gly Gln Gln Thr
145                 150                 155                 160

Tyr Ser Gln Gln Phe Asp Trp Arg Tyr Pro Pro Ser Pro Pro Pro Gln
                165                 170                 175

Pro Thr Gln Tyr Arg Gln Pro Tyr Glu Ala Leu Gly Gly Thr Arg Pro
            180                 185                 190

Gly Leu Ile Pro Gly Val Ile Pro Thr Met Thr Pro Pro Gly Met
            195                 200                 205

Val Arg Gln Arg Pro Arg Ala Gly Met Leu Ala Ile Gly Ala Val Thr
    210                 215                 220

Ile Ala Val Val Ser Ala Gly Ile Gly Gly Ala Ala Ser Leu Val
225                 230                 235                 240

Gly Phe Asn Arg Ala Pro Ala Gly Pro Ser Gly Gly Pro Val Ala Ala
            245                 250                 255

Ser Ala Ala Pro Ser Ile Pro Ala Ala Asn Met Pro Pro Gly Ser Val
            260                 265                 270

Glu Gln Val Ala Ala Lys Val Val Pro Ser Val Val Met Leu Glu Thr
    275                 280                 285

Asp Leu Gly Arg Gln Ser Glu Glu Gly Ser Gly Ile Ile Leu Ser Ala
    290                 295                 300

Glu Gly Leu Ile Leu Thr Asn Asn His Val Ile Ala Ala Ala Lys
305                 310                 315                 320

Pro Pro Leu Gly Ser Pro Pro Pro Lys Thr Thr Val Thr Phe Ser Asp
```

```
                          325                 330                 335
Gly Arg Thr Ala Pro Phe Thr Val Val Gly Ala Asp Pro Thr Ser Asp
                    340                 345                 350
Ile Ala Val Val Arg Val Gln Gly Val Ser Gly Leu Thr Pro Ile Ser
                355                 360                 365
Leu Gly Ser Ser Asp Leu Arg Val Gly Gln Pro Val Leu Ala Ile
            370                 375                 380
Gly Ser Pro Leu Gly Leu Glu Gly Thr Val Thr Thr Gly Ile Val Ser
385                 390                 395                 400
Ala Leu Asn Arg Pro Val Ser Thr Thr Gly Glu Ala Gly Asn Gln Asn
                405                 410                 415
Thr Val Leu Asp Ala Ile Gln Thr Asp Ala Ala Ile Asn Pro Gly Asn
                420                 425                 430
Ser Gly Gly Ala Leu Val Asn Met Asn Ala Gln Leu Val Gly Val Asn
                435                 440                 445
Ser Ala Ile Ala Thr Leu Gly Ala Asp Ser Ala Asp Ala Gln Ser Gly
            450                 455                 460
Ser Ile Gly Leu Gly Phe Ala Ile Pro Val Asp Gln Ala Lys Arg Ile
465                 470                 475                 480
Ala Asp Glu Leu Ile Ser Thr Gly Lys Ala Ser His Ala Ser Leu Gly
                485                 490                 495
Val Gln Val Thr Asn Asp Lys Asp Thr Pro Gly Ala Lys Ile Val Glu
                500                 505                 510
Val Val Ala Gly Gly Ala Ala Asn Ala Gly Val Pro Lys Gly Val
                515                 520                 525
Val Val Thr Lys Val Asp Asp Arg Pro Ile Asn Ser Ala Asp Ala Leu
                530                 535                 540
Val Ala Ala Val Arg Ser Lys Ala Pro Gly Ala Thr Val Ala Leu Thr
545                 550                 555                 560
Phe Gln Asp Pro Ser Gly Gly Ser Arg Thr Val Gln Val Thr Leu Gly
                565                 570                 575
Lys Ala Glu Gln
            580

(2) INFORMATION FOR SEQ ID NO:77:

(i) SEQUENCE CHARACTERISTICS:
        (A) LENGTH: 233 amino acids
        (B) TYPE: amino acid
        (C) STRANDEDNESS: single
        (D) TOPOLOGY: linear (xi) SEQUENCE DESCRIPTION: SEQ ID NO:77:

Met Asn Asp Gly Lys Arg Ala Val Thr Ser Ala Val Leu Val Val Leu
1               5                   10                  15
Gly Ala Cys Leu Ala Leu Trp Leu Ser Gly Cys Ser Ser Pro Lys Pro
                20                  25                  30
Asp Ala Glu Glu Gln Gly Val Pro Val Ser Pro Thr Ala Ser Asp Pro
            35                  40                  45
Ala Leu Leu Ala Glu Ile Arg Gln Ser Leu Asp Ala Thr Lys Gly Leu
        50                  55                  60
Thr Ser Val His Val Ala Val Arg Thr Thr Gly Lys Val Asp Ser Leu
65              70                  75                  80
Leu Gly Ile Thr Ser Ala Asp Val Asp Val Arg Ala Asn Pro Leu Ala
                85                  90                  95
```

```
Ala Lys Gly Val Cys Thr Tyr Asn Asp Glu Gln Gly Val Pro Phe Arg
            100                 105                 110

Val Gln Gly Asp Asn Ile Ser Val Lys Leu Phe Asp Asp Trp Ser Asn
            115                 120                 125

Leu Gly Ser Ile Ser Glu Leu Ser Thr Ser Arg Val Leu Asp Pro Ala
            130                 135                 140

Ala Gly Val Thr Gln Leu Leu Ser Gly Val Thr Asn Leu Gln Ala Gln
145                 150                 155                 160

Gly Thr Glu Val Ile Asp Gly Ile Ser Thr Thr Lys Ile Thr Gly Thr
                165                 170                 175

Ile Pro Ala Ser Ser Val Lys Met Leu Asp Pro Gly Ala Lys Ser Ala
            180                 185                 190

Arg Pro Ala Thr Val Trp Ile Ala Gln Asp Gly Ser His His Leu Val
            195                 200                 205

Arg Ala Ser Ile Asp Leu Gly Ser Gly Ser Ile Gln Leu Thr Gln Ser
210                 215                 220

Lys Trp Asn Glu Pro Val Asn Val Asp
225                 230

(2) INFORMATION FOR SEQ ID NO:78:

(i) SEQUENCE CHARACTERISTICS:
        (A) LENGTH: 66 amino acids
        (B) TYPE: amino acid
        (C) STRANDEDNESS: single
        (D) TOPOLOGY: linear (xi) SEQUENCE DESCRIPTION: SEQ ID NO:78:

Val Ile Asp Ile Ile Gly Thr Ser Pro Thr Ser Trp Glu Gln Ala Ala
1               5                   10                  15

Ala Glu Ala Val Gln Arg Ala Arg Asp Ser Val Asp Asp Ile Arg Val
            20                  25                  30

Ala Arg Val Ile Glu Gln Asp Met Ala Val Asp Ser Ala Gly Lys Ile
        35                  40                  45

Thr Tyr Arg Ile Lys Leu Glu Val Ser Phe Lys Met Arg Pro Ala Gln
    50                  55                  60

Pro Arg
65

(2) INFORMATION FOR SEQ ID NO:79:

(i) SEQUENCE CHARACTERISTICS:
        (A) LENGTH: 69 amino acids
        (B) TYPE: amino acid
        (C) STRANDEDNESS: single
        (D) TOPOLOGY: linear (xi) SEQUENCE DESCRIPTION: SEQ ID NO:79:

Val Pro Pro Ala Pro Leu Pro Pro Leu Pro Pro Ser Pro Ile Ser
1               5                   10                  15

Cys Ala Ser Pro Pro Ser Pro Leu Pro Ala Pro Pro Val Ala
            20                  25                  30

Pro Gly Pro Pro Met Pro Pro Leu Asp Pro Trp Pro Pro Ala Pro Pro
        35                  40                  45

Leu Pro Tyr Ser Thr Pro Pro Gly Ala Pro Leu Pro Pro Ser Pro Pro
    50                  55                  60

Ser Pro Pro Leu Pro
65
```

(2) INFORMATION FOR SEQ ID NO:80:

(i) SEQUENCE CHARACTERISTICS:
        (A) LENGTH: 355 amino acids
        (B) TYPE: amino acid
        (C) STRANDEDNESS: single
        (D) TOPOLOGY: linear (xi) SEQUENCE DESCRIPTION: SEQ ID NO:80:

```
Met Ser Asn Ser Arg Arg Ser Leu Arg Trp Ser Trp Leu Leu Ser
1               5                   10                  15

Val Leu Ala Ala Val Gly Leu Gly Leu Ala Thr Ala Pro Ala Gln Ala
            20                  25                  30

Ala Pro Pro Ala Leu Ser Gln Asp Arg Phe Ala Asp Phe Pro Ala Leu
        35                  40                  45

Pro Leu Asp Pro Ser Ala Met Val Ala Gln Val Ala Pro Gln Val Val
    50                  55                  60

Asn Ile Asn Thr Lys Leu Gly Tyr Asn Asn Ala Val Gly Ala Gly Thr
65                  70                  75                  80

Gly Ile Val Ile Asp Pro Asn Gly Val Val Leu Thr Asn Asn His Val
                85                  90                  95

Ile Ala Gly Ala Thr Asp Ile Asn Ala Phe Ser Val Gly Ser Gly Gln
            100                 105                 110

Thr Tyr Gly Val Asp Val Val Gly Tyr Asp Arg Thr Gln Asp Val Ala
        115                 120                 125

Val Leu Gln Leu Arg Gly Ala Gly Gly Leu Pro Ser Ala Ala Ile Gly
130                 135                 140

Gly Gly Val Ala Val Gly Glu Pro Val Val Ala Met Gly Asn Ser Gly
145                 150                 155                 160

Gly Gln Gly Gly Thr Pro Arg Ala Val Pro Gly Arg Val Val Ala Leu
                165                 170                 175

Gly Gln Thr Val Gln Ala Ser Asp Ser Leu Thr Gly Ala Glu Glu Thr
            180                 185                 190

Leu Asn Gly Leu Ile Gln Phe Asp Ala Ala Ile Gln Pro Gly Asp Ser
        195                 200                 205

Gly Gly Pro Val Val Asn Gly Leu Gly Gln Val Val Gly Met Asn Thr
    210                 215                 220

Ala Ala Ser Asp Asn Phe Gln Leu Ser Gln Gly Gly Gln Gly Phe Ala
225                 230                 235                 240

Ile Pro Ile Gly Gln Ala Met Ala Ile Ala Gly Gln Ile Arg Ser Gly
                245                 250                 255

Gly Gly Ser Pro Thr Val His Ile Gly Pro Thr Ala Phe Leu Gly Leu
            260                 265                 270

Gly Val Val Asp Asn Asn Gly Asn Gly Ala Arg Val Gln Arg Val Val
        275                 280                 285

Gly Ser Ala Pro Ala Ala Ser Leu Gly Ile Ser Thr Gly Asp Val Ile
    290                 295                 300

Thr Ala Val Asp Gly Ala Pro Ile Asn Ser Ala Thr Ala Met Ala Asp
305                 310                 315                 320

Ala Leu Asn Gly His His Pro Gly Asp Val Ile Ser Val Asn Trp Gln
                325                 330                 335

Thr Lys Ser Gly Gly Thr Arg Thr Gly Asn Val Thr Leu Ala Glu Gly
            340                 345                 350

Pro Pro Ala
        355
```

(2) INFORMATION FOR SEQ ID NO:81:

(i) SEQUENCE CHARACTERISTICS:
  (A) LENGTH: 205 amino acids
  (B) TYPE: amino acid
  (C) STRANDEDNESS: single
  (D) TOPOLOGY: linear (xi) SEQUENCE DESCRIPTION: SEQ ID NO:81:

```
Ser Pro Lys Pro Asp Ala Glu Glu Gln Gly Val Pro Val Ser Pro Thr
 1               5                  10                  15

Ala Ser Asp Pro Ala Leu Leu Ala Glu Ile Arg Gln Ser Leu Asp Ala
                20                  25                  30

Thr Lys Gly Leu Thr Ser Val His Val Ala Val Arg Thr Thr Gly Lys
            35                  40                  45

Val Asp Ser Leu Leu Gly Ile Thr Ser Ala Asp Val Asp Val Arg Ala
        50                  55                  60

Asn Pro Leu Ala Ala Lys Gly Val Cys Thr Tyr Asn Asp Glu Gln Gly
65                  70                  75                  80

Val Pro Phe Arg Val Gln Gly Asp Asn Ile Ser Val Lys Leu Phe Asp
                85                  90                  95

Asp Trp Ser Asn Leu Gly Ser Ile Ser Glu Leu Ser Thr Ser Arg Val
               100                 105                 110

Leu Asp Pro Ala Ala Gly Val Thr Gln Leu Leu Ser Gly Val Thr Asn
           115                 120                 125

Leu Gln Ala Gln Gly Thr Glu Val Ile Asp Gly Ile Ser Thr Thr Lys
       130                 135                 140

Ile Thr Gly Thr Ile Pro Ala Ser Ser Val Lys Met Leu Asp Pro Gly
145                 150                 155                 160

Ala Lys Ser Ala Arg Pro Ala Thr Val Trp Ile Ala Gln Asp Gly Ser
                165                 170                 175

His His Leu Val Arg Ala Ser Ile Asp Leu Gly Ser Gly Ser Ile Gln
            180                 185                 190

Leu Thr Gln Ser Lys Trp Asn Glu Pro Val Asn Val Asp
        195                 200                 205
```

(2) INFORMATION FOR SEQ ID NO:82:

(i) SEQUENCE CHARACTERISTICS:
  (A) LENGTH: 286 amino acids
  (B) TYPE: amino acid
  (C) STRANDEDNESS: single
  (D) TOPOLOGY: linear (xi) SEQUENCE DESCRIPTION: SEQ ID NO:82:

```
Gly Asp Ser Phe Trp Ala Ala Ala Asp Gln Met Ala Arg Gly Phe Val
 1               5                  10                  15

Leu Gly Ala Thr Ala Gly Arg Thr Thr Leu Thr Gly Glu Gly Leu Gln
                20                  25                  30

His Ala Asp Gly His Ser Leu Leu Asp Ala Thr Asn Pro Ala Val
            35                  40                  45

Val Ala Tyr Asp Pro Ala Phe Ala Tyr Glu Ile Gly Tyr Ile Xaa Glu
        50                  55                  60

Ser Gly Leu Ala Arg Met Cys Gly Glu Asn Pro Glu Asn Ile Phe Phe
65                  70                  75                  80

Tyr Ile Thr Val Tyr Asn Glu Pro Tyr Val Gln Pro Pro Glu Pro Glu
                85                  90                  95
```

```
Asn Phe Asp Pro Glu Gly Val Leu Gly Gly Ile Tyr Arg Tyr His Ala
            100                 105                 110

Ala Thr Glu Gln Arg Thr Asn Lys Xaa Gln Ile Leu Ala Ser Gly Val
        115                 120                 125

Ala Met Pro Ala Ala Leu Arg Ala Ala Gln Met Leu Ala Ala Glu Trp
    130                 135                 140

Asp Val Ala Ala Asp Val Trp Ser Val Thr Ser Trp Gly Glu Leu Asn
145                 150                 155                 160

Arg Asp Gly Val Val Ile Glu Thr Glu Lys Leu Arg His Pro Asp Arg
                165                 170                 175

Pro Ala Gly Val Pro Tyr Val Thr Arg Ala Leu Glu Asn Ala Arg Gly
            180                 185                 190

Pro Val Ile Ala Val Ser Asp Trp Met Arg Ala Val Pro Glu Gln Ile
        195                 200                 205

Arg Pro Trp Val Pro Gly Thr Tyr Leu Thr Leu Gly Thr Asp Gly Phe
    210                 215                 220

Gly Phe Ser Asp Thr Arg Pro Ala Gly Arg Arg Tyr Phe Asn Thr Asp
225                 230                 235                 240

Ala Glu Ser Gln Val Gly Arg Gly Phe Gly Arg Gly Trp Pro Gly Arg
                245                 250                 255

Arg Val Asn Ile Asp Pro Phe Gly Ala Gly Arg Gly Pro Pro Ala Gln
            260                 265                 270

Leu Pro Gly Phe Asp Glu Gly Gly Leu Arg Pro Xaa Lys
        275                 280                 285

(2) INFORMATION FOR SEQ ID NO:83:

(i) SEQUENCE CHARACTERISTICS:
        (A) LENGTH: 173 amino acids
        (B) TYPE: amino acid
        (C) STRANDEDNESS: single
        (D) TOPOLOGY: linear (xi) SEQUENCE DESCRIPTION: SEQ ID NO:83:

Thr Lys Phe His Ala Leu Met Gln Glu Gln Ile His Asn Glu Phe Thr
1               5                   10                  15

Ala Ala Gln Gln Tyr Val Ala Ile Ala Val Tyr Phe Asp Ser Glu Asp
            20                  25                  30

Leu Pro Gln Leu Ala Lys His Phe Tyr Ser Gln Ala Val Glu Glu Arg
        35                  40                  45

Asn His Ala Met Met Leu Val Gln His Leu Leu Asp Arg Asp Leu Arg
    50                  55                  60

Val Glu Ile Pro Gly Val Asp Thr Val Arg Asn Gln Phe Asp Arg Pro
65                  70                  75                  80

Arg Glu Ala Leu Ala Leu Ala Leu Asp Gln Glu Arg Thr Val Thr Asp
                85                  90                  95

Gln Val Gly Arg Leu Thr Ala Val Ala Arg Asp Glu Gly Asp Phe Leu
            100                 105                 110

Gly Glu Gln Phe Met Gln Trp Phe Leu Gln Glu Gln Ile Glu Glu Val
        115                 120                 125

Ala Leu Met Ala Thr Leu Val Arg Val Ala Asp Arg Ala Gly Ala Asn
    130                 135                 140

Leu Phe Glu Leu Glu Asn Phe Val Ala Arg Glu Val Asp Val Ala Pro
145                 150                 155                 160

Ala Ala Ser Gly Ala Pro His Ala Ala Gly Gly Arg Leu
```

165        170

(2) INFORMATION FOR SEQ ID NO:84:

(i) SEQUENCE CHARACTERISTICS:
        (A) LENGTH: 107 amino acids
        (B) TYPE: amino acid
        (C) STRANDEDNESS: single
        (D) TOPOLOGY: linear (xi) SEQUENCE DESCRIPTION: SEQ ID NO:84:

Arg Ala Asp Glu Arg Lys Asn Thr Thr Met Lys Met Val Lys Ser Ile
1               5                   10                  15

Ala Ala Gly Leu Thr Ala Ala Ala Ile Gly Ala Ala Ala Gly
            20                  25                  30

Val Thr Ser Ile Met Ala Gly Gly Pro Val Val Tyr Gln Met Gln Pro
            35                  40                  45

Val Val Phe Gly Ala Pro Leu Pro Leu Asp Pro Xaa Ser Ala Pro Xaa
    50                  55                  60

Val Pro Thr Ala Ala Gln Trp Thr Xaa Leu Leu Asn Xaa Leu Xaa Asp
65                  70                  75                  80

Pro Asn Val Ser Phe Xaa Asn Lys Gly Ser Leu Val Glu Gly Gly Ile
                85                  90                  95

Gly Gly Xaa Glu Gly Xaa Xaa Arg Arg Xaa Gln
            100                 105

(2) INFORMATION FOR SEQ ID NO:85:

(i) SEQUENCE CHARACTERISTICS:
        (A) LENGTH: 125 amino acids
        (B) TYPE: amino acid
        (C) STRANDEDNESS: single
        (D) TOPOLOGY: linear (xi) SEQUENCE DESCRIPTION: SEQ ID NO:85:

Val Leu Ser Val Pro Val Gly Asp Gly Phe Trp Xaa Arg Val Val Asn
1               5                   10                  15

Pro Leu Gly Gln Pro Ile Asp Gly Arg Gly Asp Val Asp Ser Asp Thr
            20                  25                  30

Arg Arg Ala Leu Glu Leu Gln Ala Pro Ser Val Val Xaa Arg Gln Gly
            35                  40                  45

Val Lys Glu Pro Leu Xaa Thr Gly Ile Lys Ala Ile Asp Ala Met Thr
    50                  55                  60

Pro Ile Gly Arg Gly Gln Arg Gln Leu Ile Ile Gly Asp Arg Lys Thr
65                  70                  75                  80

Gly Lys Asn Arg Arg Leu Cys Arg Thr Pro Ser Ser Asn Gln Arg Glu
                85                  90                  95

Glu Leu Gly Val Arg Trp Ile Pro Arg Ser Arg Cys Ala Cys Val Tyr
            100                 105                 110

Val Gly His Arg Ala Arg Arg Gly Thr Tyr His Arg Arg
            115                 120                 125

(2) INFORMATION FOR SEQ ID NO:86:

(i) SEQUENCE CHARACTERISTICS:
        (A) LENGTH: 117 amino acids
        (B) TYPE: amino acid
        (C) STRANDEDNESS: single
        (D) TOPOLOGY: linear (xi) SEQUENCE DESCRIPTION: SEQ ID NO:86:

```
Cys Asp Ala Val Met Gly Phe Leu Gly Gly Ala Gly Pro Leu Ala Val
1               5                   10                  15

Val Asp Gln Gln Leu Val Thr Arg Val Pro Gln Gly Trp Ser Phe Ala
                20                  25                  30

Gln Ala Ala Val Pro Val Val Phe Leu Thr Ala Trp Tyr Gly Leu
            35                  40                  45

Ala Asp Leu Ala Glu Ile Lys Ala Gly Glu Ser Val Leu Ile His Ala
        50                  55                  60

Gly Thr Gly Gly Val Gly Met Ala Ala Val Gln Leu Ala Arg Gln Trp
65                      70                  75                  80

Gly Val Glu Val Phe Val Thr Ala Ser Arg Gly Lys Trp Asp Thr Leu
                85                  90                  95

Arg Ala Xaa Xaa Phe Asp Asp Xaa Pro Tyr Arg Xaa Phe Pro His Xaa
            100                 105                 110

Arg Ser Ser Xaa Gly
        115

(2) INFORMATION FOR SEQ ID NO:87:

(i) SEQUENCE CHARACTERISTICS:
        (A) LENGTH: 103 amino acids
        (B) TYPE: amino acid
        (C) STRANDEDNESS: single
        (D) TOPOLOGY: linear (xi) SEQUENCE DESCRIPTION: SEQ ID NO:87:

Met Tyr Arg Phe Ala Cys Arg Thr Leu Met Leu Ala Ala Cys Ile Leu
1               5                   10                  15

Ala Thr Gly Val Ala Gly Leu Gly Val Gly Ala Gln Ser Ala Ala Gln
                20                  25                  30

Thr Ala Pro Val Pro Asp Tyr Tyr Trp Cys Pro Gly Gln Pro Phe Asp
            35                  40                  45

Pro Ala Trp Gly Pro Asn Trp Asp Pro Tyr Thr Cys His Asp Asp Phe
        50                  55                  60

His Arg Asp Ser Asp Gly Pro Asp His Ser Arg Asp Tyr Pro Gly Pro
65                      70                  75                  80

Ile Leu Glu Gly Pro Val Leu Asp Pro Gly Ala Ala Pro Pro Pro
                85                  90                  95

Pro Ala Ala Gly Gly Gly Ala
            100

(2) INFORMATION FOR SEQ ID NO:88:

(i) SEQUENCE CHARACTERISTICS:
        (A) LENGTH: 88 amino acids
        (B) TYPE: amino acid
        (C) STRANDEDNESS: single
        (D) TOPOLOGY: linear (xi) SEQUENCE DESCRIPTION: SEQ ID NO:88:

Val Gln Cys Arg Val Trp Leu Glu Ile Gln Trp Arg Gly Met Leu Gly
1               5                   10                  15

Ala Asp Gln Ala Arg Ala Gly Gly Pro Ala Arg Ile Trp Arg Glu His
                20                  25                  30

Ser Met Ala Ala Met Lys Pro Arg Thr Gly Asp Gly Pro Leu Glu Ala
            35                  40                  45

Thr Lys Glu Gly Arg Gly Ile Val Met Arg Val Pro Leu Glu Gly Gly
        50                  55                  60
```

```
Gly Arg Leu Val Val Glu Leu Thr Pro Asp Glu Ala Ala Ala Leu Gly
 65                  70                  75                  80

Asp Glu Leu Lys Gly Val Thr Ser
                 85
```

(2) INFORMATION FOR SEQ ID NO:89:

(i) SEQUENCE CHARACTERISTICS:
        (A) LENGTH: 95 amino acids
        (B) TYPE: amino acid
        (C) STRANDEDNESS: single
        (D) TOPOLOGY: linear (xi) SEQUENCE DESCRIPTION: SEQ ID NO:89:

```
Thr Asp Ala Ala Thr Leu Ala Gln Glu Ala Gly Asn Phe Glu Arg Ile
 1               5                  10                  15

Ser Gly Asp Leu Lys Thr Gln Ile Asp Gln Val Glu Ser Thr Ala Gly
                 20                  25                  30

Ser Leu Gln Gly Gln Trp Arg Gly Ala Ala Gly Thr Ala Ala Gln Ala
                 35                  40                  45

Ala Val Val Arg Phe Gln Glu Ala Ala Asn Lys Gln Lys Gln Glu Leu
 50                  55                  60

Asp Glu Ile Ser Thr Asn Ile Arg Gln Ala Gly Val Gln Tyr Ser Arg
 65                  70                  75                  80

Ala Asp Glu Glu Gln Gln Gln Ala Leu Ser Ser Gln Met Gly Phe
                 85                  90                  95
```

(2) INFORMATION FOR SEQ ID NO:90:

(i) SEQUENCE CHARACTERISTICS:
        (A) LENGTH: 166 amino acids
        (B) TYPE: amino acid
        (C) STRANDEDNESS: single
        (D) TOPOLOGY: linear (xi) SEQUENCE DESCRIPTION: SEQ ID NO:90:

```
Met Thr Gln Ser Gln Thr Val Thr Val Asp Gln Gln Glu Ile Leu Asn
 1               5                  10                  15

Arg Ala Asn Glu Val Glu Ala Pro Met Ala Asp Pro Pro Thr Asp Val
                 20                  25                  30

Pro Ile Thr Pro Cys Glu Leu Thr Xaa Xaa Lys Asn Ala Ala Gln Gln
                 35                  40                  45

Xaa Val Leu Ser Ala Asp Asn Met Arg Glu Tyr Leu Ala Ala Gly Ala
 50                  55                  60

Lys Glu Arg Gln Arg Leu Ala Thr Ser Leu Arg Asn Ala Ala Lys Xaa
 65                  70                  75                  80

Tyr Gly Glu Val Asp Glu Glu Ala Ala Thr Ala Leu Asp Asn Asp Gly
                 85                  90                  95

Glu Gly Thr Val Gln Ala Glu Ser Ala Gly Ala Val Gly Gly Asp Ser
                100                 105                 110

Ser Ala Glu Leu Thr Asp Thr Pro Arg Val Ala Thr Ala Gly Glu Pro
                115                 120                 125

Asn Phe Met Asp Leu Lys Glu Ala Ala Arg Lys Leu Glu Thr Gly Asp
                130                 135                 140

Gln Gly Ala Ser Leu Ala His Xaa Gly Asp Gly Trp Asn Thr Xaa Thr
145                 150                 155                 160

Leu Thr Leu Gln Gly Asp
                165
```

(2) INFORMATION FOR SEQ ID NO:91:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:91:

```
Arg Ala Glu Arg Met
1               5
```

(2) INFORMATION FOR SEQ ID NO:92:

(i) SEQUENCE CHARACTERISTICS:
        (A) LENGTH: 263 amino acids
        (B) TYPE: amino acid
        (C) STRANDEDNESS: single
        (D) TOPOLOGY: linear (xi) SEQUENCE DESCRIPTION: SEQ ID NO:92:

```
Val Ala Trp Met Ser Val Thr Ala Gly Gln Ala Glu Leu Thr Ala Ala
1               5                   10                  15

Gln Val Arg Val Ala Ala Ala Tyr Glu Thr Ala Tyr Gly Leu Thr
                20                  25                  30

Val Pro Pro Val Ile Ala Glu Asn Arg Ala Glu Leu Met Ile Leu
            35                  40                  45

Ile Ala Thr Asn Leu Leu Gly Gln Asn Thr Pro Ala Ile Ala Val Asn
        50                  55                  60

Glu Ala Glu Tyr Gly Glu Met Trp Ala Gln Asp Ala Ala Met Phe
65                  70                  75                  80

Gly Tyr Ala Ala Ala Thr Ala Thr Ala Thr Ala Thr Leu Leu Pro Phe
                85                  90                  95

Glu Glu Ala Pro Glu Met Thr Ser Ala Gly Gly Leu Leu Glu Gln Ala
                100                 105                 110

Ala Ala Val Glu Glu Ala Ser Asp Thr Ala Ala Ala Asn Gln Leu Met
            115                 120                 125

Asn Asn Val Pro Gln Ala Leu Lys Gln Leu Ala Gln Pro Thr Gln Gly
130                 135                 140

Thr Thr Pro Ser Ser Lys Leu Gly Gly Leu Trp Lys Thr Val Ser Pro
145                 150                 155                 160

His Arg Ser Pro Ile Ser Asn Met Val Ser Met Ala Asn Asn His Met
                165                 170                 175

Ser Met Thr Asn Ser Gly Val Ser Met Thr Asn Thr Leu Ser Ser Met
                180                 185                 190

Leu Lys Gly Phe Ala Pro Ala Ala Ala Gln Ala Val Gln Thr Ala
            195                 200                 205

Ala Gln Asn Gly Val Arg Ala Met Ser Ser Leu Gly Ser Ser Leu Gly
210                 215                 220

Ser Ser Gly Leu Gly Gly Val Ala Ala Asn Leu Gly Arg Ala Ala
225                 230                 235                 240

Ser Val Arg Tyr Gly His Arg Asp Gly Gly Lys Tyr Ala Xaa Ser Gly
                245                 250                 255

Arg Arg Asn Gly Gly Pro Ala
                260
```

(2) INFORMATION FOR SEQ ID NO:93:

(i) SEQUENCE CHARACTERISTICS:
        (A) LENGTH: 303 amino acids
        (B) TYPE: amino acid
        (C) STRANDEDNESS: single
        (D) TOPOLOGY: linear (xi) SEQUENCE DESCRIPTION: SEQ ID NO:93:

Met Thr Tyr Ser Pro Gly Asn Pro Gly Tyr Pro Gln Ala Gln Pro Ala
1               5                   10                  15

Gly Ser Tyr Gly Gly Val Thr Pro Ser Phe Ala His Ala Asp Glu Gly
            20                  25                  30

Ala Ser Lys Leu Pro Met Tyr Leu Asn Ile Ala Val Ala Val Leu Gly
        35                  40                  45

Leu Ala Ala Tyr Phe Ala Ser Phe Gly Pro Met Phe Thr Leu Ser Thr
    50                  55                  60

Glu Leu Gly Gly Gly Asp Gly Ala Val Ser Gly Asp Thr Gly Leu Pro
65                  70                  75                  80

Val Gly Val Ala Leu Leu Ala Ala Leu Leu Ala Gly Val Val Leu Val
                85                  90                  95

Pro Lys Ala Lys Ser His Val Thr Val Val Ala Val Leu Gly Val Leu
                100                 105                 110

Gly Val Phe Leu Met Val Ser Ala Thr Phe Asn Lys Pro Ser Ala Tyr
            115                 120                 125

Ser Thr Gly Trp Ala Leu Trp Val Val Leu Ala Phe Ile Val Phe Gln
        130                 135                 140

Ala Val Ala Ala Val Leu Ala Leu Leu Val Glu Thr Gly Ala Ile Thr
145                 150                 155                 160

Ala Pro Ala Pro Arg Pro Lys Phe Asp Pro Tyr Gly Gln Tyr Gly Arg
                165                 170                 175

Tyr Gly Gln Tyr Gly Gln Tyr Gly Val Gln Pro Gly Tyr Tyr Gly
            180                 185                 190

Gln Gln Gly Ala Gln Gln Ala Ala Gly Leu Gln Ser Pro Gly Pro Gln
        195                 200                 205

Gln Ser Pro Gln Pro Pro Gly Tyr Gly Ser Gln Tyr Gly Gly Tyr Ser
    210                 215                 220

Ser Ser Pro Ser Gln Ser Gly Ser Gly Tyr Thr Ala Gln Pro Pro Ala
225                 230                 235                 240

Gln Pro Pro Ala Gln Ser Gly Ser Gln Gln Ser His Gln Gly Pro Ser
                245                 250                 255

Thr Pro Pro Thr Gly Phe Pro Ser Phe Ser Pro Pro Pro Val Ser
            260                 265                 270

Ala Gly Thr Gly Ser Gln Ala Gly Ser Ala Pro Val Asn Tyr Ser Asn
        275                 280                 285

Pro Ser Gly Gly Glu Gln Ser Ser Pro Gly Gly Ala Pro Val
    290                 295                 300

(2) INFORMATION FOR SEQ ID NO:94:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO:94:

ATGAAGATGG TGAAATCGAT CGCCGCAGGT CTGACCGCCG CGGCTGCAAT CGGCGCCGCT    60

```
GCGGCCGGTG TGACTTCGAT CATGGCTGGC GGCCCGGTCG TATACCAGAT GCAGCCGGTC      120

GTCTTCGGCG CGCCACTGCC GTTGGACCCG GCATCCGCCC CTGACGTCCC GACCGCCGCC      180

CAGTTGACCA GCCTGCTCAA CAGCCTCGCC GATCCCAACG TGTCGTTTGC GAACAAGGGC      240

AGTCTGGTCG AGGGCGGCAT CGGGGGCACC GAGGCGCGCA TCGCCGACCA CAAGCTGAAG      300

AAGGCCGCCG AGCACGGGGA TCTGCCGCTG TCGTTCAGCG TGACGAACAT CCAGCCGGCG      360

GCCGCCGGTT CGGCCACCGC CGACGTTTCC GTCTCGGGTC CGAAGCTCTC GTCGCCGGTC      420

ACGCAGAACG TCACGTTCGT GAATCAAGGC GGCTGGATGC TGTCACGCGC ATCGGCGATG      480

GAGTTGCTGC AGGCCGCAGG GAACTGA                                         507

(2) INFORMATION FOR SEQ ID NO:95:

(i) SEQUENCE CHARACTERISTICS:
        (A) LENGTH: 168 amino acids
        (B) TYPE: amino acid
        (C) STRANDEDNESS: single
        (D) TOPOLOGY: linear (xi) SEQUENCE DESCRIPTION: SEQ ID NO:95:

Met Lys Met Val Lys Ser Ile Ala Ala Gly Leu Thr Ala Ala Ala
1               5                   10                  15

Ile Gly Ala Ala Ala Gly Val Thr Ser Ile Met Ala Gly Gly Pro
            20                  25                  30

Val Val Tyr Gln Met Gln Pro Val Val Phe Gly Ala Pro Leu Pro Leu
        35                  40                  45

Asp Pro Ala Ser Ala Pro Asp Val Pro Thr Ala Ala Gln Leu Thr Ser
    50                  55                  60

Leu Leu Asn Ser Leu Ala Asp Pro Asn Val Ser Phe Ala Asn Lys Gly
65                  70                  75                  80

Ser Leu Val Glu Gly Gly Ile Gly Gly Thr Glu Ala Arg Ile Ala Asp
                85                  90                  95

His Lys Leu Lys Lys Ala Ala Glu His Gly Asp Leu Pro Leu Ser Phe
            100                 105                 110

Ser Val Thr Asn Ile Gln Pro Ala Ala Ala Gly Ser Ala Thr Ala Asp
        115                 120                 125

Val Ser Val Ser Gly Pro Lys Leu Ser Ser Pro Val Thr Gln Asn Val
    130                 135                 140

Thr Phe Val Asn Gln Gly Gly Trp Met Leu Ser Arg Ala Ser Ala Met
145                 150                 155                 160

Glu Leu Leu Gln Ala Ala Gly Asn
                165

(2) INFORMATION FOR SEQ ID NO:96:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (xi) SEQUENCE DESCRIPTION: SEQ ID NO:96:

CGTGGCAATG TCGTTGACCG TCGGGGCCGG GGTCGCCTCC GCAGATCCCG TGGACGCGGT       60

CATTAACACC ACCTGCAATT ACGGGCAGGT AGTAGCTGCG CTCAACGCGA CGGATCCGGG      120

GGCTGCCGCA CAGTTCAACG CCTCACCGGT GGCGCAGTCC TATTTGCGCA ATTTCCTCGC      180

CGCACCGCCA CCTCAGCGCG CTGCCATGGC CGCGCAATTG CAAGCTGTGC CGGGGGCGGC      240
```

```
ACAGTACATC GGCCTTGTCG AGTCGGTTGC CGGCTCCTGC AACAACTATT AAGCCCATGC      300

GGGCCCCATC CCGCGACCCG GCATCGTCGC CGGGGCTAGG CCAGATTGCC CCGCTCCTCA      360

ACGGGCCGCA TCCCGCGACC CGGCATCGTC GCCGGGGCTA GGCCAGATTG CCCCGCTCCT      420

CAACGGGCCG CATCTCGTGC CGAATTCCTG CAGCCCGGGG GATCCACTAG TTCTAGAGCG      480

GCCGCCACCG CGGTGGAGCT                                                 500
```

(2) INFORMATION FOR SEQ ID NO:97:

(i) SEQUENCE CHARACTERISTICS:
  (A) LENGTH: 96 amino acids
  (B) TYPE: amino acid
  (C) STRANDEDNESS: single
  (D) TOPOLOGY: linear (xi) SEQUENCE DESCRIPTION: SEQ ID NO:97:

```
Val Ala Met Ser Leu Thr Val Gly Ala Gly Val Ala Ser Ala Asp Pro
 1               5                  10                  15

Val Asp Ala Val Ile Asn Thr Thr Cys Asn Tyr Gly Gln Val Val Ala
            20                  25                  30

Ala Leu Asn Ala Thr Asp Pro Gly Ala Ala Ala Gln Phe Asn Ala Ser
        35                  40                  45

Pro Val Ala Gln Ser Tyr Leu Arg Asn Phe Leu Ala Ala Pro Pro Pro
50                  55                  60

Gln Arg Ala Ala Met Ala Ala Gln Leu Gln Ala Val Pro Gly Ala Ala
65                  70                  75                  80

Gln Tyr Ile Gly Leu Val Glu Ser Val Ala Gly Ser Cys Asn Asn Tyr
                85                  90                  95
```

(2) INFORMATION FOR SEQ ID NO:98:

(i) SEQUENCE CHARACTERISTICS:
  (A) LENGTH: 154 base pairs
  (B) TYPE: nucleic acid
  (C) STRANDEDNESS: single
  (D) TOPOLOGY: linear (xi) SEQUENCE DESCRIPTION: SEQ ID NO:98:

```
ATGACAGAGC AGCAGTGGAA TTTCGCGGGT ATCGAGGCCG CGGCAAGCGC AATCCAGGGA       60

AATGTCACGT CCATTCATTC CCTCCTTGAC GAGGGGAAGC AGTCCCTGAC CAAGCTCGCA      120

GCGGCCTGGG GCGGTAGCGG TTCGGAAGCG TACC                                  154
```

(2) INFORMATION FOR SEQ ID NO:99:

(i) SEQUENCE CHARACTERISTICS:
  (A) LENGTH: 51 amino acids
  (B) TYPE: amino acid
  (C) STRANDEDNESS: single
  (D) TOPOLOGY: linear (xi) SEQUENCE DESCRIPTION: SEQ ID NO:99:

```
Met Thr Glu Gln Gln Trp Asn Phe Ala Gly Ile Glu Ala Ala Ala Ser
 1               5                  10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr
50
```

(2) INFORMATION FOR SEQ ID NO:100:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (xi) SEQUENCE DESCRIPTION: SEQ ID NO:100:

```
CGGTCGCGCA CTTCCAGGTG ACTATGAAAG TCGGCTTCCG NCTGGAGGAT TCCTGAACCT      60

TCAAGCGCGG CCGATAACTG AGGTGCATCA TTAAGCGACT TTTCCAGAAC ATCCTGACGC     120

GCTCGAAACG CGGCACAGCC GACGGTGGCT CCGNCGAGGC GCTGNCTCCA AAATCCCTGA     180

GACAATTCGN CGGGGCGCC TACAAGGAAG TCGGTGCTGA ATTCGNCGNG TATCTGGTCG     240

ACCTGTGTGG TCTGNAGCCG GACGAAGCGG TGCTCGACGT CG                       282
```

(2) INFORMATION FOR SEQ ID NO:101:

(i) SEQUENCE CHARACTERISTICS:
        (A) LENGTH: 3058 base pairs
        (B) TYPE: nucleic acid
        (C) STRANDEDNESS: single
        (D) TOPOLOGY: linear (xi) SEQUENCE DESCRIPTION: SEQ ID NO:101:

```
GATCGTACCC GTGCGAGTGC TCGGGCCGTT TGAGGATGGA GTGCACGTGT CTTTCGTGAT      60

GGCATACCCA GAGATGTTGG CGGCGGCGGC TGACACCCTG CAGAGCATCG GTGCTACCAC     120

TGTGGCTAGC AATGCCGCTG CGGCGGCCCC GACGACTGGG GTGGTGCCCC CCGCTGCCGA     180

TGAGGTGTCG GCGCTGACTG CGGCGCACTT CGCCGCACAT GCGGCGATGT ATCAGTCCGT     240

GAGCGCTCGG GCTGCTGCGA TTCATGACCA GTTCGTGGCC ACCCTTGCCA GCAGCGCCAG     300

CTCGTATGCG GCCACTGAAG TCGCCAATGC GGCGGCGGCC AGCTAAGCCA GGAACAGTCG     360

GCACGAGAAA CCACGAGAAA TAGGGACACG TAATGGTGGA TTTCGGGGCG TTACCACCGG     420

AGATCAACTC CGCGAGGATG TACGCCGGCC CGGGTTCGGC CTCGCTGGTG GCCGCGGCTC     480

AGATGTGGGA CAGCGTGGCG AGTGACCTGT TTTCGGCCGC GTCGGCGTTT CAGTCGGTGG     540

TCTGGGGTCT GACGGTGGGG TCGTGGATAG GTTCGTCGGC GGGTCTGATG GTGGCGGCGG     600

CCTCGCCGTA TGTGGCGTGG ATGAGCGTCA CCGCGGGGCA GGCCGAGCTG ACCGCCGCCC     660

AGGTCCGGGT TGCTGCGGCG GCCTACGAGA CGGCGTATGG GCTGACGGTG CCCCGCCGG     720

TGATCGCCGA GAACCGTGCT GAACTGATGA TTCTGATAGC GACCAACCTC TTGGGGCAAA     780

ACACCCCGGC GATCGCGGTC AACGAGGCCG AATACGGCGA GATGTGGGCC CAAGACGCCG     840

CCGCGATGTT TGGCTACGCC GCGGCGACGG CGACGGCGAC GGCGACGTTG CTGCCGTTCG     900

AGGAGGCGCC GGAGATGACC AGCGCGGGTG GGCTCCTCGA GCAGGCCGCC GCGGTCGAGG     960

AGGCCTCCGA CACCGCCGCG GCGAACCAGT TGATGAACAA TGTGCCCCAG GCGCTGCAAC    1020

AGCTGGCCCA GCCCACGCAG GGCACCACGC CTTCTTCCAA GCTGGGTGGC CTGTGGAAGA    1080

CGGTCTCGCC GCATCGGTCG CCGATCAGCA ACATGGTGTC GATGGCCAAC AACCACATGT    1140

CGATGACCAA CTCGGGTGTG TCGATGACCA ACACCTTGAG CTCGATGTTG AAGGGCTTTG    1200

CTCCGGCGGC GGCCGCCCAG GCCGTGCAAA CCGCGGCGCA AAACGGGGTC CGGGCGATGA    1260

GCTCGCTGGG CAGCTCGCTG GGTTCTTCGG GTCTGGGCGG TGGGGTGGCC GCCAACTTGG    1320

GTCGGGCGGC CTCGGTCGGT TCGTTGTCGG TGCCGCAGGC CTGGGCCGCG GCCAACCAGG    1380

CAGTCACCCC GGCGGCGCGG GCGCTGCCGC TGACCAGCCT GACCAGCGCC GCGGAAAGAG    1440
```

```
GGCCCGGGCA GATGCTGGGC GGGCTGCCGG TGGGGCAGAT GGGCGCCAGG GCCGGTGGTG    1500

GGCTCAGTGG TGTGCTGCGT GTTCCGCCGC GACCCTATGT GATGCCGCAT TCTCCGGCGG    1560

CCGGCTAGGA GAGGGGCGC AGACTGTCGT TATTTGACCA GTGATCGGCG GTCTCGGTGT     1620

TTCCGCGGCC GGCTATGACA ACAGTCAATG TGCATGACAA GTTACAGGTA TTAGGTCCAG    1680

GTTCAACAAG GAGACAGGCA ACATGGCCTC ACGTTTTATG ACGGATCCGC ACGCGATGCG    1740

GGACATGGCG GGCCGTTTTG AGGTGCACGC CCAGACGGTG GAGGACGAGG CTCGCCGGAT    1800

GTGGGCGTCC GCGCAAAACA TTTCCGGTGC GGGCTGGAGT GGCATGGCCG AGGCGACCTC    1860

GCTAGACACC ATGGCCCAGA TGAATCAGGC GTTTCGCAAC ATCGTGAACA TGCTGCACGG    1920

GGTGCGTGAC GGGCTGGTTC GCGACGCCAA CAACTACGAG CAGCAAGAGC AGGCCTCCCA    1980

GCAGATCCTC AGCAGCTAAC GTCAGCCGCT GCAGCACAAT ACTTTTACAA GCGAAGGAGA    2040

ACAGGTTCGA TGACCATCAA CTATCAATTC GGGGATGTCG ACGCTCACGG CGCCATGATC    2100

CGCGCTCAGG CCGGGTTGCT GGAGGCCGAG CATCAGGCCA TCATTCGTGA TGTGTTGACC    2160

GCGAGTGACT TTTGGGGCGG CGCCGGTTCG GCGGCCTGCC AGGGGTTCAT TACCCAGTTG    2220

GGCCGTAACT TCCAGGTGAT CTACGAGCAG GCCAACGCCC ACGGGCAGAA GGTGCAGGCT    2280

GCCGGCAACA ACATGGCGCA AACCGACAGC GCCGTCGGCT CCAGCTGGGC CTGACACCAG    2340

GCCAAGGCCA GGGACGTGGT GTACGAGTGA AGTTCCTCGC GTGATCCTTC GGGTGGCAGT    2400

CTAAGTGGTC AGTGCTGGGG TGTTGGTGGT TTGCTGCTTG GCGGGTTCTT CGGTGCTGGT    2460

CAGTGCTGCT CGGGCTCGGG TGAGGACCTC GAGGCCCAGG TAGCGCCGTC CTTCGATCCA    2520

TTCGTCGTGT TGTTCGGCGA GGACGGCTCC GACGAGGCGA ATGATCGAGG CGCGGTCGGG    2580

GAAGATGCCC ACGACGTCGG TTCGGCGTCG TACCTCTCGG TTGAGGCGTT CCTGGGGGTT    2640

GTTGGACCAG ATTTGGCGCC AGATCTGCTT GGGGAAGGCG GTGAACGCCA GCAGGTCGGT    2700

GCGGGCGGTG TCGAGGTGCT CGGCCACCGC GGGGAGTTTG TCGGTCAGAG CGTCGAGTAC    2760

CCGATCATAT TGGGCAACAA CTGATTCGGC GTCGGGCTGG TCGTAGATGG AGTGCAGCAG    2820

GGTGCGCACC CACGGCCAGG AGGGCTTCGG GGTGGCTGCC ATCAGATTGG CTGCGTAGTG    2880

GGTTCTGCAG CGCTGCCAGG CCGCTGCGGG CAGGGTGGCG CCGATCGCGG CCACCAGGCC    2940

GGCGTGGGCG TCGCTGGTGA CCAGCGCGAC CCCGGACAGG CCGCGGGCGA CCAGGTCGCG    3000

GAAGAACGCC AGCCAGCCGG CCCCGTCCTC GGCGGAGGTG ACCTGGATGC CCAGGATC     3058
```

(2) INFORMATION FOR SEQ ID NO:102:

(i) SEQUENCE CHARACTERISTICS:
        (A) LENGTH: 391 amino acids
        (B) TYPE: amino acid
        (C) STRANDEDNESS: single
        (D) TOPOLOGY: linear (xi) SEQUENCE DESCRIPTION: SEQ ID NO:102:

```
Met Val Asp Phe Gly Ala Leu Pro Pro Glu Ile Asn Ser Ala Arg Met
 1               5                  10                  15

Tyr Ala Gly Pro Gly Ser Ala Ser Leu Val Ala Ala Gln Met Trp
                20                  25                  30

Asp Ser Val Ala Ser Asp Leu Phe Ser Ala Ala Ser Ala Phe Gln Ser
            35                  40                  45

Val Val Trp Gly Leu Thr Val Gly Ser Trp Ile Gly Ser Ser Ala Gly
        50                  55                  60

Leu Met Val Ala Ala Ala Ser Pro Tyr Val Ala Trp Met Ser Val Thr
```

```
65                  70                  75                  80
Ala Gly Gln Ala Glu Leu Thr Ala Ala Gln Val Arg Val Ala Ala
                85                  90                  95
Ala Tyr Glu Thr Ala Tyr Gly Leu Thr Val Pro Pro Val Ile Ala
                100                 105                 110
Glu Asn Arg Ala Glu Leu Met Ile Leu Ile Ala Thr Asn Leu Leu Gly
                115                 120                 125
Gln Asn Thr Pro Ala Ile Ala Val Asn Glu Ala Glu Tyr Gly Glu Met
    130                 135                 140
Trp Ala Gln Asp Ala Ala Ala Met Phe Gly Tyr Ala Ala Thr Ala
145                 150                 155                 160
Thr Ala Thr Ala Thr Leu Leu Pro Phe Glu Glu Ala Pro Glu Met Thr
                165                 170                 175
Ser Ala Gly Gly Leu Leu Glu Gln Ala Ala Val Glu Glu Ala Ser
                180                 185                 190
Asp Thr Ala Ala Ala Asn Gln Leu Met Asn Asn Val Pro Gln Ala Leu
    195                 200                 205
Gln Gln Leu Ala Gln Pro Thr Gln Gly Thr Thr Pro Ser Ser Lys Leu
    210                 215                 220
Gly Gly Leu Trp Lys Thr Val Ser Pro His Arg Ser Pro Ile Ser Asn
225                 230                 235                 240
Met Val Ser Met Ala Asn Asn His Met Ser Met Thr Asn Ser Gly Val
                245                 250                 255
Ser Met Thr Asn Thr Leu Ser Ser Met Leu Lys Gly Phe Ala Pro Ala
                260                 265                 270
Ala Ala Ala Gln Ala Val Gln Thr Ala Ala Gln Asn Gly Val Arg Ala
                275                 280                 285
Met Ser Ser Leu Gly Ser Ser Leu Gly Ser Ser Gly Leu Gly Gly Gly
    290                 295                 300
Val Ala Ala Asn Leu Gly Arg Ala Ala Ser Val Gly Ser Leu Ser Val
305                 310                 315                 320
Pro Gln Ala Trp Ala Ala Ala Asn Gln Ala Val Thr Pro Ala Ala Arg
                325                 330                 335
Ala Leu Pro Leu Thr Ser Leu Thr Ser Ala Ala Glu Arg Gly Pro Gly
                340                 345                 350
Gln Met Leu Gly Gly Leu Pro Val Gly Gln Met Gly Ala Arg Ala Gly
                355                 360                 365
Gly Gly Leu Ser Gly Val Leu Arg Val Pro Pro Arg Pro Tyr Val Met
                370                 375                 380
Pro His Ser Pro Ala Ala Gly
385                 390

(2) INFORMATION FOR SEQ ID NO:103:

(i) SEQUENCE CHARACTERISTICS:
        (A) LENGTH: 1725 base pairs
        (B) TYPE: nucleic acid
        (C) STRANDEDNESS: single
        (D) TOPOLOGY: linear (xi) SEQUENCE DESCRIPTION: SEQ ID NO:103:

GACGTCAGCA CCCGCCGTGC AGGGCTGGAG CGTGGTCGGT TTTGATCTGC GGTCAAGGTG      60

ACGTCCCTCG GCGTGTCGCC GGCGTGGATG CAGACTCGAT GCCGCTCTTT AGTGCAACTA     120

ATTTCGTTGA AGTGCCTGCG AGGTATAGGA CTTCACGATT GGTTAATGTA GCGTTCACCC     180
```

-continued

```
CGTGTTGGGG TCGATTTGGC CGGACCAGTC GTCACCAACG CTTGGCGTGC GCGCCAGGCG    240

GGCGATCAGA TCGCTTGACT ACCAATCAAT CTTGAGCTCC CGGGCCGATG CTCGGGCTAA    300

ATGAGGAGGA GCACGCGTGT CTTTCACTGC GCAACCGGAG ATGTTGGCGG CCGCGGCTGG    360

CGAACTTCGT TCCCTGGGGG CAACGCTGAA GGCTAGCAAT GCCGCCGCAG CCGTGCCGAC    420

GACTGGGGTG GTGCCCCCGG CTGCCGACGA GGTGTCGCTG CTGCTTGCCA CACAATTCCG    480

TACGCATGCG GCGACGTATC AGACGGCCAG CGCCAAGGCC GCGGTGATCC ATGAGCAGTT    540

TGTGACCACG CTGGCCACCA GCGCTAGTTC ATATGCGGAC ACCGAGGCCG CCAACGCTGT    600

GGTCACCGGC TAGCTGACCT GACGGTATTC GAGCGGAAGG ATTATCGAAG TGGTGGATTT    660

CGGGGCGTTA CCACCGGAGA TCAACTCCGC GAGGATGTAC GCCGGCCCGG GTTCGGCCTC    720

GCTGGTGGCC GCCGCGAAGA TGTGGGACAG CGTGGCGAGT GACCTGTTTT CGGCCGCGTC    780

GGCGTTTCAG TCGGTGGTCT GGGGTCTGAC GGTGGGGTCG TGGATAGGTT CGTCGGCGGG    840

TCTGATGGCG GCGGCGGCCT CGCCGTATGT GGCGTGGATG AGCGTCACCG CGGGGCAGGC    900

CCAGCTGACC GCCGCCCAGG TCCGGGTTGC TGCGGCGGCC TACGAGACAG CGTATAGGCT    960

GACGGTGCCC CCGCCGGTGA TCGCCGAGAA CCGTACCGAA CTGATGACGC TGACCGCGAC   1020

CAACCTCTTG GGGCAAAACA CGCCGGCGAT CGAGGCCAAT CAGGCCGCAT ACAGCCAGAT   1080

GTGGGGCCAA GACGCGGAGG CGATGTATGG CTACGCCGCC ACGGCGGCGA CGGCGACCGA   1140

GGCGTTGCTG CCGTTCGAGG ACGCCCCACT GATCACCAAC CCCGGCGGGC TCCTTGAGCA   1200

GGCCGTCGCG GTCGAGGAGG CCATCGACAC CGCCGCGGCG AACCAGTTGA TGAACAATGT   1260

GCCCCAAGCG CTGCAACAGC TGGCCCAGCC AGCGCAGGGC GTCGTACCTT CTTCCAAGCT   1320

GGGTGGGCTG TGGACGGCGG TCTCGCCGCA TCTGTCGCCG CTCAGCAACG TCAGTTCGAT   1380

AGCCAACAAC CACATGTCGA TGATGGGCAC GGGTGTGTCG ATGACCAACA CCTTGCACTC   1440

GATGTTGAAG GGCTTAGCTC CGGCGGCGGC TCAGGCCGTG GAAACCGCGG CGGAAAACGG   1500

GGTCTGGGCG ATGAGCTCGC TGGGCAGCCA GCTGGGTTCG TCGCTGGGTT CTTCGGGTCT   1560

GGGCGCTGGG GTGGCCGCCA ACTTGGGTCG GCGGCCTCG GTCGGTTCGT TGTCGGTGCC   1620

GCCAGCATGG GCCGCGGCCA ACCAGGCGGT CACCCCGGCG GCGCGGGCGC TGCCGCTGAC   1680

CAGCCTGACC AGCGCCGCCC AAACCGCCCC CGGACACATG CTGGG                   1725
```

(2) INFORMATION FOR SEQ ID NO:104:

(i) SEQUENCE CHARACTERISTICS:
        (A) LENGTH: 359 amino acids
        (B) TYPE: amino acid
        (C) STRANDEDNESS:
        (D) TOPOLOGY: linear (xi) SEQUENCE DESCRIPTION: SEQ ID NO:104:

```
Val Val Asp Phe Gly Ala Leu Pro Pro Glu Ile Asn Ser Ala Arg Met
 1               5                  10                  15

Tyr Ala Gly Pro Gly Ser Ala Ser Leu Val Ala Ala Lys Met Trp
            20                  25                  30

Asp Ser Val Ala Ser Asp Leu Phe Ser Ala Ala Ser Ala Phe Gln Ser
        35                  40                  45

Val Val Trp Gly Leu Thr Val Gly Ser Trp Ile Gly Ser Ser Ala Gly
    50                  55                  60

Leu Met Ala Ala Ala Ser Pro Tyr Val Ala Trp Met Ser Val Thr
65                  70                  75                  80

Ala Gly Gln Ala Gln Leu Thr Ala Ala Gln Val Arg Val Ala Ala Ala
```

```
                        85                  90                       95
Ala Tyr Glu Thr Ala Tyr Arg Leu Thr Val Pro Pro Val Ile Ala
                    100                 105                 110

Glu Asn Arg Thr Glu Leu Met Thr Leu Thr Ala Thr Asn Leu Leu Gly
            115                 120                 125

Gln Asn Thr Pro Ala Ile Glu Ala Asn Gln Ala Ala Tyr Ser Gln Met
        130                 135                 140

Trp Gly Gln Asp Ala Glu Ala Met Tyr Gly Tyr Ala Ala Thr Ala Ala
145                 150                 155                 160

Thr Ala Thr Glu Ala Leu Leu Pro Phe Glu Asp Ala Pro Leu Ile Thr
                165                 170                 175

Asn Pro Gly Gly Leu Leu Glu Gln Ala Val Ala Val Glu Glu Ala Ile
            180                 185                 190

Asp Thr Ala Ala Ala Asn Gln Leu Met Asn Asn Val Pro Gln Ala Leu
        195                 200                 205

Gln Gln Leu Ala Gln Pro Ala Gln Gly Val Val Pro Ser Ser Lys Leu
    210                 215                 220

Gly Gly Leu Trp Thr Ala Val Ser Pro His Leu Ser Pro Leu Ser Asn
225                 230                 235                 240

Val Ser Ser Ile Ala Asn Asn His Met Ser Met Met Gly Thr Gly Val
                245                 250                 255

Ser Met Thr Asn Thr Leu His Ser Met Leu Lys Gly Leu Ala Pro Ala
            260                 265                 270

Ala Ala Gln Ala Val Glu Thr Ala Ala Glu Asn Gly Val Trp Ala Met
        275                 280                 285

Ser Ser Leu Gly Ser Gln Leu Gly Ser Ser Leu Gly Ser Ser Gly Leu
    290                 295                 300

Gly Ala Gly Val Ala Ala Asn Leu Gly Arg Ala Ala Ser Val Gly Ser
305                 310                 315                 320

Leu Ser Val Pro Pro Ala Trp Ala Ala Ala Asn Gln Ala Val Thr Pro
                325                 330                 335

Ala Ala Arg Ala Leu Pro Leu Thr Ser Leu Thr Ser Ala Ala Gln Thr
            340                 345                 350

Ala Pro Gly His Met Leu Gly
        355

(2) INFORMATION FOR SEQ ID NO:105:

(i) SEQUENCE CHARACTERISTICS:
        (A) LENGTH: 3027 base pairs
        (B) TYPE: nucleic acid
        (C) STRANDEDNESS: single
        (D) TOPOLOGY: linear (xi) SEQUENCE DESCRIPTION: SEQ ID NO:105:

AGTTCAGTCG AGAATGATAC TGACGGGCTG TATCCACGAT GGCTGAGACA ACCGAACCAC      60

CGTCGGACGC GGGGACATCG CAAGCCGACG CGATGGCGTT GGCCGCCGAA GCCGAAGCCG     120

CCGAAGCCGA AGCGCTGGCC GCCGCGGCGC GGGCCCGTGC CCGTGCCGCC CGGTTGAAGC     180

GTGAGGCGCT GGCGATGGCC CCAGCCGAGG ACGAGAACGT CCCCGAGGAT ATGCAGACTG     240

GGAAGACGCC GAAGACTATG ACGACTATGA CGACTATGAG GCCGCAGACC AGGAGGCCGC     300

ACGGTCGGCA TCCTGGCGAC GGCGGTTGCG GGTGCGGTTA CCAAGACTGT CCACGATTGC     360

CATGGCGGCC GCAGTCGTCA TCATCTGCGG CTTCACCGGG CTCAGCGGAT ACATTGTGTG     420

GCAACACCAT GAGGCCACCG AACGCCAGCA GCGCGCCGCG GCGTTCGCCG CCGGAGCCAA     480
```

-continued

```
GCAAGGTGTC ATCAACATGA CCTCGCTGGA CTTCAACAAG GCCAAAGAAG ACGTCGCGCG    540

TGTGATCGAC AGCTCCACCG GCGAATTCAG GGATGACTTC CAGCAGCGGG CAGCCGATTT    600

CACCAAGGTT GTCGAACAGT CCAAAGTGGT CACCGAAGGC ACGGTGAACG CGACAGCCGT    660

CGAATCCATG AACGAGCATT CCGCCGTGGT GCTCGTCGCG GCGACTTCAC GGGTCACCAA    720

TTCCGCTGGG GCGAAAGACG AACCACGTGC GTGGCGGCTC AAAGTGACCG TGACCGAAGA    780

GGGGGGACAG TACAAGATGT CGAAAGTTGA GTTCGTACCG TGACCGATGA CGTACGCGAC    840

GTCAACACCG AAACCACTGA CGCCACCGAA GTCGCTGAGA TCGACTCAGC CGCAGGCGAA    900

GCCGGTGATT CGGCGACCGA GGCATTTGAC ACCGACTCTG CAACGGAATC TACCGCGCAG    960

AAGGGTCAGC GGCACCGTGA CCTGTGGCGA ATGCAGGTTA CCTTGAAACC CGTTCCGGTG   1020

ATTCTCATCC TGCTCATGTT GATCTCTGGG GGCGCGACGG GATGGCTATA CCTTGAGCAA   1080

TACGACCCGA TCAGCAGACG GACTCCGGCG CCGCCCGTGC TGCCGTCGCC GCGGCGTCTG   1140

ACGGGACAAT CGCGCTGTTG TGTATTCACC CGACACGTCG ACCAAGACTT CGCTACCGCC   1200

AGGTCGCACC TCGCCGGCGA TTTCCTGTCC TATACGACCA GTTCACGCAG CAGATCGTGG   1260

CTCCGGCGGC CAAACAGAAG TCACTGAAAA CCACCGCCAA GGTGGTGCGC GCGGCCGTGT   1320

CGGAGCTACA TCCGGATTCG GCCGTCGTTC TGGTTTTTGT CGACCAGAGC ACTACCAGTA   1380

AGGACAGCCC CAATCCGTCG ATGGCGGCCA GCAGCGTGAT GGTGACCCTA GCCAAGGTCG   1440

ACGGCAATTG GCTGATCACC AAGTTCACCC CGGTTTAGGT TGCCGTAGGC GGTCGCCAAG   1500

TCTGACGGGG GCGCGGGTGG CTGCTCGTGC GAGATACCGG CCGTTCTCCG GACAATCACG   1560

GCCCGACCTC AAACAGATCT CGGCCGCTGT CTAATCGGCC GGGTTATTTA AGATTAGTTG   1620

CCACTGTATT TACCTGATGT TCAGATTGTT CAGCTGGATT TAGCTTCGCG GCAGGGCGGC   1680

TGGTGCACTT TGCATCTGGG GTTGTGACTA CTTGAGAGAA TTTGACCTGT TGCCGACGTT   1740

GTTTGCTGTC CATCATTGGT GCTAGTTATG GCCGAGCGGA AGGATTATCG AAGTGGTGGA   1800

CTTCGGGGCG TTACCACCGG AGATCAACTC CGCGAGGATG TACGCCGGCC CGGGTTCGGC   1860

CTCGCTGGTG GCCGCCGCGA AGATGTGGGA CAGCGTGGCG AGTGACCTGT TTTCGGCCGC   1920

GTCGGCGTTT CAGTCGGTGG TCTGGGGTCT GACGACGGGA TCGTGGATAG GTTCGTCGGC   1980

GGGTCTGATG GTGGCGGCGG CCTCGCCGTA TGTGGCGTGG ATGAGCGTCA CCGCGGGGCA   2040

GGCCGAGCTG ACCGCCGCCC AGGTCCGGGT TGCTGCGGCG GCCTACGAGA CGGCGTATGG   2100

GCTGACGGTG CCCCCGCCGG TGATCGCCGA GAACCGTGCT GAACTGATGA TTCTGATAGC   2160

GACCAACCTC TTGGGGCAAA ACACCCCGGC GATCGCGGTC AACGAGGCCG AATACGGGGA   2220

GATGTGGGCC CAAGACGCCG CCGCGATGTT TGGCTACGCC GCCACGGCGG CGACGGCGAC   2280

CGAGGCGTTG CTGCCGTTCG AGGACGCCCC ACTGATCACC AACCCCGCG GGCTCCTTGA   2340

GCAGGCCGTC GCGGTCGAGG AGGCCATCGA CACCGCCGCG GCGAACCAGT TGATGAACAA   2400

TGTGCCCCAA GCGCTGCAAC AACTGGCCCA GCCCACGAAA AGCATCTGGC CGTTCGACCA   2460

ACTGAGTGAA CTCTGGAAAG CCATCTCGCC GCATCTGTCG CCGCTCAGCA ACATCGTGTC   2520

GATGCTCAAC AACCACGTGT CGATGACCAA CTCGGGTGTG TCGATGGCCA GCACCTTGCA   2580

CTCAATGTTG AAGGGCTTTG CTCCGGCGGC GGCTCAGGCC GTGGAAACCG CGGCGCAAAA   2640

CGGGGTCCAG GCGATGAGCT CGCTGGGCAG CCAGCTGGGT TCGTCGCTGG GTTCTTCGGG   2700

TCTGGGCGCT GGGGTGGCCG CCAACTTGGG TCGGGCGGCC TCGGTCGGTT CGTTGTCGGT   2760

GCCGCAGGCC TGGGCCGCGG CCAACCAGGC GGTCACCCCG GCGGCGCGGG CGCTGCCGCT   2820
```

```
GACCAGCCTG ACCAGCGCCG CCCAAACCGC CCCCGGACAC ATGCTGGGCG GGCTACCGCT       2880

GGGGCAACTG ACCAATAGCG GCGGCGGGTT CGGCGGGGTT AGCAATGCGT TGCGGATGCC       2940

GCCGCGGGCG TACGTAATGC CCCGTGTGCC CGCCGCCGGG TAACGCCGAT CCGCACGCAA       3000

TGCGGGCCCT CTATGCGGGC AGCGATC                                           3027
```

(2) INFORMATION FOR SEQ ID NO:106:

(i) SEQUENCE CHARACTERISTICS:
        (A) LENGTH: 396 amino acids
        (B) TYPE: amino acid
        (C) STRANDEDNESS:
        (D) TOPOLOGY: linear (xi) SEQUENCE DESCRIPTION: SEQ ID NO:106:

```
Val Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Lys Met Trp
            20                  25                  30

Asp Ser Val Ala Ser Asp Leu Phe Ser Ala Ala Ser Ala Phe Gln Ser
            35                  40                  45

Val Val Trp Gly Leu Thr Thr Gly Ser Trp Ile Gly Ser Ser Ala Gly
50                  55                  60

Leu Met Val Ala Ala Ala Ser Pro Tyr Val Ala Trp Met Ser Val Thr
65                  70                  75                  80

Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Val Ile Ala
            100                 105                 110

Glu Asn Arg Ala Glu Leu Met Ile Leu Ile Ala Thr Asn Leu Leu Gly
            115                 120                 125

Gln Asn Thr Pro Ala Ile Ala Val Asn Glu Ala Glu Tyr Gly Glu Met
            130                 135                 140

Trp Ala Gln Asp Ala Ala Ala Met Phe Gly Tyr Ala Ala Thr Ala Ala
145                 150                 155                 160

Thr Ala Thr Glu Ala Leu Leu Pro Phe Glu Asp Ala Pro Leu Ile Thr
                165                 170                 175

Asn Pro Gly Gly Leu Leu Glu Gln Ala Val Ala Val Glu Glu Ala Ile
            180                 185                 190

Asp Thr Ala Ala Ala Asn Gln Leu Met Asn Asn Val Pro Gln Ala Leu
            195                 200                 205

Gln Gln Leu Ala Gln Pro Thr Lys Ser Ile Trp Pro Phe Asp Gln Leu
            210                 215                 220

Ser Glu Leu Trp Lys Ala Ile Ser Pro His Leu Ser Pro Leu Ser Asn
225                 230                 235                 240

Ile Val Ser Met Leu Asn Asn His Val Ser Met Thr Asn Ser Gly Val
                245                 250                 255

Ser Met Ala Ser Thr Leu His Ser Met Leu Lys Gly Phe Ala Pro Ala
            260                 265                 270

Ala Ala Gln Ala Val Glu Thr Ala Ala Gln Asn Gly Val Gln Ala Met
            275                 280                 285

Ser Ser Leu Gly Ser Gln Leu Gly Ser Ser Leu Gly Ser Ser Gly Leu
            290                 295                 300

Gly Ala Gly Val Ala Ala Asn Leu Gly Arg Ala Ala Ser Val Gly Ser
305                 310                 315                 320
```

Leu Ser Val Pro Gln Ala Trp Ala Ala Asn Gln Ala Val Thr Pro
                325                 330                 335

Ala Ala Arg Ala Leu Pro Leu Thr Ser Leu Thr Ser Ala Ala Gln Thr
            340                 345                 350

Ala Pro Gly His Met Leu Gly Gly Leu Pro Leu Gly Gln Leu Thr Asn
        355                 360                 365

Ser Gly Gly Gly Phe Gly Gly Val Ser Asn Ala Leu Arg Met Pro Pro
    370                 375                 380

Arg Ala Tyr Val Met Pro Arg Val Pro Ala Ala Gly
385                 390                 395

(2) INFORMATION FOR SEQ ID NO:107:

(i) SEQUENCE CHARACTERISTICS:
        (A) LENGTH: 1616 base pairs
        (B) TYPE: nucleic acid
        (C) STRANDEDNESS: single
        (D) TOPOLOGY: linear (xi) SEQUENCE DESCRIPTION: SEQ ID NO:107:

```
CATCGGAGGG AGTGATCACC ATGCTGTGGC ACGCAATGCC ACCGGAGTAA ATACCGCACG      60

GCTGATGGCC GGCGCGGGTC CGGCTCCAAT GCTTGCGGCG GCCGCGGGAT GGCAGACGCT     120

TTCGGCGGCT CTGGACGCTC AGGCCGTCGA GTTGACCGCG CGCCTGAACT CTCTGGGAGA     180

AGCCTGGACT GGAGGTGGCA GCGACAAGGC GCTTGCGGCT GCAACGCCGA TGGTGGTCTG     240

GCTACAAACC GCGTCAACAC AGGCCAAGAC CCGTGCGATG CAGGCGACGG CGCAAGCCGC     300

GGCATACACC CAGGCCATGG CCACGACGCC GTCGCTGCCG GAGATCGCCG CCAACCACAT     360

CACCCAGGCC GTCCTTACGG CCACCAACTT CTTCGGTATC AACACGATCC CGATCGCGTT     420

GACCGAGATG GATTATTTCA TCCGTATGTG GAACCAGGCA GCCCTGGCAA TGGAGGTCTA     480

CCAGGCCGAG ACCGCGGTTA ACACGCTTTT CGAGAAGCTC GAGCCGATGG CGTCGATCCT     540

TGATCCCGGC GCGAGCCAGA GCACGACGAA CCCGATCTTC GGAATGCCCT CCCCTGGCAG     600

CTCAACACCG GTTGGCCAGT TGCCGCCGGC GGCTACCCAG ACCCTCGGCC AACTGGGTGA     660

GATGAGCGGC CCGATGCAGC AGCTGACCCA GCCGCTGCAG CAGGTGACGT CGTTGTTCAG     720

CCAGGTGGGC GGCACCGGCG GCGGCAACCC AGCCGACGAG GAAGCCGCGC AGATGGGCCT     780

GCTCGGCACC AGTCCGCTGT CGAACCATCC GCTGGCTGGT GGATCAGGCC CCAGCGCGGG     840

CGCGGGCCTG CTGCGCGCGG AGTCGCTACC TGGCGCAGGT GGGTCGTTGA CCCGCACGCC     900

GCTGATGTCT CAGCTGATCG AAAAGCCGGT TGCCCCCTCG GTGATGCCGG CGGCTGCTGC     960

CGGATCGTCG GCGACGGGTG GCGCCGCTCC GGTGGGTGCG GGAGCGATGG GCCAGGGTGC    1020

GCAATCCGGC GGCTCCACCA GGCCGGGTCT GGTCGCGCCG GCACCGCTCG CGCAGGAGCG    1080

TGAAGAAGAC GACGAGGACG ACTGGGACGA AGAGGACGAC TGGTGAGCTC CCGTAATGAC    1140

AACAGACTTC CCGGCCACCC GGGCCGGAAG ACTTGCCAAC ATTTTGGCGA GGAAGGTAAA    1200

GAGAGAAAGT AGTCCAGCAT GGCAGAGATG AAGACCGATG CCGCTACCCT CGCGCAGGAG    1260

GCAGGTAATT TCGAGCGGAT CTCCGGCGAC CTGAAAACCC AGATCGACCA GGTGGAGTCG    1320

ACGGCAGGTT CGTTGCAGGG CCAGTGGCGC GGCGCGGCGG GGACGGCCGC CCAGGCCGCG    1380

GTGGTGCGCT TCCAAGAAGC AGCCAATAAG CAGAAGCAGG AACTCGACGA GATCTCGACG    1440

AATATTCGTC AGGCCGGCGT CCAATACTCG AGGGCCGACG AGGAGCAGCA GCAGGCGCTG    1500

TCCTCGCAAA TGGGCTTCTG ACCCGCTAAT ACGAAAAGAA ACGGAGCAAA AACATGACAG    1560

AGCAGCAGTG GAATTTCGCG GGTATCGAGG CCGCGGCAAG CGCAATCCAG GGAAAT        1616
```

(2) INFORMATION FOR SEQ ID NO:108:

(i) SEQUENCE CHARACTERISTICS:
        (A) LENGTH: 432 base pairs
        (B) TYPE: nucleic acid
        (C) STRANDEDNESS: single
        (D) TOPOLOGY: linear (xi) SEQUENCE DESCRIPTION: SEQ ID NO:108:

```
CTAGTGGATG GGACCATGGC CATTTTCTGC AGTCTCACTG CCTTCTGTGT TGACATTTTG      60

GCACGCCGGC GGAAACGAAG CACTGGGGTC GAAGAACGGC TGCGCTGCCA TATCGTCCGG     120

AGCTTCCATA CCTTCGTGCG GCCGGAAGAG CTTGTCGTAG TCGGCCGCCA TGACAACCTC     180

TCAGAGTGCG CTCAAACGTA TAAACACGAG AAAGGGCGAG ACCGACGGAA GGTCGAACTC     240

GCCCGATCCC GTGTTTCGCT ATTCTACGCG AACTCGGCGT TGCCCTATGC GAACATCCCA     300

GTGACGTTGC CTTCGGTCGA AGCCATTGCC TGACCGGCTT CGCTGATCGT CCGCGCCAGG     360

TTCTGCAGCG CGTTGTTCAG CTCGGTAGCC GTGGCGTCCC ATTTTTGCTG GACACCCTGG     420

TACGCCTCCG AA                                                        432
```

(2) INFORMATION FOR SEQ ID NO:109:

(i) SEQUENCE CHARACTERISTICS:
        (A) LENGTH: 368 amino acids
        (B) TYPE: amino acid
        (C) STRANDEDNESS: single
        (D) TOPOLOGY: linear (xi) SEQUENCE DESCRIPTION: SEQ ID NO:109:

```
Met Leu Trp His Ala Met Pro Pro Glu Xaa Asn Thr Ala Arg Leu Met
1               5                  10                  15

Ala Gly Ala Gly Pro Ala Pro Met Leu Ala Ala Ala Gly Trp Gln
            20                  25                  30

Thr Leu Ser Ala Ala Leu Asp Ala Gln Ala Val Glu Leu Thr Ala Arg
        35                  40                  45

Leu Asn Ser Leu Gly Glu Ala Trp Thr Gly Gly Ser Asp Lys Ala
    50                  55                  60

Leu Ala Ala Ala Thr Pro Met Val Val Trp Leu Gln Thr Ala Ser Thr
65                  70                  75                  80

Gln Ala Lys Thr Arg Ala Met Gln Ala Thr Gln Ala Ala Tyr
                85                  90                  95

Thr Gln Ala Met Ala Thr Thr Pro Ser Leu Pro Glu Ile Ala Ala Asn
                100                 105                 110

His Ile Thr Gln Ala Val Leu Thr Ala Thr Asn Phe Gly Ile Asn
        115                 120                 125

Thr Ile Pro Ile Ala Leu Thr Glu Met Asp Tyr Phe Ile Arg Met Trp
    130                 135                 140

Asn Gln Ala Ala Leu Ala Met Glu Val Tyr Gln Ala Glu Thr Ala Val
145                 150                 155                 160

Asn Thr Leu Phe Glu Lys Leu Glu Pro Met Ala Ser Ile Leu Asp Pro
                165                 170                 175

Gly Ala Ser Gln Ser Thr Thr Asn Pro Ile Phe Gly Met Pro Ser Pro
                180                 185                 190

Gly Ser Ser Thr Pro Val Gly Gln Leu Pro Pro Ala Ala Thr Gln Thr
            195                 200                 205

Leu Gly Gln Leu Gly Glu Met Ser Gly Pro Met Gln Gln Leu Thr Gln
```

```
                210                 215                 220
Pro Leu Gln Gln Val Thr Ser Leu Phe Ser Gln Val Gly Gly Thr Gly
225                 230                 235                 240

Gly Gly Asn Pro Ala Asp Glu Glu Ala Ala Gln Met Gly Leu Leu Gly
                245                 250                 255

Thr Ser Pro Leu Ser Asn His Pro Leu Ala Gly Gly Ser Gly Pro Ser
                260                 265                 270

Ala Gly Ala Gly Leu Leu Arg Ala Glu Ser Leu Pro Gly Ala Gly Gly
            275                 280                 285

Ser Leu Thr Arg Thr Pro Leu Met Ser Gln Leu Ile Glu Lys Pro Val
290                 295                 300

Ala Pro Ser Val Met Pro Ala Ala Ala Gly Ser Ser Ala Thr Gly
305                 310                 315                 320

Gly Ala Ala Pro Val Gly Ala Gly Ala Met Gly Gln Gly Ala Gln Ser
                325                 330                 335

Gly Gly Ser Thr Arg Pro Gly Leu Val Ala Pro Ala Pro Leu Ala Gln
                340                 345                 350

Glu Arg Glu Glu Asp Asp Glu Asp Asp Trp Asp Glu Glu Asp Asp Trp
            355                 360                 365

(2) INFORMATION FOR SEQ ID NO:110:

(i) SEQUENCE CHARACTERISTICS:
        (A) LENGTH: 100 amino acids
        (B) TYPE: amino acid
        (C) STRANDEDNESS:
        (D) TOPOLOGY: linear (xi) SEQUENCE DESCRIPTION: SEQ ID NO:110:

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
                20                  25                  30

Glu Ser Thr Ala Gly Ser Leu Gln Gly Gln Trp Arg Gly Ala Ala Gly
            35                  40                  45

Thr Ala Ala Gln Ala Ala Val Val Arg Phe Gln Glu Ala Ala Asn Lys
50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Ala Leu Ser Ser
                85                  90                  95

Gln Met Gly Phe
            100

(2) INFORMATION FOR SEQ ID NO:111:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (xi) SEQUENCE DESCRIPTION: SEQ ID NO:111:

GATCTCCGGC GACCTGAAAA CCCAGATCGA CCAGGTGGAG TCGACGGCAG GTTCGTTGCA        60

GGGCCAGTGG CGCGGCGCGG CGGGGACGGC CGCCCAGGCC GCGGTGGTGC GCTTCCAAGA       120

AGCAGCCAAT AAGCAGAAGC AGGAACTCGA CGAGATCTCG ACGAATATTC GTCAGGCCGG       180

CGTCCAATAC TCGAGGGCCG ACGAGGAGCA GCAGCAGGCG CTGTCCTCGC AAATGGGCTT       240
```

```
CTGACCCGCT AATACGAAAA GAAACGGAGC AAAAACATGA CAGAGCAGCA GTGGAATTTC      300

GCGGGTATCG AGGCCGCGGC AAGCGCAATC CAGGGAAATG TCACGTCCAT TCATTCCCTC      360

CTTGACGAGG GGAAGCAGTC CCTGACCAAG CTCGCA                                396

(2) INFORMATION FOR SEQ ID NO:112:

(i) SEQUENCE CHARACTERISTICS:
        (A) LENGTH: 80 amino acids
        (B) TYPE: amino acid
        (C) STRANDEDNESS: single
        (D) TOPOLOGY: linear (xi) SEQUENCE DESCRIPTION: SEQ ID NO:112:

Ile Ser Gly Asp Leu Lys Thr Gln Ile Asp Gln Val Glu Ser Thr Ala
1               5                   10                  15

Gly Ser Leu Gln Gly Gln Trp Arg Gly Ala Ala Gly Thr Ala Ala Gln
            20                  25                  30

Ala Ala Val Val Arg Phe Gln Glu Ala Ala Asn Lys Gln Lys Gln Glu
        35                  40                  45

Leu Asp Glu Ile Ser Thr Asn Ile Arg Gln Ala Gly Val Gln Tyr Ser
    50                  55                  60

Arg Ala Asp Glu Glu Gln Gln Gln Ala Leu Ser Ser Gln Met Gly Phe
65                  70                  75                  80

(2) INFORMATION FOR SEQ ID NO:113:

(i) SEQUENCE CHARACTERISTICS:
        (A) LENGTH: 387 base pairs
        (B) TYPE: nucleic acid
        (C) STRANDEDNESS: single
        (D) TOPOLOGY: linear (xi) SEQUENCE DESCRIPTION: SEQ ID NO:113:

GTGGATCCCG ATCCCGTGTT TCGCTATTCT ACGCGAACTC GGCGTTGCCC TATGCGAACA       60

TCCCAGTGAC GTTGCCTTCG GTCGAAGCCA TTGCCTGACC GGCTTCGCTG ATCGTCCGCG      120

CCAGGTTCTG CAGCGCGTTG TTCAGCTCGG TAGCCGTGGC GTCCCATTTT TGCTGGACAC      180

CCTGGTACGC CTCCGAACCG CTACCGCCCC AGGCCGCTGC GAGCTTGGTC AGGGACTGCT      240

TCCCCTCGTC AAGGAGGGAA TGAATGGACG TGACATTTCC CTGGATTGCG CTTGCCGCGG      300

CCTCGATACC CGCGAAATTC CACTGCTGCT CTGTCATGTT TTTGCTCCGT TTCTTTTCGT      360

ATTAGCGGGT CAGAAGCCCA TTTGCGA                                         387

(2) INFORMATION FOR SEQ ID NO:114:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (xi) SEQUENCE DESCRIPTION: SEQ ID NO:114:

CGGCACGAGG ATCTCGGTTG GCCCAACGGC GCTGGCGAGG GCTCCGTTCC GGGGGCGAGC       60

TGCGCGCCGG ATGCTTCCTC TGCCCGCAGC CGCGCCTGGA TGGATGGACC AGTTGCTACC      120

TTCCCGACGT TCGTTCGGT GTCTGTGCGA TAGCGGTGAC CCCGGCGCGC ACGTCGGGAG       180

TGTTGGGGGG CAGGCCGGGT CGGTGGTTCG GCCGGGACG CAGACGGTCT GGACGGAACG       240

GGCGGGGGTT CGCCGATTGG CATCTTTGCC CA                                    272
```

(2) INFORMATION FOR SEQ ID NO:115:

(i) SEQUENCE CHARACTERISTICS:
        (A) LENGTH: 20 amino acids
        (B) TYPE: amino acid
        (C) STRANDEDNESS:
        (D) TOPOLOGY: linear (xi) SEQUENCE DESCRIPTION: SEQ ID NO:115:

```
Asp Pro Val Asp Ala Val Ile Asn Thr Thr Cys Asn Tyr Gly Gln Val
1               5                   10                  15
Val Ala Ala Leu
            20
```

(2) INFORMATION FOR SEQ ID NO:116:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:116:

```
Ala Val Glu Ser Gly Met Leu Ala Leu Gly Thr Pro Ala Pro Ser
1               5                   10                  15
```

(2) INFORMATION FOR SEQ ID NO:117:

(i) SEQUENCE CHARACTERISTICS:
        (A) LENGTH: 19 amino acids
        (B) TYPE: amino acid
        (C) STRANDEDNESS:
        (D) TOPOLOGY: linear (xi) SEQUENCE DESCRIPTION: SEQ ID NO:117:

```
Ala Ala Met Lys Pro Arg Thr Gly Asp Gly Pro Leu Glu Ala Ala Lys
1               5                   10                  15
Glu Gly Arg
```

(2) INFORMATION FOR SEQ ID NO:118:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:118:

```
Tyr Tyr Trp Cys Pro Gly Gln Pro Phe Asp Pro Ala Trp Gly Pro
1               5                   10                  15
```

(2) INFORMATION FOR SEQ ID NO:119:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:119:

```
Asp Ile Gly Ser Glu Ser Thr Glu Asp Gln Gln Xaa Ala Val
1               5                   10
```

(2) INFORMATION FOR SEQ ID NO:120:

(i) SEQUENCE CHARACTERISTICS:

(A) LENGTH: 13 amino acids
        (B) TYPE: amino acid
        (C) STRANDEDNESS:
        (D) TOPOLOGY: linear (xi) SEQUENCE DESCRIPTION: SEQ ID NO:120:

Ala Glu Glu Ser Ile Ser Thr Xaa Glu Xaa Ile Val Pro
1               5                  10

(2) INFORMATION FOR SEQ ID NO:121:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:121:

Asp Pro Glu Pro Ala Pro Pro Val Pro Thr Thr Ala Ala Ser Pro Pro
1               5                  10                  15

Ser (2) INFORMATION FOR SEQ ID NO:122:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:122:

Ala Pro Lys Thr Tyr Xaa Glu Glu Leu Lys Gly Thr Asp Thr Gly
1               5                  10                  15

(2) INFORMATION FOR SEQ ID NO:123:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:123:

Asp Pro Ala Ser Ala Pro Asp Val Pro Thr Ala Ala Gln Leu Thr Ser
1               5                  10                  15

Leu Leu Asn Ser Leu Ala Asp Pro Asn Val Ser Phe Ala Asn
            20                  25                  30

(2) INFORMATION FOR SEQ ID NO:124:

(i) SEQUENCE CHARACTERISTICS:
        (A) LENGTH: 22 amino acids
        (B) TYPE: amino acid
        (C) STRANDEDNESS:
        (D) TOPOLOGY: linear (xi) SEQUENCE DESCRIPTION: SEQ ID NO:124:

Asp Pro Pro Asp Pro His Gln Xaa Asp Met Thr Lys Gly Tyr Tyr Pro
1               5                  10                  15

Gly Gly Arg Arg Xaa Phe
            20

(2) INFORMATION FOR SEQ ID NO:125:

(i) SEQUENCE CHARACTERISTICS:
        (A) LENGTH: 7 amino acids

```
            (B) TYPE: amino acid
            (C) STRANDEDNESS:
            (D) TOPOLOGY: linear (xi) SEQUENCE DESCRIPTION: SEQ ID NO:125:

Asp Pro Gly Tyr Thr Pro Gly
1               5

(2) INFORMATION FOR SEQ ID NO:126:

(i) SEQUENCE CHARACTERISTICS:
            (A) LENGTH: 10 amino acids
            (B) TYPE: amino acid
            (C) STRANDEDNESS:
            (D) TOPOLOGY: linear (ix) FEATURE:
            (D) OTHER INFORMATION: /note= "The Second Residue Can Be
                Either a Pro or Thr"

(xi) SEQUENCE DESCRIPTION: SEQ ID NO:126:

Xaa Xaa Gly Phe Thr Gly Pro Gln Phe Tyr
1               5                   10

(2) INFORMATION FOR SEQ ID NO:127:

(i) SEQUENCE CHARACTERISTICS:
            (A) LENGTH: 9 amino acids
            (B) TYPE: amino acid
            (C) STRANDEDNESS:
            (D) TOPOLOGY: linear (ix) FEATURE:
            (D) OTHER INFORMATION: /note= "The Third Residue Can Be Either
                a Gln or Leu"

(xi) SEQUENCE DESCRIPTION: SEQ ID NO:127:

Xaa Pro Xaa Val Thr Ala Tyr Ala Gly
1               5

(2) INFORMATION FOR SEQ ID NO:128:

(i) SEQUENCE CHARACTERISTICS:
            (A) LENGTH: 9 amino acids
            (B) TYPE: amino acid
            (C) STRANDEDNESS:
            (D) TOPOLOGY: linear (xi) SEQUENCE DESCRIPTION: SEQ ID NO:128:

Xaa Xaa Xaa Glu Lys Pro Phe Leu Arg
1               5

(2) INFORMATION FOR SEQ ID NO:129:

(i) SEQUENCE CHARACTERISTICS:
            (A) LENGTH: 15 amino acids
            (B) TYPE: amino acid
            (C) STRANDEDNESS:
            (D) TOPOLOGY: linear (xi) SEQUENCE DESCRIPTION: SEQ ID NO:129:

Xaa Asp Ser Glu Lys Ser Ala Thr Ile Lys Val Thr Asp Ala Ser
1               5                   10                  15

(2) INFORMATION FOR SEQ ID NO:130:

(i) SEQUENCE CHARACTERISTICS:
            (A) LENGTH: 15 amino acids
            (B) TYPE: amino acid
```

```
            (C) STRANDEDNESS:
            (D) TOPOLOGY: linear (xi) SEQUENCE DESCRIPTION: SEQ ID NO:130:

Ala Gly Asp Thr Xaa Ile Tyr Ile Val Gly Asn Leu Thr Ala Asp
 1               5                  10                  15

(2) INFORMATION FOR SEQ ID NO:131:

(i) SEQUENCE CHARACTERISTICS:
            (A) LENGTH: 15 amino acids
            (B) TYPE: amino acid
            (C) STRANDEDNESS:
            (D) TOPOLOGY: linear (xi) SEQUENCE DESCRIPTION: SEQ ID NO:131:

Ala Pro Glu Ser Gly Ala Gly Leu Gly Gly Thr Val Gln Ala Gly
 1               5                  10                  15

(2) INFORMATION FOR SEQ ID NO:132:

(i) SEQUENCE CHARACTERISTICS:
            (A) LENGTH: 21 amino acids
            (B) TYPE: amino acid
            (C) STRANDEDNESS:
            (D) TOPOLOGY: linear (xi) SEQUENCE DESCRIPTION: SEQ ID NO:132:

Xaa Tyr Ile Ala Tyr Xaa Thr Thr Ala Gly Ile Val Pro Gly Lys Ile
 1               5                  10                  15

Asn Val His Leu Val
            20

(2) INFORMATION FOR SEQ ID NO:133:

(i) SEQUENCE CHARACTERISTICS:
            (A) LENGTH: 882 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:133:

GCAACGCTGT CGTGGCCTTT GCGGTGATCG GTTTCGCCTC GCTGGCGGTG GCGGTGGCGG       60

TCACCATCCG ACCGACCGCG GCCTCAAAAC CGGTAGAGGG ACACCAAAAC GCCCAGCCAG      120

GGAAGTTCAT GCCGTTGTTG CCGACGCAAC AGCAGGCGCC GGTCCCGCCG CCTCCGCCCG      180

ATGATCCCAC CGCTGGATTC CAGGGCGGCA CCATTCCGGC TGTACAGAAC GTGGTGCCGC      240

GGCCGGGTAC CTCACCCGGG GTGGGTGGGA CGCCGGCTTC GCCTGCGCCG GAAGCGCCGG      300

CCGTGCCCGG TGTTGTGCCT GCCCCGGTGC CAATCCCGGT CCCGATCATC ATTCCCCCGT      360

TCCCGGGTTG GCAGCCTGGA ATGCCGACCA TCCCCACCGC ACCGCCGACG ACGCCGGTGA      420

CCACGTCGGC GACGACGCCG CCGACCACGC CGCCGACCAC GCCGGTGACC ACGCCGCCAA      480

CGACGCCGCC GACCACGCCG GTGACCACGC CGCCAACGAC GCCGCCGACC ACGCCGGTGA      540

CCACGCCACC AACGACCGTC GCCCCGACGA CCGTCGCCCC GACGACGGTC GCTCCGACCA      600

CCGTCGCCCC GACCACGGTC GCTCCAGCCA CCGCCACGCC GACGACCGTC GCTCCGCAGC      660

CGACGCAGCA GCCCACGCAA CAACCAACCC AACAGATGCC AACCCAGCAG CAGACCGTGG      720

CCCCGCAGAC GGTGGCGCCG GCTCCGCAGC CGCCGTCCGG TGGCCGCAAC GGCAGCGGCG      780

GGGGCGACTT ATTCGGCGGG TTCTGATCAC GGTCGCGGCT TCACTACGGT CGGAGGACAT      840
```

```
GGCCGGTGAT GCGGTGACGG TGGTGCTGCC CTGTCTCAAC GA                882

(2) INFORMATION FOR SEQ ID NO:134:

(i) SEQUENCE CHARACTERISTICS:
        (A) LENGTH: 815 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:134:

CCATCAACCA ACCGCTCGCG CCGCCCGCGC CGCCGGATCC GCCGTCGCCG CCACGCCCGC   60

CGGTGCCTCC GGTGCCCCCG TTGCCGCCGT CGCCGCCGTC GCCGCCGACC GGCTGGGTGC  120

CTAGGGCGCT GTTACCGCCC TGGTTGGCGG GGACGCCGCC GGCACCACCG GTACCGCCGA  180

TGGCGCCGTT GCCGCCGGCG GCACCGTTGC CACCGTTGCC ACCGTTGCCA CCGTTGCCGA  240

CCAGCCACCC GCCGCGACCA CCGGCACCGC CGGCGCCGCC CGCACCGCCG GCGTGCCCGT  300

TCGTGCCCGT ACCGCCGGCA CCGCCGTTGC CGCCGTCACC GCCGACGGAA CTACCGGCGG  360

ACGCGGCCTG CCCGCCGGCG CCGCCCGCAC CGCCATTGGC ACCGCCGTCA CCGCCGGCTG  420

GGAGTGCCGC GATTAGGGCA CTGACCGGCG CAACCAGCGC AAGTACTCTC GGTCACCGAG  480

CACTTCCAGA CGACACCACA GCACGGGGTT GTCGGCGGAC TGGGTGAAAT GGCAGCCGAT  540

AGCGGCTAGC TGTCGGCTGC GGTCAACCTC GATCATGATG TCGAGGTGAC CGTGACCGCG  600

CCCCCCGAAG GAGGCGCTGA ACTCGGCGTT GAGCCGATCG GCGATCGGTT GGGGCAGTGC  660

CCAGGCCAAT ACGGGGATAC CGGGTGTCNA AGCCGCCGCG AGCGCAGCTT CGGTTGCGCG  720

ACNGTGGTCG GGGTGGCCTG TTACGCCGTT GTCNTCGAAC ACGAGTAGCA GGTCTGCTCC  780

GGCGAGGGCA TCCACCACGC GTTGCGTCAG CTCGT                            815

(2) INFORMATION FOR SEQ ID NO:135:

(i) SEQUENCE CHARACTERISTICS:
        (A) LENGTH: 1152 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:135:

ACCAGCCGCC GGCTGAGGTC TCAGATCAGA GAGTCTCCGG ACTCACCGGG GCGGTTCAGC   60

CTTCTCCCAG AACAACTGCT GAAGATCCTC GCCCGCGAAA CAGGCGCTGA TTTGACGCTC  120

TATGACCGGT TGAACGACGA GATCATCCGG CAGATTGATA TGGCACCGCT GGGCTAACAG  180

GTGCGCAAGA TGGTGCAGCT GTATGTCTCG GACTCCGTGT CGCGGATCAG CTTTGCCGAC  240

GGCCGGGTGA TCGTGTGGAG CGAGGAGCTC GGCGAGAGCC AGTATCCGAT CGAGACGCTG  300

GACGGCATCA CGCTGTTTGG GCGGCCGACG ATGACAACGC CCTTCATCGT TGAGATGCTC  360

AAGCGTGAGC GCGACATCCA GCTCTTCACG ACCGACGGCC ACTACCAGGG CCGGATCTCA  420

ACACCCGACG TGTCATACGC GCCGCGGCTC CGTCAGCAAG TTCACCGCAC CGACGATCCT  480

GCGTTCTGCC TGTCGTTAAG CAAGCGGATC GTGTCGAGGA AGATCCTGAA TCAGCAGGCC  540

TTGATTCGGG CACACACGTC GGGGCAAGAC GTTGCTGAGA GCATCCGCAC GATGAAGCAC  600

TCGCTGGCCT GGGTCGATCG ATCGGGCTCC CTGGCGGAGT TGAACGGGTT CGAGGGAAAT  660
```

```
GCCGCAAAGG CATACTTCAC CGCGCTGGGG CATCTCGTCC CGCAGGAGTT CGCATTCCAG      720

GGCCGCTCGA CTCGGCCGCC GTTGGACGCC TTCAACTCGA TGGTCAGCCT CGGCTATTCG      780

CTGCTGTACA AGAACATCAT AGGGGCGATC GAGCGTCACA GCCTGAACGC GTATATCGGT      840

TTCCTACACC AGGATTCACG AGGGCACGCA ACGTCTCGTG CCGAATTCGG CACGAGCTCC      900

GCTGAAACCG CTGGCCGGCT GCTCAGTGCC CGTACGTAAT CCGCTGCGCC CAGGCCGGCC      960

CGCCGGCCGA ATACCAGCAG ATCGGACAGC GAATTGCCGC CCAGCCGGTT GGAGCCGTGC     1020

ATACCGCCGG CACACTCACC GGCAGCGAAC AGGCCTGGCA CCGTGGCGGC GCCGGTGTCC     1080

GCGTCTACTT CGACACCGCC CATCACGTAG TGACACGTCG GCCCGACTTC CATTGCCTGC     1140

GTTCGGCACG AG                                                        1152
```

(2) INFORMATION FOR SEQ ID NO:136:

(i) SEQUENCE CHARACTERISTICS:
        (A) LENGTH: 655 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:136:

```
CTCGTGCCGA TTCGGCAGGG TGTACTTGCC GGTGGTGTAN GCCGCATGAG TGCCGACGAC       60

CAGCAATGCG GCAACAGCAC GGATCCCGGT CAACGACGCC ACCCGGTCCA CGTGGGCGAT      120

CCGCTCGAGT CCGCCCTGGG CGGCTCTTTC CTTGGGCAGG GTCATCCGAC GTGTTTCCGC      180

CGTGGTTTGC CGCCATTATG CCGGCGCGCC GCGTCGGGCG GCCGGTATGG CCGAANGTCG      240

ATCAGCACAC CCGAGATACG GGTCTGTGCA AGCTTTTTGA GCGTCGCGCG GGGCAGCTTC      300

GCCGGCAATT CTACTAGCGA GAAGTCTGGC CCGATACGGA TCTGACCGAA GTCGCTGCGG      360

TGCAGCCCAC CCTCATTGGC GATGGCGCCG ACGATGGCGC CTGGACCGAT CTTGTGCCGC      420

TTGCCGACGG CGACGCGGTA GGTGGTCAAG TCCGGTCTAC GCTTGGGCCT TTGCGGACGG      480

TCCCGACGCT GGTCGCGGTT GCGCCGCGAA AGCGGCGGGT CGGGTGCCAT CAGGAATGCC      540

TCACCGCCGC GGCACTGCAC GGCCAGTGCC GCGGCGATGT CAGCCATCGG GACATCATGC      600

TCGCGTTCAT ACTCCTCGAC CAGTCGGCGG AACAGCTCGA TTCCCGGACC GCCCA          655
```

(2) INFORMATION FOR SEQ ID NO:137:

(i) SEQUENCE CHARACTERISTICS:
        (A) LENGTH: 267 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:137:

```
Asn Ala Val Val Ala Phe Ala Val Ile Gly Phe Ala Ser Leu Ala Val
 1               5                  10                  15

Ala Val Ala Val Thr Ile Arg Pro Thr Ala Ala Ser Lys Pro Val Glu
            20                  25                  30

Gly His Gln Asn Ala Gln Pro Gly Lys Phe Met Pro Leu Leu Pro Thr
        35                  40                  45

Gln Gln Gln Ala Pro Val Pro Pro Pro Pro Asp Asp Pro Thr Ala
    50                  55                  60

Gly Phe Gln Gly Gly Thr Ile Pro Ala Val Gln Asn Val Val Pro Arg
```

```
65                  70                  75                  80
Pro Gly Thr Ser Pro Gly Val Gly Gly Thr Pro Ala Ser Pro Ala Pro
                85                  90                  95
Glu Ala Pro Ala Val Pro Gly Val Val Pro Ala Pro Val Pro Ile Pro
                100                 105                 110
Val Pro Ile Ile Ile Pro Pro Phe Pro Gly Trp Gln Pro Gly Met Pro
                115                 120                 125
Thr Ile Pro Thr Ala Pro Pro Thr Thr Pro Val Thr Thr Ser Ala Thr
                130                 135                 140
Thr Pro Pro Thr Thr Pro Thr Thr Pro Val Thr Thr Pro Pro Thr
145                 150                 155                 160
Thr Pro Pro Thr Thr Pro Val Thr Thr Pro Pro Thr Thr Pro Pro Thr
                165                 170                 175
Thr Pro Val Thr Thr Pro Pro Thr Thr Val Ala Pro Thr Thr Val Ala
                180                 185                 190
Pro Thr Thr Val Ala Pro Thr Thr Val Ala Pro Thr Thr Val Ala Pro
                195                 200                 205
Ala Thr Ala Thr Pro Thr Thr Val Ala Pro Gln Pro Thr Gln Gln Pro
                210                 215                 220
Thr Gln Gln Pro Thr Gln Gln Met Pro Thr Gln Gln Gln Thr Val Ala
225                 230                 235                 240
Pro Gln Thr Val Ala Pro Ala Pro Gln Pro Pro Ser Gly Gly Arg Asn
                245                 250                 255
Gly Ser Gly Gly Gly Asp Leu Phe Gly Phe
                260                 265
```

(2) INFORMATION FOR SEQ ID NO:138:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:138:

```
Ile Asn Gln Pro Leu Ala Pro Pro Ala Pro Pro Asp Pro Pro Ser Pro
1               5                   10                  15
Pro Arg Pro Pro Val Pro Pro Val Pro Pro Leu Pro Pro Ser Pro Pro
                20                  25                  30
Ser Pro Pro Thr Gly Trp Val Pro Arg Ala Leu Leu Pro Pro Trp Leu
                35                  40                  45
Ala Gly Thr Pro Pro Ala Pro Pro Val Pro Pro Met Ala Pro Leu Pro
50                  55                  60
Pro Ala Ala Pro Leu Pro Pro Leu Pro Pro Leu Pro Pro Leu Pro Thr
65                  70                  75                  80
Ser His Pro Pro Arg Pro Pro Ala Pro Pro Ala Pro Pro Ala Pro Pro
                85                  90                  95
Ala Cys Pro Phe Val Pro Val Pro Pro Ala Pro Pro Leu Pro Pro Ser
                100                 105                 110
Pro Pro Thr Glu Leu Pro Ala Asp Ala Ala Cys Pro Pro Ala Pro Pro
                115                 120                 125
Ala Pro Pro Leu Ala Pro Pro Ser Pro Pro Ala Gly Ser Ala Ala Ile
                130                 135                 140
Arg Ala Leu Thr Gly Ala Thr Ser Ala Ser Thr Leu Gly His Arg Ala
```

```
                145                 150                 155                 160
Leu Pro Asp Asp Thr Thr Ala Arg Gly Cys Arg Arg Thr Gly
                    165                 170
```

(2) INFORMATION FOR SEQ ID NO:139:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:139:

```
Gln Pro Pro Ala Glu Val Ser Asp Gln Arg Val Ser Gly Leu Thr Gly
1               5                   10                  15
Ala Val Gln Pro Ser Pro Arg Thr Thr Ala Glu Asp Pro Arg Pro Arg
                20                  25                  30
Asn Arg Arg
        35
```

(2) INFORMATION FOR SEQ ID NO:140:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:140:

```
Arg Ala Asp Ser Ala Gly Cys Thr Cys Arg Trp Cys Xaa Pro His Glu
1               5                   10                  15
Cys Arg Arg Pro Ala Met Arg Gln Gln His Gly Ser Arg Ser Thr Thr
                20                  25                  30
Pro Pro Gly Pro Arg Gly Arg Ser Ala Arg Val Arg Pro Gly Arg Leu
            35                  40                  45
Phe Pro Trp Ala Gly Ser Ser Asp Val Phe Pro Pro Trp Phe Ala Ala
        50                  55                  60
Ile Met Pro Ala Arg Arg Val Gly Arg Pro Val Trp Pro Xaa Val Asp
65                  70                  75                  80
Gln His Thr Arg Asp Thr Gly Leu Cys Lys Leu Phe Glu Arg Arg Ala
                85                  90                  95
Gly Gln Leu Arg Arg Gln Phe Tyr
            100
```

(2) INFORMATION FOR SEQ ID NO:141:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(vi) ORIGINAL SOURCE:
        (A) ORGANISM: Mycobacterium tuberculosis (xi) SEQUENCE DESCRIPTION: SEQ ID NO:141:

```
GGATCCATAT GGGCCATCAT CATCATCATC ACGTGATCGA CATCATCGGG ACC           53
```

(2) INFORMATION FOR SEQ ID NO:142:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR Primer"

(vi) ORIGINAL SOURCE:
        (A) ORGANISM: Mycobacterium tuberculosis (xi) SEQUENCE DESCRIPTION: SEQ ID NO:142:

CCTGAATTCA GGCCTCGGTT GCGCCGGCCT CATCTTGAAC GA                        42

(2) INFORMATION FOR SEQ ID NO:143:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR Primer"

(vi) ORIGINAL SOURCE:
        (A) ORGANISM: Mycobacterium tuberculosis (xi) SEQUENCE DESCRIPTION: SEQ ID NO:143:

GGATCCTGCA GGCTCGAAAC CACCGAGCGG T                                    31

(2) INFORMATION FOR SEQ ID NO:144:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(vi) ORIGINAL SOURCE:
        (A) ORGANISM: Mycobacterium tuberculosis (xi) SEQUENCE DESCRIPTION: SEQ ID NO:144:

CTCTGAATTC AGCGCTGGAA ATCGTCGCGA T                                    31

(2) INFORMATION FOR SEQ ID NO:145:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(vi) ORIGINAL SOURCE:
        (A) ORGANISM: Mycobacterium tuberculosis (xi) SEQUENCE DESCRIPTION: SEQ ID NO:145:

GGATCCAGCG CTGAGATGAA GACCGATGCC GCT                                33

(2) INFORMATION FOR SEQ ID NO:146:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR primer"

(vi) ORIGINAL SOURCE:
            (A) ORGANISM: Mycobacterium tuberculosis (xi) SEQUENCE DESCRIPTION: SEQ ID NO:146:

GAGAGAATTC TCAGAAGCCC ATTTGCGAGG ACA                                    33

(2) INFORMATION FOR SEQ ID NO:147:

(i) SEQUENCE CHARACTERISTICS:
            (A) LENGTH: 1993 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Mycobacterium tuberculosis (ix) FEATURE:
            (A) NAME/KEY: CDS
            (B) LOCATION: 152..1273

(xi) SEQUENCE DESCRIPTION: SEQ ID NO:147:

TGTTCTTCGA CGGCAGGCTG GTGGAGGAAG GGCCCACCGA ACAGCTGTTC TCCTCGCCGA        60

AGCATGCGGA AACCGCCCGA TACGTCGCCG GACTGTCGGG GGACGTCAAG GACGCCAAGC      120

GCGGAAATTG AAGAGCACAG AAAGGTATGG C GTG AAA ATT CGT TTG CAT ACG         172
                                  Val Lys Ile Arg Leu His Thr
                                    1               5

CTG TTG GCC GTG TTG ACC GCT GCG CCG CTG CTG CTA GCA GCG GCG GGC        220
Leu Leu Ala Val Leu Thr Ala Ala Pro Leu Leu Leu Ala Ala Ala Gly
         10                  15                  20

TGT GGC TCG AAA CCA CCG AGC GGT TCG CCT GAA ACG GGC GCC GGC GCC        268
Cys Gly Ser Lys Pro Pro Ser Gly Ser Pro Glu Thr Gly Ala Gly Ala
 25                  30                  35

GGT ACT GTC GCG ACT ACC CCC GCG TCG TCG CCG GTG ACG TTG GCG GAG        316
Gly Thr Val Ala Thr Thr Pro Ala Ser Ser Pro Val Thr Leu Ala Glu
 40                  45                  50                  55

ACC GGT AGC ACG CTG CTC TAC CCG CTG TTC AAC CTG TGG GGT CCG GCC        364
Thr Gly Ser Thr Leu Leu Tyr Pro Leu Phe Asn Leu Trp Gly Pro Ala
                 60                  65                  70

TTT CAC GAG AGG TAT CCG AAC GTC ACG ATC ACC GCT CAG GGC ACC GGT        412
Phe His Glu Arg Tyr Pro Asn Val Thr Ile Thr Ala Gln Gly Thr Gly
             75                  80                  85

TCT GGT GCC GGG ATC GCG CAG GCC GCC GCC GGG ACG GTC AAC ATT GGG        460
Ser Gly Ala Gly Ile Ala Gln Ala Ala Ala Gly Thr Val Asn Ile Gly
             90                  95                 100

GCC TCC GAC GCC TAT CTG TCG GAA GGT GAT ATG GCC GCG CAC AAG GGG        508
Ala Ser Asp Ala Tyr Leu Ser Glu Gly Asp Met Ala Ala His Lys Gly
        105                 110                 115

CTG ATG AAC ATC GCG CTA GCC ATC TCC GCT CAG CAG GTC AAC TAC AAC        556
Leu Met Asn Ile Ala Leu Ala Ile Ser Ala Gln Gln Val Asn Tyr Asn
120                 125                 130                 135

CTG CCC GGA GTG AGC GAG CAC CTC AAG CTG AAC GGA AAA GTC CTG GCG        604
Leu Pro Gly Val Ser Glu His Leu Lys Leu Asn Gly Lys Val Leu Ala

```
                  140                 145                 150
GCC ATG TAC CAG GGC ACC ATC AAA ACC TGG GAC GAC CCG CAG ATC GCT       652
Ala Met Tyr Gln Gly Thr Ile Lys Thr Trp Asp Asp Pro Gln Ile Ala
            155                 160                 165

GCG CTC AAC CCC GGC GTG AAC CTG CCC GGC ACC GCG GTA GTT CCG CTG       700
Ala Leu Asn Pro Gly Val Asn Leu Pro Gly Thr Ala Val Val Pro Leu
        170                 175                 180

CAC CGC TCC GAC GGG TCC GGT GAC ACC TTC TTG TTC ACC CAG TAC CTG       748
His Arg Ser Asp Gly Ser Gly Asp Thr Phe Leu Phe Thr Gln Tyr Leu
185                 190                 195

TCC AAG CAA GAT CCC GAG GGC TGG GGC AAG TCG CCC GGC TTC GGC ACC       796
Ser Lys Gln Asp Pro Glu Gly Trp Gly Lys Ser Pro Gly Phe Gly Thr
200                 205                 210                 215

ACC GTC GAC TTC CCG GCG GTG CCG GGT GCG CTG GGT GAG AAC GGC AAC       844
Thr Val Asp Phe Pro Ala Val Pro Gly Ala Leu Gly Glu Asn Gly Asn
                220                 225                 230

GGC GGC ATG GTG ACC GGT TGC GCC GAG ACA CCG GGC TGC GTG GCC TAT       892
Gly Gly Met Val Thr Gly Cys Ala Glu Thr Pro Gly Cys Val Ala Tyr
            235                 240                 245

ATC GGC ATC AGC TTC CTC GAC CAG GCC AGT CAA CGG GGA CTC GGC GAG       940
Ile Gly Ile Ser Phe Leu Asp Gln Ala Ser Gln Arg Gly Leu Gly Glu
        250                 255                 260

GCC CAA CTA GGC AAT AGC TCT GGC AAT TTC TTG TTG CCC GAC GCG CAA       988
Ala Gln Leu Gly Asn Ser Ser Gly Asn Phe Leu Leu Pro Asp Ala Gln
265                 270                 275

AGC ATT CAG GCC GCG GCG GCT GGC TTC GCA TCG AAA ACC CCG GCG AAC      1036
Ser Ile Gln Ala Ala Ala Ala Gly Phe Ala Ser Lys Thr Pro Ala Asn
280                 285                 290                 295

CAG GCG ATT TCG ATG ATC GAC GGG CCC GCC CCG GAC GGC TAC CCG ATC      1084
Gln Ala Ile Ser Met Ile Asp Gly Pro Ala Pro Asp Gly Tyr Pro Ile
                300                 305                 310

ATC AAC TAC GAG TAC GCC ATC GTC AAC AAC CGG CAA AAG GAC GCC GCC      1132
Ile Asn Tyr Glu Tyr Ala Ile Val Asn Asn Arg Gln Lys Asp Ala Ala
            315                 320                 325

ACC GCG CAG ACC TTG CAG GCA TTT CTG CAC TGG GCG ATC ACC GAC GGC      1180
Thr Ala Gln Thr Leu Gln Ala Phe Leu His Trp Ala Ile Thr Asp Gly
        330                 335                 340

AAC AAG GCC TCG TTC CTC GAC CAG GTT CAT TTC CAG CCG CTG CCG CCC      1228
Asn Lys Ala Ser Phe Leu Asp Gln Val His Phe Gln Pro Leu Pro Pro
345                 350                 355

GCG GTG GTG AAG TTG TCT GAC GCG TTG ATC GCG ACG ATT TCC AGC          1273
Ala Val Val Lys Leu Ser Asp Ala Leu Ile Ala Thr Ile Ser Ser
360                 365                 370

TAGCCTCGTT GACCACCACG CGACAGCAAC CTCCGTCGGG CCATCGGGCT GCTTTGCGGA    1333
GCATGCTGGC CCGTGCCGGT GAAGTCGGCC GCGCTGGCCC GGCCATCCGG TGGTTGGGTG    1393
GGATAGGTGC GGTGATCCCG CTGCTTGCGC TGGTCTTGGT GCTGGTGGTG CTGGTCATCG    1453
AGGCGATGGG TGCGATCAGG CTCAACGGGT TGCATTTCTT CACCGCCACC GAATGGAATC    1513
CAGGCAACAC CTACGGCGAA ACCGTTGTCA CCGACGCGTC GCCCATCCGG TCGGCGCCTA    1573
CTACGGGGCG TTGCCGCTGA TCGTCGGGAC GCTGGCGACC TCGGCAATCG CCCTGATCAT    1633
CGCGGTGCCG GTCTCTGTAG GAGCGGCGCT GGTGATCGTG GAACGGCTGC CGAAACGGTT    1693
GGCCGAGGCT GTGGGAATAG TCCTGGAATT GCTCGCCGGA ATCCCCAGCG TGGTCGTCGG    1753
TTTGTGGGGG GCAATGACGT TCGGGCCGTT CATCGCTCAT CACATCGCTC CGGTGATCGC    1813
TCACAACGCT CCCGATGTGC CGGTGCTGAA CTACTTGCGC GGCGACCCGG GCAACGGGGA    1873
GGGCATGTTG GTGTCCGGTC TGGTGTTGGC GGTGATGGTC GTTCCCATTA TCGCCACCAC    1933
```

CACTCATGAC CTGTTCCGGC AGGTGCCGGT GTTGCCCCGG GAGGGCGCGA TCGGGAATTC    1993

(2) INFORMATION FOR SEQ ID NO:148:

(i) SEQUENCE CHARACTERISTICS:
        (A) LENGTH: 374 amino acids
        (B) TYPE: amino acid
        (D) TOPOLOGY: linear (ii) MOLECULE TYPE: protein (xi) SEQUENCE DESCRIPTION: SEQ ID NO:148:

```
Val Lys Ile Arg Leu His Thr Leu Leu Ala Val Leu Thr Ala Ala Pro
 1               5                  10                  15

Leu Leu Leu Ala Ala Gly Cys Gly Ser Lys Pro Pro Ser Gly Ser
            20                  25                  30

Pro Glu Thr Gly Ala Gly Ala Gly Thr Val Ala Thr Thr Pro Ala Ser
            35                  40                  45

Ser Pro Val Thr Leu Ala Glu Thr Gly Ser Thr Leu Leu Tyr Pro Leu
        50                  55                  60

Phe Asn Leu Trp Gly Pro Ala Phe His Glu Arg Tyr Pro Asn Val Thr
65                  70                  75                  80

Ile Thr Ala Gln Gly Thr Gly Ser Gly Ala Gly Ile Ala Gln Ala Ala
                85                  90                  95

Ala Gly Thr Val Asn Ile Gly Ala Ser Asp Ala Tyr Leu Ser Glu Gly
            100                 105                 110

Asp Met Ala Ala His Lys Gly Leu Met Asn Ile Ala Leu Ala Ile Ser
            115                 120                 125

Ala Gln Gln Val Asn Tyr Asn Leu Pro Gly Val Ser Glu His Leu Lys
        130                 135                 140

Leu Asn Gly Lys Val Leu Ala Ala Met Tyr Gln Gly Thr Ile Lys Thr
145                 150                 155                 160

Trp Asp Asp Pro Gln Ile Ala Ala Leu Asn Pro Gly Val Asn Leu Pro
                165                 170                 175

Gly Thr Ala Val Val Pro Leu His Arg Ser Asp Gly Ser Gly Asp Thr
            180                 185                 190

Phe Leu Phe Thr Gln Tyr Leu Ser Lys Gln Asp Pro Glu Gly Trp Gly
            195                 200                 205

Lys Ser Pro Gly Phe Gly Thr Thr Val Asp Phe Pro Ala Val Pro Gly
210                 215                 220

Ala Leu Gly Glu Asn Gly Asn Gly Gly Met Val Thr Gly Cys Ala Glu
225                 230                 235                 240

Thr Pro Gly Cys Val Ala Tyr Ile Gly Ile Ser Phe Leu Asp Gln Ala
                245                 250                 255

Ser Gln Arg Gly Leu Gly Glu Ala Gln Leu Gly Asn Ser Ser Gly Asn
            260                 265                 270

Phe Leu Leu Pro Asp Ala Gln Ser Ile Gln Ala Ala Ala Gly Phe
            275                 280                 285

Ala Ser Lys Thr Pro Ala Asn Gln Ala Ile Ser Met Ile Asp Gly Pro
        290                 295                 300

Ala Pro Asp Gly Tyr Pro Ile Ile Asn Tyr Glu Tyr Ala Ile Val Asn
305                 310                 315                 320

Asn Arg Gln Lys Asp Ala Ala Thr Ala Gln Thr Leu Gln Ala Phe Leu
                325                 330                 335

His Trp Ala Ile Thr Asp Gly Asn Lys Ala Ser Phe Leu Asp Gln Val
```

-continued

```
                340                 345                 350
His Phe Gln Pro Leu Pro Pro Ala Val Val Lys Leu Ser Asp Ala Leu
        355                 360                 365
Ile Ala Thr Ile Ser Ser
    370
```

COMPOUNDS AND METHODS FOR DIAGNOSIS OF TUBERCULOSIS

CROSS-REFERENCE TO RELATED APPLICATIONS

This application is a continuation-in-part of U.S. application Ser. No. 08/729,622 filed Oct. 11, 1996; which claims priority from PCT Application No. PCT/US 96/14675, filed Aug. 30, 1996; and is a continuation-in-part of U.S. application Ser. No. 08/680,574, filed Jul. 12, 1996; which is a continuation-in-part of U.S. application Ser. No. 08/658,800 filed Jun. 5, 1996; which is a continuation-in-part of U.S. application Ser. No. 08/620,280, filed Mar. 22, 1996, now abandoned; which is a continuation-in-part of U.S. application Ser. No. 08/532,136, filed Sept. 22, 1995, now abandoned; which is a continuation of U.S. application Ser. No. 08/523,435, filed September 1, 1995, now abandoned.

The U.S. Government has a paid-up license in this invention and the right in limited circumstances to require the patent owner to license others on reasonable tenns as provided for by the terms of Phase I Grant No. AI39879 awarded by National Institute of Health.

TECHNICAL FIELD

The present invention relates generally to the detection of *Mycobacterium tuberculosis* infection. The invention is more particularly related to polypeptides comprising a *Mycobacterium tuberculosis* antigen, or a portion or other variant thereof, and the use of such polypeptides for the serodiagnosis of *Mycobacterium tuberculosis* infection.

BACKGROUND OF THE INVENTION

Tuberculosis is a chronic, infectious disease, that is generally caused by infection with *Mycobacterium tuberculosis*. It is a major disease in developing countries, as well as an increasing problem in developed areas of the world, with about 8 million new cases and 3 million deaths each year. Although the infection may be asymptomatic for a considerable period of time, the disease is most commonly manifested as an acute inflammation of the lungs, resulting in fever and a nonproductive cough. If left untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

Inhibiting the spread of tuberculosis will require effective vaccination and accurate, early diagnosis of the disease. Currently, vaccination with live bacteria is the most efficient method for inducing protective immunity. The most common Mycobacterium for this purpose is Bacillus Calmette-Guerin (BCG), an avirulent strain of *Mycobacterium bovis*. However, the safety and efficacy of BCG is a source of controversy and some countries, such as the United States, do not vaccinate the general public. Diagnosis is commonly achieved using a skin test, which involves intradermal exposure to tuberculin PPD (protein-purified derivative). Antigen-specific T cell responses result in measurable incubation at the injection site by 48–72 hours after injection, which indicates exposure to Mycobacterial antigens. Sensitivity and specificity have, however, been a problem with this test, and individuals vaccinated with BCG cannot be distinguished from infected individuals.

While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in AIDS patients, due to the depletion of CD4 T cells associated with human immunodeficiency virus (HIV) infection. Mycobacterium-reactive CD4 T cells have been shown to be potent producers of gamma-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, IL-12 has been shown to play a role in stimulating resistance to *M. tuberculosis* infection. For a review of the immunology of *M. tuberculosis* infection see Chan and Kaufmann, in *Tuberculosis: Pathogenesis, Protection and Control*, Bloom (ed.), ASM Press, Washington, DC, 1994.

Accordingly, there is a need in the art for improved diagnostic methods for detecting tuberculosis. The present invention fulfills this need and further provides other related advantages.

SUMMARY OF THE INVENTION

Briefly stated, the present invention provides compositions and methods for diagnosing tuberculosis. In one aspect, polypeptides are provided comprising an antigenic portion of a soluble *M. tuberculosis* antigen, or a variant of such an antigen that differs only in conservative substitutions and/or modifications. In one embodiment of this aspect, the soluble antigen has one of the following N-terrninal sequences:

(a) Asp-Pro-Val-Asp-Ala-Val-Ile-Asn-Thr-Thr-Cys-Asn-Tyr-Gly-Gln-Val-Val-Ala-Ala-Leu (SEQ ID No. 115);

(b) Ala-Val-Glu-Ser-Gly-Met-Leu-Ala-Leu-Gly-Thr-Pro-Ala-Pro-Ser (SEQ ID No. 116);

(c) Ala-Ala-Met-Lys-Pro-Arg-Thr-Gly-Asp-Gly-Pro-Leu-Glu-Ala-Ala-Lys-Glu-Gly-Arg (SEQ ID No. 117);

(d) Tyr-Tyr-Trp-Cys-Pro-Gly-Gln-Pro-Phe-Asp-Pro-Ala-Trp-Gly-Pro (SEQ ID No. 118);

(e) Asp-Ile-Gly-Ser-Glu-Ser-Thr-Glu-Asp-Gln-Gln-Xaa-Ala-Val (SEQ ID No. 119);

(f) Ala-Glu-Glu-Ser-Ile-Ser-Thr-Xaa-Glu-Xaa-Ile-Val-Pro (SEQ ID No. 120);

(g) Asp-Pro-Glu-Pro-Ala-Pro-Pro-Val-Pro-Thr-Thr-Ala-Ala-Ser-Pro-Pro-Ser (SEQ ID No. 121);

(h) Ala-Pro-Lys-Thr-Tyr-Xaa-Glu-Glu-Leu-Lys-Gly-Thr-Asp-Thr-Gly (SEQ ID No. 122);

(i) Asp-Pro-Ala-Ser-Ala-Pro-Asp-Val-Pro-Thr-Ala-Ala-Gln-Leu-Thr-Ser-Leu-Leu-Asn-Ser-Leu-Ala-Asp-Pro-Asn-Val-Ser-Phe-Ala-Asn (SEQ ID No. 123);

(j) Xaa-Asp-Ser-Glu-Lys-Ser-Ala-Thr-Ile-Lys-Val-Thr-Asp-Ala-Ser; (SEQ ID No. 129)

(k) Ala-Gly-Asp-Thr-Xaa-Ile-Tyr-Ile-Val-Gly-Asn-Leu-Thr-Ala-Asp; (SEQ ID No. 130) or (1) Ala-Pro-Glu-Ser-Gly-Ala-Gly-Leu-Gly-Gly-Thr-Val-Gln-Ala-Gly; (SEQ ID No. 131)

wherein Xaa may be any amino acid.

In a related aspect, polypeptides are provided comprising an immunogenic portion of an *M. tuberculosis* antigen, or a variant of such an antigen that differs only in conservative substitutions and/or modifications, the antigen having one of the following N-terminal sequences:

(m) Xaa-Tyr-Ile-Ala-Tyr-Xaa-Thr-Thr-Ala-Gly-Ile-Val-Pro-Gly-Lys-Ile-Asn-Val-His-Leu-Val; (SEQ ID No. 132) or (n) Asp-Pro-Pro-Asp-Pro-His-Gln-Xaa-Asp-Met-Thr-Lys-Gly-Tyr-Tyr-Pro-Gly-Gly-Arg-Arg-Xaa-Phe; (SEQ ID No. 124)

wherein Xaa may be any amino acid.

In another embodiment, the antigen comprises an amino acid sequence encoded by a DNA sequence selected from the group consisting of the sequences recited in SEQ ID Nos. 1, 2, 4–10, 13–25, 52, 94 and 96, the complements of said sequences, and DNA sequences that hybridize to a sequence recited in SEQ ID Nos. 1, 2, 4–10, 13–25, 52, 94 and 96 or a complement thereof under moderately stringent conditions.

In a related aspect, the polypeptides comprise an antigenic portion of a *M. tuberculosis* antigen, or a variant of such an antigen that differs only in conservative substitutions and/or modifications, wherein the antigen comprises an amino acid sequence encoded by a DNA sequence selected from the group consisting of the sequences recited in SEQ ID Nos. 26–51, 133 and 134, the complements of said sequences, and DNA sequences that hybridize to a sequence recited in SEQ ID Nos. 26–51, 133 and 134 or a complement thereof under moderately stringent conditions.

In related aspects, DNA sequences encoding the above polypeptides, recombinant expression vectors comprising these DNA sequences and host cells transformed or transfected with such expression vectors are also provided.

In another aspect, the present invention provides fusion proteins comprising a first and a second inventive polypeptide or, alternatively, an inventive polypeptide and a known *M. tuberculosis* antigen.

In further aspects of the subject invention, methods and diagnostic kits are provided for detecting tuberculosis in a patient. The methods comprise: (a) contacting a biological sample with at least one of the above polypeptides; and (b) detecting in the sample the presence of antibodies that bind to the polypeptide or polypeptides, thereby detecting *M. tuberculosis* infection in the biological sample. Suitable biological samples include whole blood, sputum, serum, plasma, saliva, cerebrospinal fluid and urine. The diagnostic kits comprise one or more of the above polypeptides in combination with a detection reagent.

The present invention also provides methods for detecting *M. tuberculosis* infection comprising: (a) obtaining a biological sample from a patient; (b) contacting the sample with at least one oligonucleotide primer in a polymerase chain reaction, the oligonucleotide primer being specific for a DNA sequence encoding the above polypeptides; and (c) detecting in the sample a DNA sequence that amplifies in the presence of the first and second oligonucleotide primers. In one embodiment, the oligonucleotide primer comprises at least about 10 contiguous nucleotides of such a DNA sequence.

In a further aspect, the present invention provides a method for detecting *M. tuberculosis* infection in a patient comprising: (a) obtaining a biological sample from the patient; (b) contacting the sample with an oligonucleotide probe specific for a DNA sequence encoding the above polypeptides; and (c) detecting in the sample a DNA sequence that hybridizes to the oligonucleotide probe. In one embodiment, the oligonucleotide probe comprises at least about 15 contiguous nucleotides of such a DNA sequence.

In yet another aspect, the present invention provides antibodies, both polyclonal and monoclonal, that bind to the polypeptides described above, as well as methods for their use in the detection of *M. tuberculosis* infection.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

FIGS. 1A and B illustrate the stimulation of proliferation and interferon-γ production in T cells derived from a first and a second *M. tuberculosis*-immune donor, respectively, by the 14 Kd, 20 Kd and 26 Kd antigens described in Example 1.

FIGS. 2A–D illustrate the reactivity of antisera raised against secretory *M. tuberculosis* proteins, the known *M. tuberculosis* antigen 85b and the inventive antigens Tb38-1 and TbH-9, respectively, with *M. tuberculosis* lysate (lane 2), *M. tuberculosis* secretory proteins (lane 3), recombinant Tb38-1 (lane 4), recombinant TbH-9 (lane 5) and recombinant 85b (lane 5).

FIG. 3A illustrates the stimulation of proliferation in a TbH-9-specific T cell clone by secretory *M. tuberculosis* proteins, recombinant TbH-9 and a control antigen, TbRa11.

FIG. 3B illustrates the stimulation of interferon-γ production in a TbH-9-specific F cell clone by secretory *M. tuberculosis* proteins, PPD and recombinant TbH-9.

FIG. 4 illustrates the reactivity of two representative polypeptides with sera from *M. tuberculosis*-infected and uninfected individuals, as compared to the reactivity of bacterial lysate.

FIG. 5 shows the reactivity of four representative polypeptides with sera from *M. tuberculosis*-infected and uninfected individuals, as compared to the reactivity of the 38 kD antigen.

FIG. 6 shows the reactivity of recombinant 38 kD and TbRa11 antigens with sera from *M. tuberculosis* patients, PPD positive donors and normal donors.

FIG. 7 shows the reactivity of the antigen TbRa2A with 38 kD negative sera.

FIG. 8 shows the reactivity of the antigen of SEQ ID No. 60 with sera from *M. tuberculosis* patients and normal donors.

FIG. 9 illustrates the reactivity of the recombinant antigen TbH-29 (SEQ ID NO: 137) with sera from *M. tuberculosis* patients, PPD positive donors and normal donors as determined by indirect ELISA.

FIG. 10 illustrates the reactivity of the recombinant antigen TbH-33 (SEQ ID NO: 140) with sera from *M. tuberculosis* patients and from normal donors, and with a pool of sera from *M. tuberculosis* patients, as determined both by direct and indirect ELISA FIG. 11 illustrates the reactivity of increasing concentrations of the recombinant antigen TbH-33 (SEQ ID NO: 140) with sera from *M. tuberculosis* patients and from normal donors as determined by EILISA.

SEQ. ID NO. 1 is the DNA sequence of TbRa1.

SEQ. ID NO. 2 is the DNA sequence of TbRa10.

SEQ. ID NO. 3 is the DNA sequence of TbRa11.

SEQ. ID NO. 4 is the DNA sequence of TbRa12.
SEQ. ID NO. 5 is the DNA sequence of TbRa13.
SEQ. ID NO. 6 is the DNA sequence of TbRa16.
SEQ. ID NO. 7 is the DNA sequence of TbRa17.
SEQ. ID NO. 8 is the DNA sequence of TbRa18.
SEQ. ID NO. 9 is the DNA sequence of TbRa19.
SEQ. ID NO. 10 is the DNA sequence of TbRa24.
SEQ. ID NO. 11 is the DNA sequence of TbRa26.
SEQ. ID NO. 12 is the DNA sequence of TbRa28.
SEQ. ID NO. 13 is the DNA sequence of TbRa29.
SEQ. ID NO. 14 is the DNA sequence of TbRa2A.
SEQ. ID NO. 15 is the DNA sequence of TbRa3.
SEQ. ID NO. 16 is the DNA sequence of TbRa32.
SEQ. ID NO. 17 is the DNA sequence of TbRa35.
SEQ. ID NO. 18 is the DNA sequence of TbRa36.
SEQ. ID NO. 19 is the DNA sequence of TbRa4.
SEQ. ID NO. 20 is the DNA sequence of TbRa9 .
SEQ. ID NO. 21 is the DNA sequence of TbRaB.
SEQ. ID NO. 22 is the DNA sequence of TbRaC.
SEQ. ID NO. 23 is the DNA sequence of TbRaD.
SEQ. ID NO. 24 is the DNA sequence of YYWCPG.
SEQ. ID NO. 25 is the DNA sequence of AAMK.
SEQ. ID NO. 26 is the DNA sequence of TbL-23.
SEQ. ID NO. 27 is the DNA sequence of TbL-24.
SEQ. ID NO. 28 is the DNA sequence of TbL-25.
SEQ. ID NO. 29 is the DNA sequence of TbL-28.
SEQ. ID NO. 30 is the DNA sequence of TbL-29.
SEQ. ID NO. 31 is the DNA sequence of TbH-5.
SEQ. ID NO. 32 is the DNA sequence of TbH-8.
SEQ. ID NO. 33 is the DNA sequence of TbH-9.
SEQ. ID NO. 34 is the DNA sequence of TbM-1.
SEQ. ID NO. 35 is the DNA sequence of TbM-3.
SEQ. ID NO. 36 is the DNA sequence of TbM-6.
SEQ. ID NO. 37 is the DNA sequence of TbM-7.
SEQ. ID NO. 38 is the DNA sequence of TbM-9.
SEQ. ID NO. 39 is the DNA sequence of TbM-12.
SEQ. ID NO. 40 is the DNA sequence of TbM-13.
SEQ. ID NO. 41 is the DNA sequence of TbM-14.
SEQ. ID NO. 42 is the DNA sequence of TbM-15.
SEQ. ID NO. 43 is the DNA sequence of TbH-4.
SEQ. ID NO. 44 is the DNA sequence of TbH-4-FWD.
SEQ. ID NO. 45 is the DNA sequence of TbH-12.
SEQ. ID NO. 46 is the DNA sequence of Tb38-1.
SEQ. ID NO. 47 is the DNA sequence of Tb38-4.
SEQ. ID NO. 48 is the DNA sequence of TbL-17.
SEQ. ID NO. 49 is the DNA sequence of TbL-20.
SEQ. ID NO. 50 is the DNA sequence of TbL-21.
SEQ. ID NO. 51 is the DNA sequence of TbH-16.
SEQ. ID NO. 52 is the DNA sequence of DPEP.
SEQ. ID NO. 53 is the deduced amino acid sequence of DPEP.
SEQ. ID NO. 54 is the protein sequence of DPV N-terminal Antigen.
SEQ. ID NO. 55 is the protein sequence of AVGS N-terminal Antigen.
SEQ. ID NO. 56 is the protein sequence of AAMK N-terminal Antigen.
SEQ. ID NO. 57 is the protein sequence of YYWC N-terminal Antigen.
SEQ. ID NO. 58 is the protein sequence of DIGS N-terminal Antigen.
SEQ. ID NO. 59 is the protein sequence of AEES N-terminal Antigen.
SEQ. ID NO. 60 is the protein sequence of DPEP N-terminal Antigen.
SEQ. ID NO. 61 is the protein sequence of APKT N-terminal Antigen.
SEQ. ID NO. 62 is the protein sequence of DPAS N-terminal Antigen.
SEQ. ID NO. 63 is the deduced amino acid sequence of TbM-1 Peptide.
SEQ. ID NO. 64 is the deduced amino acid sequence of TbRa1.
SEQ. ID NO. 65 is the deduced amino acid sequence of TbRa10.
SEQ. ID NO. 66 is the deduced amino acid sequence of TbRa11.
SEQ. ID NO. 67 is the deduced amino acid sequence of TbRa12.
SEQ. ID NO. 68 is the deduced amino acid sequence of TbRa13.
SEQ. ID NO. 69 is the deduced amino acid sequence of TbRa16.
SEQ. ID NO. 70 is the deduced amino acid sequence of TbRa17.
SEQ. ID NO. 71 is the deduced amino acid sequence of TbRa18.
SEQ. ID NO. 72 is the deduced amino acid sequence of TbRa19.
SEQ. ID NO. 73 is the deduced amino acid sequence of TbRa24.
SEQ. ID NO. 74 is the deduced amino acid sequence of TbRa26.
SEQ. ID NO. 75 is the deduced amino acid sequence of TbRa28.
SEQ. ID NO. 76 is the deduced amino acid sequence of TbRa29.
SEQ. ID NO. 77 is the deduced amino acid sequence of TbRa2A.
SEQ. ID NO. 78 is the deduced amino acid sequence of TbRa3.
SEQ. ID NO. 79 is the deduced amino acid sequence of TbRa32.
SEQ. ID NO. 80 is the deduced amino acid sequence of TbRa35.
SEQ. ID NO. 81 is the deduced amino acid sequence of TbRa36.
SEQ. ID NO. 82 is the deduced amino acid sequence of TbRa4.
SEQ. ID NO. 83 is the deduced amino acid sequence of TbRa9.
SEQ. ID NO. 84 is the deduced amino acid sequence of TbRaB.
SEQ. ID NO. 85 is the deduced amino acid sequence of TbRaC.
SEQ. ID NO. 86 is the deduced amino acid sequence of TbRaD.
SEQ. ID NO. 87 is the deduced amino acid sequence of YYWCPG.
SEQ. ID NO. 88 is the deduced amino acid sequence of TbAAMK.
SEQ. ID NO. 89 is the deduced amino acid sequence of Tb38-1.
SEQ. ID NO. 90 is the deduced amino acid sequence of TbH-4.
SEQ. ID NO. 91 is the deduced amino acid sequence of TbH-8.
SEQ. ID NO. 92 is the deduced amino acid sequence of TbH-9.
SEQ. ID NO. 93 is the deduced amino acid sequence of TbH-12.
SEQ. ID NO. 94 is the DNA sequence of DPAS.
SEQ. ID NO. 95 is the deduced amino acid sequence of DPAS.

SEQ. ID NO. 96 is the DNA sequence of DPV.

SEQ. ID NO. 97 is the deduced amino acid sequence of DPV.

SEQ. ID NO. 98 is the DNA sequence of ESAT-6.

SEQ. ID NO. 99 is the deduced amino acid sequence of ESAT-6.

SEQ. ID NO. 100 is the DNA sequence of TbH-8-2.

SEQ. ID NO. 101 is the DNA sequence of TbH-9FL.

SEQ. ID NO. 102 is the deduced amino acid sequence of TbH-9FL.

SEQ. ID NO. 103 is the DNA sequence of TbH-9-1.

SEQ. ID NO. 104 is the deduced amino acid sequence of TbH-9-1.

SEQ. ID NO. 105 is the DNA sequence of TbH-9-4.

SEQ. ID NO. 106 is the deduced amino acid sequence of TbH-9-4.

SEQ. ID NO. 107 is the DNA sequence of Tb38-1F2 IN.

SEQ. ID NO. 108 is the DNA sequence of Tb38-1F2 RP.

SEQ. ID NO. 109 is the deduced amino acid sequence of Tb37-FL.

SEQ. ID NO. 110 is the deduced amino acid sequence of Tb38-IN.

SEQ. ID NO. 111 is the DNA sequence of Tb38-1F3.

SEQ. ID NO. 112 is the deduced amino acid sequence of Tb38-1F3.

SEQ. ID NO. 113 is the DNA sequence of Tb38-1F5.

SEQ. ID NO. 114 is the DNA sequence of Tb38-1F6.

SEQ. ID NO. 115 is the deduced N-terminal amino acid sequence of DPV.

SEQ. ID NO. 116 is the deduced N-terminal amino acid sequence of AVGS.

SEQ. ID NO. 117 is the deduced N-terminal amino acid sequence of AAMK.

SEQ. ID NO. 118 is the deduced N-terminal amino acid sequence of YYWC.

SEQ. ID NO. 119 is the deduced N-terminal amino acid sequence of DIGS.

SEQ. ID NO. 120 is the deduced N-terminal amino acid sequence of AAES.

SEQ. ID NO. 121 is the deduced N-terminal amino acid sequence of DPEP.

SEQ. ID NO. 122 is the deduced N-terminal amino acid sequence of APKT.

SEQ. ID NO. 123 is the deduced N-terminal amino acid sequence of DPAS.

SEQ. ID NO. 124 is the protein sequence of DPPD N-terminal Antigen.

SEQ ID NO. 125–128 are the protein sequences of four DPPD cyanogen bromide fragments.

SEQ ID NO. 129 is the N-terminal protein sequence of XDS antigen.

SEQ ID NO. 130 is the N-terminal protein sequence of AGD antigen.

SEQ ID NO. 131 is the N-terminal protein sequence of APE antigen.

SEQ ID NO. 132 is the N-terminal protein sequence of XYI antigen.

SEQ ID NO. 133 is the DNA sequence of TbH-29.

SEQ ID NO. 134 is the DNA sequence of TbH-30.

SEQ ID NO. 135 is the DNA sequence of TbH-32.

SEQ ID NO. 136 is the DNA sequence of TbH-33.

SEQ ID NO. 137 is the predicted amino acid sequence of TbH-29.

SEQ ID NO. 138 is the predicted amino acid sequence of TbH-30.

SEQ ID NO. 139 is the predicted amino acid sequence of TbH-32.

SEQ ID NO. 140 is the predicted amino acid sequence of TbH-33.

SEQ ID NO: 141–146 are PCR primers used in the preparation of a fusion protein containing TbRa3, 38 kD and Tb38-1.

SEQ ID NO: 147 is the DNA sequence of the fusion protein containing TbRa3, 38 kD and Tb38-1.

SEQ ID NO: 148 is the amino acid sequence of the fusion protein containing TbRa3, 38 kD and Tb38-1.

SEQ ID NO: 149 is the DNA sequence of the *M. tuberculosis* antigen 38 kD.

SEQ ID NO: 150 is the amino acid sequence of the *M. tuberculosis* antigen 38 kD.

DETAILED DESCRIPTION OF THE INVENTION

As noted above, the present invention is generally directed to compositions and methods for diagnosing tuberculosis. The compositions of the subject invention include polypeptides that comprise at least one antigenic portion of a *M. tuberculosis* antigen, or a variant of such an antigen that differs only in conservative substitutions and/or modifications. Polypeptides within the scope of the present invention include, but are not limited to, soluble *M. tuberculosis* antigens. A "soluble *M. tuberculosis* antigen" is a protein of *M. tuberculosis* origin that is present in *M. tuberculosis* culture filtrate. As used herein, the term "polypeptide" encompasses amino acid chains of any length, including full length proteins (i.e., antigens), wherein the amino acid residues are linked by covalent peptide bonds. Thus, a polypeptide comprising an antigenic portion of one of the above antigens may consist entirely of the antigenic portion, or may contain additional sequences. The additional sequences may be derived from the native *M. tuberculosis* antigen or may be heterologous, and such sequences may (but need not) be antigenic.

An "antigenic portion" of an antigen (which may or may not be soluble) is a portion that is capable of reacting with sera obtained from an *M. tuberculosis*-infected individual (i.e., generates an absorbance reading with sera from infected individuals that is at least three standard deviations above the absorbance obtained with sera from uninfected individuals, in a representative ELISA assay described herein). An "*M. tuberculosis*-infected individual" is a human who has been infected with *M. tuberculosis* (e.g., has an intradermal skin test response to PPD that is at least 0.5 cm in diameter). Infected individuals may display symptoms of tuberculosis or may be free of disease symptoms. Polypeptides comprising at least an antigenic portion of one or more *M. tuberculosis* antigens as described herein may generally be used, alone or in combination, to detect tuberculosis in a patient.

The compositions and methods of this invention also encompass variants of the above polypeptides. A "variant," as used herein, is a polypeptide that differs from the native antigen only in conservative substitutions and/or modifications, such that the antigenic properties of the polypeptide are retained. Such variants may generally be identified by modifying one of the above polypeptide sequences, and evaluating the antigenic properties of the modified polypeptide using, for example, the representative procedures described herein.

A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also (or alternatively) be modified by, for example, the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In a related aspect, combination polypeptides are disclosed. A "combination polypeptide" is a polypeptide comprising at least one of the above antigenic portions and one or more additional antigenic M. tuberculosis sequences, which are joined via a peptide linkage into a single amino acid chain. The sequences may be joined directly (i.e., with no intervening amino acids) or may be joined by way of a linker sequence (e.g., Gly-Cys-Gly) that does not significantly diminish the antigenic properties of the component polypeptides.

In general, M. tuberculosis antigens, and DNA sequences encoding such antigens, may be prepared using any of a variety of procedures. For example, soluble antigens may be isolated from M. tuberculosis culture filtrate by procedures known to those of ordinary skill in the art, including anion-exchange and reverse phase chromatography. Purified antigens may then be evaluated for a desired property, such as the ability to react with sera obtained from an M. tuberculosis-infected individual. Such screens may be performed using the representative methods described herein. Antigens may then be partially sequenced using, for example, traditional Edman chemistry. See Edman and Berg, Eur. J. Biochem. 80:116–132, 1967.

Antigens may also be produced recombinantly using a DNA sequence that encodes the antigen, which has been inserted into an expression vector and expressed in an appropriate host. DNA molecules encoding soluble antigens may be isolated by screening an appropriate M. tuberculosis expression library with anti-sera (e.g., rabbit) raised specifically against soluble M. tuberculosis antigens. DNA sequences encoding antigens that may or may not be soluble may be identified by screening an appropriate M. tuberculosis genomic or cDNA expression library with sera obtained from patients infected with M. tuberculosis. Such screens may generally be performed using techniques well known in the art, such as those described in Sambrook et al., Molecular Cloning: A Laboratory Manual, Cold Spring Harbor Laboratories, Cold Spring Harbor, N.Y., 1989.

DNA sequences encoding soluble antigens may also be obtained by screening an appropriate M. tuberculosis cDNA or genomic DNA library for DNA sequences that hybridize to degenerate oligonucleotides derived from partial amino acid sequences of isolated soluble antigens. Degenerate oligonucleotide sequences for use in such a screen may be designed and synthesized, and the screen may be performed, as described (for example) in Sambrook et al., Molecular Cloning: A Laboratory Manual, Cold Spring Harbor Laboratories, Cold Spring Harbor, N.Y (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

Regardless of the method of preparation, the antigens described herein are "antigenic." More specifically, the antigens have the ability to react with sera obtained from an M. tuberculosis-infected individual. Reactivity may be evaluated using, for example, the representative EILISA assays described herein, where an absorbance reading with sera from infected individuals that is at least three standard deviations above the absorbance obtained with sera from uninfected individuals is considered positive.

Antigenic portions of M. tuberculosis antigens may be prepared and identified using well known techniques, such as those summarized in Paul, Fundamental Immunology, 3d ed., Raven Press, 1993, pp. 243–247 and references cited therein. Such techniques include screening polypeptide portions of the native antigen for antigenic properties. The representative ELISAs described herein may generally be employed in these screens. An antigenic portion of a polypeptide is a portion that, within such representative assays, generates a signal in such assays that is substantially similar to that generated by the full length antigen. In other words, an antigenic portion of a M. tuberculosis antigen generates at least about 20%, and preferably about 100%, of the signal induced by the full length antigen in a model ELISA as described herein.

Portions and other variants of M. tuberculosis antigens may be generated by synthetic or recombinant means. Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149–2146, 1963. Equipment for automated synthesis of polypeptides is commercially available from suppliers such as Applied BioSystems, Inc., Foster City, Calif., and may be operated according to the manufacturer's instructions. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Recombinant polypeptides containing portions and/or variants of a native antigen may be readily prepared from a DNA sequence encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides as described herein. Expression may be achieved in any appropriate host cell that has been transformed or transfected with an expression vector containing a DNA molecule that encodes a recombinant polypeptide.

Suitable host cells include prokaryotes, yeast and higher eukaryotic cells. Preferably, the host cells employed are *E. coli*, yeast or a mammalian cell line, such as COS or CHO. The DNA sequences expressed in this manner may encode naturally occurring antigens, portions of naturally occurring antigens, or other variants thereof.

In general, regardless of the method of preparation, the polypeptides disclosed herein are prepared in substantially pure form. Preferably, the polypeptides are at least about 80% pure, more preferably at least about 90% pure and most preferably at least about 99% pure. For use in the methods described herein, however, such substantially pure polypeptides may be combined.

In certain specific embodiments, the subject invention discloses polypeptides comprising at least an antigenic portion of a soluble *M. tuberculosis* antigen (or a variant of such an antigen), where the antigen has one of the following N-terminal sequences:

(a) Asp-Pro-Val-Asp-Ala-Val-Ile-Asn-Thr-Thr-Cys-Asn-Tyr-Gly-Gln-Val-Val-Ala-Ala-Leu (SEQ ID No. 115);

(b) Ala-Val-Glu-Ser-Gly-Met-Leu-Ala-Leu-Gly-Thr-Pro-Ala-Pro-Ser (SEQ ID No. 116);

(c) Ala-Ala-Met-Lys-Pro-Arg-Thr-Gly-Asp-Gly-Pro-Leu-Glu-Ala-Ala-Lys-Glu-Gly-Arg (SEQ ID No. 117);

(d) Tyr-Tyr-Trp-Cys-Pro-Gly-Gln-Pro-Phe-Asp-Pro-Ala-Trp-Gly-Pro (SEQ ID No. 118);

(e) Asp-Ile-Gly-Ser-Glu-Ser-Thr-Glu-Asp-Gln-Gln-Xaa-Ala-Val (SEQ ID No. 119);

(f) Ala-Glu-Glu-Ser-Ile-Ser-Thr-Xaa-Glu-Xaa-Ile-Val-Pro (SEQ ID No. 120);

(g) Asp-Pro-Glu-Pro-Ala-Pro-Pro-Val-Pro-Thr-Thr-Ala-Ala-Ser-Pro-Pro-Ser (SEQ ID No. 121);

(h) Ala-Pro-Lys-Thr-Tyr-Xaa-Glu-Glu-Leu-Lys-Gly-Thr-Asp-Thr-Gly (SEQ ID No. 122);

(i) Asp-Pro-Ala-Ser-Ala-Pro-Asp-Val-Pro-Thr-Ala-Ala-Gln-Gln-Thr-Ser-Leu-Leu-Asn-Ser-Leu-Ala-Asp-Pro-Asn-Val-Ser-Phe-Ala-Asn (SEQ ID No. 123);

(j) Xaa-Asp-Ser-Glu-Lys-Ser-Ala-Thr-Ile-Lys-Val-Thr-Asp-Ala-Ser; (SEQ ID No. 129)

(k) Ala-Gly-Asp-Thr-Xaa-Ile-Tyr-Ile-Val-Gly-Asn-Leu-Thr-Ala-Asp; (SEQ ID No. 130) or (l) Ala-Pro-Glu-Ser-Gly-Ala-Gly-Leu-Gly-Gly-Thr-Val-Gln-Ala-Gly; (SEQ ID No. 131)

wherein Xaa may be any amino acid, preferably a cysteine residue. A DNA sequence encoding the antigen identified as (g) above is provided in SEQ ID No. 52, the deduced amino acid sequence of which is provided in SEQ ID No. 53. A DNA sequence encoding the antigen identified as (a) above is provided in SEQ ID No. 96; its deduced amino acid sequence is provided in SEQ ID No. 97. A DNA sequence corresponding to antigen (d) above is provided in SEQ ID No. 24, a DNA sequence corresponding to antigen (c) is provided in SEQ ID No. 25 and a DNA sequence corresponding to antigen (I) is disclosed in SEQ ID No. 94 and its deduced amino acid sequence is provided in SEQ ID No. 95.

In a further specific embodiment, the subject invention discloses polypeptides comprising at least an immunogenic portion of an *M. tuberculosis* antigen having one of the following N-terminal sequences, or a variant thereof that differs only in conservative substitutions and/or modifications:

(m) Xaa-Tyr-Ile-Ala-Tyr-Xaa-Thr-Thr-Ala-Gly-Ile-Val-Pro-Gly-Lys-Ile-Asn-Val-His-Leu-Val; (SEQ ID No. 132) or (n) Asp-Pro-Pro-Asp-Pro-His-Gln-Xaa-Asp-Met-Thr-Lys-Gly-Tyr-Tyr-Pro-Gly-Gly-Arg-Arg-Xaa-Phe; (SEQ ID No. 124)

wherein Xaa may be any amino acid, preferably a cysteine residue.

In other specific embodiments, the subject invention discloses polypeptides comprising at least an antigenic portion of a soluble *M. tuberculosis* antigen (or a variant of such an antigen) that comprises one or more of the amino acid sequences encoded by (a) the DNA sequences of SEQ ID Nos. 1, 2, 4–10, 13–25, 52, 94 and 96, (b) the complements of such DNA sequences, or (c) DNA sequences substantially homologous to a sequence in (a) or (b).

In further specific embodiments, the subject invention discloses polypeptides comprising at least an antigenic portion of a *M. tuberculosis* antigen (or a variant of such an antigen), which may or may not be soluble, that comprises one or more of the amino acid sequences encoded by (a) the DNA sequences of SEQ ID Nos. 26–51, 133 and 134, (b) the complements of such DNA sequences or (c) DNA sequences substantially homologous to a sequence in (a) or (b).

In the specific embodiments discussed above, the *M. tuberculosis* antigens include variants that are encoded DNA sequences which are substantially homologous to one or more of DNA sequences specifically recited herein. "Substantial homology," as used herein, refers to DNA sequences that are capable of hybridizing under moderately stringent conditions. Suitable moderately stringent conditions include prewashing in a solution of 5×SSC, 0.5% SDS, 1.0 mM EDTA (pH 8.0); hybridizing at 50° C.–65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS). Such hybridizing DNA sequences are also within the scope of this invention, as are nucleotide sequences that, due to code degeneracy, encode an immunogenic polypeptide that is encoded by a hybridizing DNA sequence.

In a related aspect, the present invention provides fusion proteins comprising a first and a second inventive polypeptide or, alternatively, a polypeptide of the present invention and a known *M. tuberculosis* antigen, such as the 38 kD antigen described above or ESAT-6 (SEQ ID Nos. 98 and 99), together with variants of such fusion proteins. The fusion proteins of the present invention may also include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3)

the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8562, 1986; U.S. Pat. No. 4,935,233 and U.S. Pat. No. 4,751,180. The linker sequence may be from 1 to about 50 amino acids in length. Peptide linker sequences are not required when the first and second polypeptides have non-essential N-terminal amino acid regions that can be used to separate the functional domains and prevent steric hindrance.

In another aspect, the present invention provides methods for using the polypeptides described above to diagnose tuberculosis. In this aspect, methods are provided for detecting *M. tuberculosis* infection in a biological sample, using one or more of the above polypeptides, alone or in combination. In embodiments in which multiple polypeptides are employed, polypeptides other than those specifically described herein, such as the 38 kD antigen described in Andersen and Hansen, *Infect. Immun.* 57:2481–2488, 1989, may be included. As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient or a blood supply. The polypeptide(s) are used in an assay, as described below, to determine the presence or absence of antibodies to the polypeptide(s) in the sample, relative to a predetermined cut-off value. The presence of such antibodies indicates previous sensitization to mycobacteria antigens which may be indicative of tuberculosis.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with *M. tuberculosis*. After determining which samples test positive (as described below) with each polypeptide, combinations of two or more polypeptides may be formulated that are capable of detecting infection in most, or all, of the samples tested. Such polypeptides are complementary. For example, approximately 25–30% of sera from tuberculosis-infected individuals are negative for antibodies to any single protein, such as the 38 kD antigen mentioned above. Complementary polypeptides may, therefore, be used in combination with the 38 kD antigen to improve sensitivity of a diagnostic test.

There are a variety of assay formats known to those of ordinary skill in the art for using one or more polypeptides to detect antibodies in a sample. See, e.g., Harlow and Lane, *Antibodies: A Laboratory Manual*, Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art, which are amply described in the patent and scientific literature. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time (i.e., incubation time) is that period of time that is sufficient to detect the presence of antibody within a *M. tuberculosis*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-*M. tuberculosis* antibodies in the sample, the signal detected from the reporter group that remains bound to the solid support is generally compared to a signal that corresponds to a predetermined cut- off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for tuberculosis. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, pp. 106–107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for tuberculosis.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-*M. tuberculosis* antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 $\mu$g, and more preferably from about 50 ng to about 500 ng. Such tests can typically be performed with a very small amount (e.g., one drop) of patient serum or blood.

Of course, numerous other assay protocols exist that are suitable for use with the polypeptides of the present invention. The above descriptions are intended to be exemplary only.

In yet another aspect, the present invention provides antibodies to the inventive polypeptides. Antibodies may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Antibodies may be used in diagnostic tests to detect the presence of M. tuberculosis antigens using assays similar to those detailed above and other techniques well known to those of skill in the art, thereby providing a method for detecting M. tuberculosis infection in a patient.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify M. tuberculosis-specific cDNA derived from a biological sample, wherein at least one of the oligonucleotide primers is specific for a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80%, preferably at least about 90% and more preferably at least about 95%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule encoding one of the polypeptides disclosed herein. Preferably, oligonucleotide probes for use in the inventive diagnostic methods comprise at least about 15 contiguous oligonucleotides of a DNA molecule encoding one of the polypeptides disclosed herein. Techniques for both PCR based assays and hybridization assays are well known in the art (see, for example, Mullis et al. Ibid; Ehrlich, Ibid). Primers or probes may thus be used to detect M. tuberculosis-specific sequences in biological samples. DNA probes or primers comprising oligonucleotide sequences described above may be used alone, in combination with each other, or with previously identified sequences, such as the 38 kD antigen discussed above.

The following Examples are offered by way of illustration and not by way of limitation.

EXAMPLES

Example 1

PURIFICATION AND CHARACTERIZATION OF POLYPEPTIDES FROM M. TUBERCULOSIS CULTURE FILTRATE

This example illustrates the preparation of M. tuberculosis* soluble polypeptides from culture filtrate. Unless otherwise noted, all percentages in the following example are weight per volume.

*M. tuberculosis* (either H37Ra, ATCC No. 25177, or H37Rv, ATCC No. 25618) was cultured in sterile GAS media at 37° C. for fourteen days. The media was then vacuum filtered (leaving the bulk of the cells) through a 0.45$\mu$ filter into a sterile 2.5 L bottle. The media was then filtered through a 0.2$\mu$ filter into a sterile 4 L bottle. $NaN_3$ was then added to the culture filtrate to a concentration of 0.04%. The bottles were then placed in a 4° C. cold room.

The culture filtrate was concentrated by placing the filtrate in a 12 L reservoir that had been autoclaved and feeding the filtrate into a 400 ml Amicon stir cell which had been rinsed with ethanol and contained a 10,000 kDa MWCO membrane. The pressure was maintained at 60 psi using nitrogen gas. This procedure reduced the 12 L volume to approximately 50 ml.

The culture filtrate was then dialyzed into 0.1% ammonium bicarbonate using a 8,000 kDa MWCO cellulose ester membrane, with two changes of ammonium bicarbonate solution. Protein concentration was then determined by a commercially available BCA assay (Pierce, Rockford, Ill.).

The dialyzed culture filtrate was then lyophilized, and the polypeptides resuspended in distilled water. The polypeptides were then dialyzed against 0.01 mM 1,3 bis[tris (hydroxymethyl)-methylamino]propane, pH 7.5 (Bis-Tris propane buffer), the initial conditions for anion exchange chromatography. Fractionation was performed using gel profusion chromatography on a POROS 146 II Q/M anion exchange column 4.6 mm×100 mm (Perseptive BioSystems, Framingham, Mass.) equilibrated in 0.01 mM Bis-Tris propane buffer pH 7.5. Polypeptides were eluted with a linear 0–0.5 M NaCl gradient in the above buffer system. The column eluent was monitored at a wavelength of 220 nm.

The pools of polypeptides eluting from the ion exchange column were dialyzed against distilled water and lyophilized. The resulting material was dissolved in 0.1% trifluoroacetic acid (TFA) pH1.9 in water, and the polypeptides were purified on a Delta-Pak C18 column (Waters, Milford, Mass.) 300 Angstrom pore size, 5 micron particle size (3.9×150 mm). The polypeptides were eluted from the column with a linear gradient from 0–60% dilution buffer (0.1% TFA in acetonitrile). The flow rate was 0.75 ml/minute and the HPLC eluent was monitored at 214 nm. Fractions containing the eluted polypeptides were collected to maximize the purity of the individual samples. Approximately 200 purified polypeptides were obtained.

The purified polypeptides were then screened for the ability to induce T-cell proliferation in PBMC preparations. The PBMCs from donors known to be PPD skin test positive and whose T cells were shown to proliferate in response to PPD and crude soluble proteins from MTB were cultured in medium comprising RPMI 1640 supplemented with 10% pooled human serum and 50 µg/ml gentamicin. Purified polypeptides were added in duplicate at concentrations of 0.5 to 10 µg/mL. After six days of culture in 96-well round-bottom plates in a volume of 200 µl, 50 µl of medium was removed from each well for determination of IFN-γ levels, as described below. The plates were then pulsed with 1 µCi/well of tritiated thymidine for a further 18 hours, harvested and tritium uptake determined using a gas scintillation counter. Fractions that resulted in proliferation in both replicates three fold greater than the proliferation observed in cells cultured in medium alone were considered positive.

IFN-γ was measured using an enzyme-linked immunosorbent assay (ELISA). ELISA plates were coated with a mouse monoclonal antibody directed to human IFN-γ (Chemicon) in PBS for four hours at room temperature. Wells were then blocked with PBS containing 5% (WNV) non-fat dried milk for 1 hour at room temperature. The plates were then washed six times in PBS/0.2% TWEEN-20 and samples diluted 1:2 in culture medium in the ELISA plates were incubated overnight at room temperature. The plates were again washed and a polyclonal rabbit anti-human IFN-γ serum diluted 1:3000 in PBS/10% normal goat serum was added to each well. The plates were then incubated for two hours at room temperature, washed and horseradish peroxidase-coupled anti-rabbit IgG (Jackson Labs.) was added at a 1:2000 dilution in PBS/5% non-fat dried milk. After a further two hour incubation at room temperature, the plates were washed and TMB substrate added. The reaction was stopped after 20 min with 1 N sulfuric acid. Optical density was determined at 450 nm using 570 nm as a reference wavelength. Fractions that resulted in both replicates giving an OD two fold greater than the mean OD from cells cultured in medium alone, plus 3 standard deviations, were considered positive.

For sequencing, the polypeptides were individually dried onto Biobrene™ (Perkin Elmer/Applied BioSystems Division, Foster City, Calif.) treated glass fiber filters. The filters with polypeptide were loaded onto a Perkin Elmer/Applied BioSystems Division Procise 492 protein sequencer. The polypeptides were sequenced from the amino terminal and using traditional Edman chemistry. The amino acid sequence was determined for each polypeptide by comparing the retention time of the PTH amino acid derivative to the appropriate PTH derivative standards.

Using the procedure described above, antigens having the following N-terminal sequences were isolated:

(a) Asp-Pro-Val-Asp-Ala-Val-Ile-Asn-Thr-Thr-Xaa-Asn-Tyr-Gly-Gln-Val-Val-Ala-Ala-Leu (SEQ ID No. 54);

(b) Ala-Val-Glu-Ser-Gly-Met-Leu-Ala-Leu-Gly-Thr-Pro-Ala-Pro-Ser (SEQ ID No. 55);

(c) Ala-Ala-Met-Lys-Pro-Arg-Thr-Gly-Asp-Gly-Pro-Leu-Glu-Ala-Ala-Lys-Glu-Gly-Arg (SEQ ID No. 56);

(d) Tyr-Tyr-Trp-Cys-Pro-Gly-Gln-Pro-Phe-Asp-Pro-Ala-Trp-Gly-Pro (SEQ ID No. 57);

(e) Asp-Ile-Gly-Ser-Glu-Ser-Thr-Glu-Asp-Gln-Gln-Xaa-Ala-Val (SEQ ID No. 58);

(f) Ala-Glu-Glu-Ser-Ile-Ser-Thr-Xaa-Glu-Xaa-Ile-Val-Pro (SEQ ID No. 59);

(g) Asp-Pro-Glu-Pro-Ala-Pro-Pro-Val-Pro-Thr-Ala-Ala-Ala-Ala-Pro-Pro-Ala (SEQ ID No. 60); and (h) Ala-Pro-Lys-Thr-Tyr-Xaa-Glu-Glu-Leu-Lys-Gly-Thr-Asp-Thr-Gly (SEQ ID No. 61);

wherein Xaa may be any amino acid.

An additional antigen was isolated employing a microbore HPLC purification step in addition to the procedure described above. Specifically, 20 µl of a fraction comprising a mixture of antigens from the chromatographic purification step previously described, was purified on an Aquapore C18 column (Perkin Elmer/Applied Biosystems Division, Foster City, Calif.) with a 7 micron pore size, column size 1 mm×100 mm, in a Perkin Elmer/Applied Biosystems Division Model 172 HPLC. Fractions were eluted from the column with a linear gradient of 1%/minute of acetonitrile (containing 0.05% TFA) in water (0.05% TFA) at a flow rate of 80 µl/minute. The eluent was monitored at 250 nm. The original fraction was separated into 4 major peaks plus other smaller components and a polypeptide was obtained which was shown to have a molecular weight of 12.054 Kd (by mass spectrometry) and the following N-terminal sequence:

(i) Asp-Pro-Ala-Ser-Ala-Pro-Asp-Val-Pro-Thr-Ala-Ala-Gln-Gln-Thr-Ser-Leu-Leu-Asn-Asn-Leu-Ala-Asp-Pro-Asp-Val-Ser-Phe-Ala-Asp (SEQ ID No. 62).

This polypeptide was shown to induce proliferation and IFN-γ production in PBMC preparations using the assays described above.

Additional soluble antigens were isolated from *M. tuberculosis* culture filtrate as follows. *M. tuberculosis* culture filtrate was prepared as described above. Following dialysis against Bis-Tris propane buffer, at pH 5.5, fractionation was performed using anion exchange chromatography on a Poros QE column 4.6 x 100 mm (Perseptive Biosystems) equilibrated in Bis-Tris propane buffer pH 5.5. Polypeptides were eluted with a linear 0–1.5 M NaCl gradient in the above buffer system at a flow rate of 10 ml/min. The column eluent was monitored at a wavelength of 214 nm.

The fractions eluting from the ion exchange column were pooled and subjected to reverse phase chromatography using a Poros R2 column 4.6×100 mm (Perseptive Biosystems). Polypeptides were eluted from the column with a linear gradient from 0–100% acetonitrile (0.1% TFA) at a flow rate of 5 ml/min. The eluent was monitored at 214 nm.

Fractions containing the eluted polypeptides were lyophilized and resuspended in 80 µl of aqueous 0.1% TFA and further subjected to reverse phase chromatography on a Vydac C4 column 4.6×150 mm (Western Analytical, Temecula, Calif.) with a linear gradient of 0–100% acetonitrile (0.1% TFA) at a flow rate of 2 ml/min. Eluent was monitored at 214 nm.

The fraction with biological activity was separated into one major peak plus other smaller components. Western blot of this peak onto PVDF membrane revealed three major bands of molecular weights 14 Kd, 20 Kd and 26 Kd. These polypeptides were determined to have the following N-terminal sequences, respectively:

(j) Xaa-Asp-Ser-Glu-Lys-Ser-Ala-Thr-Ile-Lys-Val-Thr-Asp-Ala-Ser; (SEQ ID No. 129)

(k) Ala-Gly-Asp-Thr-Xaa-lle-Tyr-Ile-Val-Gly-Asn-Leu-Thr-Ala-Asp; (SEQ ID No. 130) and (l) Ala-Pro-Glu-Ser-Gly-Ala-Gly-Leu-Gly-Gly-Thr-Val-Gln-Ala-Gly; (SEQ ID No. 131), wherein Xaa may be any amino acid.

Using the assays described above, these polypeptides were shown to induce proliferation and IFN-γ production in PBMC preparations. FIGS. 1A and B show the results of such assays using PBMC preparations from a first and a second donor, respectively.

DNA sequences that encode the antigens designated as (a), (c), (d) and (g) above were obtained by screening a *M. tuberculosis* genomic library using $^{32}$P end labeled degenerate oligonucleotides corresponding to the N-terminal sequence and containing *M. tuberculosis* codon bias. The screen performed using a probe corresponding to antigen (a) above identified a clone having the sequence provided in SEQ ID No. 96. The polypeptide encoded by SEQ ID No. 96 is provided in SEQ ID No. 97. The screen performed using a probe corresponding to antigen (g) above identified a clone having the sequence provided in SEQ ID No. 52. The polypeptide encoded by SEQ ID No. 52 is provided in SEQ ID No. 53. The screen performed using a probe corresponding to antigen (d) above identified a clone having the sequence provided in SEQ ID No. 24, and the screen performed with a probe corresponding to antigen (c) identified a clone having the sequence provided in SEQ ID No. 25.

The above amino acid sequences were compared to known amino acid sequences in the gene bank using the DNA STAR system. The database searched contains some 173,000 proteins and is a combination of the Swiss, PIR databases along with translated protein sequences (Version 87). No significant homologies to the amino acid sequences for antigens (a)–(h) and (I) were detected.

The amino acid sequence for antigen (i) was found to be homologous to a sequence from *M. leprae*. The full length *M. leprae* sequence was amplified from genomic DNA using the sequence obtained from GENBANK. This sequence was then used to screen an *M. tuberculosis* library and a full length copy of the *M. tuberculosis* homologue was obtained (SEQ ID No. 94).

The amino acid sequence for antigen (j) was found to be homologous to a known *M. tuberculosis* protein translated from a DNA sequence. To the best of the inventors' knowledge, this protein has not been previously shown to possess T-cell stimulatory activity. The amino acid sequence for antigen (k) was found to be related to a sequence from *M. leprae*.

In the proliferation and IFN-γ assays described above, using three PPD positive donors, the results for representative antigens provided above are presented in Table 1:

TABLE 1

RESULTS OF PBMC PROLIFERATION AND IFN-γ ASSAYS

| Sequence | Proliferation | IFN-γ |
|---|---|---|
| (a) | + | – |
| (c) | +++ | +++ |
| (d) | ++ | ++ |
| (g) | +++ | +++ |
| (h) | +++ | +++ |

In Table 1, responses that gave a stimulation index (SI) of between 2 and 4 (compared to cells cultured in medium alone) were scored as +, as SI of 4–8 or 2–at a concentration of 1 μg or less was scored as ++ and an SI of greater than 8 was scored as +++. The antigen of sequence (i) was found to have a high SI (+++) for one donor and lower SI (++ and +) for the two other donors in both proliferation and IFN-γ assays. These results indicate that these antigens are capable of inducing proliferation and/or interferon-γ production.

Example 2

Use Of Patient Sera To Isolate *M. Tuberculosis* Antigens

This example illustrates the isolation of antigens from *M. tuberculosis* lysate by screening with serum from *M. tuberculosis*-infected individuals.

Dessicated *M. tuberculosis* H37Ba (Difco Laboratories) was added to a 2% NP40 solution, and alternately homogenized and sonicated three times. The resulting suspension was centrifuged at 13,000 rpm in microfuge tubes and the supernatant put through a 0.2 micron syringe filter. The filtrate was bound to Macro Prep DEAE beads (BioRad, Hercules, Calif.). The beads were extensively washed with 20 mM Tris pH 7.5 and bound proteins eluted with 1M NaCl. The NaCl elute was dialyzed overnight against 10 mM Tris, pH 7. Dialyzed solution was treated with DNase and RNase at 0.05 mg/ml for 30 min. at room temperature and then with α-D-mannosidase, 0.5 U/mg at pH 4.5 for 3–4 hours at room temperature. After returning to pH 7.5, the material was fractionated via FPILC over a Bio Scale-Q-20 column (BioRad). Fractions were combined into nine pools, concentrated in a Centriprep 10 (Amicon, Beverley, Mass.) and screened by Western blot for serological activity using a serum pool from *M. tuberculosis*-infected patients which was not immunoreactive with other antigens of the present invention.

The most reactive fraction was run in SDS-PAGE and transferred to PVDF. A band at approximately 85 Kd was cut cut yielding the sequence:

(m) Xaa-Tyr-Ile-Ala-Tyr-Xaa-Thr-Thr-Ala-Gly-Ile-Val-Pro-Gly-Lys-Ile-Asn-Val-His-Leu-Val; SEQ ID No. 132), wherein Xaa may be any amino acid.

Comparison of this sequence with those in the gene bank as described above, revealed no significant homologies to known sequences.

Example 3

Preparation Of DNA Sequences Encofding *M. Tuberculosis* Antigens

This example illustrates the preparation of DNA sequences encoding *M. tuberculosis* antigens by screening a *M. tuberculosis* expression library with sera obtained from patients infected with *M. tuberculosis*, or with anti-sera raised against *M. tuberculosis* antigens.

A. Preparation of *M. Tuberculosis* Soluble Antigens using Rabbit Anti-sera

Genomic DNA was isolated from the *M. tuberculosis* strain H37Ra. The DNA was randomly sheared and used to construct an expression library using the Lambda ZAP expression system (Stratagene, La Jolla, Calif.). Rabbit anti-sera was generated against secretory proteins of the *M. tuberculosis* strains H37Ra, H37Rv and Erdman by immunizing a rabbit with concentrated supernatant of the *M. tuberculosis* cultures. Specifically, the rabbit was first immunized subcutaneously with 200 μg of protein antigen in a total volume of 2 ml containing 100 μg muramyl dipeptide (Calbiochem, La Jolla, Calif.) and 1 ml of incomplete Freund's adjuvant. Four weeks later the rabbit was boosted subcutaneously with 100 μg antigen in incomplete Freund's adjuvant. Finally, the rabbit was immunized intravenously four weeks later with 50 μg protein antigen. The anti-sera were used to screen the expression library as described in Sambrook et al., *Molecular Cloning: A Laboratory Manual*, Cold Spring Harbor Laboratories, Cold Spring Harbor, N.Y, 1989. Bacteriophage plaques expressing immunoreactive antigens were purified. Phagemid from the plaques was rescued and the nucleotide sequences of the *M. tuberculosis* clones deduced.

Thirty two clones were purified. Of these, 25 represent sequences that have not been previously identified in *M. tuberculosis*. Proteins were induced by IPTG and purified by gel elution, as described in Skeiky et al., *J. Exp. Med.*

181:1527–1537, 1995. Representative partial sequences of DNA molecules identified in this screen are provided in SEQ ID Nos. 1–25. The corresponding predicted amino acid sequences are shown in SEQ ID Nos. 64–88.

On comparison of these sequences with known sequences in the gene bank using the databases described above, it was found that the clones referred to hereinafter as TbRA2A, TbRA16, TbRA18, and TbRA29 (SEQ ID Nos. 77, 69, 71, 76) show some homology to sequences previously identified in *Mycobacterium leprae* but not in *M. tuberculosis*. TbRA11, TbRA26, TbRA28 and TbDPEP (SEQ ID Nos. 66, 74, 75, 53) have been previously identified in *M. tuberculosis*. No significant homologies were found to TbRA1, TbRA3, TbRA4, TbRA9, TbRA10, TbRA13, TbRA17, TbRA19, TbRA29, TbRA32, TbRA36 and the overlapping clones TbRA35 and TbRA12 (SEQ ID Nos. 64, 78, 82, 83, 65, 68, 76, 72, 76, 79, 81, 80, 67, respectively). The clone TbRa24 is overlapping with clone TbRa29.

B. USE OF PATIENT SERA TO IDENTIFY DNA SEQUENCES ENCODING *M. TUBERCULOSIS* ANTIGENS

The genomic DNA library described above, and an additional H37Rv library, were screened using pools of sera obtained from patients with active tuberculosis. To prepare the H37Rv library, *M. tuberculosis* strain H37Rv genomic DNA was isolated, subjected to partial Sau3A digestion and used to construct an expression library using the Lambda Zap expression system (Stratagene, La Jolla, Calif.). Three different pools of sera, each containing sera obtained from three individuals with active pulmonary or pleural disease, were used in the expression screening. The pools were designated TbL, TbM and TbH, referring to relative reactivity with H37Ra lysate (i.e., TbL=low reactivity, TbM= medium reactivity and TbH=high reactivity) in both ELISA and immunoblot format. A fourth pool of sera from seven patients with active pulmonary tuberculosis was also employed. All of the sera lacked increased reactivity with the recombinant 38 kD *M. tuberculosis* H37Ra phosphate-binding protein.

All pools were pre-adsorbed with *E. coli* lysate and used to screen the H37Ra and H37Rv expression libraries, as described in Sambrook et al., *Molecular Cloning: A Laboratory Manual*, Cold Spring Harbor Laboratories, Cold Spring Harbor, N.Y., 1989. Bacteriophage plaques expressing immunoreactive antigens were purified. Phagemid from the plaques was rescued and the nucleotide sequences of the *M. tuberculosis* clones deduced.

Thirty two clones were purified. Of these, 31 represented sequences that had not been previously identified in human *M. tuberculosis*. Representative sequences of the DNA molecules identified are provided in SEQ ID NOS.: 26–51 and 100. Of these, TbH-8-2 (SEQ. ID NO. 100) is a partial clone of TbH-8, and TbH-4 (SEQ. ID NO. 43) and TbH-4-FWD (SEQ. ID NO. 44) are non-contiguous sequences from the same clone. Amino acid sequences for the antigens hereinafter identified as Tb38-1, TbH-4, TbH-8, TbH-9, and TbH-12 are shown in SEQ ID NOS.: 89–93. Comparison of these sequences with known sequences in the gene bank using the databases identified above revealed no significant homologies to TbH-4, TbH-8, TbH-9 and TbM-3, although weak homologies were found to TbH-9. TbH-12 was found to be homologous to a 34 kD antigenic protein previously identified in *M. paratuberculosis* (Acc. No. S28515). Tb38-1 was found to be located 34 base pairs upstream of the open reading frame for the antigen ESAT-6 previously identified in *M. bovis* (Acc. No. U34848) and in *M. tuberculosis* (Sorensen et al., *Infec. Immun.* 63:1710–1717, 1995).

Probes derived from Tb38-1 and TbH-9, both isolated from an H37Ra library, were used to identify clones in an H37Rv library. Tb38-1 hybridized to Tb38-1F2, Tb38-1F3, Tb38-1F5 and Tb38-1F6 (SEQ. ID NOS. 107, 108, 111, 113, and 114). (SEQ ID NOS. 107 and 108 are non-contiguous sequences from clone Tb38-1F2.) Two open reading frames were deduced in Tb38-1F2; one corresponds to Tb37FL (SEQ. ID. NO. 109), the second, a partial sequence, may be the homologue of Tb38-1 and is called Tb38-IN (SEQ. ID NO. 110). The deduced amino acid sequence of Tb38-1F3 is presented in SEQ. ID. NO. 112. A Tbl-1-9 probe identified three clones in the H37Rv library: TbH-9-FL (SEQ. ID NO. 101), which may be the homologue of TbH-9 (R37Ra), TbH-9-1 (SEQ. ID NO. 103), and TbH-8-2 (SEQ. ID NO. 105) is a partial clone of TbH-8. The deduced amino acid sequences for these three clones are presented in SEQ IDNOS. 102,104 and 106.

Further screening of the *M. tuberculosis* genomic DNA library, as described above, resulted in the recovery of ten additional reactive clones, representing seven different genes. One of these genes was identified as the 38 Kd antigen discussed above, one was determined to be identical to the 14 Kd alpha crystalline heat shock protein previously shown to be present in *M. tuberculosis*, and a third was determined to be identical to the antigen TbH-8 described above. The determined DNA sequences for the remaining five clones (hereinafter referred to as TbH-29, TbH-30, TbH-32 and TbH-33) are provided in SEQ ID NO: 133–136, respectively, with the corresponding predicted amino acid sequences being provided n SEQ ID NO: 137–140, respectively. The DNA and amino acid sequences for these antigens were compared with those in the gene bank as described above. No homologies were found to the 5' end of TbH-29 (which contains the reactive open reading frame), although the 3' end of TbH-29 was found to be identical to the *M. tuberculosis* cosinid Y227. TbH-32 and TbH-33 were found to be identical to the previously identified *M. tuberculosis* insertion element IS6110 and to the *M. tuberculosis* cosmid Y50, respectively. No significant homologies to TbH-30 were found.

Positive phagemid from this additional screening were used to infect *E. coli* XL-1 Blue MRF', as described in Sambrook et al., supra. Induction of recombinant protein was accomplished by the addition of IPTG. Induced and uninduced lysates were run in duplicate on SDS-PAGE and transferred to nitrocellulose filters. Filters were reacted with human *M. tuberculosis* sera (1:200 dilution) reactive with TbH and a rabbit sera (1:200 or 1:250 dilution) reactive with the N-terminal 4 Kd portion of lacZ. Sera incubations were performed for 2 hours at room temperature. Bound antibody was detected by addition of $^{25}$I-labeled Protein A and subsequent exposure to film for variable times ranging from 16 hours to 11 day. The results of the immunoblots are summarized in Table 2.

TABLE 2

| Antigen | Human M. tb Sera | Anti-lacZ Sera |
| --- | --- | --- |
| TbH-29 | 45 Kd | 45 Kd |
| TbH-30 | No reactivity | 29 Kd |
| ThH-32 | 12 Kd | 12 Kd |
| TbH-33 | 16 Kd | 16 Kd |

Positive reaction of the recombinant human *M. tuberculosis* antigens with both the human *M. tuberculosis* sera and znti-lacZ sera indicate that reactivity of the human *M. tuberculosis* sera is directed towards the fusion protein. Antigens reactive with the anti-lacZ sera but not with the human *M. tuberculosis* sera may be the result of the human

*M. tuberculosis* sera recognizing conformational epitopes, or the antigen-antibody binding kinetics may be such that the 2 hour sera exposure in the immunoblot is not sufficient.

Studies were undertaken to determine whether the antigens TbH-9 and Tb38-1 represent cellular proteins or are secreted into *M. tuberculosis* culture media. In the first study, rabbit sera were raised against A) secretory proteins of *M. tuberculosis*, B) the known secretory recombinant *M. tuberculosis* antigen 85b, C) recombinant Tb38-1 and D) recombinant TbH-9, using protocols substantially as described in Example 3A. Total *M. tuberculosis* lysate, concentrated supernatant of *M. tuberculosis* cultures and the recombinant antigens 85b, TbH-9 and Tb38-1 were resolved on denaturing gels, immobilized on nitrocellulose membranes and duplicate blots were probed using the rabbit sera described above.

Figure 2A:
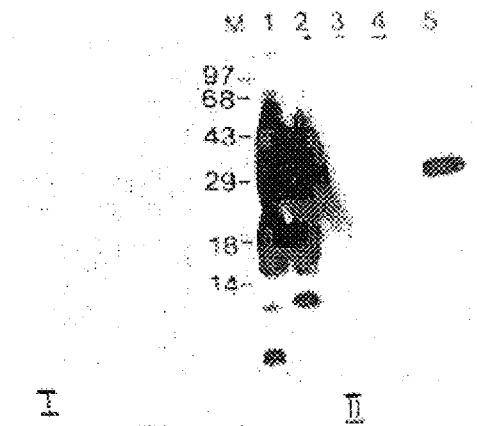
Figure 2B:
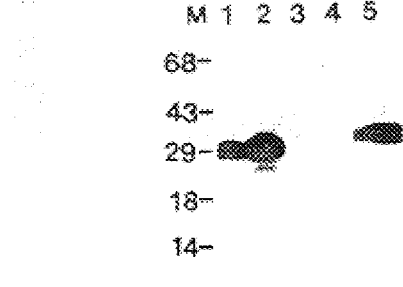
Figure 2C:
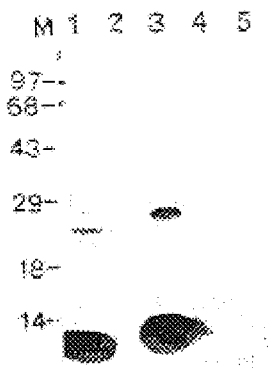
Figure 2D:
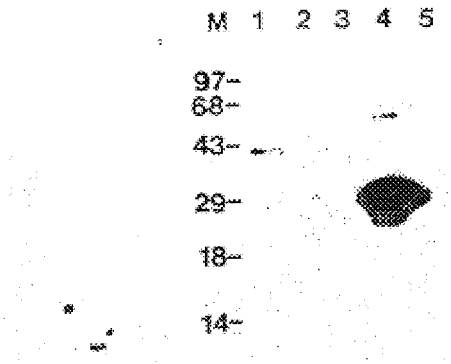

The results of this analysis using control sera (panel I) and antisera (panel II) against secretory proteins, recombinant 85b, recombinant Tb3 8-1 and recombinant TbH-9 are shown in FIGS. 2A–D, respectively, wherein the lane designations are as follows: 1) molecular weight protein standards; 2) 5 tg of M tuberculosis lysate; 3) 5 $\mu$g secretory proteins; 4) 50 ng recombinant Tb38-1; 5) 50 ng recombinant TbH-9; and 6) 50 ng recombinant 85b. The recombinant antigens were engineered with six terminal histidine residues and would therefore be expected to migrate with a mobility approximately 1 kD larger that the native protein. In FIG. 2D, recombinant TbH-9 is lacking approximately 10 kD of the full-length 42 kD antigen, hence the significant difference in the size of the immunoreactive native TbH-9 antigen in the lysate lane (indicated by an arrow). These results demonstrate that Tb38-1 and TbH-9 are intracellular antigens and are not actively secreted by *M. tuberculosis*.

Figure 3A:
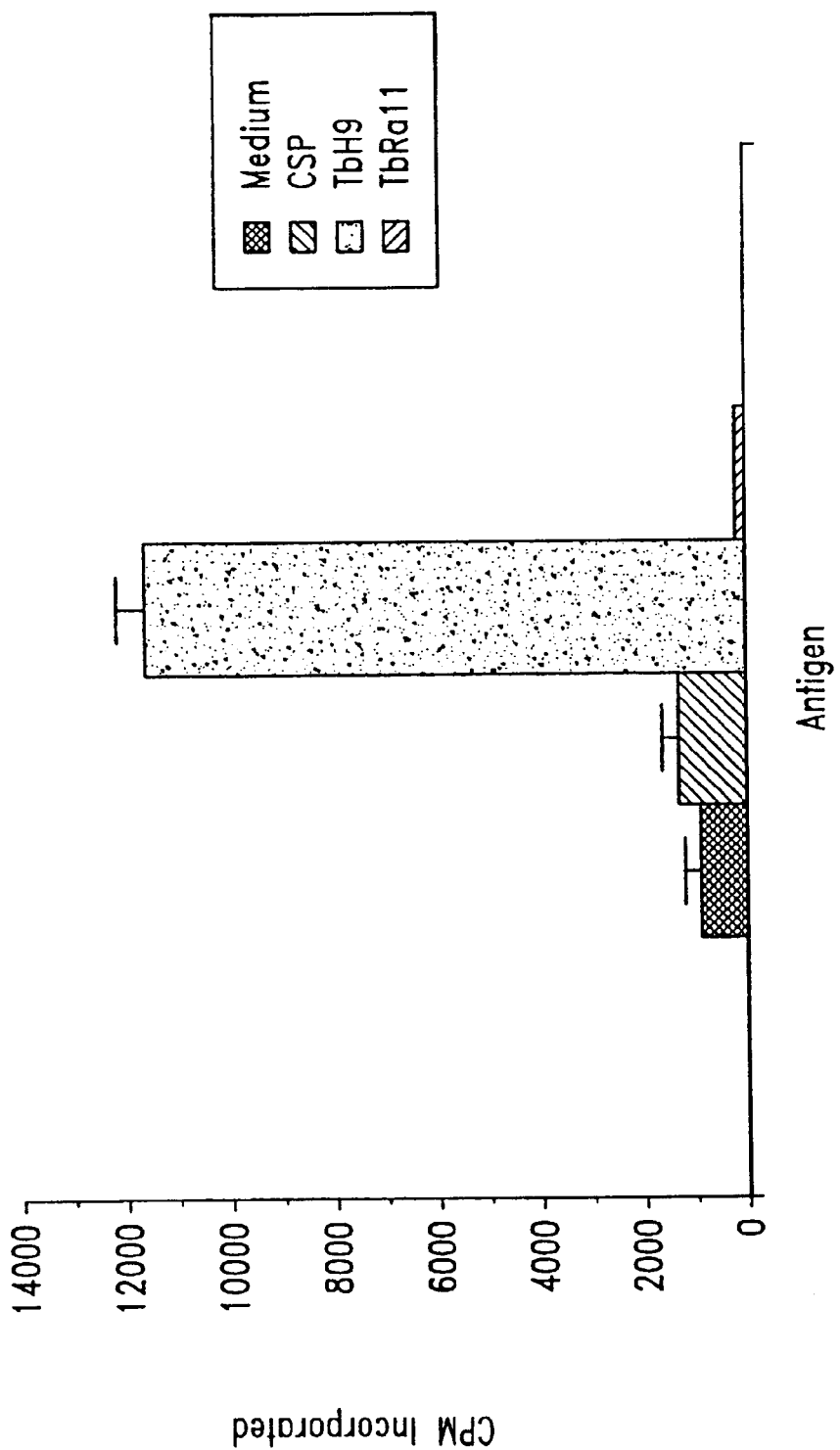
Figure 3B:
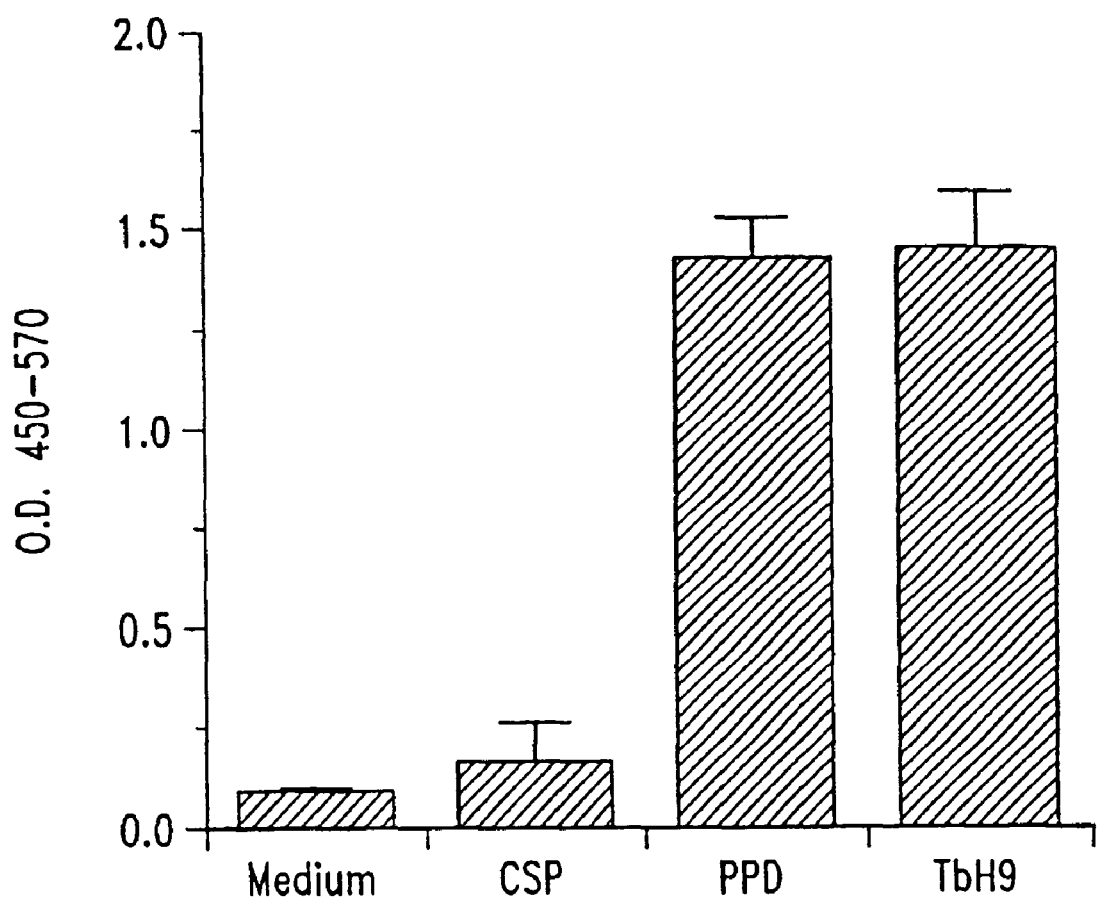

The finding that TbH-9 is an intracellular antigen was confirmed by determining the reactivity of TbH-9-specific human T cell clones to recombinant TbH-9, secretory *M. tuberculosis* proteins and PPD. A TbH-9-specific T cell clone (designated 131TbH-9) was generated from PB,MC of a healthy PPD-positive donor. The proliferative response of 131 TbH-9 to secretory proteins, recombinant TbH-9 and a control *M. tuberculosis* antigen, TbRa11, was determined by measuring uptake of tritiated thymidine, as described in Example 1. As shown in FIG. 3A, the clone 131TbH-9 responds specifically to TbH-9, showing that TbH-9 is not a significant component of *M. tuberculosis* secretory proteins. FIG. 3B shows the production of IFN-γ by a second TbH-9-specific T cell clone (designated PPD 800-10) prepared from PBMC from a healthy PPD-positive donor, following stimulation of the T cell clone with secretory proteins, PPD or recombinant TbH-9. These results further confirm that TbH-9 is not secreted by *M. tuberculosis*.

Example 4

PURIFICATION AND CHARACTERIZATION OF A POLYPEPTIDE FROM TUBERCULIN PURIFIED PROTEIN DERIVATIVE

An *M. tuberculosis* polypeptide was isolated from tuberculin purified protein derivative (PPD) as follows.

PPD was prepared as published with some modification (Seibert, F. et al., Tuberculin purified protein derivative. Prepiration and analyses of a large quantity for standard. *The American Review of Tuberculosis* 44:9–25, 1941). *M. tuberculosis* Rv strain was grown for 6 weeks in synthetic medium in roller bottles at 37° C. Bottles containing the bacterial growth were then heated to 100° C. in water vapor for 3 hours. Cultures were sterile filtered using a 0.22μ filter and the liquid phase was concentrated 20 times using a 3 kD cut-off membrane. Proteins were precipitated once with 50% ammonium sulfate solution and eight times with 25% ammonium sulfate solution. The resulting proteins (PPD) were fractionated by reverse phase liquid chromatography (RP-HPLC) using a C18 column (7.8×300 mM; Waters, Milford, Mass.) in a Biocad HPLC system (Perseptive Biosystems, Framingham, Mass.). Fractions were eluted from the column with a linear gradient from 0–100% buffer (0.1% TFA in acetonitrile). The flow rate was 10 ml/minute and eluent was monitored at 214 nm and 280 nm.

Six fractions were collected, dried, suspended in PBS and tested individually in *M. tuberculosis*-infected guinea pigs for induction of delayed type hypersensitivity (DTH) reaction. One fraction was found to induce a strong DTH reaction and was subsequently fractionated further by RP-HPLC on a microbore Vydac C18 column (Cat. No. 218TP5115) in a Perkin Elmer/Applied Biosystems Division Model 172 HPLC. Fractions were eluted with a linear gradient from 5–100% buffer (0.05% TFA in acetonitrile) with a flow rate of 80 μl/minute. Eluent was monitored at 215 nm. Eight fractions were collected and tested for induction of DTH in *M. tuberculosis*-infected guinea pigs. One fraction was found to induce strong DTH of about 16 mm induration. The other fractions did not induce detectable DTH. The positive fraction was submitted to SDS-PAGE gel electrophoresis and found to contain a single protein band of approximately 12 kD molecular weight.

This polypeptide, herein after referred to as DPPD, was sequenced from the amino terminal using a Perkin Elmer/Applied Biosystems Division Procise 492 protein sequencer as described above and found to have the N-terminal sequence shown in SEQ ID No.: 124. Comparison of this sequence with known sequences in the gene bank as described above revealed no known homologies. Four cyanogen bromide fragments of DPPD were isolated and found to have the sequences shown in SEQ ID Nos.: 125–128.

Example 5

Synthesis of Synthetic Polypeptides

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoro-.acetic acid (TFA) and lyophilized prior to purification by C18 reverse phase HPLC. A gradient of 0–60% acetonitrile (containing 0.1% TFA) in water (containing 0.1% TFA) may be used to elute the peptides. Following lyophilization of the pDure fractions, the peptides may be characterized using electrospray mass spectrometry and by amino acid analysis.

This procedure was used to synthesize a TbM-1 peptide that contains one and a half repeats of a TbM-1 sequence. The TbM-1 peptide has the sequence GCGDRSGGNLD-QIRLRRDRSGGNL (SEQ ID No. 63).

Example 6

USE OF REPRESENTATIVE ANTIGENS FOR SERODIAGNOSIS OF TUBERCULOSIS

This Example illustrates the diagnostic properties of several representative antigens.

Assays were performed in 96-well plates were coated with 200 ng antigen diluted to 50 μL in carbonate coating buffer, pH 9.6. The wells were coated overnight at 4° C. (or 2 hours at 37° C.). The plate contents were then removed and the wells were blocked for 2 hours with 200 μL of PBS/1% BSA. After the blocking step, the wells were washed five times with PBS/0. 1% Tween 20™. 50 μL sera, diluted 1:100 in PBS/0.1% Tween 20™/0.1% BSA, was, then added to each well and incubated for 30 minutes at room temperature. The plates were then washed again five times with PBS/0.1% Tween 20™.

The enzyme conjugate (horseradish peroxidase—Protein A, Zymed, San Francisco, Calif.) was then diluted 1:10,000 in PBS/0.1% Tween 20™/0.1% BSA, and 50 μL of the diluted conjugate was added to each well and incubated for 30 minutes at room temperature. Following incubation, the wells were washed five times with PBS/0.1% Tween 20™. 100 μL of tetramethylbenzidine peroxidase (TMB) substrate (Kirkegaard and Perry Laboratories, Gaithersburg, Md.) was added, undiluted, and incubated for about 15 minutes. The reaction was stopped with the addition of 100 μL of 1 N $H_2SO_4$ to each well, and the plates were read at 450 nm.

Figure 4:
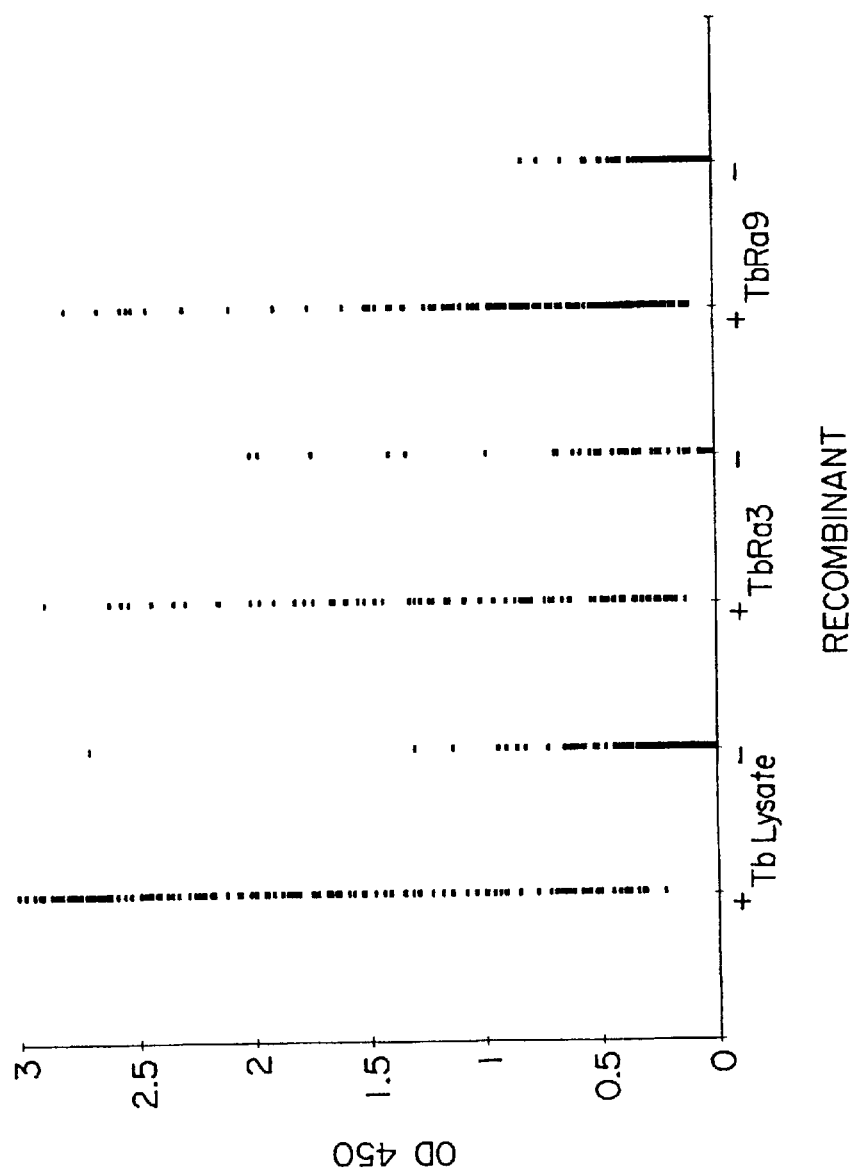

FIG. 4 shows the ELISA reactivity of two recombinant antigens isolated using method A in Example 3 (TbRa3 and TbRa9) with sera from *M. tuberculosis* positive and negative patients. The reactivity of these antigens is compared to that of bacterial lysate isolated from *M. tuberculosis* strain H37Ra (Difco, Detroit, Mich.). In both cases, the recombinant antigens differentiated positive from negative sera. Based on cut-off values obtained from receiver-operator curves, TbRa3 detected 56 out of 87 positive sera, and TbRa9 detected 111 out of 165 positive sera.

Figure 5:
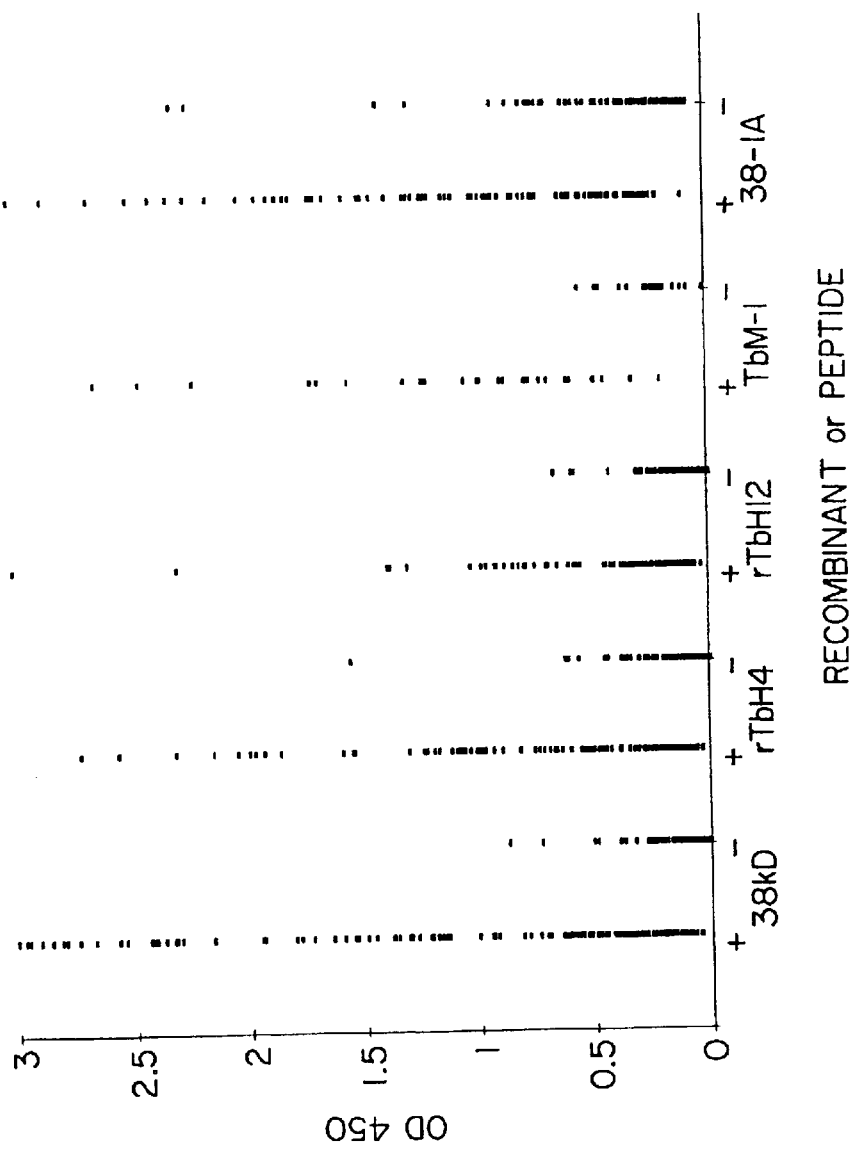

FIG. 5 illustrates the ELISA reactivity of representative antigens isolated using method B of Example 3. The reactivity of the recombinant antigens TbH4, TbH12, Tb38-1 and the peptide TbM-1 (as described in Example 4) is compared to that of the 38 kD antigen described by Andersen and Hansen, *Infect. Immun.* 57:2481–2488, 1989. Again, all of the polypeptides tested differentiated positive from negative sera. Based on cut-off values obtained from receiver-operator curves, TbH4 detected 67 out of 126 positive sera, TbHl2 detected 50 out of 125 positive sera, 38-1 detected 61 out of 101 positive sera and the rbM-1 peptide detected 25 out of 30 positive sera.

The reativity of four antigens (TbRa3, TbRa9, TbH4 and TbH12) with sera from a group of *M. tuberculosis* infected patients with differing reactivity in the acid fast stain of sputum (Smithwick and David, *Tubercle* 52:226, 1971) was also examined, and compared to the reactivity of *M. tuberculosis* lysate and the 38 kD antigen. The results are presented in Table 3, below:

TABLE 3

REACTIVITY OF ANTIGENS WITR SERA FROM *M. TUBERCULOSIS* PATIENTS

| Patient | Acid Fast Sputum | ELISA Values | | | | | |
|---|---|---|---|---|---|---|---|
| | | Lysate | 38kD | TbRa9 | TbH12 | TbH4 | TbRa3 |
| Tb01B93I-2 | ++++ | 1.853 | 0.634 | 0.998 | 1.022 | 1.030 | 1.314 |
| Tb01B93I-19 | ++++ | 2.657 | 2.322 | 0.608 | 0.837 | 1.857 | 2.335 |
| Tb01B93I-8 | +++ | 2.703 | 0.527 | 0.492 | 0.281 | 0.501 | 2.002 |
| Tb01B93I-10 | +++ | 1.665 | 1.301 | 0.685 | 0.216 | 0.448 | 0.458 |
| Th01B931-11 | +++ | 2.817 | 0.697 | 0.509 | 0.301 | 0.173 | 2.608 |
| Tb01B93I-15 | +++ | 1.28 | 0.283 | 0.808 | 0.218 | 1.537 | 0.811 |
| Tb01B93I-16 | +++ | 2.908 | >3 | 0.899 | 0.441 | 0.593 | 1.080 |
| Tb01B93I-25 | +++ | 0.395 | 0.131 | 0.335 | 0.211 | 0.107 | 0.948 |
| Tb01B93I-87 | +++ | 2.653 | 2.432 | 2.282 | 0.977 | 1.221 | 0.857 |
| Tb01B93I-89 | +++ | 1.912 | 2.370 | 2.436 | 0.876 | 0.520 | 0.952 |
| Tb01B94I-108 | +++ | 1.639 | 0.341 | 0.797 | 0.368 | 0.654 | 0.798 |
| Tb01B94I-201 | +++ | 1.721 | 0.419 | 0.661 | 0.137 | 0.064 | 0.692 |
| Th01B931-88 | ++ | 1.939 | 1.269 | 2.519 | 1.381 | 0.214 | 0.530 |
| Tb01B931-92 | ++ | 2.355 | 2.329 | 2.78 | 0.685 | 0.997 | 2.527 |
| Tb01B941-109 | ++ | 0.993 | 0.620 | 0.574 | 0.441 | 0.5 | 2.558 |
| Tb01B941-210 | ++ | 2.777 | >3 | 0.393 | 0.367 | 1.004 | 1.315 |
| Tb01B941-224 | ++ | 2.913 | 0.476 | 0.251 | 1.297 | 1.990 | 0.256 |
| Tb01B931-9 | + | 2.649 | 0.278 | 0.210 | 0.140 | 0.181 | 1.586 |
| Tb01B931-14 | + | >3 | 1.538 | 0.282 | 0.291 | 0.549 | 2.880 |
| Tb01B931-21 | + | 2.645 | 0.739 | 2.499 | 0.783 | 0.536 | 1.770 |
| Tb01B931-22 | + | 0.714 | 0.451 | 2.082 | 0.285 | 0.269 | 1.159 |
| Tb01B931-31 | + | 0.956 | 0.490 | 1.019 | 0.812 | 0.176 | 1.293 |
| Tb01B931-32 | − | 2.261 | 0.786 | 0.668 | 0.273 | 0.535 | 0.405 |
| Tb01B931-52 | − | 0.658 | 0.114 | 0.434 | 0.330 | 0.273 | 1.140 |
| Tb01B931-99 | − | 2.118 | 0.584 | 1.62 | 0.119 | 0.977 | 0.729 |
| Tb01B941-130 | − | 1.349 | 0.224 | 0.86 | 0.282 | 0.383 | 2.146 |
| Th01B941-131 | − | 0.685 | 0.324 | 1.173 | 0.059 | 0.118 | 1.431 |
| AT4-0070 | Normal | 0.072 | 0.043 | 0.092 | 0.071 | 0.040 | 0.039 |
| AT4-0105 | Normal | 0.397 | 0.121 | 0.118 | 0.103 | 0.078 | 0.390 |
| 3/15/94-1 | Normal | 0.227 | 0.064 | 0.098 | 0.026 | 0.001 | 0.228 |
| 4/15/93-2 | Normal | 0.114 | 0.240 | 0.071 | 0.034 | 0.041 | 0.264 |
| 5/26/94-4 | Normal | 0.089 | 0.259 | 0.096 | 0.046 | 0.008 | 0.053 |
| 5/26/94-3 | Normal | 0.139 | 0.093 | 0.085 | 0.019 | 0.067 | 0.01 |

Based on cut-off values obtained from receiver-operator curves, TbRa3 detected 23 out of 27 positive sera, TbRa9 detected 22 out of 27, TbH4 detected 18 out of 27 and TbH12 detected 15 out of 27. If used in combination, these four antigens would have a theoretical sensitivity of 27 out of 27, indicating that these antigens should complement each other in the serological detection of *M. tuberculosis* infection. In addition, several of the recombinant antigens detected positive sera that were not detected using the 38 kD antigen, indicating that these antigens may be complementary to the 38 kD antigen.

Figure 6:
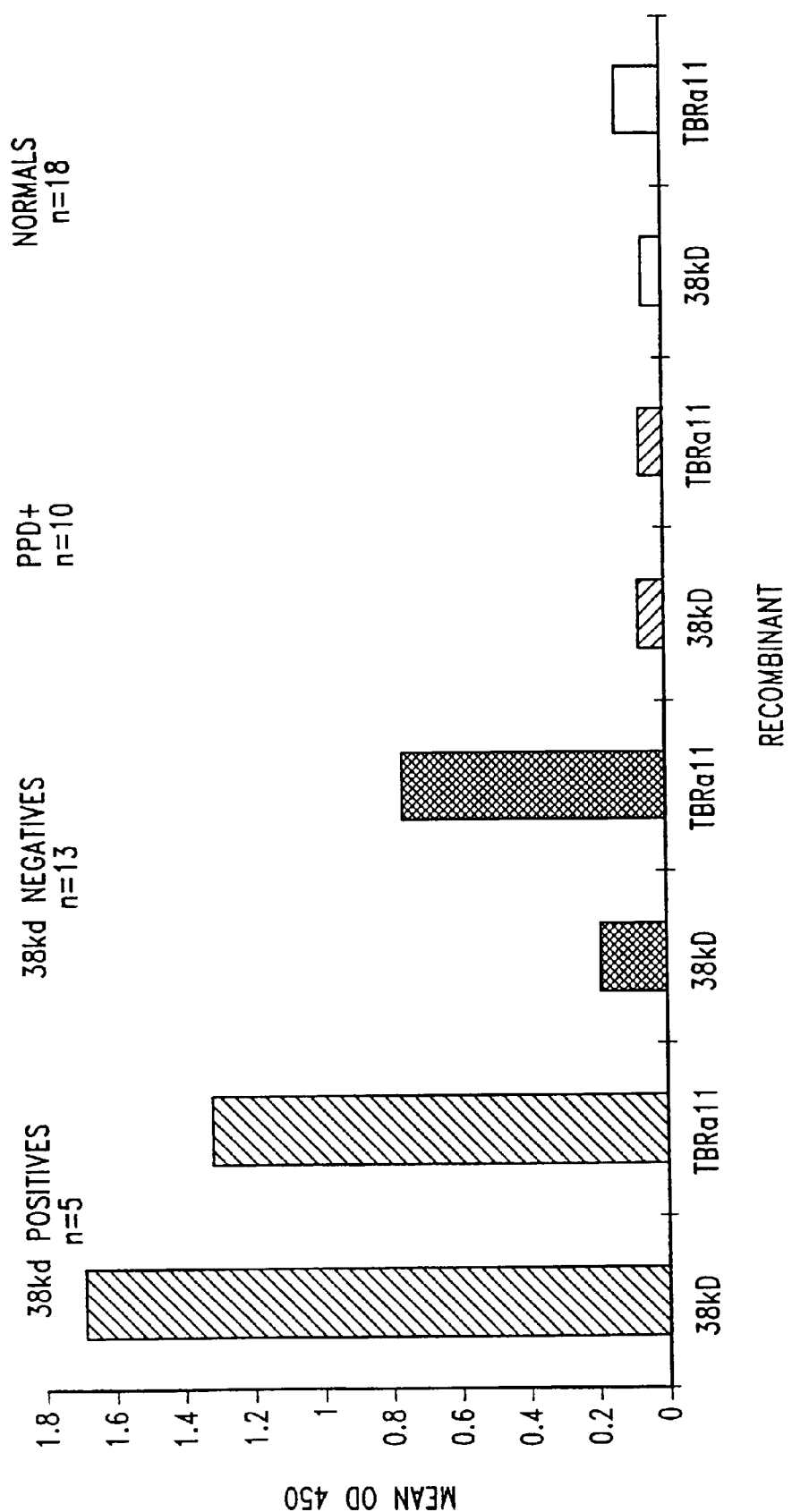

The reactivity of the recombinant antigen TbRa11 with sera from *M. tuberculosis* patients shown to be negative for the 38 kD antigen, as well as with sera from PPD positive and normal donors, was determined by ELISA as described above. The results are shown in FIG. 6 which indicates that TbRa11, while being negative with sera from PPD positive and normal donors, detected sera that were negative with the 38 kD antigen. Of the thirteen 38 kD negative sera tested, nine were positive with TbRa11, indicating that this antigen may be reacting with a sub-group of 38 kD antigen negative sera. In contrast, in a group of 38 kD positive sera where TbRa11 was reactive, the mean OD 450 for TbRa11 was lower than that for the 38 kD antigen. The data indicate an inverse relationship between the presence of TbRa11 activity and 38 kD positivity.

Figure 7:
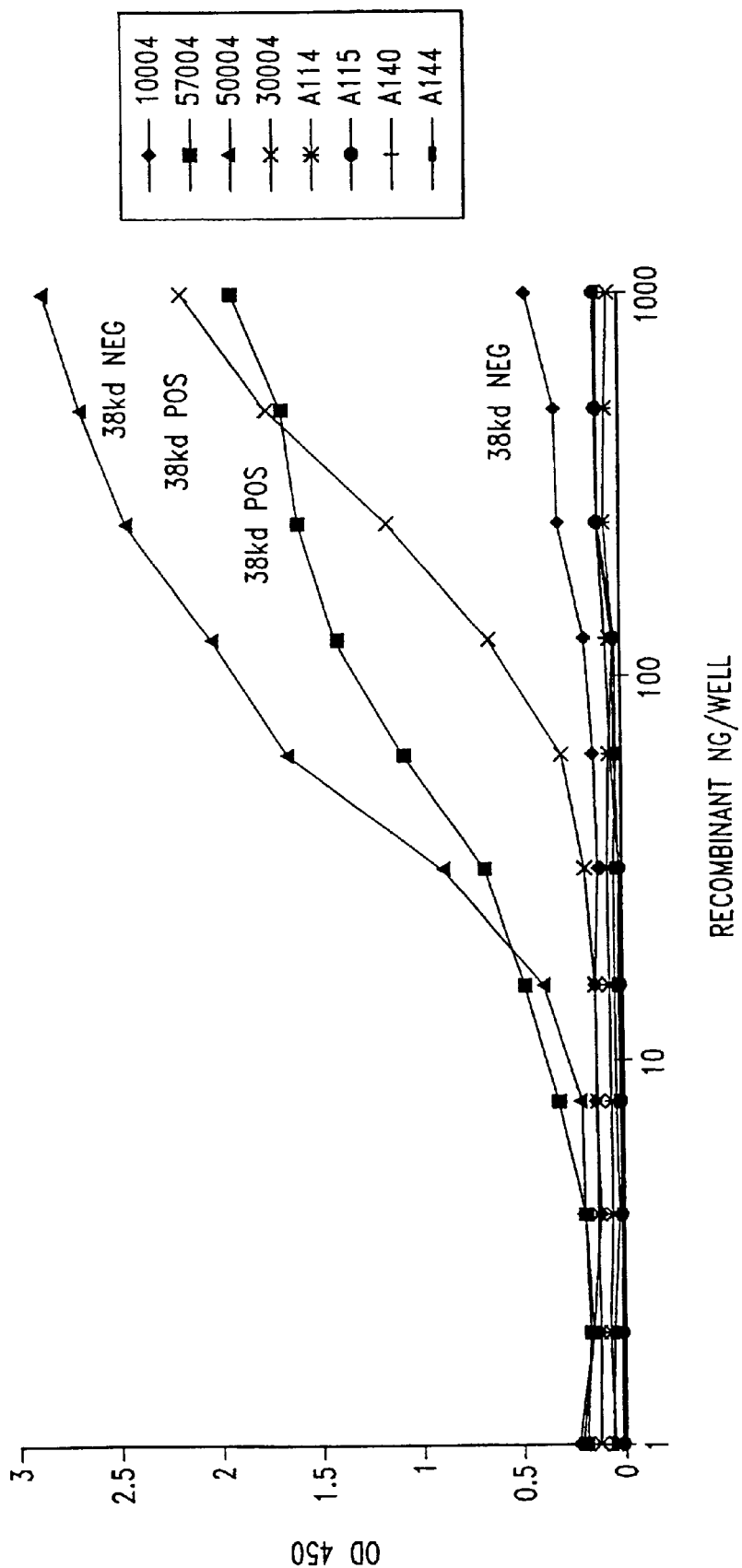

The antigen TbRa2A was tested in an indirect ELISA using initially 50 μl of serum at 1:100 dilution for 30 minutes at room temperature followed by washing in PBS Tween and incubating for 30 minutes with biotinylated Protein A (Zymed, San Francisco, Calif.) at a 1:10,000 dilution. Following washing, 50 μl of streptavidin-horseradish peroxidase (Zymed) at 1:10,000 dilution was added and the mixture incubated for 30 minutes. After washing, the assay was developed with TMB substrate as described above. The reactivity of TbRa2A with sera from *M. tuberculosis* patients and normal donors in shown in Table 4. The mean value for reactivity of TbRa2A with sera from *M. tuberculosis* patients was 0.444 with a standard deviation of 0.309. The mean for reactivity with sera from normal donors was 0.109 with a standard deviation of 0.029. Testing of 38 kD negative sera (FIG. 7) also indicated that the TbRa2A antigen was capable of detecting sera in this category.

TABLE 4

REACTIVITY OF TBRA2A WITH SERA FROM *M. TUBERCULOSIS* PATIENTS AND FROM NORMAL DONORS

| Serum ID | Status | OD 450 |
|---|---|---|
| Tb85 | TB | 0.680 |
| Tb86 | TB | 0.450 |
| Tb87 | TB | 0.263 |
| Tb88 | TB | 0.275 |
| Tb89 | TB | 0.403 |
| Tb91 | TB | 0.393 |
| Tb92 | TB | 0.401 |
| Tb93 | TB | 0.232 |
| Tb94 | TB | 0.333 |
| Tb95 | TB | 0.435 |
| Tb96 | TB | 0.284 |
| Tb97 | TB | 0.320 |
| Tb99 | TB | 0.328 |
| Tb100 | TB | 0.817 |
| Tb101 | TB | 0.607 |
| Tb102 | TB | 0.191 |
| Tb103 | TB | 0.228 |
| Tb107 | TB | 0.324 |

TABLE 4-continued

REACTIVITY OF TBRA2A WITH SERA FROM *M. TUBERCULOSIS* PATIENTS AND FROM NORMAL DONORS

| Serum ID | Status | OD 450 |
|---|---|---|
| Tb109 | TB | 1.572 |
| Tb112 | TB | 0.338 |
| DL4-0176 | Normal | 0.036 |
| AT4-0043 | Normal | 0.126 |
| AT4-0044 | Normal | 0.130 |
| AT4-0052 | Normal | 0.135 |
| AT4-0053 | Normal | 0.133 |
| AT4-0062 | Normal | 0.128 |
| AT4-0070 | Normal | 0.088 |
| AT4-0091 | Normal | 0.108 |
| AT4-0100 | Normal | 0.106 |
| AT4-0105 | Normal | 0.108 |
| AT4-0109 | Normal | 0.105 |

Figure 8:
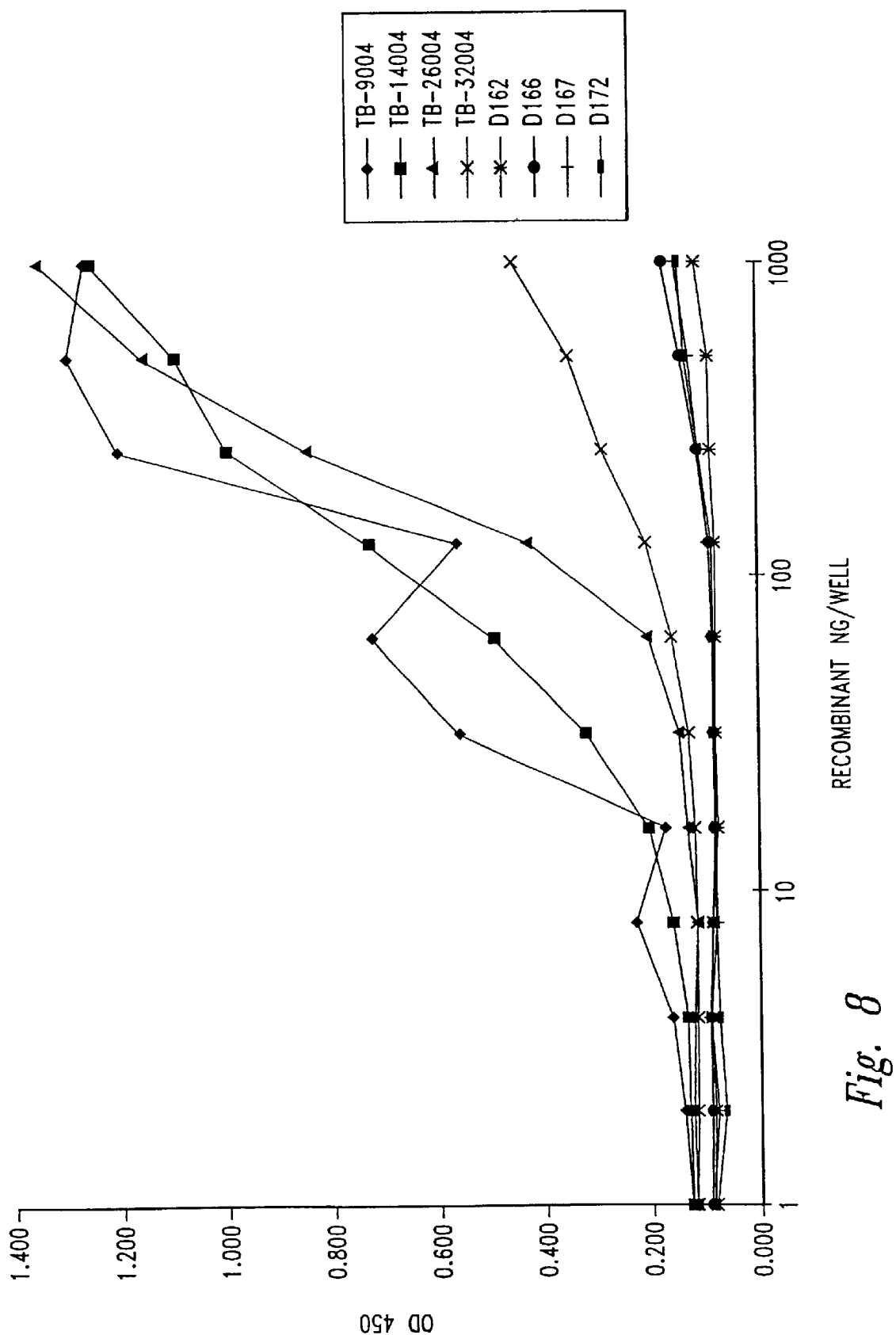

The reactivity of the recombinant antigen (g) (SEQ ID No. 60) with sera from *M. tuberculosis* patients and normal donors was determined by ELISA as described above. FIG. 8 shows the results of the titration of antigen (g) with four *M. tuberculosis* positive sera that were all reactive with the 38 kD antigen and with four donor sera. All four positive sera were reactive with antigen (g).

Figure 9:
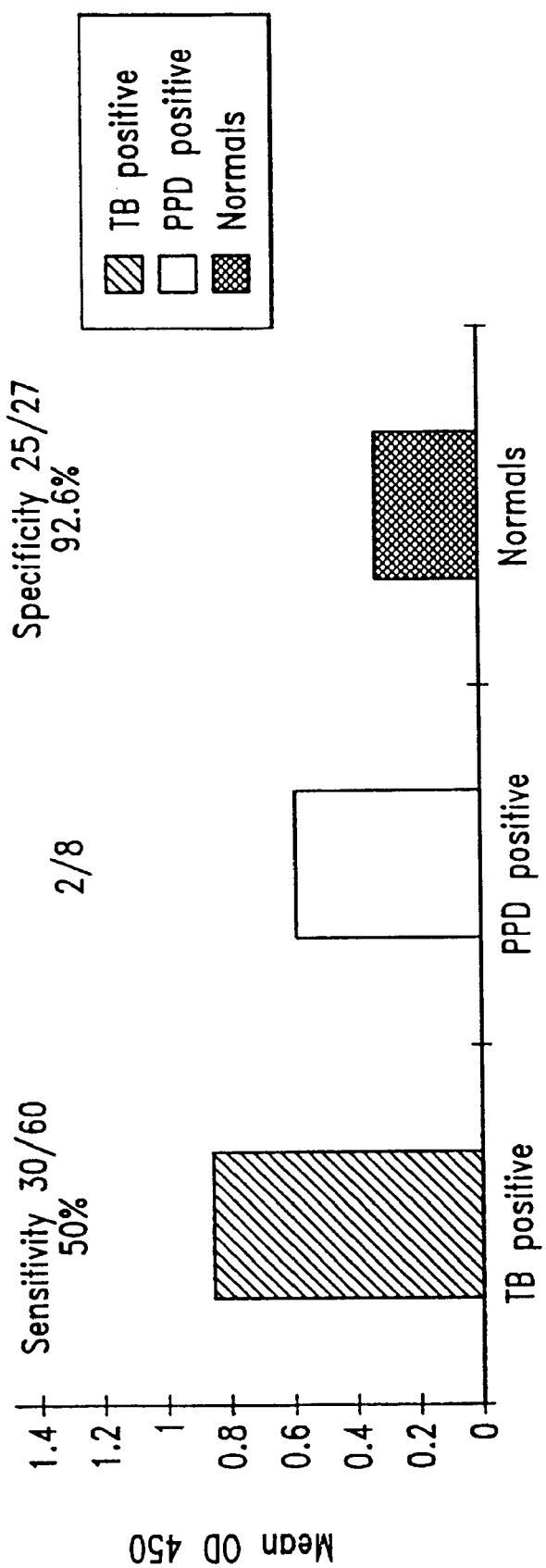

The reactivity of the recombinant antigen TbH-29 (SEQ ID NO: 137) with sera from *M. tuberculosis* patients, PPD positive donors and normal donors was determined by indirect ELISA as described above. The results are shown in FIG. 9. TbH-29 detected 30 out of 60 *M. tuberculosis* sera, 2 out of 8 PPD positive sera and 2 out of 27 normal sera.

Figure 10:
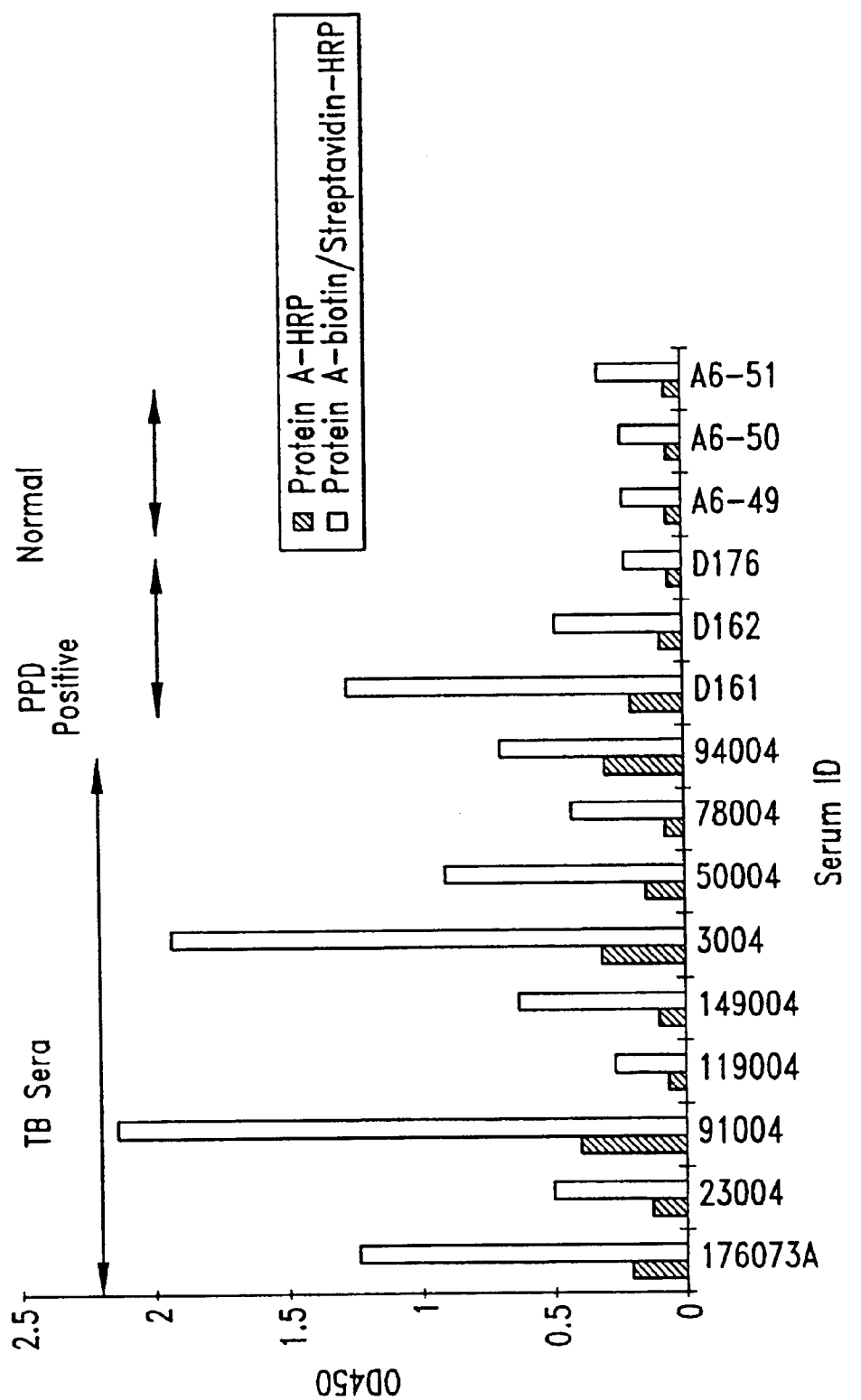
Figure 11:
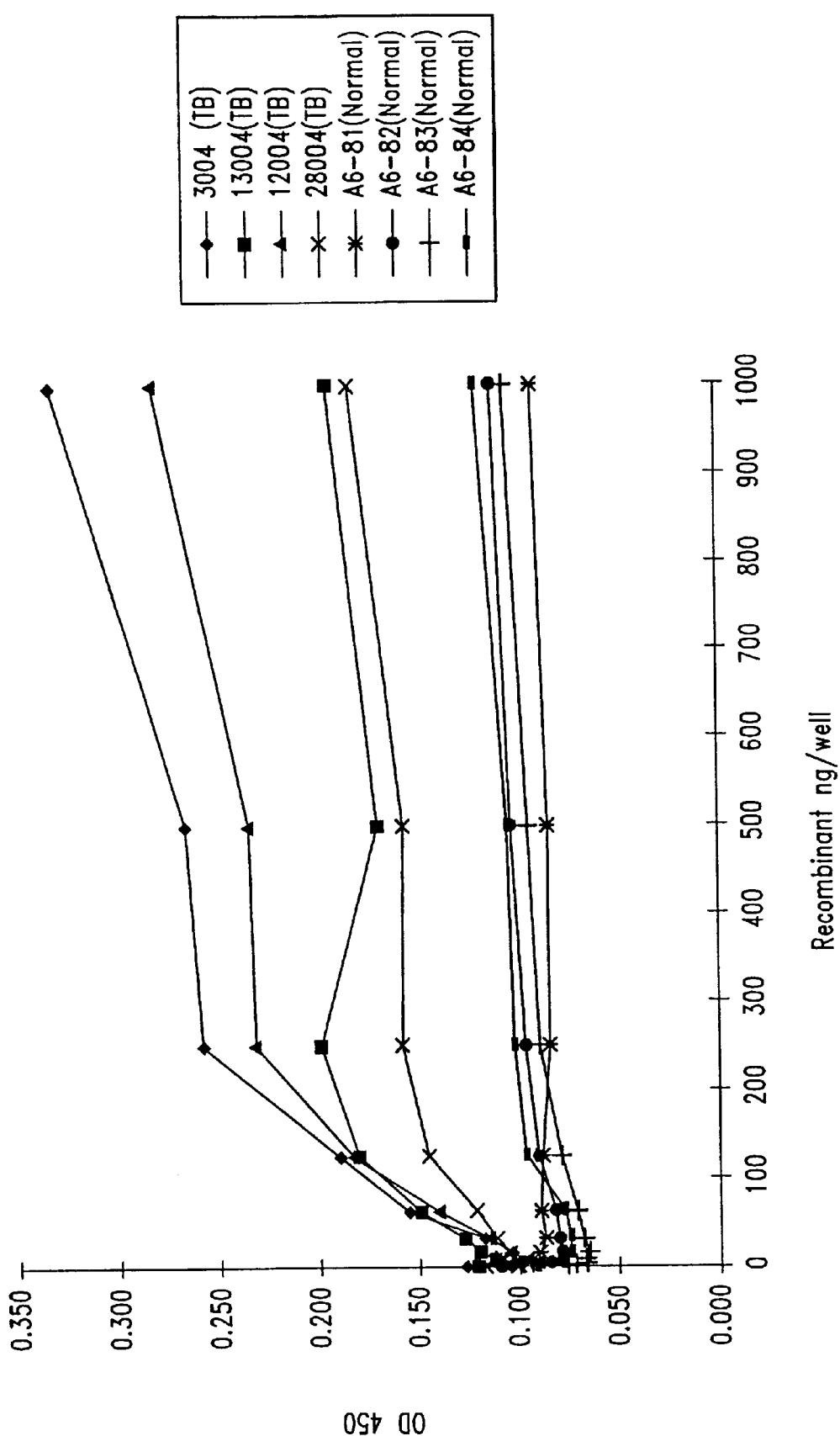

FIG. 10 shows the results of ELISA tests (both direct and indirect) of the antigen TbH-33 (SEQ ID NO: 140) with sera from *M. tuberculosis* patients and from normal donors and with a pool of sera from *M. tuberculosis* patients. The mean OD 450 was demonstrated to be higher with sera from *M. tuberculosis* patients than from normal donors, with the mean OD 450 being significantly higher in the indirect ELISA than in the direct ELISA. FIG. 11 is a titration curve for the reactivity of recombinant TbH-33 with sera from *M. tuberculosis* patients and from normal donors showing an increase in OD 450 with increasing concentration of antigen.

Example 7

PREPARATION AND CHARACTERIZATION OF *M. TUBERCULOSIS* FUSION PROTEINS

A fusion protein containing TbRa3, the 38 kD antigen and Tb38-1 was prepared as follows.

Each of the DNA constructs TbRa3, 38 kD and Tb38-1 were modified by PCR in order to facilitate their fusion and the subsequent expression of the fusion protein TbRa3-38 kD-Tb38-1. TbRa3, 38 kD and Tb38-1 DNA was used to perform PCR using the primers PDM-64 and PDM-65 (SEQ ID NO: 141 and 142), PDM-57 and PDM-58 (SEQ ID NO: 143 and 144), and PDNI-69 and PDM-60 (SEQ ID NO: 145–146), respectively. In each case, the DNA amplification was performed using 10 μl 10X Pfu buffer, 2 μl 10 mM dNTPs, 2 μl each of the PCR primers at 10 μM concentration, 81.5 μl water, 1.5 μl Pfu DNA polymerase (Stratagene, La Jolla, Calif.) and 1 μl DNA at either 70 ng/μl (for TbRa3) or 50 ng/μl (for 38 kD and Tb38-1). For TbRa3, denaturation at 94° C. was performed for 2 min, followed by 40 cycles of 96° C. for 15 sec and 72° C. for 1 min, and lastly by 72° C. for 4 min. For 38 kD, denaturation at 96° C. was performed for 2 min, followed by 40 cycles of 96° C. for 30 sec, 68° C. for 15 sec and 72° C. for 3 min, and finally by 72° C. for 4 min. For Tb38-1 denaturation at 94° C. for 2 min was followed by 10 cycles of 96° C. for 15 sec, 68° C. for 15 sec and for 1.5 min, 30 cycles of 96° C. for 15 sec, 64° C. for 15 sec and 72° C. for 1.5, and finally by 72° C. for 4 min.

The TbRa3 PCR fragment was digested with NdeI and EcoRI and cloned directly into pT70L2 IL 1 vector using NdeI and EcoRI sites. The 38 kD PCR fragment was digested with Sse83871, treated with T4 DNA polymerase to make blunt ends and then digested with EcoRI for direct cloning into the pT70L2Ra3-1 vector which was digested with StuI and EcoRI. The 38-1 PCR fragment was digested with Eco47III and EcoRI and directly subcloned into pT70L2Ra3/38kD-17 digested with the same enzymes. The whole fusion was then transferred to pET28b NT LMEIF—1 using NdeI and EcoRI sites. The fusion construct was confirmed by DNA sequencing.

The expression construct was transformed to BLR pLys S *E. coli* (Novagen, Madison, Wis.) and grown overnight in LB broth with kanamycin (30 μg/ml) and chloramphenicol (34 μg/ml). This culture (12 ml) was used to inoculate 500 ml 2XYT with the same antibiotics and the culture was induced with IPTG at an OD560 of 0.44 to a final concentration of 1.2 mM. Four hours post-induction, the bacteria were harvested and sonicated in 20 mM Tris (8.0), 100 mM NaCl, 0.1% DOC, 20 μg/ml Leupeptin, 20 mM PMSF followed by centrifugation at 26,000×g. The resulting pellet was resuspended in 8 M urea, 20 mM Tris (8.0), 100 mM NaCl and bound to Pro-bond nickel resin (Invitrogen, Carlsbad, Calif.). The column was washed several times with the above buffer then eluted with an imidazole gradient (50 mM, 100 mM, 500 mM imidazole was added to 8 M urea, 20 mM Tris (8.0), 100 mM NaCl). The eluates containing the protein of interest were then dialkyed against 10 mM Tris (8.0).

The DNA and amino acid sequences for the resulting fusion protein (hereinafter referred to as TbRa3–38 kD-Tb38-1) are provided in SEQ ID NO: 147 and 148, respectively.

A fusion protein containing the two antigens TbH-9 and Tb38-1 (hereinafter referred to as TbH9-Tb38-1) without a hinge sequence, was prepared using a similar procedure to that described above. The DNA sequence for the TbH9-Tb38-1 fusion protein is provided in SEQ ID NO: 151.

Example 8

USE OF *M. TUBERCULOSIS* FUSION PROTEINS FOR SERODIAGNOSIS OF TUBERCULOSIS

The effectiveness of the fusion protein TbRa3–38 kD-Tb38-1, prepared as described above, in the serodiagnosis of tuberculosis infection was examined by ELISA.

The ELISA protocol was as described above in Example 6, with the fusion protein being coated at 200 ng/well. A panel of sera was chosen from a group of tuberculosis patients previously shown, either by ELISA or by western blot analysis, to react with each of the three antigens individually or in combination. Such a panel enabled the dissection of the serological reactivity of the fusion protein to determine if all three epitopes functioned with the fusion protein. As shown in Table 5, all four sera that reacted with TbRa3 only were detectable with the fusion protein. Three sera that reacted only with Tb38-1 were also detectable, as were two sear that reacted with 38 kD alone. The remaining 15 sera were all positive with the fusion protein based on a cut-off in the assay of mean negatives +3 standard deviations. This data demonstrates the functional activity of all three epitopes in the fusion protein.

TABLE 5

REACTIVITY OF FUSION PROTEIN WITH SERA FROM *M. TUBERCULOSIS* PATIENTS

| Serum ID | Status | ELISA and/or Western Blot Reactivity with Individual proteins 38kd | Tb38-1 | TbRa3 | Fusion recombinant OD 450 | Fusion Recombinant Status |
|---|---|---|---|---|---|---|
| 01B93I-40 | TB | − | − | + | 0.413 | + |
| 01B93I-41 | TB | − | + | + | 0.392 | + |
| 01B93I-29 | TB | + | − | + | 2.217 | + |
| 01B93I-109 | TB | + | ± | + | 0.522 | + |
| 01B93I-132 | TB | + | + | + | 0.937 | + |
| 5004 | TB | ± | + | ± | 1.098 | + |
| 15004 | TB | + | + | + | 2.077 | + |
| 39004 | TB | + | + | + | 1.675 | + |
| 68004 | TB | + | + | + | 2.388 | + |
| 99004 | TB | − | + | ± | 0.607 | + |
| 107004 | TB | − | + | ± | 0.667 | + |
| 92004 | TB | + | ± | ± | 1.070 | + |
| 97004 | TB | + | − | ± | 1.152 | + |
| 118004 | TB | + | − | ± | 2.694 | + |
| 173004 | TB | + | + | + | 3.258 | + |
| 175004 | TB | + | − | + | 2.514 | + |
| 274004 | TB | − | − | + | 3.220 | + |
| 276004 | TB | − | + | − | 2.991 | + |
| 282004 | TB | + | − | − | 0.824 | + |
| 289004 | TB | − | − | + | 0.848 | + |
| 308004 | TB | − | + | − | 3.338 | + |
| 314004 | TB | − | + | − | 1362 | + |
| 317004 | TB | + | − | − | 0.763 | + |
| 312004 | TB | − | − | + | 1.079 | + |
| D176 | PPD | − | − | − | 0.145 | − |
| D162 | PPD | − | − | − | 0.073 | − |

TABLE 5-continued

REACTIVITY OF FUSION PROTEIN WITH SERA FROM *M. TUBERCULOSIS* PATIENTS

| Serum ID | Status | ELISA and/or Western Blot Reactivity with Individual proteins | | | Fusion recombinant OD 450 | Fusion Recombinant Status |
|---|---|---|---|---|---|---|
| | | 38kd | Tb38-1 | TbRa3 | | |
| D161 | PPD | – | – | – | 0.097 | – |
| D27 | PPD | – | – | – | 0.082 | – |
| A6-124 | NORMAL | – | – | – | 0.053 | – |
| A6-125 | NORMAL | – | – | – | 0.087 | – |
| A6-126 | NORMAL | – | – | – | 0.346 | ± |
| A6-127 | NORMAL | – | – | – | 0.064 | – |
| A6-128 | NORMAL | – | – | – | 0.034 | – |
| A6-129 | NORMAL | – | – | – | 0.037 | – |
| A6-130 | NORMAL | – | – | – | 0.057 | – |
| A6-131 | NORMAL | – | – | – | 0.054 | – |
| A6-132 | NORMAL | – | – | | 0.022 | – |
| A6-133 | NORMAL | – | – | | 0.147 | – |
| A6-134 | NORMAL | – | – | – | 0.101 | – |
| A6-135 | NORMAL | – | – | | 0.066 | – |
| A6-136 | NORMAL | – | – | | 0.054 | – |
| A6-137 | NORMAL | – | – | – | 0.065 | – |
| A6-138 | NORMAL | – | – | – | 0.041 | – |
| A6-139 | NORMAL | – | – | – | 0.103 | – |
| A6-140 | NORMAL | – | – | – | 0.212 | – |
| A6-141 | NORMAL | – | – | – | 0.056 | – |
| A6-142 | NORMAL | – | – | – | 0.051 | – |

From the foregoing, it will be appreciated that, although specific embodiments of the invention have been described herein for the purpose of illustration, various modifications may be made without deviating from the spirit and scope of the invention.

We claim:

1. An isolated polypeptide comprising an amino acid sequence as set forth in SEQ ID NOs: 53, 63–65, 67–73, 76–88, 90, 92, 93, 95, 97, 115–121, 123, 124, 131, or 132 or an amino acid sequence comprising an immunogenic portion of SEQ ID NOs: 53, 63–65, 67–73, 76–88, 90, 92, 93, 95, 97, 115–121, 123, 124, 131, or 132.

2. The polypeptide of claim 1, wherein the amino acid sequence is as set forth in SEQ ID NO:53 or an immunogenic portion thereof.

3. The polypeptide of claim 1, wherein the amino acid sequence is as set forth in SEQ ID NO:63 or an immunogenic portion thereof.

4. The polypeptide of claim 1, wherein the amino acid sequence is as set forth in SEQ ID NO:64 or an immunogenic portion thereof.

5. The polypeptide of claim 1, wherein the a o acid sequence is as set forth in SEQ ID NO:65 or an immunogenic portion thereof.

6. The polypeptide of claim 1, wherein the amino acid sequence is as set forth in SEQ ID NO:67 or an immunogenic portion thereof.

7. The polypeptide of claim 1, wherein the amino acid sequence is as set forth in SEQ ID NO:68 or an immunuogenic portion thereof.

8. The polypeptide of claim 1, wherein the amino acid sequence is as set forth in SEQ ID NO:69 or an immunogenic portion thereof.

9. The polypeptide of claim 1, wherein the amino acid sequence is as set forth in SEQ ID NO:70 or an immunogenic portion thereof.

10. The polypeptide of claim 1, wherein the amino acid sequence is as set forth in SEQ ID NO:71 or an immunogenic portion thereof.

11. The polypeptide of claim 1, wherein the amino acid sequence is as set forth in SEQ ID NO:72 or an immunogenic portion thereof.

12. The polypeptide of claim 1, wherein the amino acid sequence is as set forth in SEQ ID NO:73 or an immunogenic portion thereof.

13. The polypeptide of claim 1, wherein the amino acid sequence is as set forth in SEQ ID NO:76 or an immunogenic portion thereof.

14. The polypeptide of claim 1, wherein the amino acid sequence is as set forth in SEQ ID NO:77 or an immunogenic portion thereof.

15. The polypeptide of claim 1, wherein the amino acid sequence is as set forth in SEQ ID NO:78 or an immunogenic portion thereof.

16. The polypeptide of claim 1, wherein the amino acid sequence is as set forth in SEQ ID NO:79 or an immunogenic portion thereof.

17. The polypeptide of claim 1, wherein the amino acid sequence is as set forth in SEQ ID NO:80 or an immunogenic portion thereof.

18. The polypeptide of claim 1, wherein the amino acid sequence is as set forth in SEQ ID NO:81 or an immunogenic portion thereof.

19. The polypeptide of claim 1, wherein the amino acid sequence is as set forth in SEQ ID NO:82 or an immunogenic portion thereof.

20. The polypeptide of claim 1, wherein the amino acid sequence is as set forth in SEQ ID NO:83 or an immunogenic portion thereof.

21. The polypeptide of claim 1, wherein the amino acid sequence is as set forth in SEQ ID NO:84 or an immunogenic portion thereof.

22. The polypeptide of claim 1, wherein the amino acid sequence is as set forth in SEQ ID NO:85 or an immunogenic portion thereof.

23. The polypeptide of claim 1, wherein the amino acid sequence is as set forth in SEQ ID NO:86 or an immunogenic portion thereof.

24. The polypeptide of claim 1, wherein the amino acid sequence is as set forth in SEQ ID NO:87 or an immunogenic portion thereof.

25. The polypeptide of claim 1, wherein the amino acid sequence is as set forth in SEQ ID NO:88 or an immunogenic portion thereof.

26. The polypeptide of claim 1, wherein the o acid sequence is as set forth in SEQ ID NO:90 or an immunogenic portion thereof.

27. The polypeptide of claim 1, wherein the amino acid sequence is as set forth in SEQ ID NO:92 or an immunogenic portion thereof.

28. The polypeptide of claim 1, wherein the amino acid sequence is as set forth in SEQ ID NO:93 or an immunogenic portion thereof.

29. The polypeptide of claim 1, wherein the amino acid sequence is as set forth in SEQ ID NO:95 or an immunogenic portion thereof.

30. The polypeptide of claim 1, wherein the amino acid sequence is as set forth in SEQ ID NO:97 or an immunogenic portion thereof.

31. The polypeptide of claim 1, wherein the amino acid sequence is as set forth in SEQ ID NO:115 or an immunogenic portion thereof.

32. The polypeptide of claim 1, wherein the amino acid sequence is as set forth in SEQ ID NO:116 or an immunogenic portion thereof.

33. The polypeptide of claim 1, wherein the amino acid sequence is as set forth in SEQ ID NO:117 or an immunogenic portion thereof.

34. The polypeptide of claim 1, wherein the amino acid sequence is as set forth in SEQ ID NO:118 or an immunogenic portion thereof.

35. The polypeptide of claim 1, wherein the amino acid sequence is as set forth in SEQ ID NO:119 or an immunogenic portion thereof.

36. The polypeptide of claim 1, wherein the amino acid sequence is as set forth in SEQ ID NO:120 or an immunogenic portion thereof.

37. The polypeptide of claim 1, wherein the amino acid sequence is as set forth in SEQ ID NO:121 or an immunogenic portion thereof.

38. The polypeptide of claim 1, wherein the amino acid sequence is as set forth in SEQ ID NO:123 or an immunogenic portion thereof.

39. The polypeptide of claim 1, wherein the amino acid sequence is as set forth in SEQ ID NO:124 or an immunogenic portion thereof.

40. The polypeptide of claim 1, wherein the amino acid sequence is as set forth in SEQ ID NO:131 or an immunogenic portion thereof.

41. The polypeptide of claim 1, wherein the amino acid sequence is as set forth in SEQ ID NO:132 or an immunogenic portion thereof.

42. A polypeptide comprising an amino acid sequence encoded by a polynucleotide sequence as set forth in SEQ ID NOs:1, 2, 4–10, 13–43, 45, 47–52, 94, 96, 133, or 134, or a polypeptide comprising an immunogenic portion of a polypeptide encoded by SEQ ID NOs:1, 2, 4–10, 13–43, 45, 47–52, 94, 96, 133, or 134.

43. The polypeptide of claim 42, wherein the polypeptide comprises an amino acid sequence encoded by SEQ ID NO:1 or an immunogenic portion of the polypeptide encoded by SEQ ID NO:1.

44. The polypeptide of claim 42, wherein the polypeptide comprises an amino acid sequence encoded by SEQ ID NO:2 or an immunogenic portion of the polypeptide encoded by SEQ ID NO:2.

45. The polypeptide of claim 42, wherein the polypeptide comprises an amino acid sequence encoded by SEQ ID NO:4 or an immunogenic portion of the polypeptide encoded by SEQ ID NO:4.

46. The polypeptide of claim 42, wherein the polypeptide comprises an amino acid sequence encoded by SEQ ID NO:5 or an immunogenic portion of the polypeptide encoded by SEQ ID NO:5.

47. The polypeptide of claim 42, wherein the polypeptide comprises an ammo acid sequence encoded by SEQ ID NO:6 or an immunogenic portion of the polypeptide encoded by SEQ ID NO:6.

48. The polypeptide of claim 42, wherein the polypeptide comprises an amino acid sequence encoded by SEQ ID NO:7 or an immunogenic portion of the polypeptide encoded by SEQ ID NO:7.

49. The polypeptide of claim 42, wherein the polypeptide comprises an amino acid sequence encoded by SEQ ID NO:8 or an immunogenic portion of the polypeptide encoded by SEQ ID NO:8.

50. The polypeptide of claim 42, wherein the polypeptide comprises an amino acid sequence encoded by SEQ ID NO:9 or an immunogenic portion of the polypeptide encoded by SEQ ID NO:9.

51. The polypeptide of claim 42, wherein the polypeptide comprises an amino acid sequence encoded by SEQ ID NO:10 or an immunogenic portion of the polypeptide encoded by SEQ ID NO:10.

52. The polypeptide of claim 42, wherein the polypeptide comprises an amino acid sequence encoded by SEQ ID NO:13 or an immunogenic portion of the polypeptide encoded by SEQ ID NO:13.

53. The polypeptide of claim 42, wherein the polypeptide comprises an amino acid sequence encoded by SEQ ID NO:14 or an immunogenic portion of the polypeptide encoded by SEQ ID NO:14.

54. The polypeptide of claim 42, wherein the polypeptide comprises an amino acid sequence encoded by SEQ ID NO:15 or an immunogenic portion of the polypeptide encoded by SEQ ID NO:15.

55. The polypeptide of claim 42, wherein the polypeptide comprises an amino acid sequence encoded by SEQ ID NO:16 or an immunogenic portion of the polypeptide encoded by SEQ ID NO:16.

56. The polypeptide of claim 42, wherein the polypeptide comprises an amino acid sequence encoded by SEQ ID NO:17 or an immunogenic portion of the polypeptide encoded by SEQ ID NO:17.

57. The polypeptide of claim 42, wherein the polypeptide comprises an amino acid sequence encoded by SEQ ID NO:18 or an immunogenic portion of the polypeptide encoded by SEQ ID NO:18.

58. The polypeptide of claim 42, wherein the polypeptide comprises an amino acid sequence encoded by SEQ ID NO:19 or an immunogenic portion of the polypeptide encoded by SEQ ID NO:19.

59. The polypeptide of claim 42, wherein the polypeptide comprises an amino acid sequence encoded by SEQ ID NO:20 or an immunogenic portion of the polypeptide encoded by SEQ ID NO:20.

60. The polypeptide of claim 42, wherein the polypeptide comprises an amino acid sequence encoded by SEQ ID NO:21 or an immunogenic portion of the polypeptide encoded by SEQ ID NO:21.

61. The polypeptide of claim 42, wherein the polypeptide comprises an amino acid sequence encoded by SEQ ID NO:22 or an immunogenic portion of the polypeptide encoded by SEQ ID NO:22.

62. The polypeptide of claim 42, wherein the polypeptide comprises an amino acid sequence encoded by SEQ ID NO:23 or an immunogenic portion of the polypeptide encoded by SEQ ID NO:23.

63. The polypeptide of claim 42, wherein the polypeptide comprises an amino acid sequence encoded by SEQ ID NO:24 or an immunogenic portion of the polypeptide encoded by SEQ ID NO:24.

64. The polypeptide of claim 42, wherein the polypeptide comprises an amino acid sequence encoded by SEQ ID NO:25 or an immunogenic portion of the polypeptide encoded by SEQ ID NO:25.

65. The polypeptide of claim 42, wherein the polypeptide comprises an amino acid sequence encoded by SEQ ID NO:26 or an immunogenic portion of the polypeptide encoded by SEQ ID NO:26.

66. The polypeptide of claim 42, wherein the polypeptide comprises an amino acid sequence encoded by SEQ ID NO:27 or an immunogenic portion of the polypeptide encoded by SEQ ID NO:27.

67. The polypeptide of claim 42, wherein the polypeptide comprises an amino acid sequence encoded by SEQ ID NO:28 or an immunogenic portion of the polypeptide encoded by SEQ ID NO:28.

68. The polypeptide of claim 42, wherein the polypeptide comprises an amino acid sequence encoded by SEQ ID NO:29 or an immunogenic portion of the polypeptide encoded by SEQ ID NO:29.

69. The polypeptide of claim 42, wherein the polypeptide comprises an amino acid sequence encoded by SEQ ID NO:30 or an immunogenic portion of the polypeptide encoded by SEQ ID NO:30.

70. The polypeptide of claim 42, wherein the polypeptide comprises an amino acid sequence encoded by SEQ ID NO:31 or an immunogenic portion of the polypeptide encoded by SEQ ID NO:31.

71. The polypeptide of claim 42, wherein the polypeptide comprises an amino acid sequence encoded by SEQ ID NO:32 or an immunogenic portion of the polypeptide encoded by SEQ ID NO:32.

72. The polypeptide of claim 42, wherein the polypeptide comprises an amino acid sequence encoded by SEQ ID NO:33 or an immunogenic portion of the polypeptide encoded by SEQ ID NO:33.

73. The polypeptide of claim 42, wherein the polypeptide comprises an amino acid sequence encoded by SEQ ID NO:34 or an immunogenic portion of the polypeptide encoded by SEQ ID NO:34.

74. The polypeptide of claim 42, wherein the polypeptide comprises an amino acid sequence encoded by SEQ ID NO:35 or an immunogenic portion of the polypeptide encoded by SEQ ID NO:35.

75. The polypeptide of claim 42, wherein the polypeptide comprises an amino acid sequence encoded by SEQ ID NO:36 or an immunogenic portion of the polypeptide encoded by SEQ ID NO:36.

76. The polypeptide of claim 42, wherein the polypeptide comprises an amino acid sequence encoded by SEQ ID NO:37 or an immunogenic portion of the polypeptide encoded by SEQ ID NO:37.

77. The polypeptide of claim 42, wherein the polypeptide comprises an amino acid sequence encoded by SEQ ID NO:38 or an immunogenic portion of the polypeptide encoded by SEQ ID NO:33.

78. The polypeptide of claim 42, wherein the polypeptide comprises an amino acid sequence encoded by SEQ ID NO:39 or an immunogenic portion of the polypeptide encoded by SEQ ID NO:39.

79. The polypeptide of claim 42, wherein the polypeptide comprises an amino acid sequence encoded by SEQ ID NO:40 or an immunogenic portion of the polypeptide encoded by SEQ ID NO:40.

80. The polypeptide of claim 42, wherein the polypeptide comprises an amino acid sequence encoded by SEQ ID NO:41 or an immunogenic portion of the polypeptide encoded by SEQ ID NO:41.

81. The polypeptide of claim 42, wherein the polypeptide comprises an amino acid sequence encoded by SEQ ID NO:42 or an immunogenic portion of the polypeptide encoded by SEQ ID NO:42.

82. The polypeptide of claim 42, wherein the polypeptide comprises an amino acid sequence encoded by SEQ ID NO:43 or an immunogenic portion of the polypeptide encoded by SEQ ID NO:43.

83. The polypeptide of claim 42, wherein the polypeptide comprises an amino acid sequence encoded by SEQ ID NO:45 or an immunogenic portion of the polypeptide encoded by SEQ ID NO:45.

84. The polypeptide of claim 42, wherein the polypeptide comprises an amino acid sequence encoded by SEQ ID NO:47 or an immunogenic portion of the polypeptide encoded by SEQ ID NO:47.

85. The polypeptide of claim 42, wherein the polypeptide comprises an amino acid sequence encoded by SEQ ID NO:48 or an immunogenic portion of the polypeptide encoded by SEQ ID NO:48.

86. The polypeptide of claim 42, wherein the polypeptide comprises an amino acid sequence encoded by SEQ ID NO:49 or an immunogenic portion of the polypeptide encoded by SEQ ID NO:49.

87. The polypeptide of claim 42, wherein the polypeptide comprises an amino acid sequence encoded by SEQ ID NO:50 or an immunuogenic portion of the polypeptide encoded by SEQ ID NO:50.

88. The polypeptide of claim 42, wherein the polypeptide comprises an amino acid sequence encoded by SEQ ID NO:51 or an immunogenic portion of the polypeptide encoded by SEQ ID NO:51.

89. The polypeptide of claim 42, wherein the polypeptide comprises an amino acid sequence encoded by SEQ ID NO:52 or an immunogenic portion of the polypeptide encoded by SEQ ID NO:52.

90. The polypeptide of claim 42, wherein tie polypeptide comprises an amino acid sequence encoded by SEQ ID NO:94 or an immunogenic portion of the polypeptide encoded by SEQ ID NO:94.

91. The polypeptide of claim 42, wherein the polypeptide comprises an amino acid sequence encoded by SEQ ID NO:96 or an immunogenic portion of the polypeptide encoded by SEQ ID NO:96.

92. The polypeptide of claim 42, wherein the polypeptide comprises an amino acid sequence encoded by SEQ ID NO:133 or an immunogenic portion of the polypeptide encoded by SEQ ID NO:133.

93. The polypeptide of claim 42, wherein the polypeptide comprises an amino acid sequence encoded by SEQ ID NO:134 or an immunogenic portion of the polypeptide encoded by SEQ ID NO:134.

\* \* \* \* \*